US010428084B2

(12) United States Patent
Park et al.

(10) Patent No.: US 10,428,084 B2
(45) Date of Patent: Oct. 1, 2019

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si, Chungcheongnam-do (KR)

(72) Inventors: Jeongkeun Park, Seoul (KR); Wonsam Kim, Hwaseong-si (KR); Moonsung Kang, Cheonan-si (KR); Boram Park, Mokpo-si (KR); Hoyoung Jung, Cheonan-si (KR); Jong-jin Ha, Cheonan-si (KR); Junghwan Park, Hwaseong-si (KR); Sunhee Lee, Hwaseong-si (KR); Gyumin Lee, Cheonan-si (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 128 days.

(21) Appl. No.: 15/561,707

(22) PCT Filed: Mar. 11, 2016

(86) PCT No.: PCT/KR2016/002435
§ 371 (c)(1),
(2) Date: Sep. 26, 2017

(87) PCT Pub. No.: WO2016/153198
PCT Pub. Date: Sep. 29, 2016

(65) Prior Publication Data
US 2018/0201621 A1 Jul. 19, 2018

(30) Foreign Application Priority Data
Mar. 26, 2015 (KR) .................. 10-2015-0042166

(51) Int. Cl.
C07D 495/04 (2006.01)
C09K 11/06 (2006.01)
C07D 491/048 (2006.01)
C07D 513/04 (2006.01)
H01L 27/32 (2006.01)
H01L 51/50 (2006.01)
H01L 51/52 (2006.01)
H01L 51/00 (2006.01)

(52) U.S. Cl.
CPC ....... *C07D 495/04* (2013.01); *C07D 491/048* (2013.01); *C07D 513/04* (2013.01); *C09K 11/06* (2013.01); *H01L 27/3211* (2013.01); *H01L 51/006* (2013.01); *H01L 51/0052* (2013.01); *H01L 51/0059* (2013.01); *H01L 51/0061* (2013.01); *H01L 51/0071* (2013.01); *H01L 51/0074* (2013.01); *H01L 51/508* (2013.01); *H01L 51/5024* (2013.01); *H01L 51/5092* (2013.01); *H01L 51/5206* (2013.01); *H01L 51/5221* (2013.01); *C09K 2211/1022* (2013.01); *C09K 2211/1033* (2013.01); *C09K 2211/1037* (2013.01); *C09K 2211/1059* (2013.01); *C09K 2211/1088* (2013.01); *H01L 51/5056* (2013.01); *H01L 51/5096* (2013.01); *Y02E 10/549* (2013.01)

(58) Field of Classification Search
CPC .................................................... C07D 491/048
See application file for complete search history.

(56) References Cited

U.S. PATENT DOCUMENTS

2014/0353640 A1  12/2014  Haketa et al.
2018/0047914 A1* 2/2018  Cha .................. C07D 491/048
2018/0141957 A1* 5/2018  Park .................. C07D 495/04

FOREIGN PATENT DOCUMENTS

| KR | 10-2011-0004408 A | 1/2011 |
| KR | 10-2013-0127563 A | 11/2013 |
| KR | 10-2013-0134202 A | 12/2013 |
| KR | 10-2014-0067910 A | 6/2014 |

* cited by examiner

*Primary Examiner* — Peter F Godenschwager
(74) *Attorney, Agent, or Firm* — Vorys, Sater, Seymour & Pease LLP; Mih Suhn Koh

(57) ABSTRACT

Provided are a compound represented by Formula 1, and an organic electric element comprising a first electrode, a second electrode, and an organic material layer formed between the first electrode and the second electrode, wherein the organic material layer comprise the compound represented by Formula 1, and the driving voltage of an organic electronic device can be lowered, and the luminous efficiency, color purity and life time of an organic electronic device can be improved by comprising the compound represented by Formula 1 in the organic material layer.

10 Claims, 1 Drawing Sheet

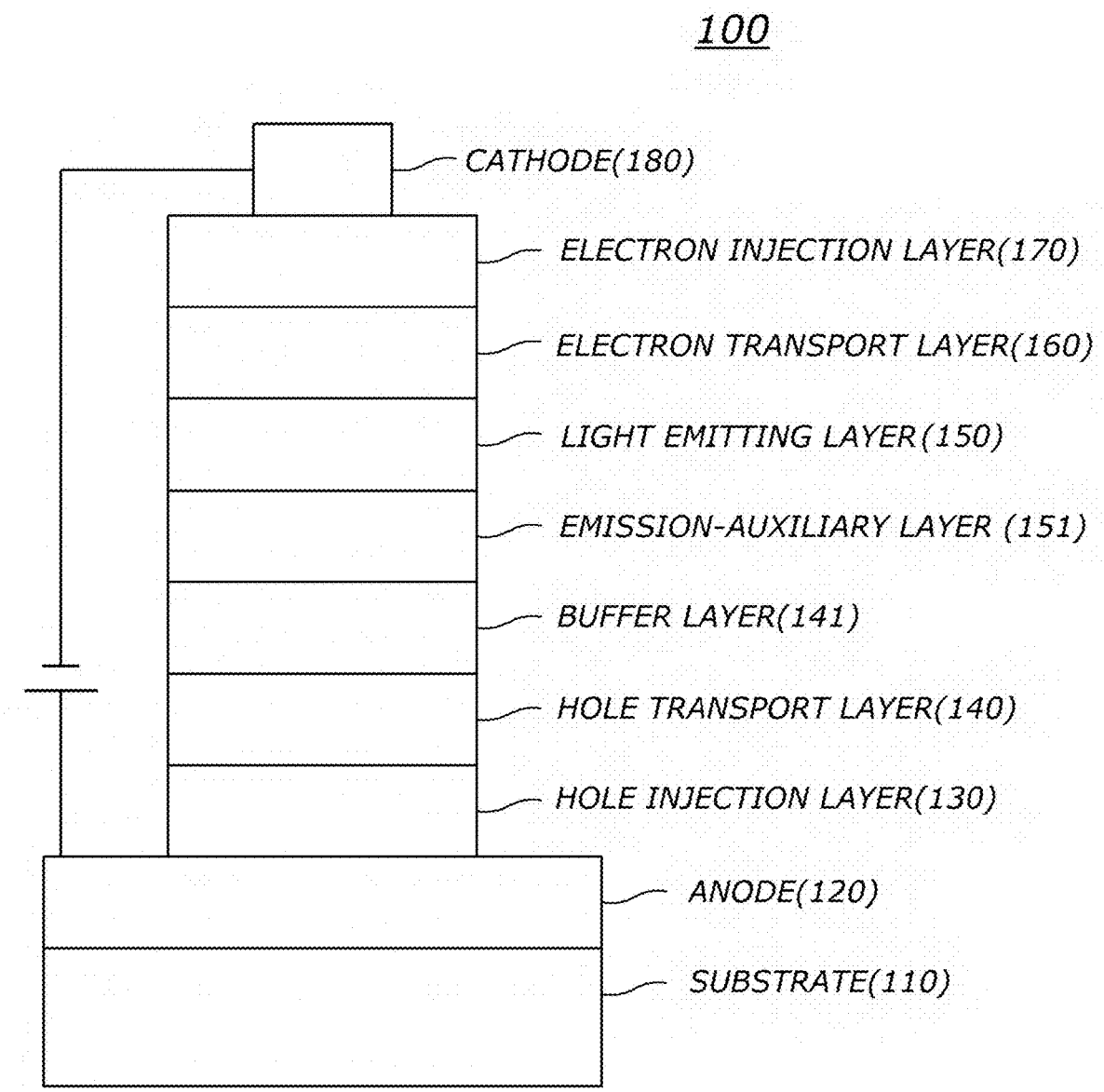

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This patent application claims priority from and the benefit under 35 U.S.C. 119(a) of Korean Patent Application No. 10-2015-0042166, filed on Mar. 26, 2015, which is hereby incorporated by reference for all purposes as if fully set forth herein. Further, this application claims the benefit of priority in countries other than U.S.A., which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Further, recently, in order to solve the emission problem in a hole transport layer and driving voltage of an organic electric element, it is needed to form an emission-auxiliary layer (multilayered hole transport layer) between the hole transport layer and a light emitting layer, and it is time to develop different emission-auxiliary layers according to respective light emitting layers.

In general, an electron which is transferred from an electron transport layer to a light emitting layer and a hole which is transferred from a hole transport layer to the light emitting layer are recombined to form an exciton in a light emitting layer. However, when a material having a high hole mobility is used to lower a driving voltage, a positive polaron is accumulated at the interface between the light emitting layer and the hole transporting layer, thereby causing interface deterioration, as a result the lifetime and efficiency are reduced, and charge is out of balance, so that a surplus polaron in the light emitting layer attacks the weak bonding of the light emitting material to deform the light emitting material, thereby exhibiting a phenomenon such as a reduction in the lifetime, efficiency and color purity.

Therefore, the emission-auxiliary layer should be present between a hole transport layer and the light-emitting layer and be a material having an appropriate HOMO value between the light-emitting layer and the hole transport layer in order to prevent the positive polaron from being accumulated on the interface of the light-emitting layer, and be a material having hole mobility within proper driving voltage (within the blue device driving voltage range of the full device) in order to increase charge balance in the light-emitting layer.

However, this cannot be achieved simply by the structural properties of the core of an emission-auxiliary layer material. High efficiency and long lifespan of device can be achieved when the characteristics of the core and the sub-substituent and the proper combination of the emission-auxiliary layer and the hole transport layer and of the emission-auxiliary layer and the light-emitting layer are met.

That is, it should be preceded that the materials consisting an organic material layer of the element, for example, a hole injection material, a hole transport material, a light emitting material, an electron transport material, an electron injection material, or the like, are supported by a stable and efficient material. Particularly, it is strongly required to develop materials of the emission-auxiliary layer and the hole transport layer.

SUMMARY

In order to solve one or more of the above-mentioned problems in prior art, an aspect of the present invention is to provide a compound having efficient electron blocking ability and hole transport ability and allowing to improve luminous efficiency, to lower a driving voltage, to have a high heat-resistance, and to improve color purity and lifetime of the element, an organic electric element comprising the same, and an electronic device thereof.

In accordance with an aspect of the present invention, the compound represented by the following formula 1 is provided.

[Formula 1]

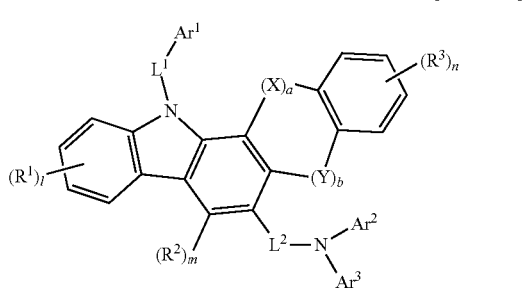

In another aspect of the present invention, organic electric elements comprising the compound represented by the formula 1 above and electronic devices including the organic electric element are provided.

According to the embodiments of the present invention, by using compound of the present invention as a material of the organic electric device, luminous efficiency, heat-resistance, color purity and lifetime of the organic electric elements can be improved and a driving voltage of the organic electric elements can be lowered due to HOMO energy level and the high T1 value that facilitate charge balancing in the light emitting layer.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below, "substituted fluorenyl group" or "substituted fluorenylene group" means, functional group which at least any one of R, R' and R" is a functional group other than hydrogen, and fluorenyl group" or "fluorenylene group" comprises spiro compound which is formed by linking R and R' together with the carbon bonded to them.

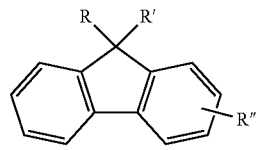

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P, and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes compound below.

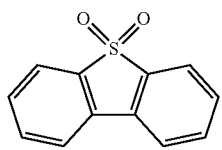 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom, fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a fluorenyl group, a $C_8$-$C_{20}$ arylalkenyl group, a silane group, a boron group, a germanium group, and a $C_5$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene, which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula.

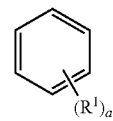

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. when a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

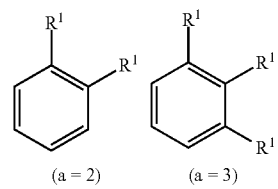

FIG. 1 illustrates an organic electric element according to an embodiment of the present invention.

Referring to FIG. 1, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may not be formed, the organic material layer may further include a hole blocking layer, an electron blocking layer, an emission-auxiliary layer 151, an electron transport auxiliary layer, a buffer layer 141, etc., the electron transport layer 160 and the like may serve as the hole blocking layer.

Although not shown, the organic electric element according to an embodiment of the present invention may further include a protective layer or a layer for improving luminous efficiency (capping layer), wherein they are formed on at least one side of the first and second electrodes opposite to the organic material layer.

The inventive compound employed in the organic material layer may be used as a material of a hole injection layer 130, an emission-auxiliary layer 151, a hole transport layer 140, an electron transport auxiliary layer, an electron transport layer 160, and an electron injection layer 170, as a host material or a dopant material of a light emitting layer 150, or as a material a capping layer material. For example, the inventive compound may be used as material of the light emitting layer 150, the hole transport layer 140, and/or the emission-auxiliary layer 151, preferably, as the hole transport layer 140, and/or the emission-auxiliary layer 151.

On the other hand, even if the core is the same core, the band gap, the electrical characteristics, the interface characteristics, and the like may be different depending on which substituent is bonded at which position. Therefore, it is necessary to study the selection of the core and the combination of the sub-substituent. Specially, long life span and high efficiency can be simultaneously achieved when the optimal combination of energy levels and T1 values, inherent material properties (mobility, interfacial properties, etc.), and the like among the respective layers of an organic material layer is achieved.

As already described above, generally, in order to solve the emission problem with a hole transport layer of an organic electric element, it is preferable that an emission-auxiliary layer is formed between the hole transport layer and a light emitting layer, and it is necessary to develop different emission-auxiliary layers according to respective light emitting layers (R, G, B).

On the other hand, it is very difficult to infer the characteristics of an emission-auxiliary layer, even if the core of an emission-auxiliary layer is similar, because it is necessary to grasp the correlation between the emission-auxiliary layer and a hole transport layer and a light emitting layer (host).

According to the present invention, energy levels and T1 values between organic material layers, inherent material properties (mobility, interfacial properties, etc.), and the like can be optimized by forming a hole transport layer and/or an emission-auxiliary layer which comprise the compound represented by the Formula 1, and thus it is possible to simultaneously improve the life span and efficiency of the organic electronic element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

And also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

A WOLED (White Organic Light Emitting Device) readily allows for the formation of ultra-high definition images, and is of excellent processability as well as enjoying the advantage of WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R (Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

The compound according to an aspect of the present invention is represented by the following Formula 1.

[Formula 1]

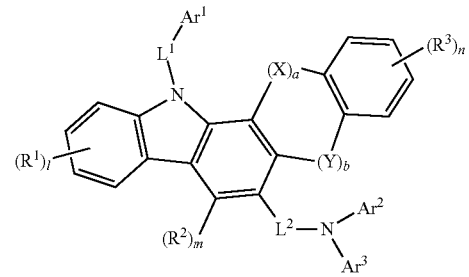

In formula 1 above, symbols may be each defined as follows.

X and Y are each independently O or S, "a" and "b" are each an integer of 0 or 1 and at least one of "a" and "b" is an integer of 1. Here, when "a" or "b" is "0", it means that X or Y is not present and thus carbons of both benzene rings are directly bonded. That is, when a or b is "0", X or Y is a single bond.

$Ar^1$ to $Ar^3$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, $C_1$-$C_{60}$ alkyl group, a fused ring group of a $C_6$-$C_{60}$ aromatic ring and a $C_3$-$C_{60}$ aliphatic ring, and -L'-N(R')(R").

When $Ar^1$ to $Ar^3$ are an aryl group, $Ar^1$ to $Ar^3$ may be preferably a $C_6$-$C_{30}$ aryl group, more preferably $C_6$-$C_{18}$ aryl group, also more preferably $C_6$-$C_{12}$ aryl group, for example, phenyl, biphenyl, terphenyl, naphthyl, phenanthryl and the like. When $Ar^1$ to $Ar^3$ are a heterocyclic group, $Ar^1$ to $Ar^3$ may be preferably a $C_2$-$C_{30}$ heterocyclic group, more preferably a $C_2$-$C_{12}$ heterocyclic group, for example, pyridyl, pyrimidyl, triazinyl, carbazole, dibenzothienyl, dibenzofuryl, and the like. When $Ar^1$ to $Ar^3$ are a fluorenyl group, $Ar^1$ to $Ar^3$ may be, for example, 9,9-dimethyl-9H-fluorenyl, 9,9-diphenyl-9H-fluorenyl, 9,9'-spirobifluorenyl, and the like.

$R^1$ to $R^3$ are each independently selected from the group consisting of deuterium, tritium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group, and -L'-N(R')(R"). Here, neighboring groups of $R^1$, neighboring groups of $R^2$ or neighboring groups of $R^3$ may be linked each other to form a ring when a plurality of $R^1$ to $R^3$ are present.

"l" and "n" are each an integer of 0~4, and "m" is an integer of 0 or 1. A plurality of $R^1$ and A plurality of $R^3$ are the same or different from each other when "l" and "n" are each an integer of 2. Hydrogen is attached in the position of $R^1$-$R^3$ when "l", "m, and "n" are each an integer of 0. Preferably, all of "l", "m, and "n" are an integer of 0.

When $R^1$ to $R^3$ are an aryl group, $R^1$ to $R^3$ may be preferably a $C_6$-$C_{30}$ aryl group, more preferably $C_6$-$C_{12}$ aryl group; when $R^1$ to $R^3$ are a heterocyclic group, $R^1$ to $R^3$ may be preferably a $C_2$-$C_{30}$ heterocyclic group, more preferably $C_2$-$C_5$ heterocyclic group; for example, $R^1$ to $R^3$ may be phenyl, biphenyl, naphthyl, pyridine, pyrimidine, triazine, and the like.

$L^1$, $L^2$ and L' may be each independently selected from the group consisting of a single bond, a $C_6$-$C_{60}$ arylene group, a fluorenylene group, a $C_2$-$C_{60}$ heterocyclic group containing at least one heteroatom selected from O, N, S, Si, and P, a fused ring group of a $C_3$-$C_{60}$ aliphatic ring and a $C_6$-$C_{60}$ aromatic ring, and an aliphatic hydrocarbon group.

When $L^1$, $L^2$ and L' are an arylene group, $L^1$, $L^2$ and L' may be preferably a $C_6$-$C_{30}$ arylene group, more preferably $C_6$-$C_{12}$ arylene group; when $L^1$, $L^2$ and L' are a heterocyclic group, $L^1$, $L^2$ and L' may be preferably a $C_2$-$C_{30}$ heterocyclic group, more preferably $C_2$-$C_{12}$ heterocyclic group; for example, $L^1$, $L^2$ and L' may be phenylene, biphenylene, naphthylene, dimethylfluorene, diphenylfluorene, spirobifluorene, dibenzothiophene, dibenzofuran, pyridine, and the like.

When $Ar^1$ to $Ar^3$, and $R^1$ to $R^3$ are -L'-N(R')(R"), R' and R" may be each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring.

When $Ar^1$ to $Ar^3$, $R^1$ to $R^3$, R' and R" are each the aryl group, fluorenyl group, heterocyclic group, or fused ring group, when $Ar^1$ to $Ar^3$ are each the alkyl group, when $R^1$ to $R^3$ are each the alkyl group, alkenyl group, alkynyl group, alkoxyl group or aryloxy group, or when $L^1$, $L^2$ and L' are each the arylene group, fluorenylene group, heterocyclic group, or fused ring group, each of them may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

In Formula 1, $Ar^2$ may be biphenyl. In this case, Formula 1 may be represented by the following Formula 2.

[Formula 2]

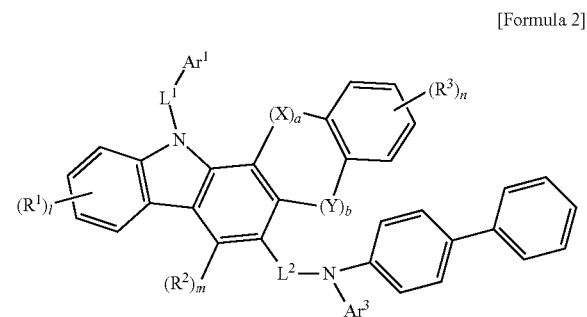

Further, Formula 1 above may be represented by the following Formulas 3 or 4. Formula 1 may be represented by the following Formulas 3 when "a" is "0" in Formula 1, and Formula 1 may be represented by the following Formulas 4 when "b" is "0" in Formula 1.

<Formula 3>

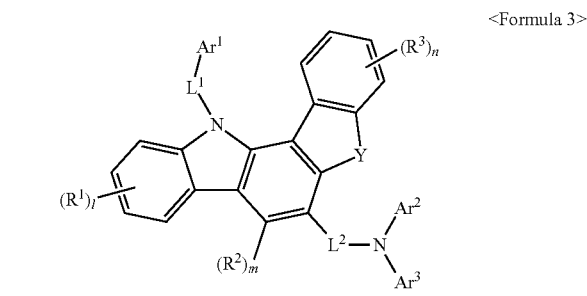

<Formula 4>

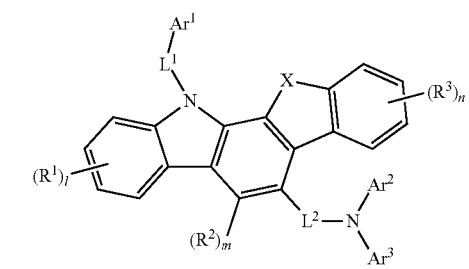

In the above Formulas 2 to 4, symbols may be each the same as defined in Formula 1. That is, in the above Formulas 2 to 4, X, Y, $Ar^1$ to $Ar^3$, $R^1$ to $R^3$, $L^1$, $L^2$, a, b, l, m, and n may be each the same as defined in Formula 1.

Specifically, the compound represented by Formula 1 may be any one of the following compounds.
1-1
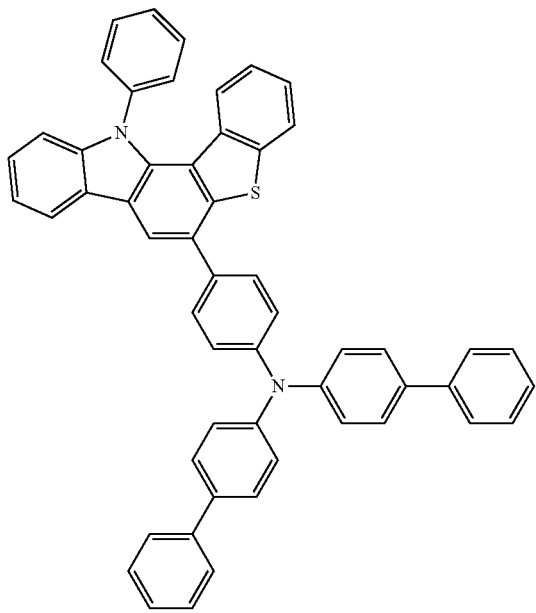
1-2
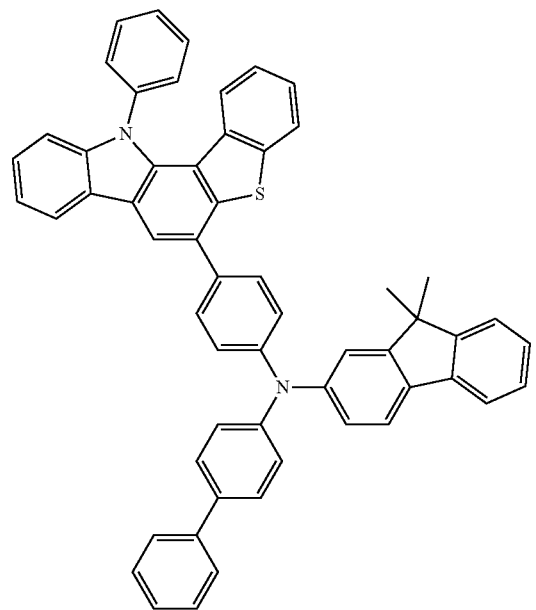
1-3
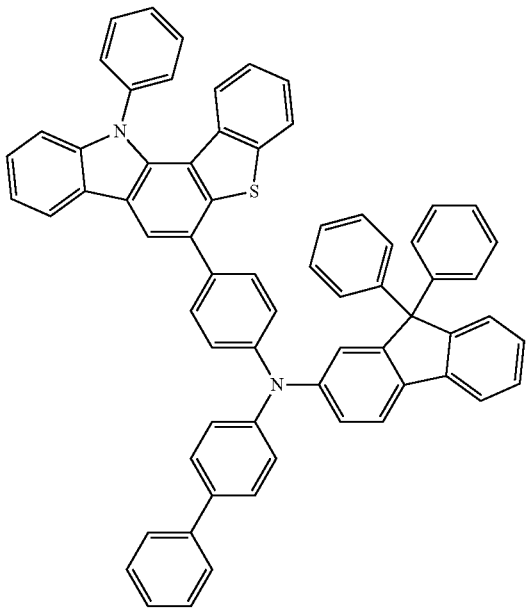
1-4
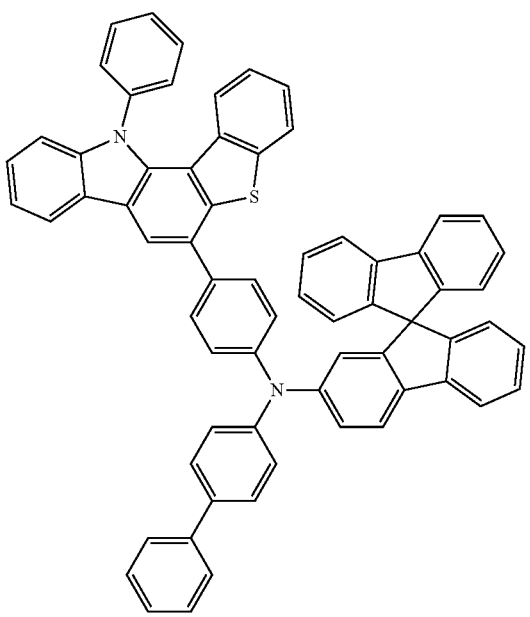

1-5
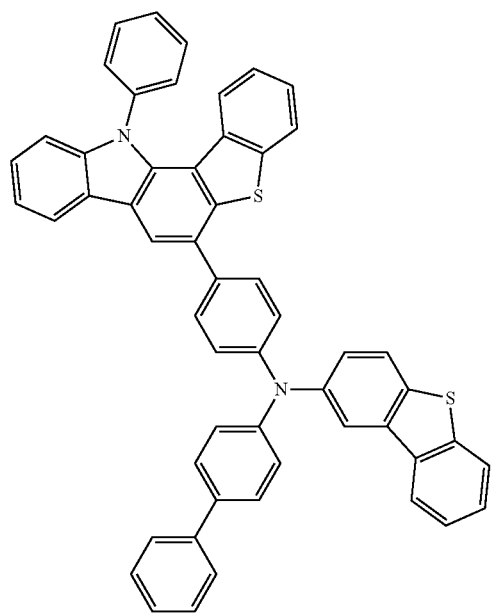
1-6
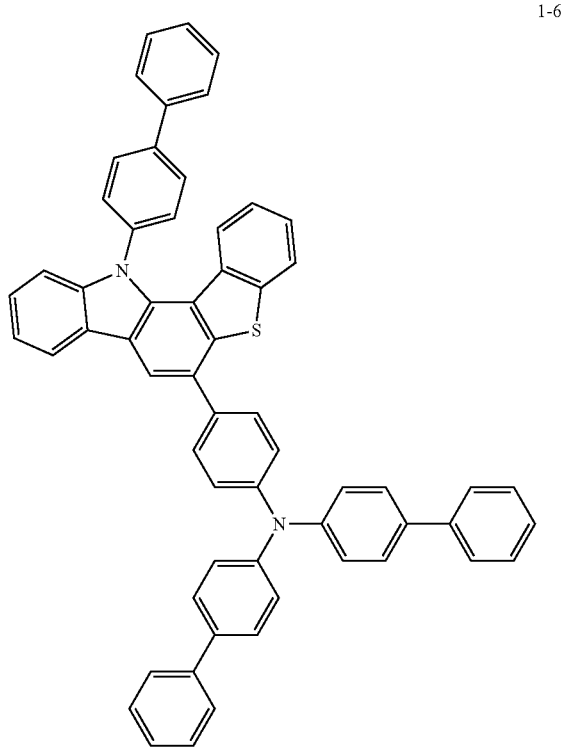
1-7
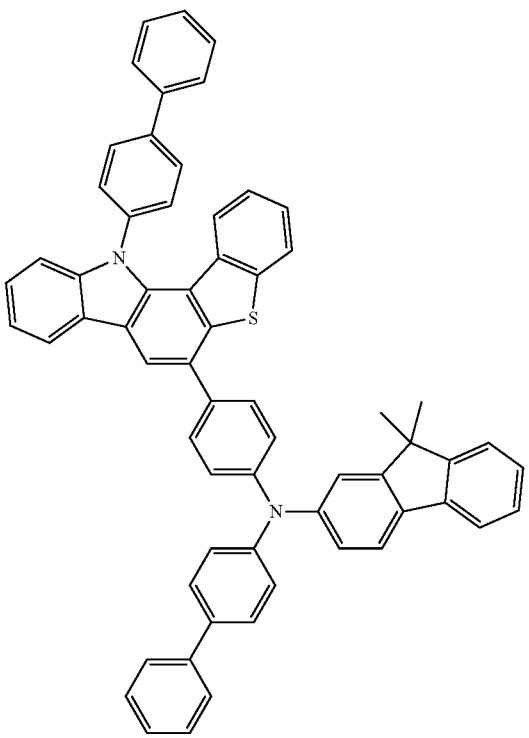
1-8
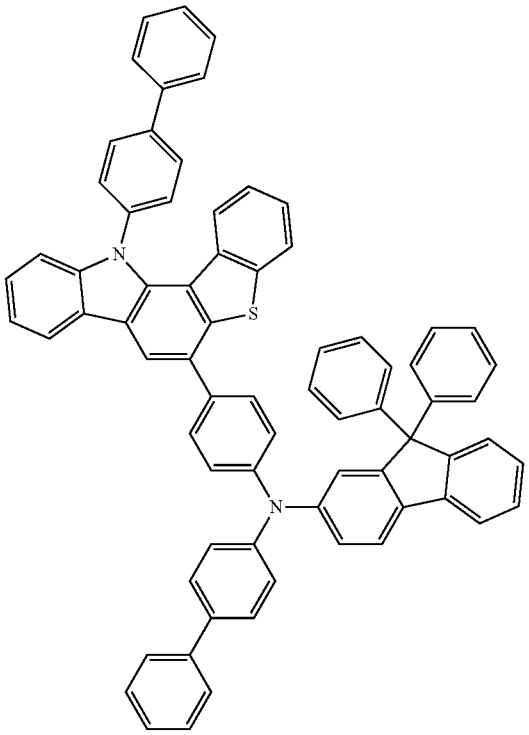

1-9
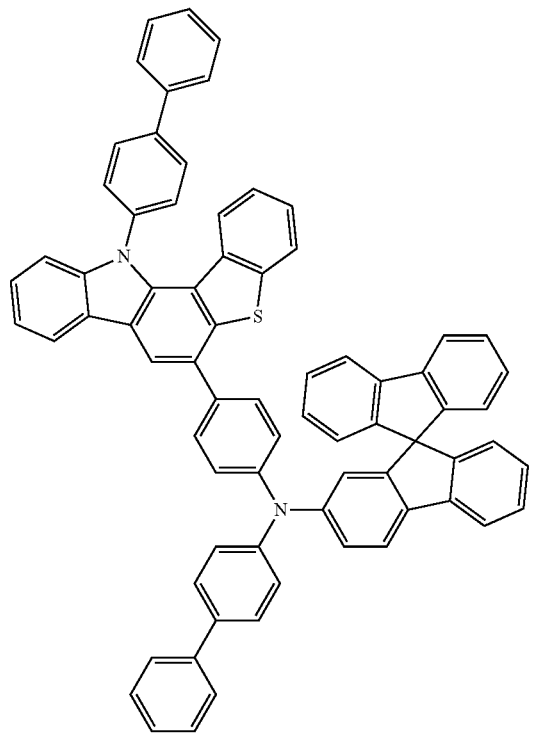
1-10
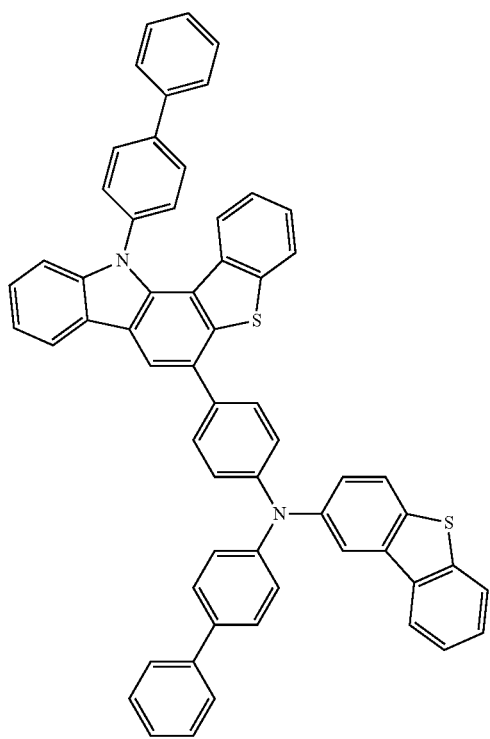
1-11
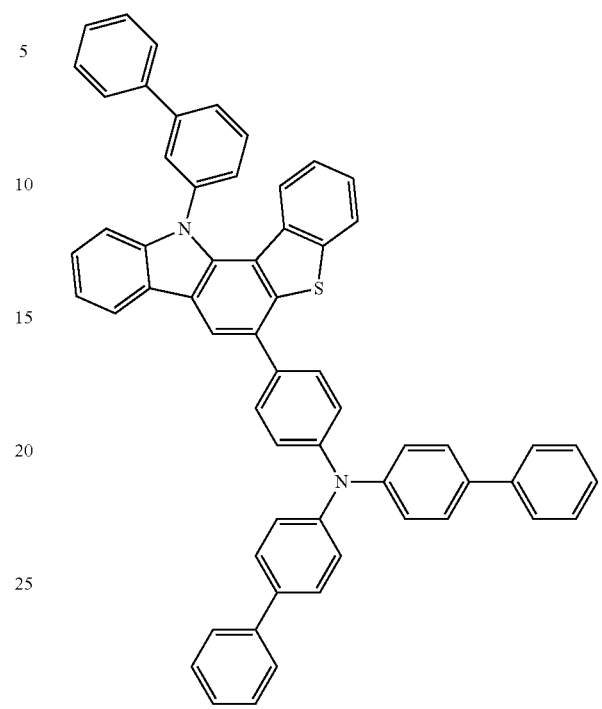
1-12
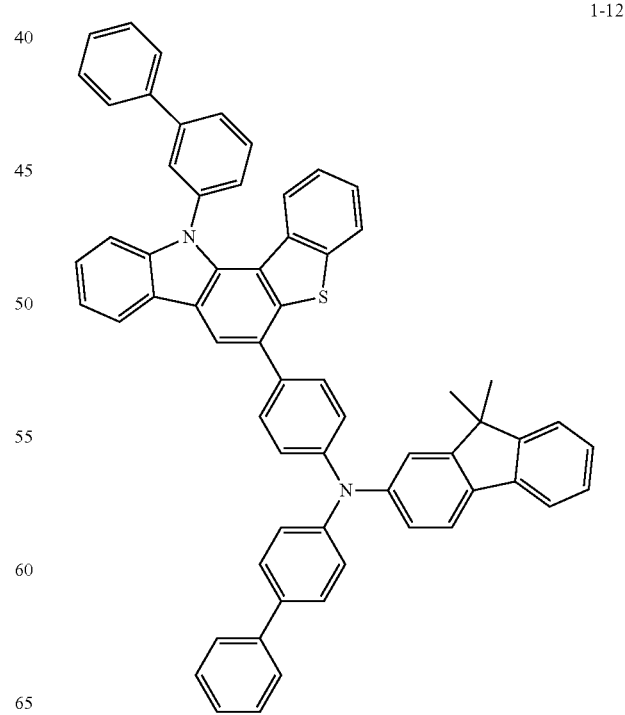

1-13
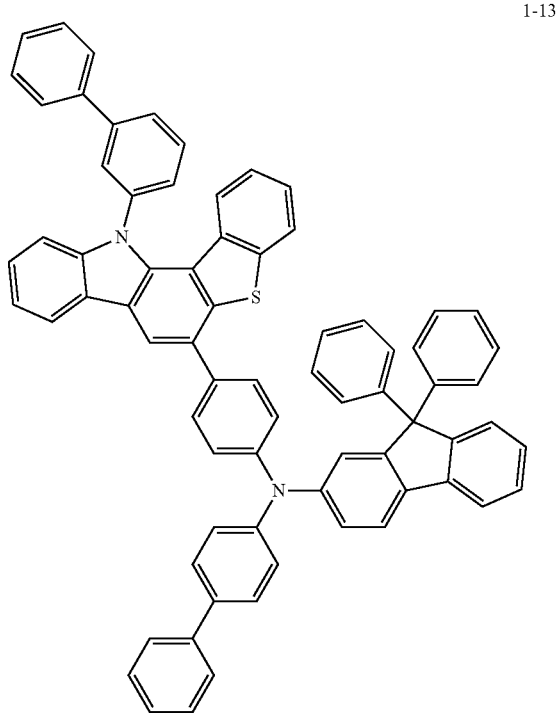 [SMILES: c1ccc(-c2ccc(N(c3ccc(-c4cc5c6ccccc6n(-c6ccc7ccccc7c6)c5c5c4sc4ccccc45)cc3)c3ccc4c(c3)C(c3ccccc3)(c3ccccc3)c3ccccc3-4)cc2)cc1]
1-15
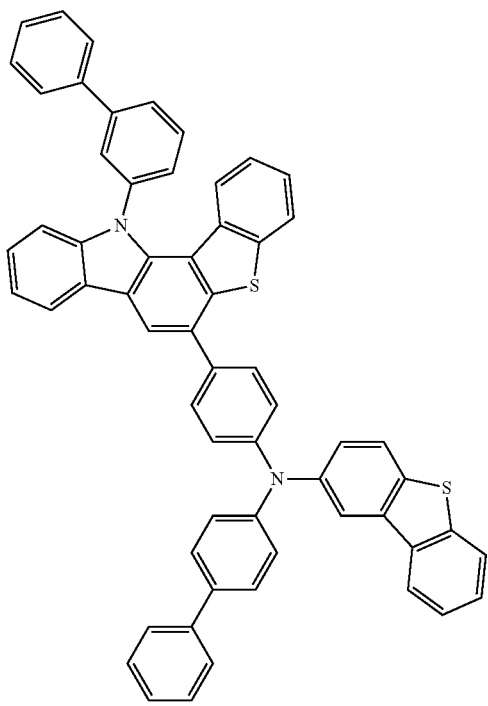
1-14
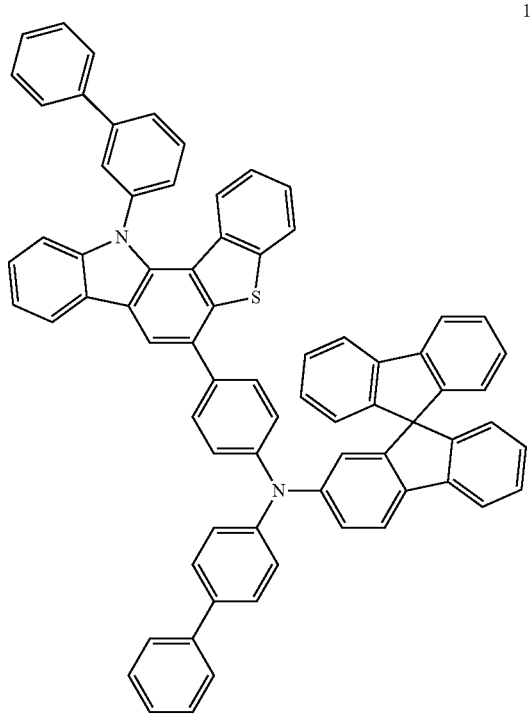
1-16
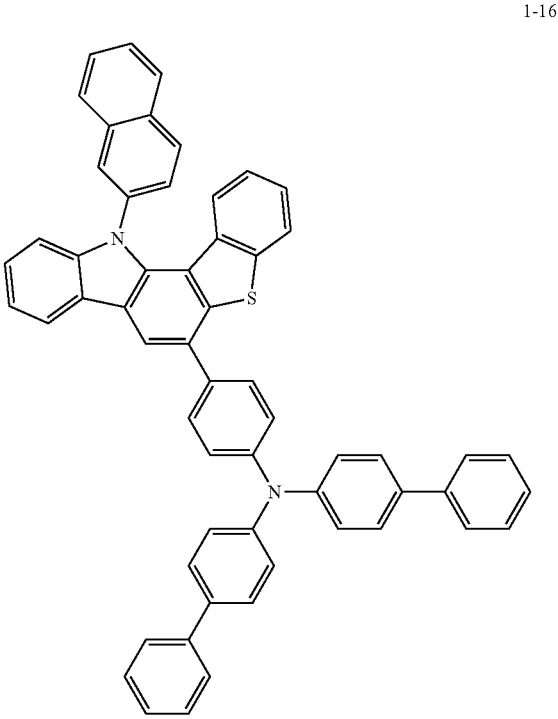

1-17
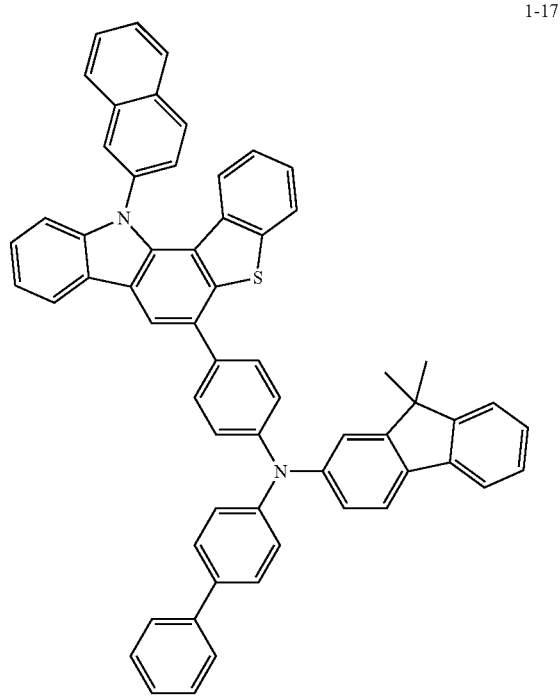
1-19
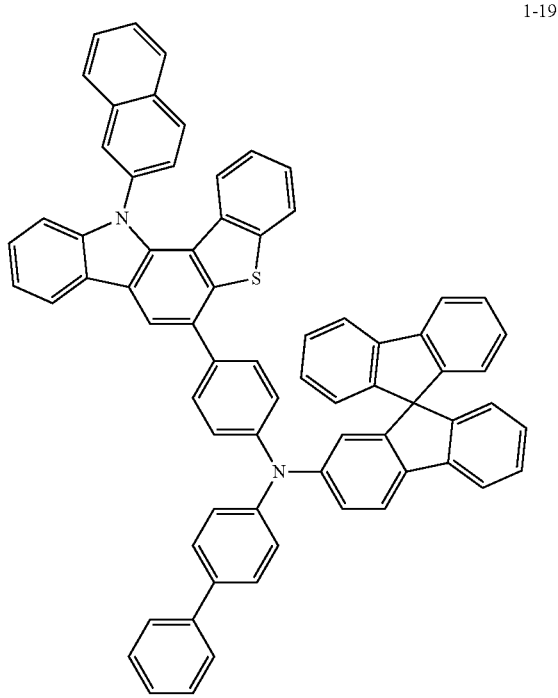
1-18
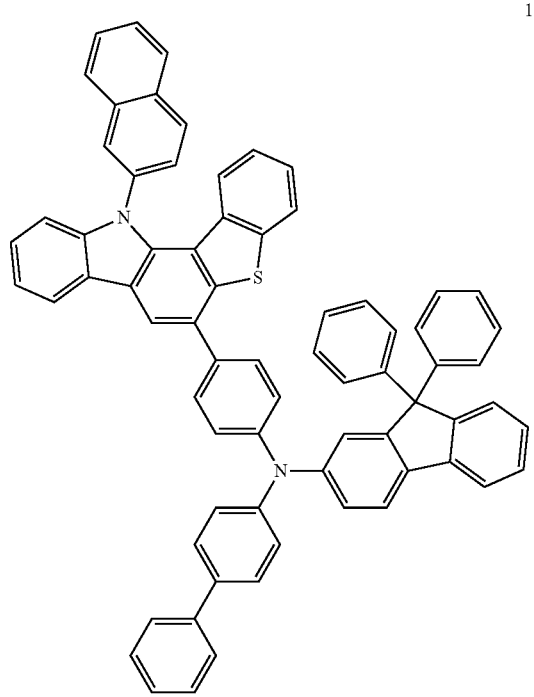
1-20
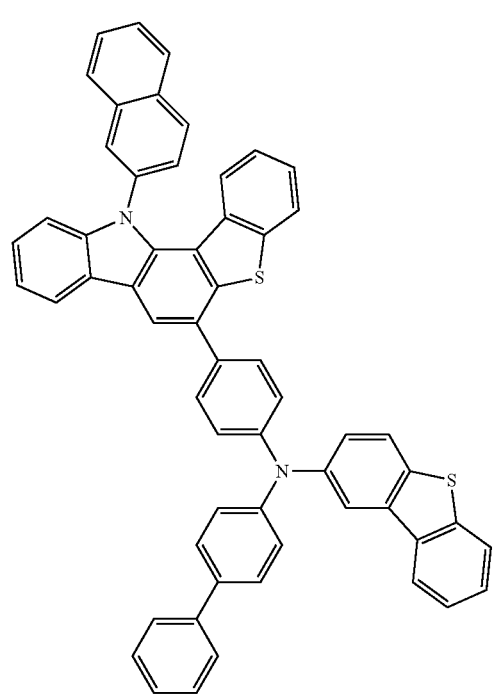

1-21
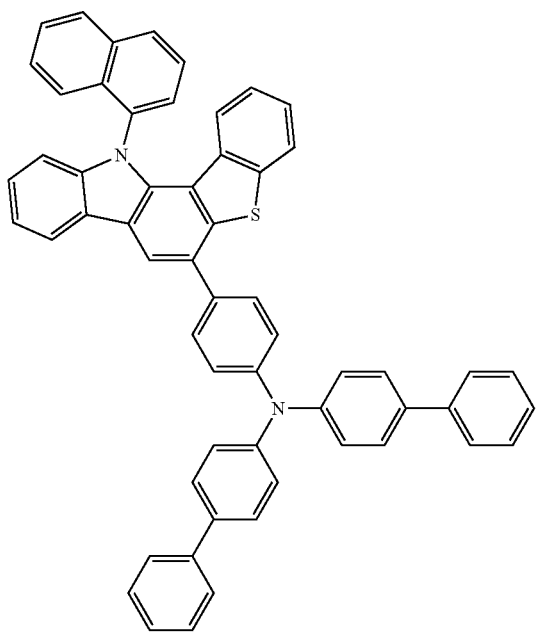
1-23
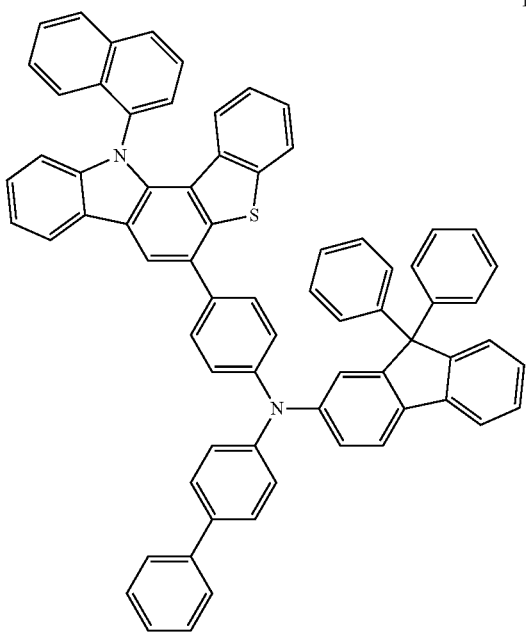
1-22
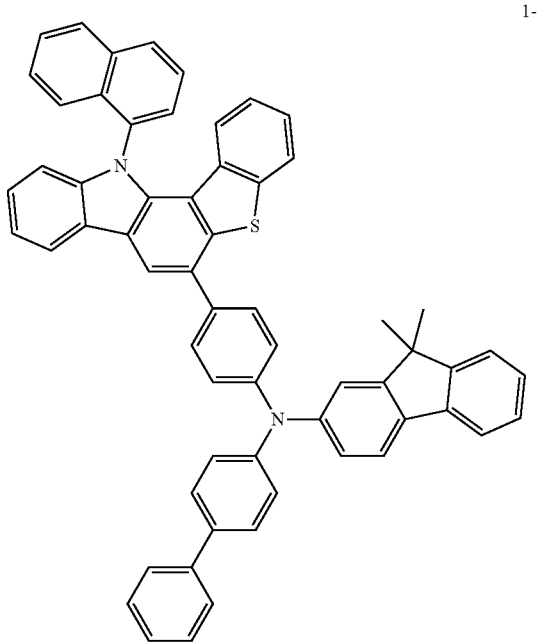
1-24
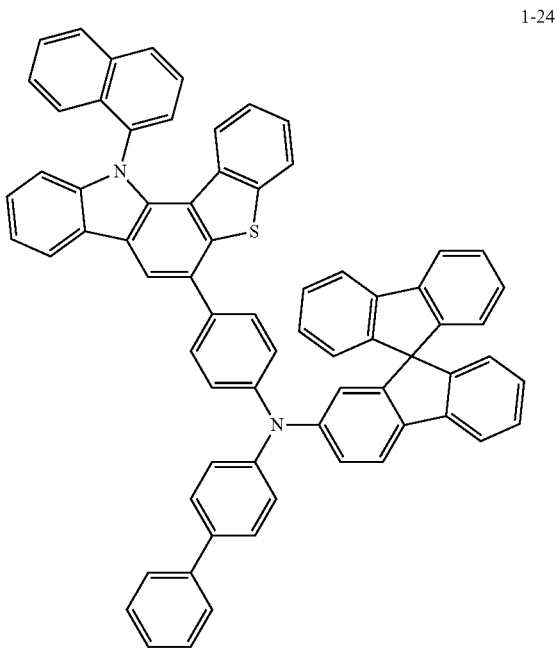

1-25
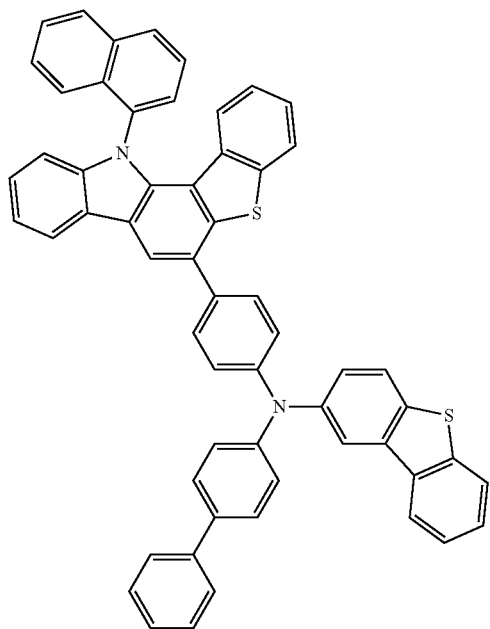
1-26
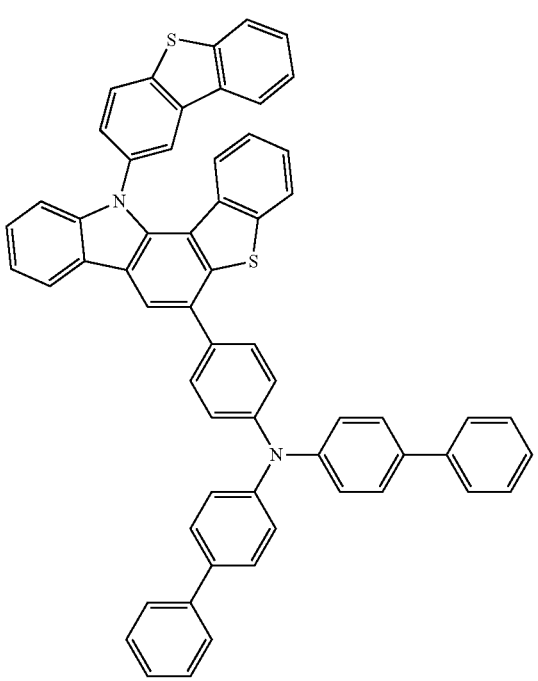
1-27
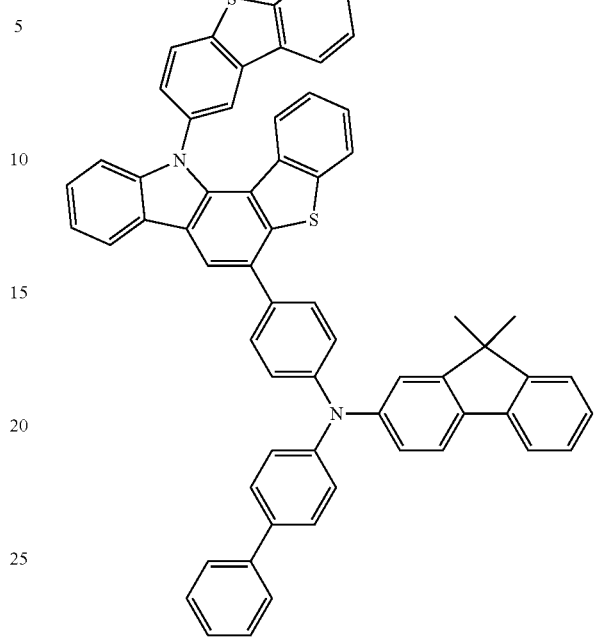
1-28

1-29
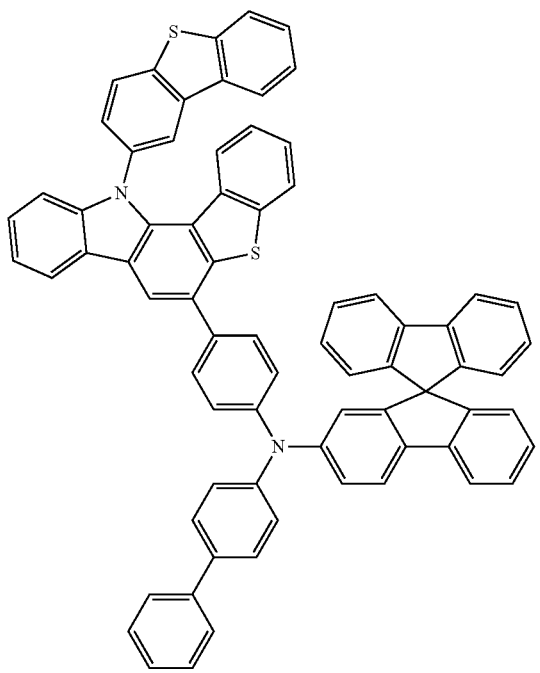
1-30
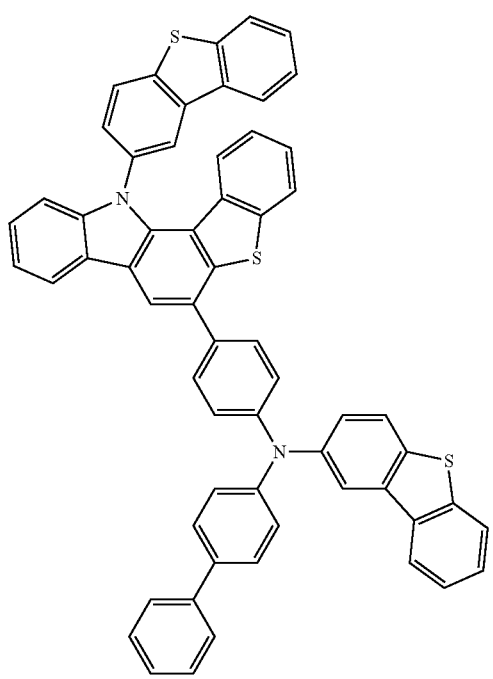
1-31
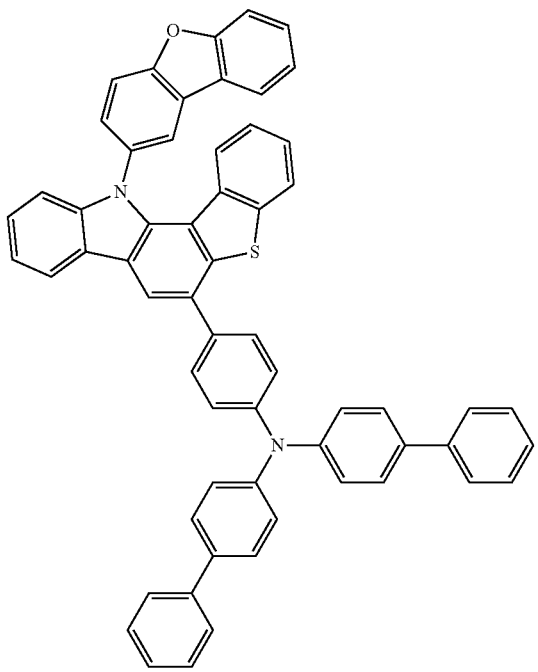
1-32
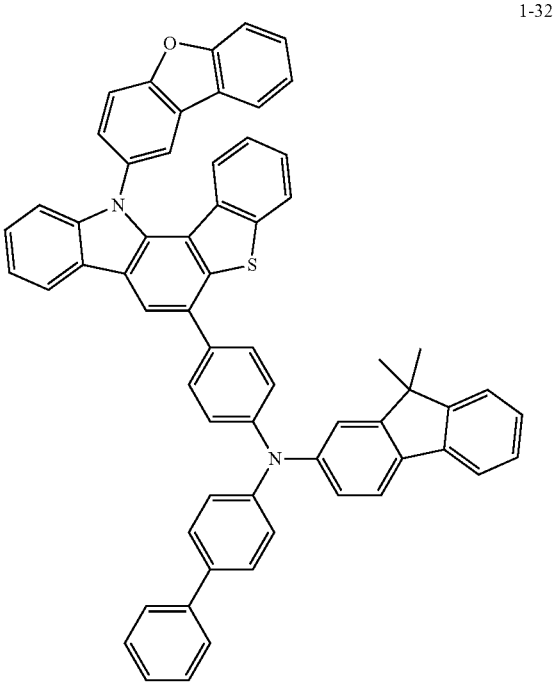

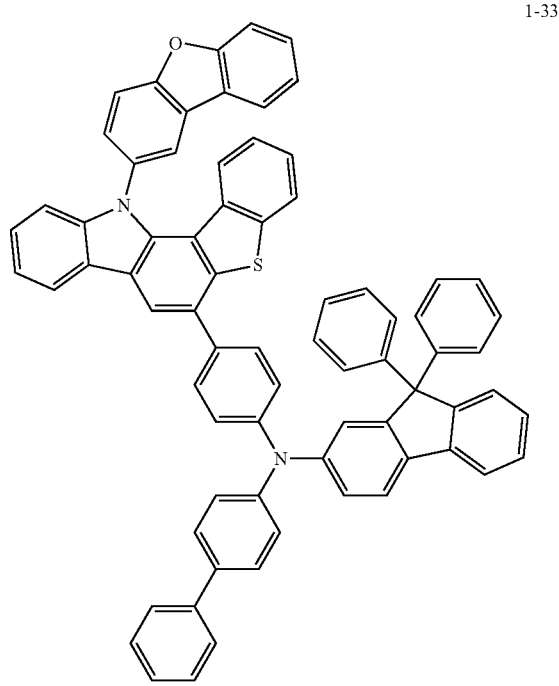
1-33
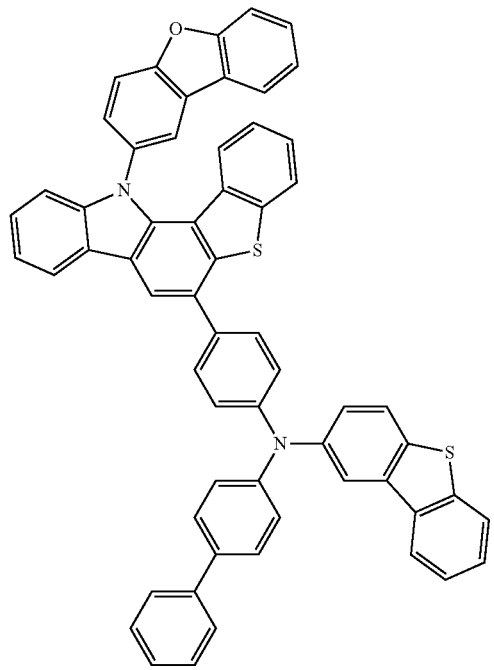
1-35
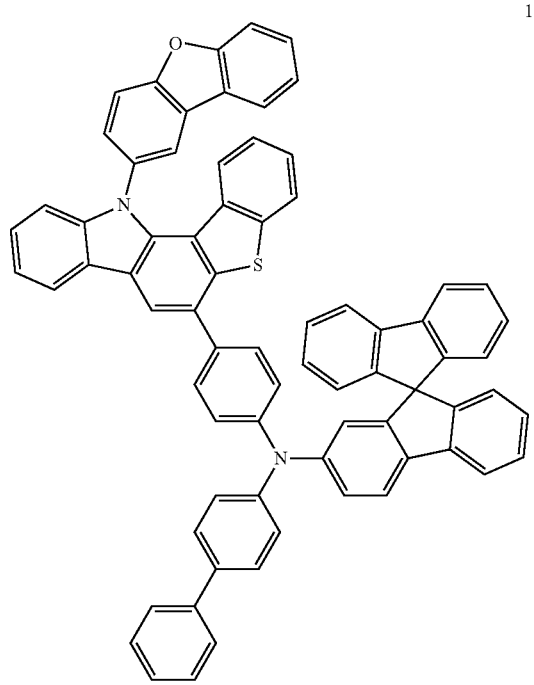
1-34
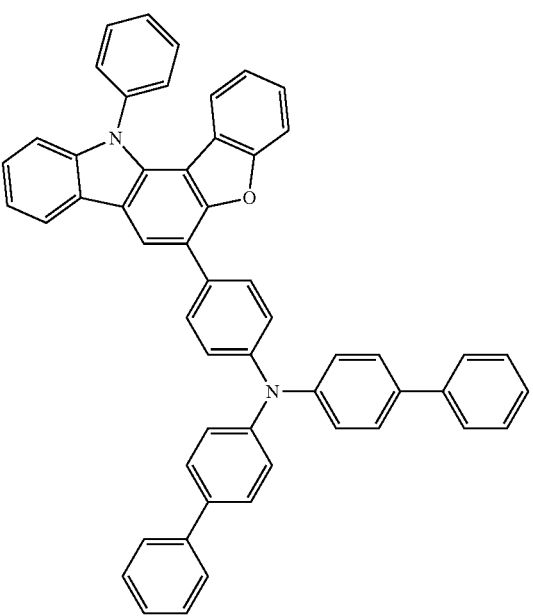
1-36

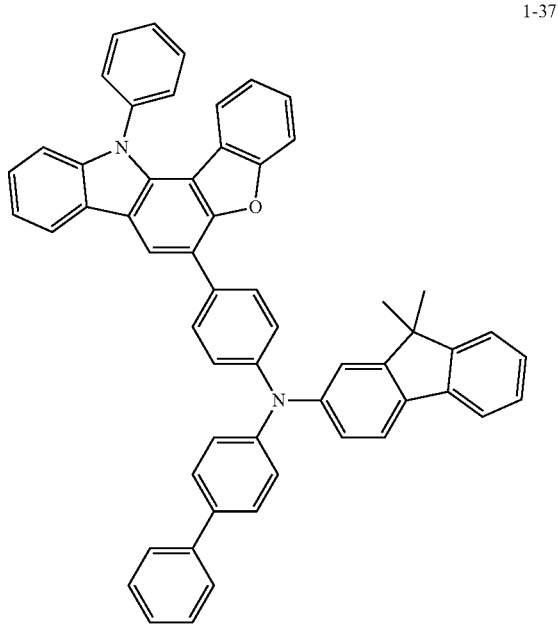
1-37
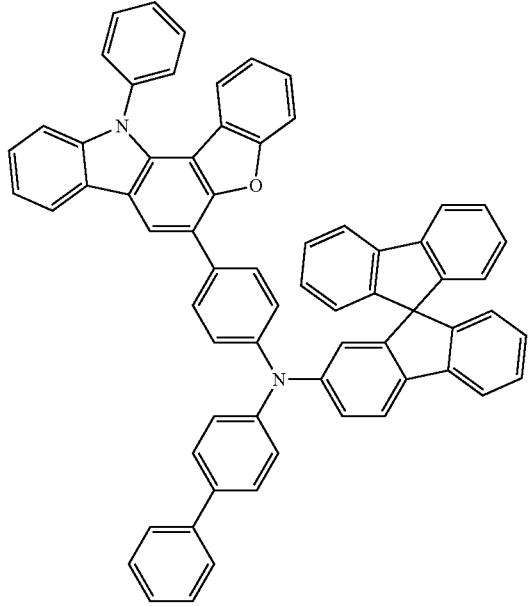
1-39
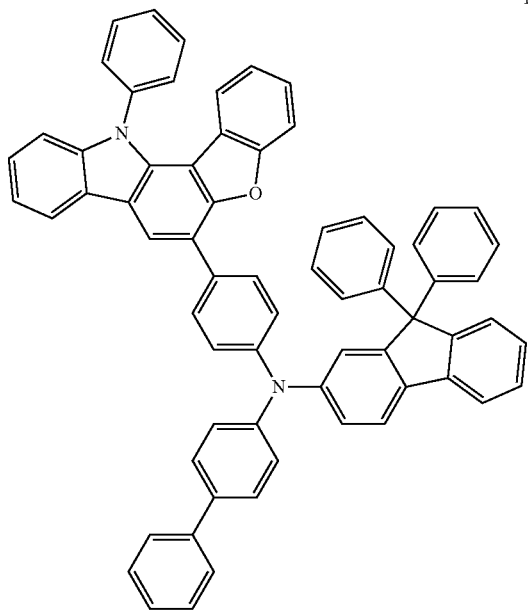
1-38
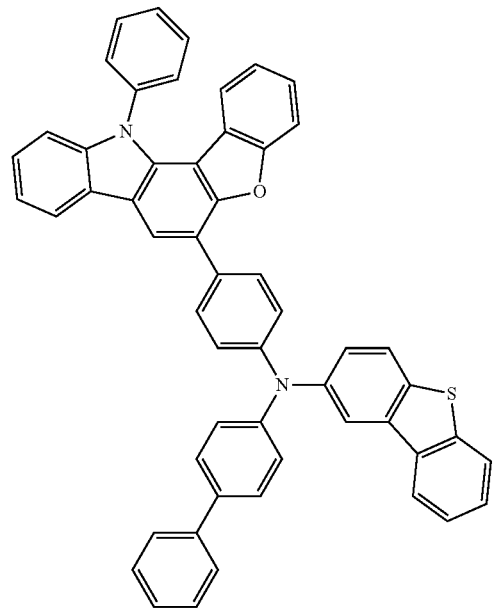
1-40

-continued
1-41
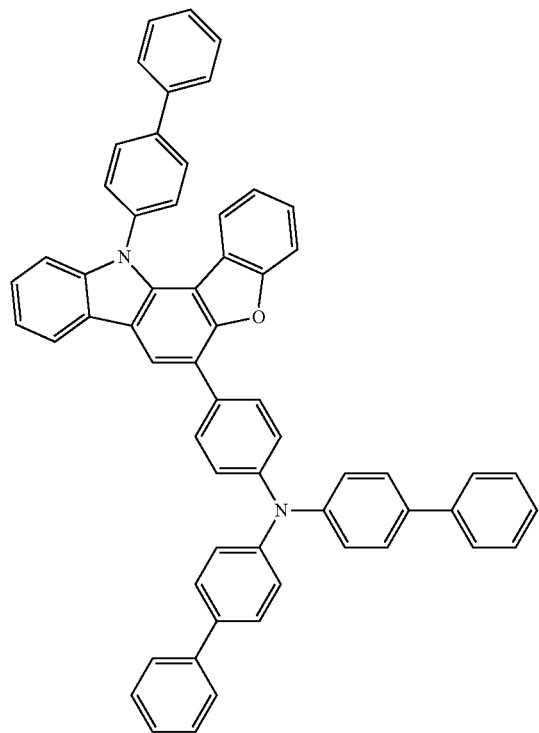
1-42
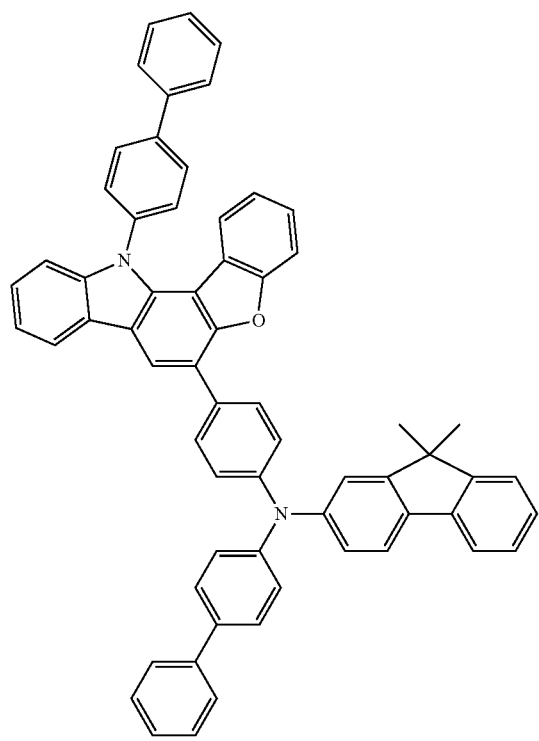
1-43
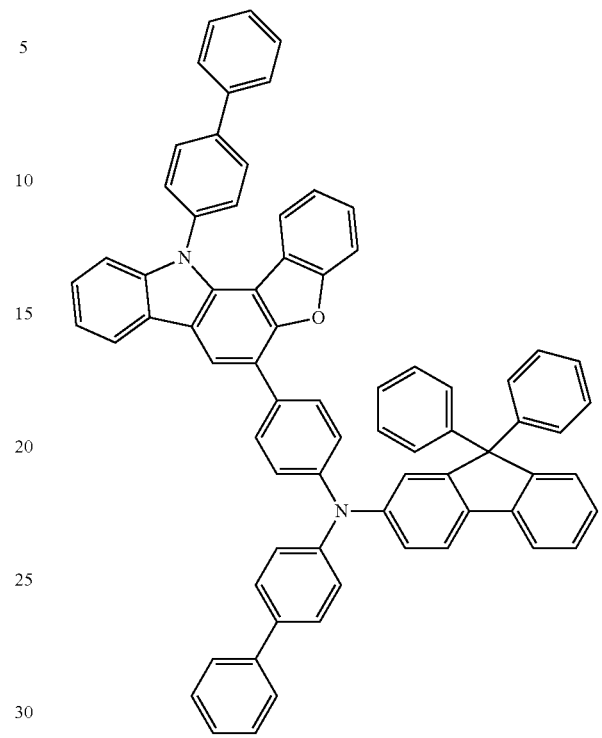
1-44
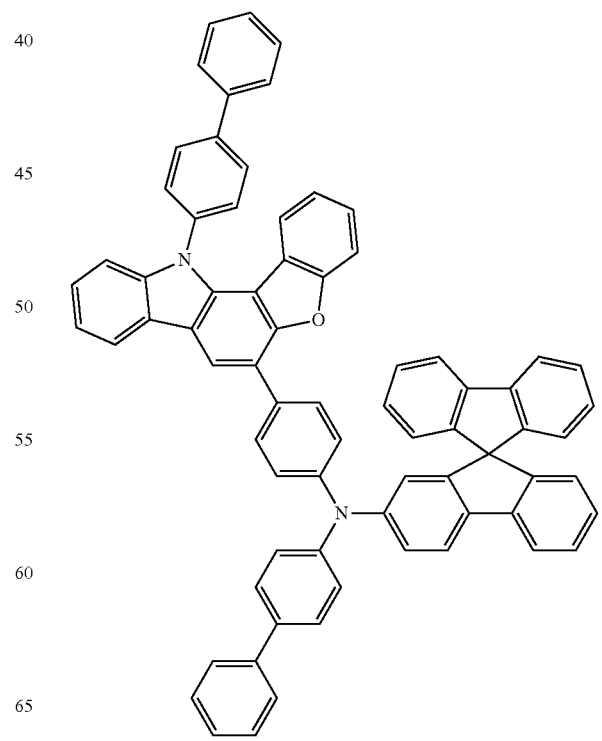

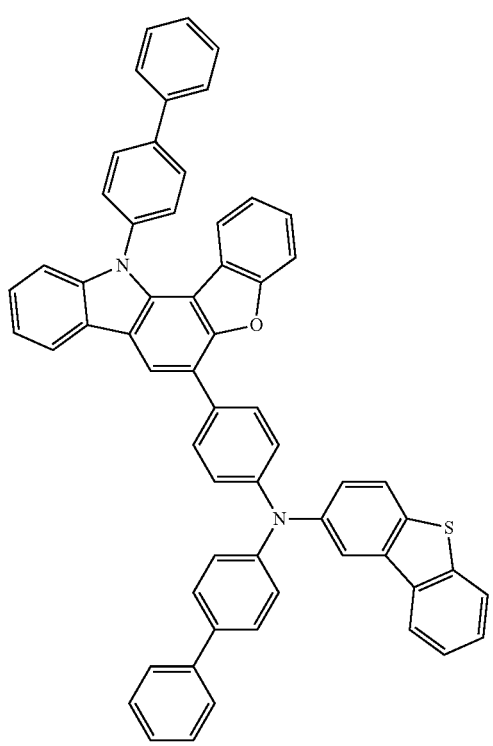
1-45
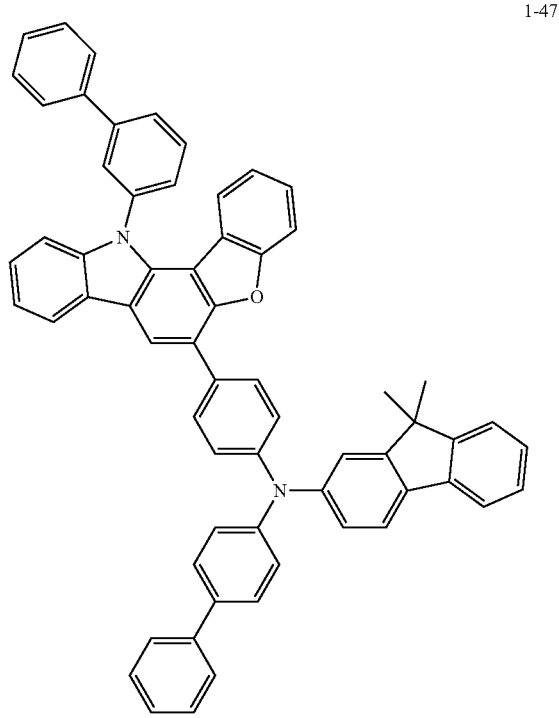
1-47
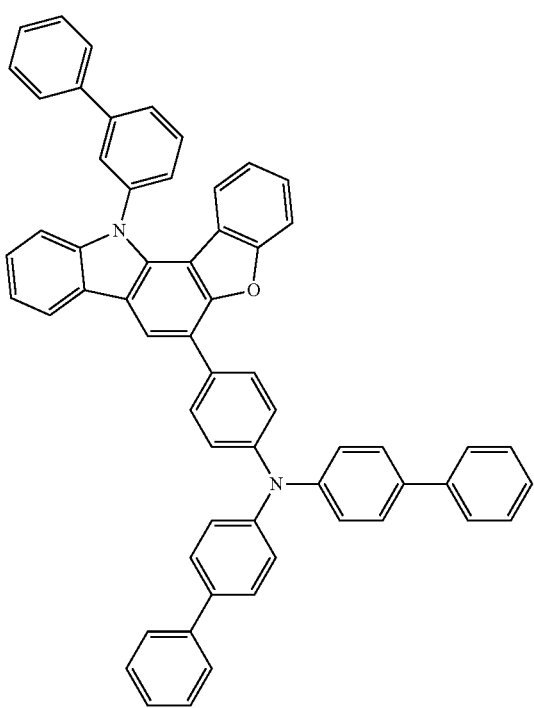
1-46
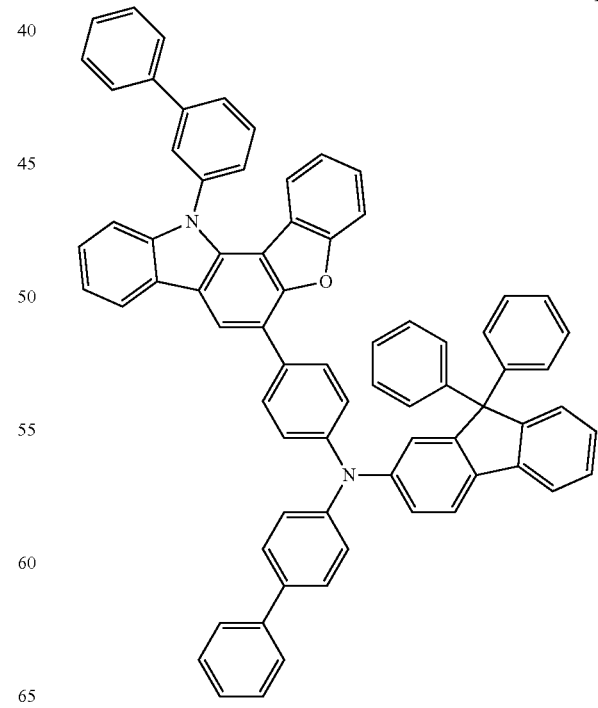
1-48

1-49
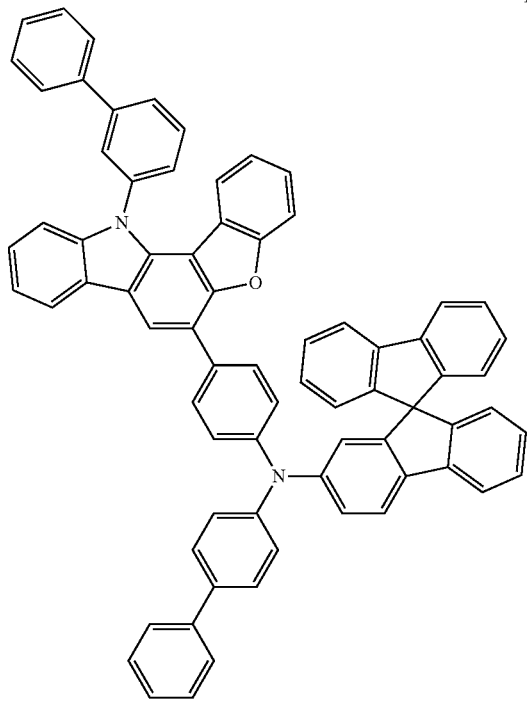
1-50
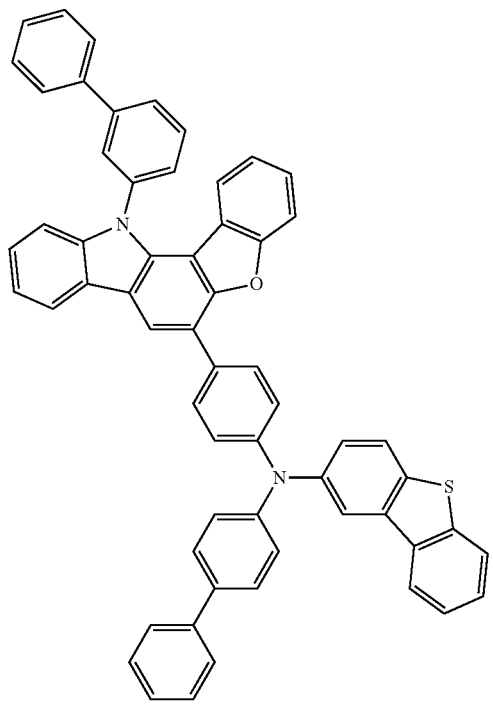
1-51
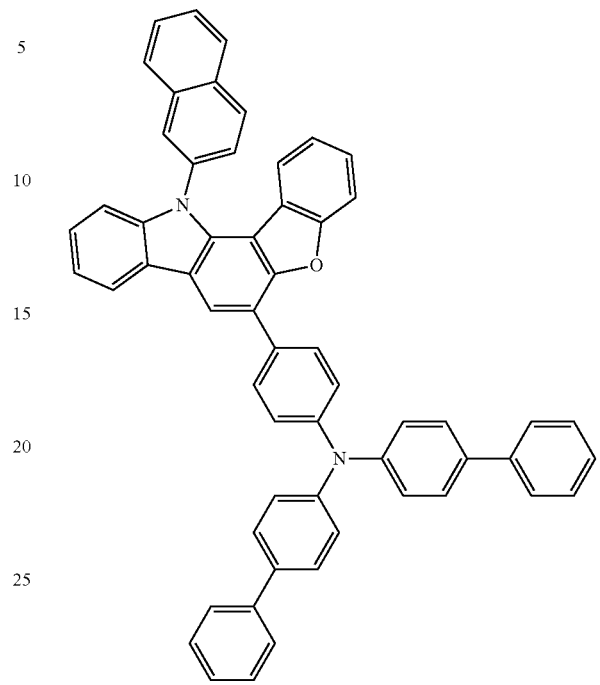
1-52
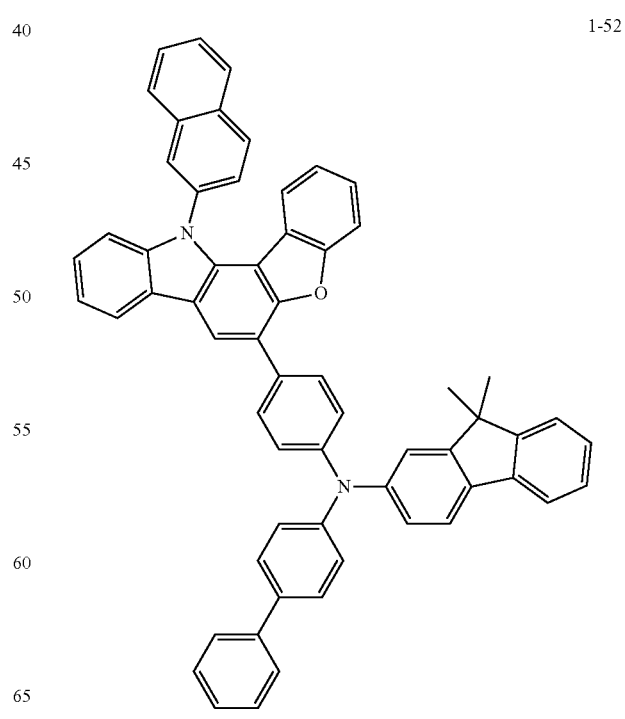

1-53
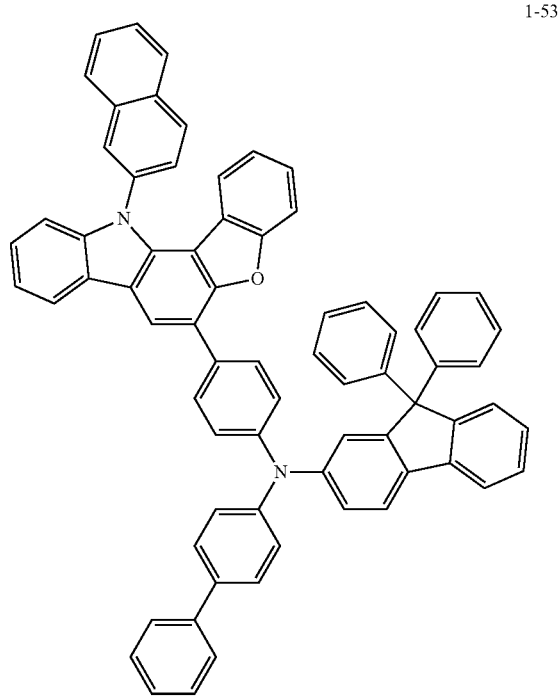
1-55
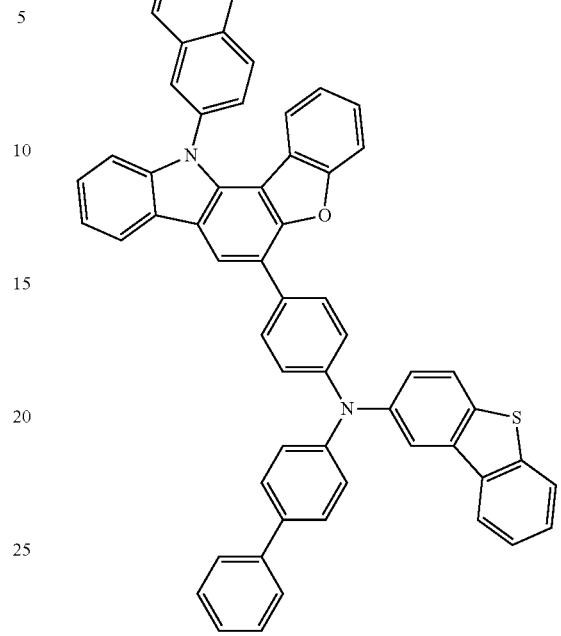
1-54
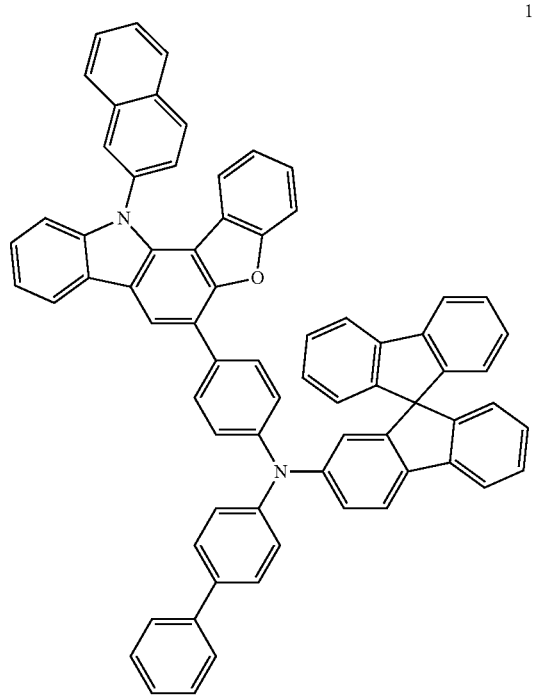
1-56
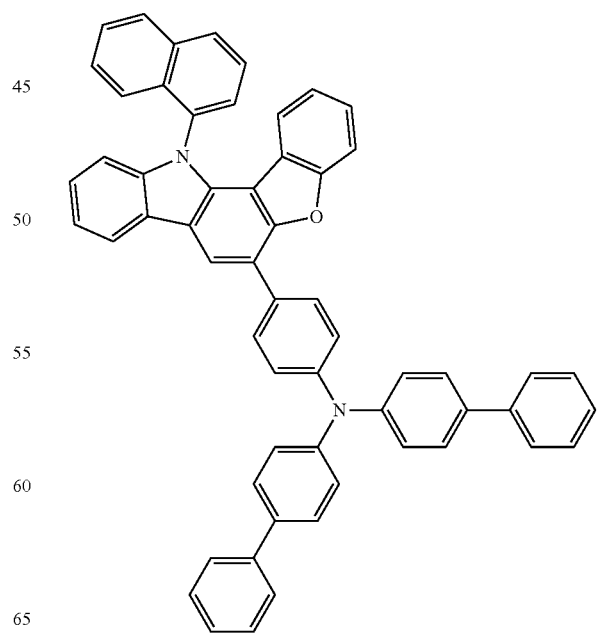

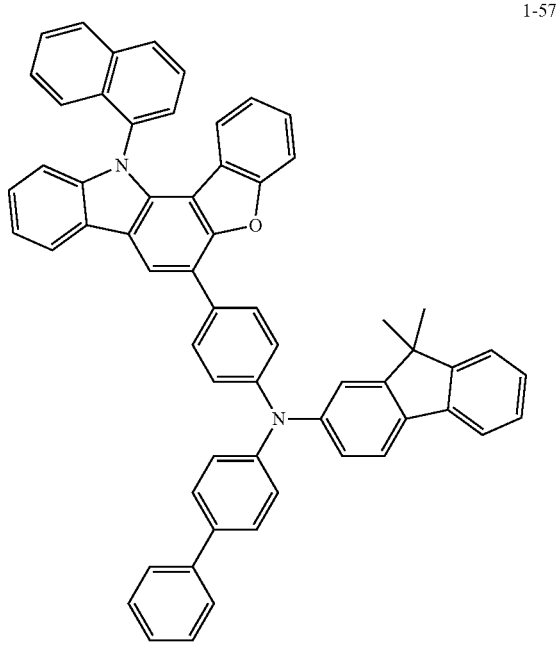
1-57
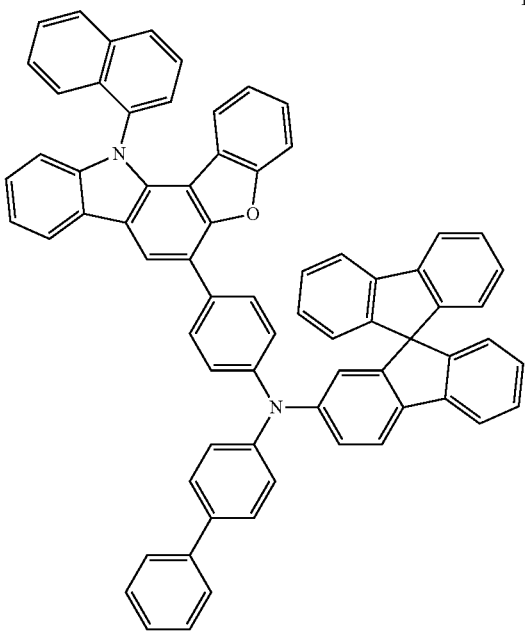
1-59
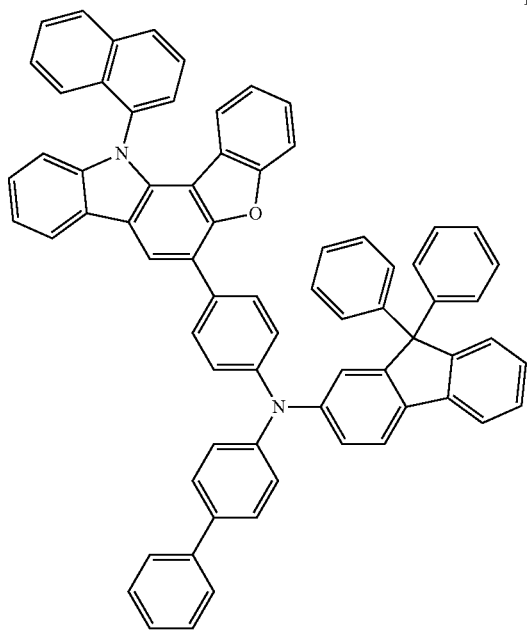
1-58
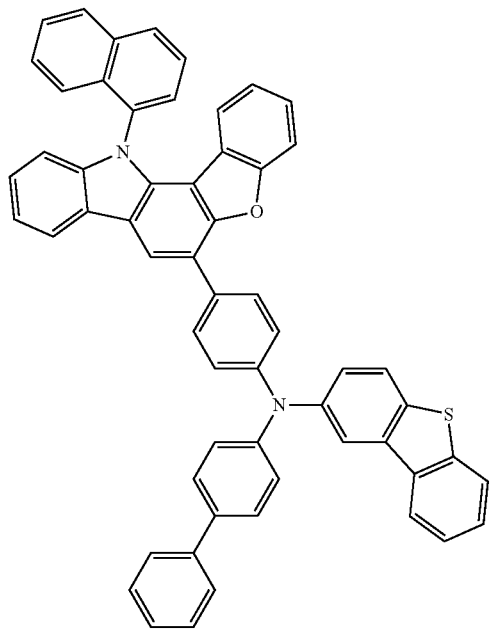
1-60

1-61
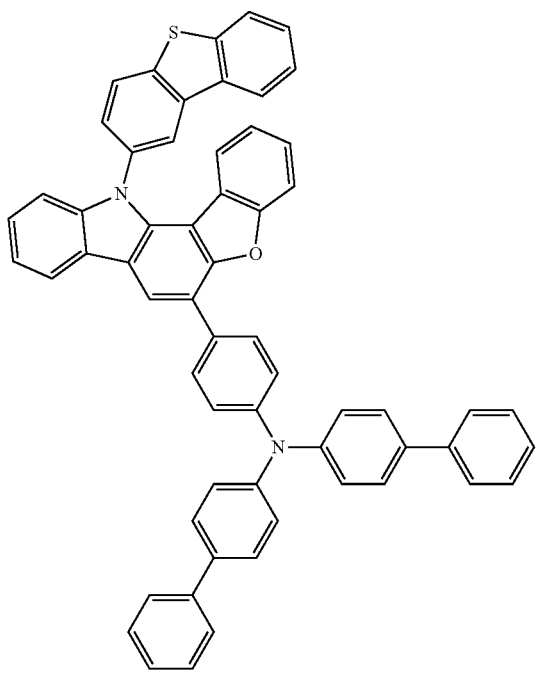
1-63
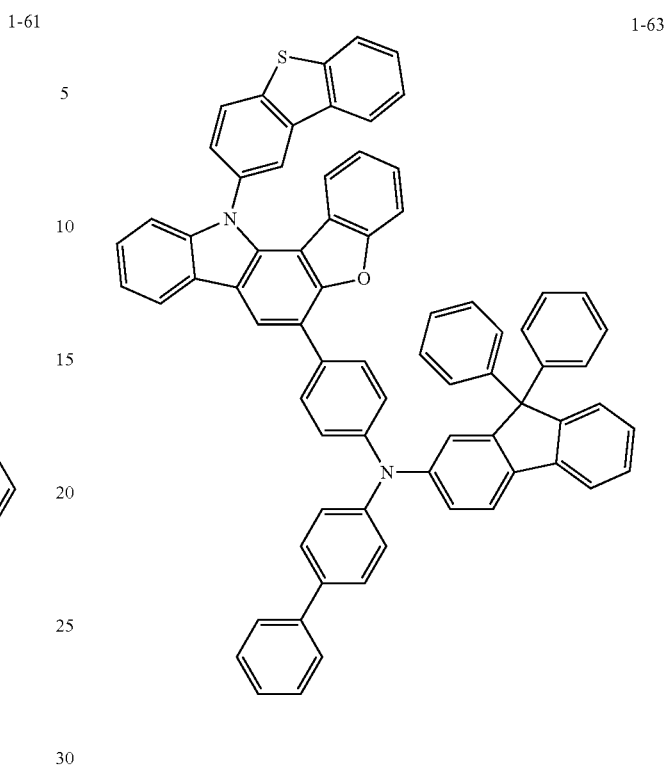
1-62
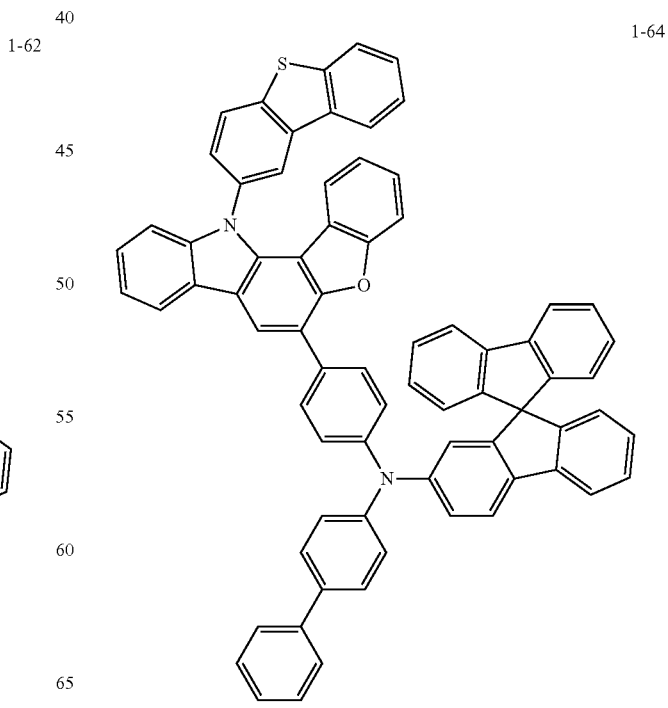
1-64

1-65
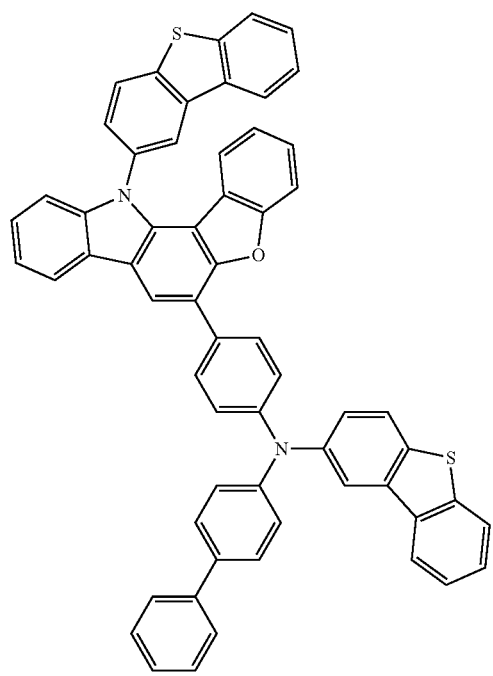
1-67
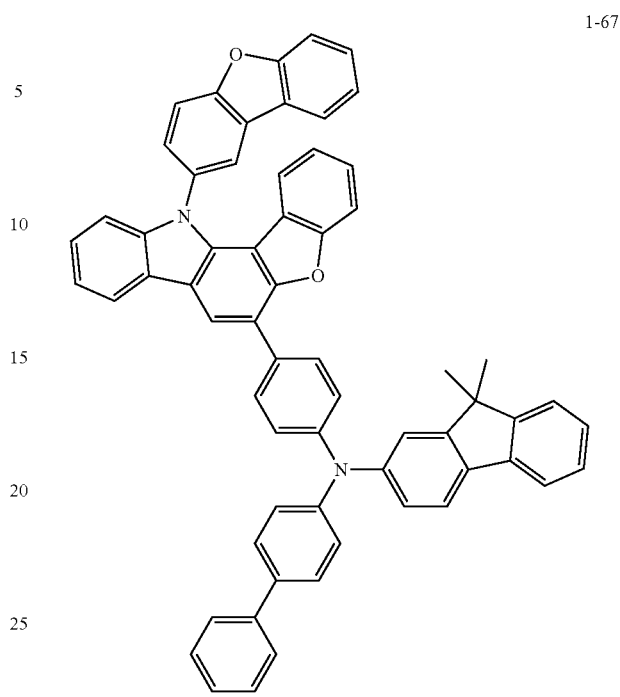
1-66
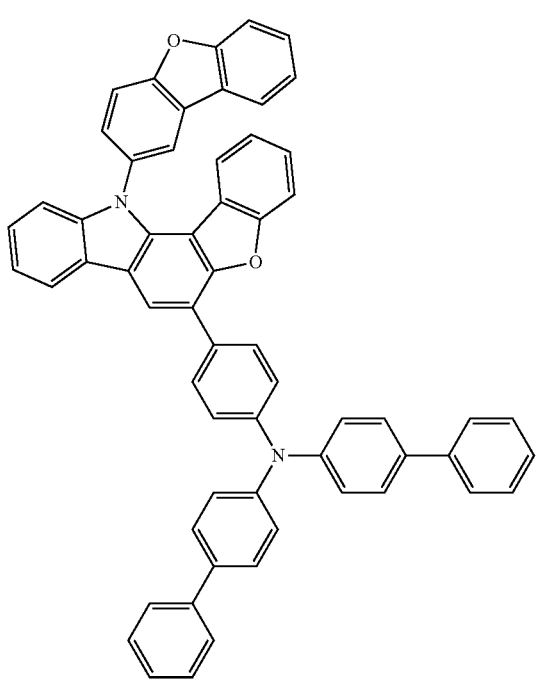
1-68
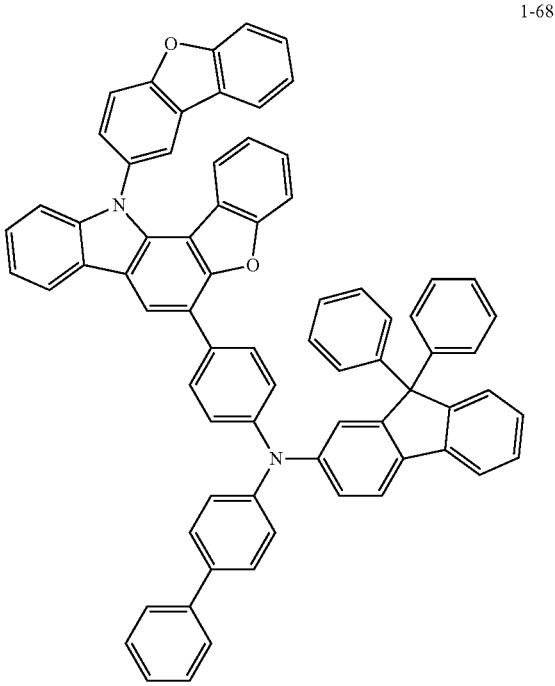

1-69
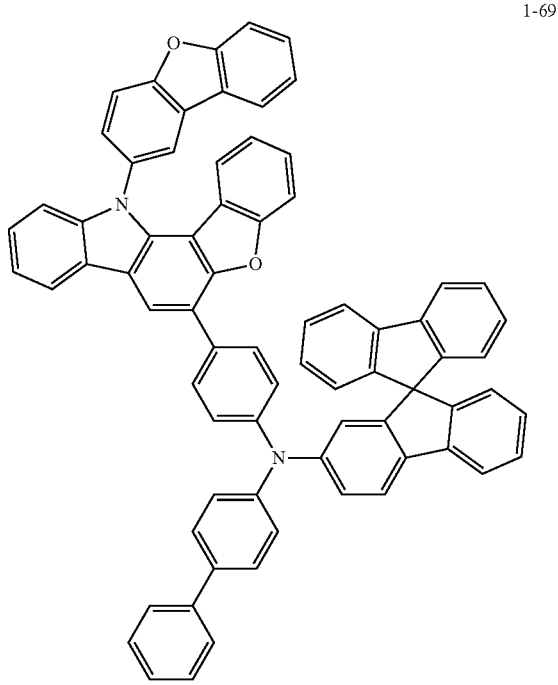
1-70
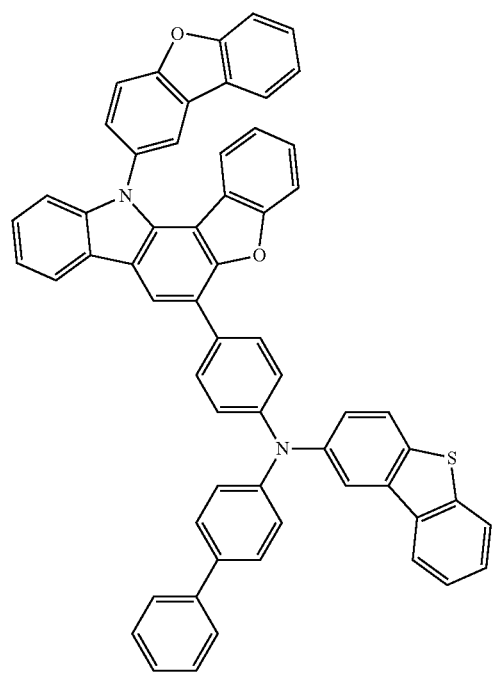
1-71
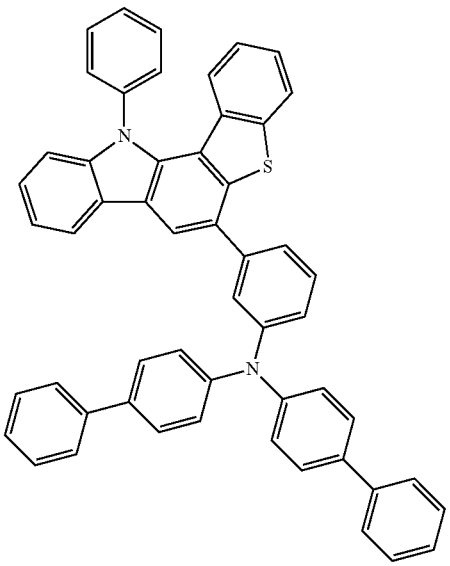
1-72
1-73
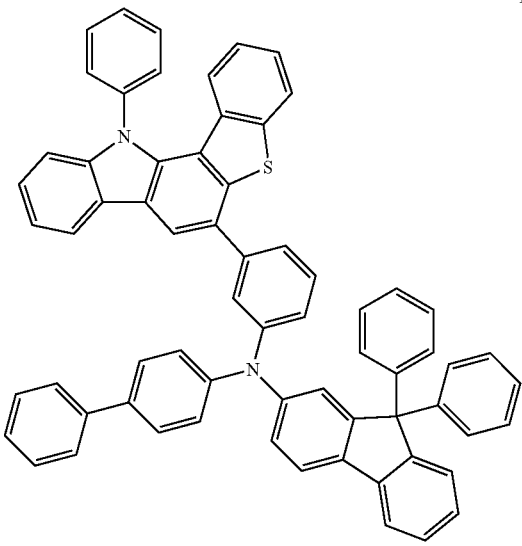

-continued
1-74
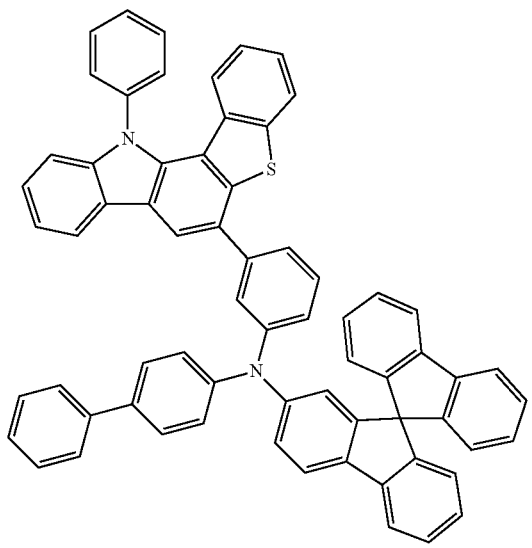
1-76
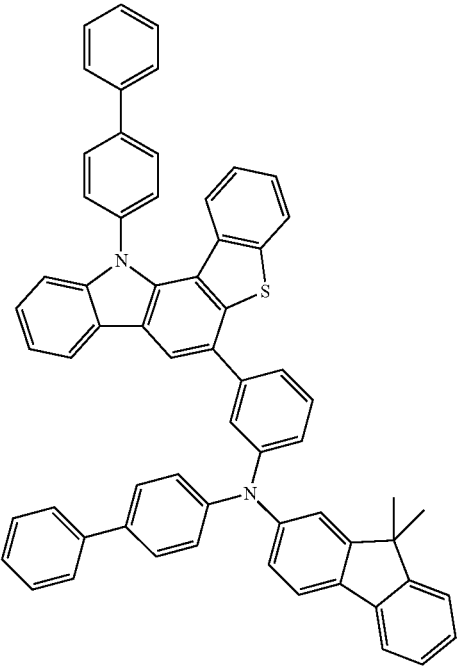
1-75
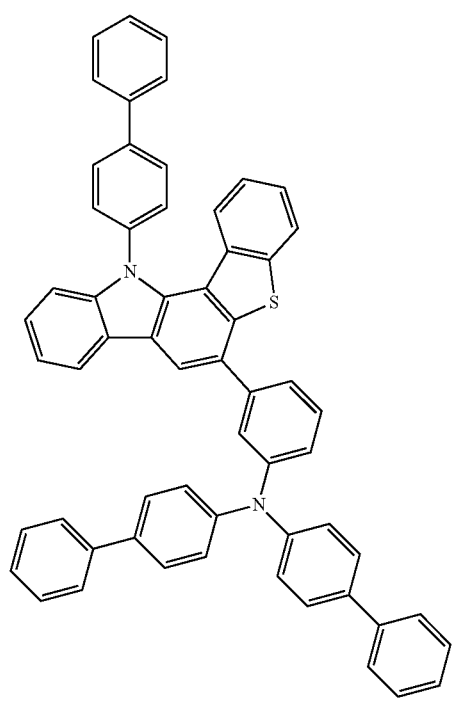
1-77
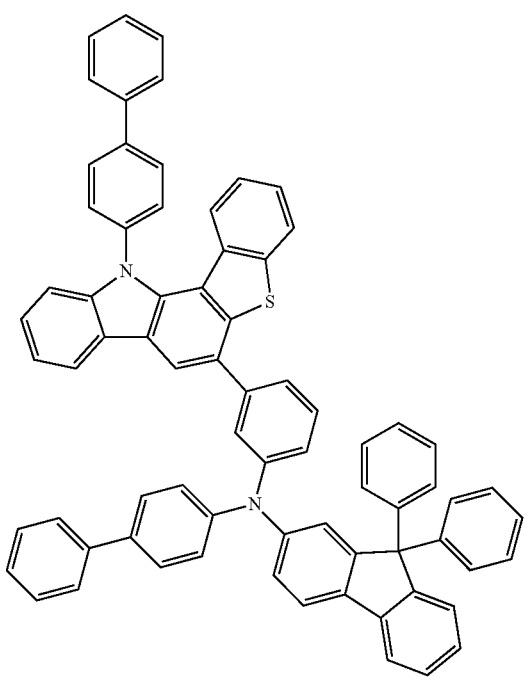

1-78
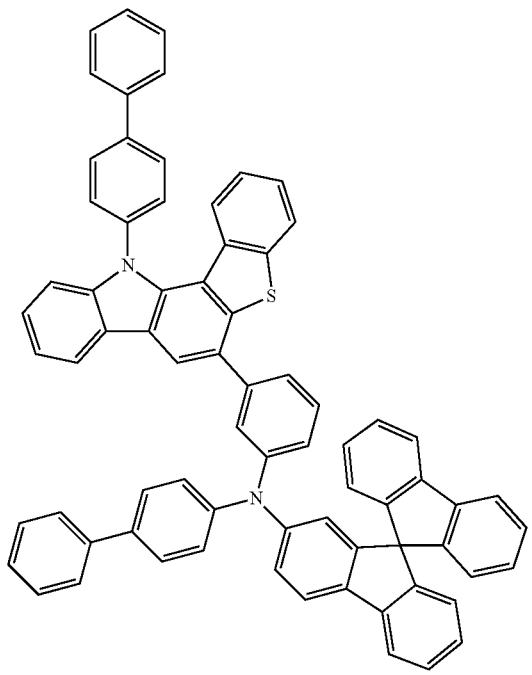
1-80
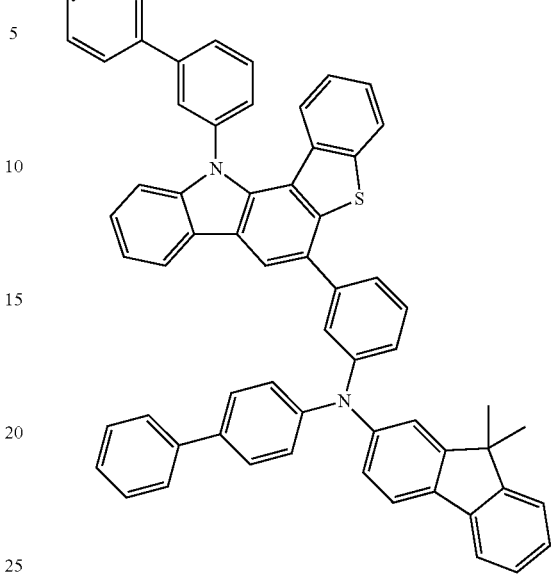
1-79
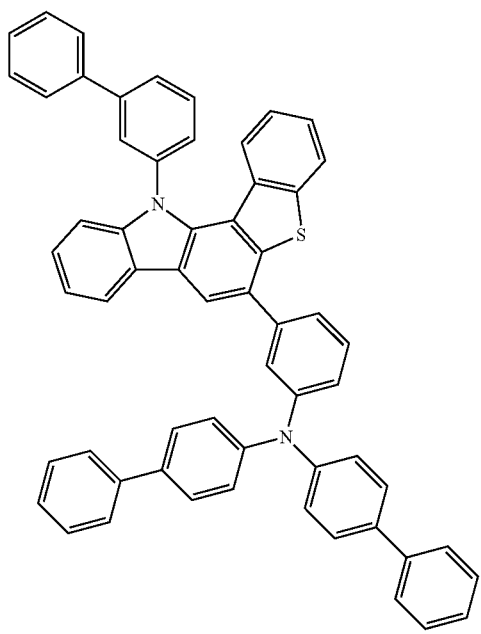
1-81
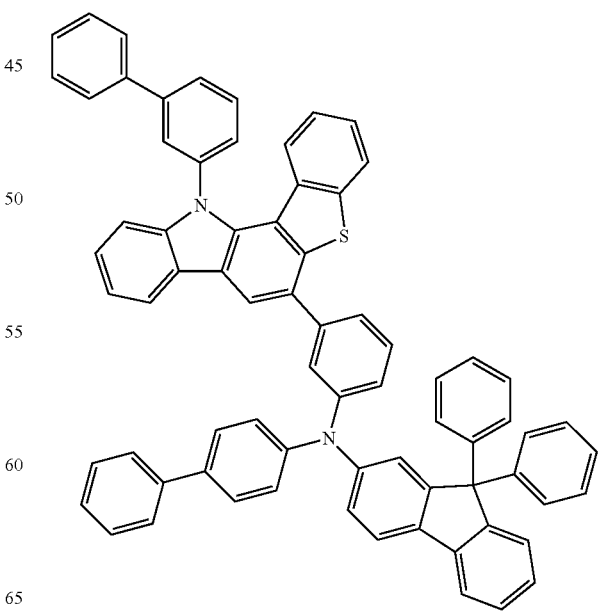

1-82
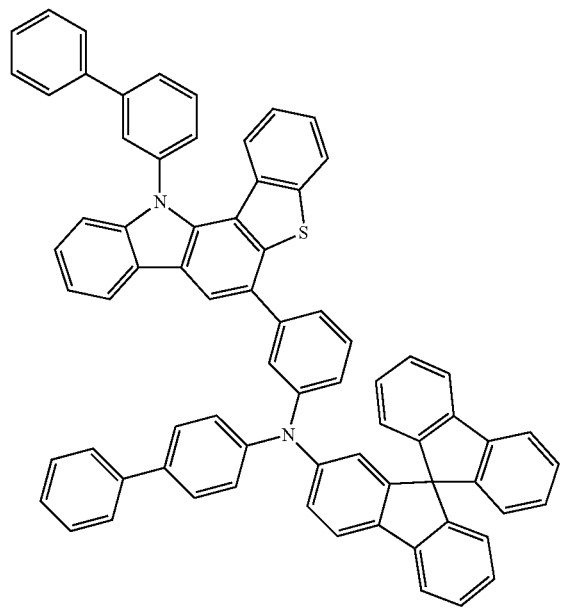
1-83
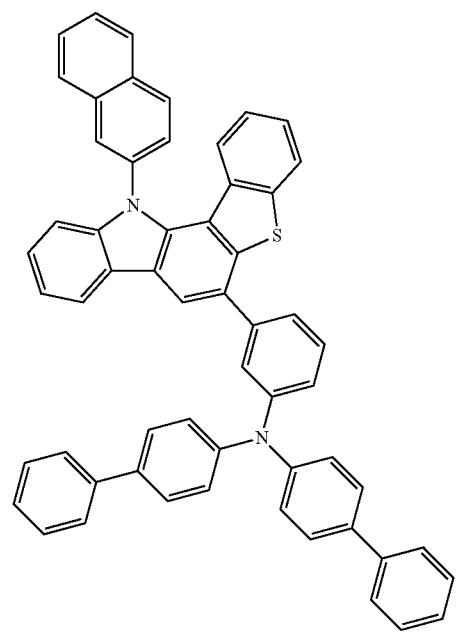
1-84
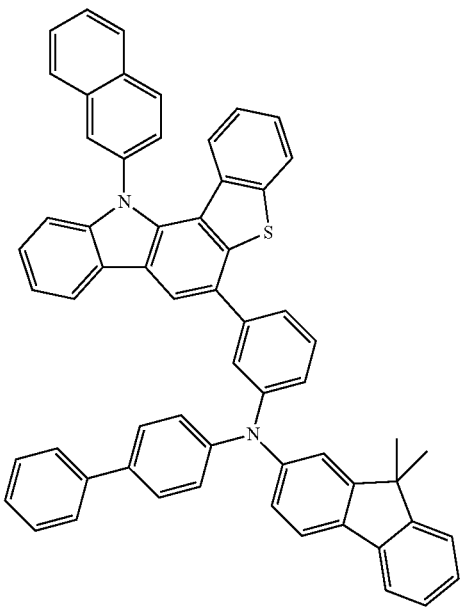
1-85
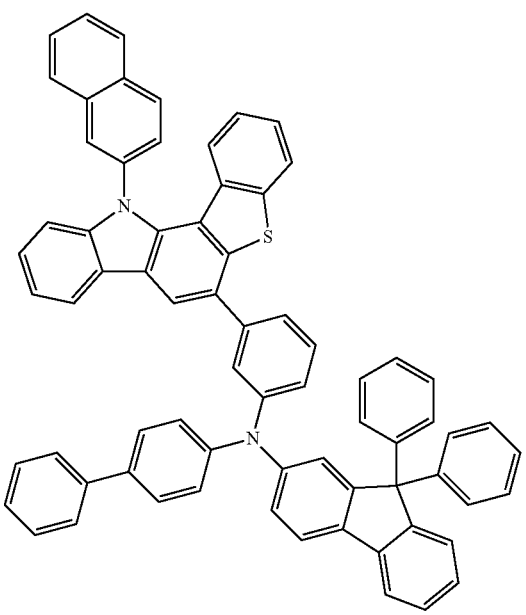

1-86
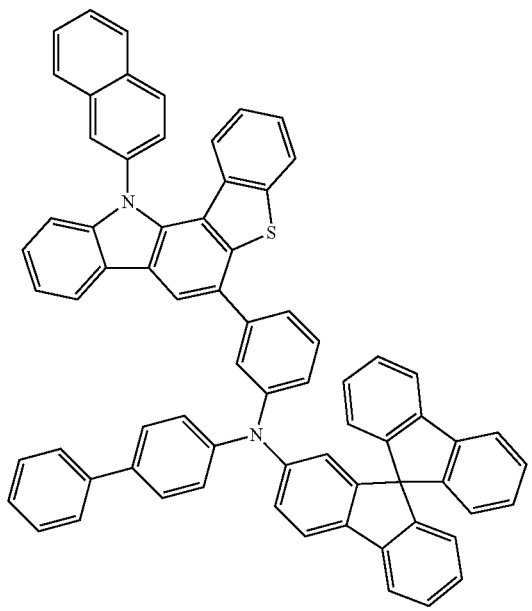
1-87
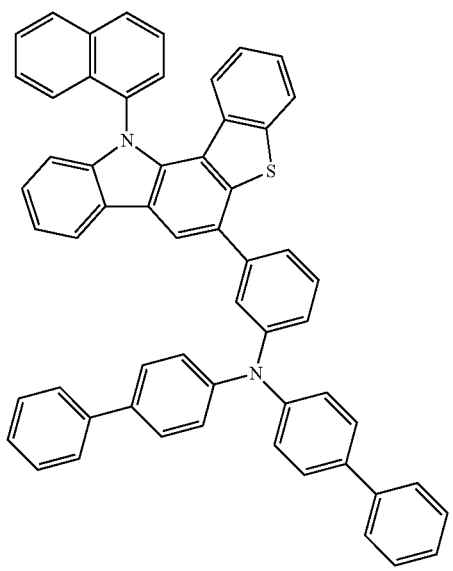
1-88
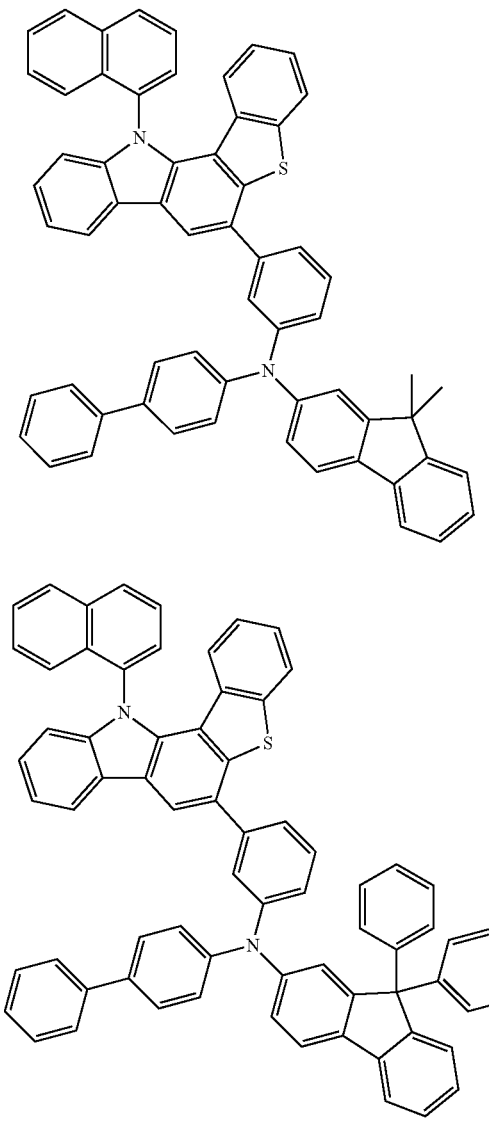
1-89
1-90
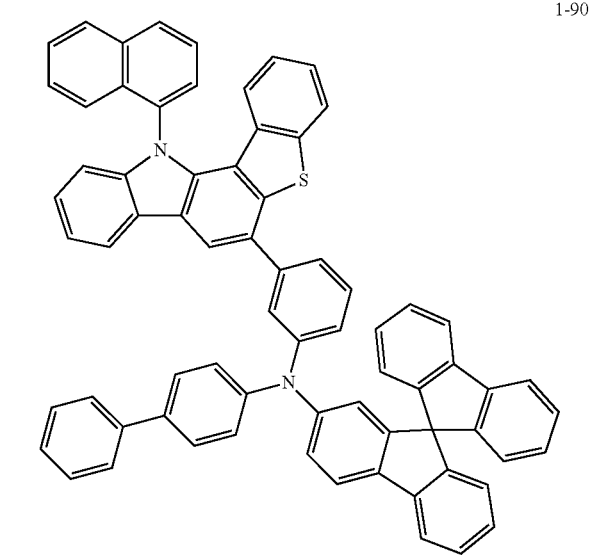

1-91
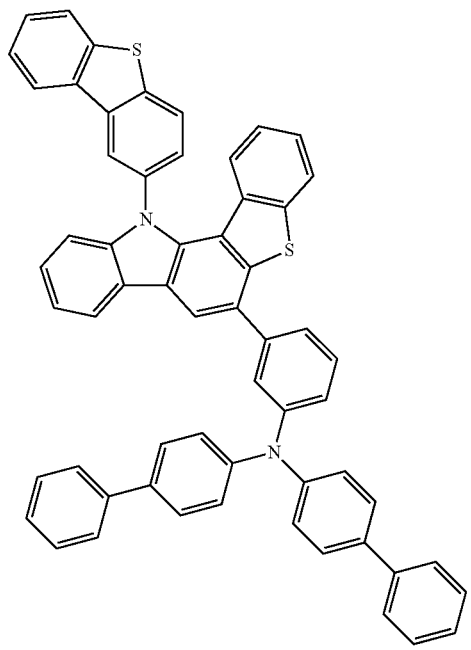
1-92
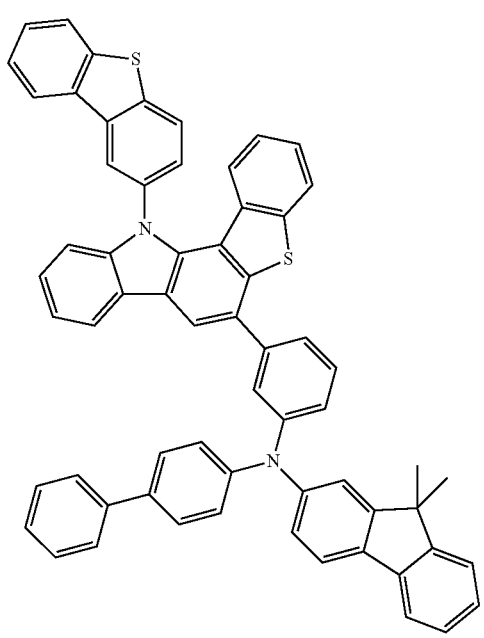
1-93
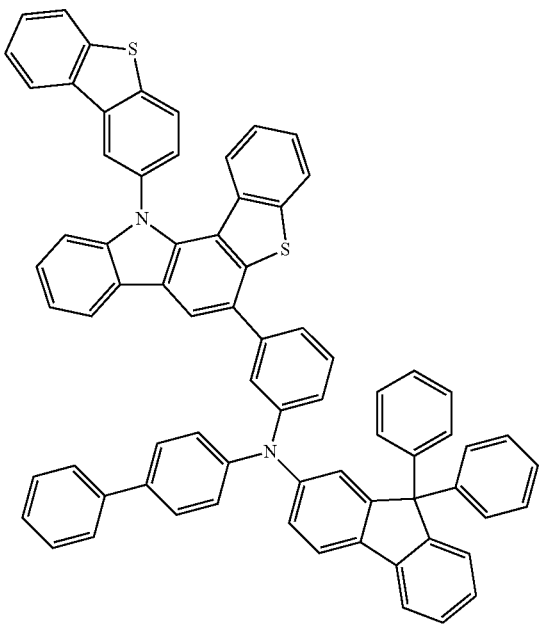
1-94
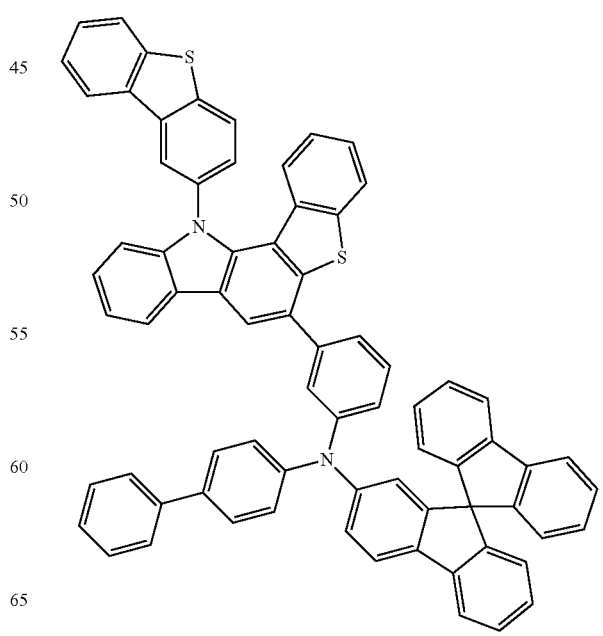

1-95
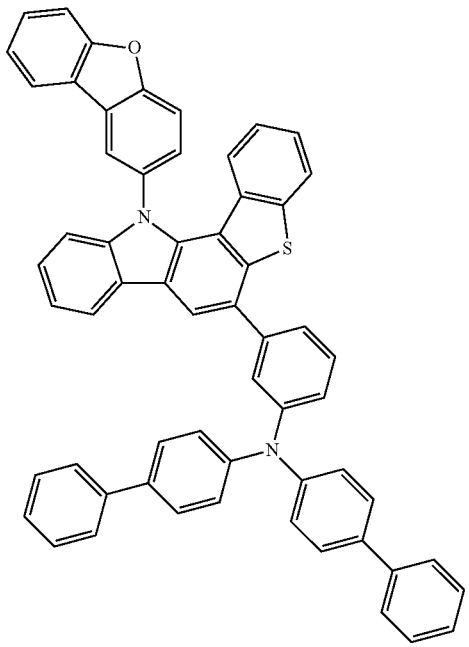
1-96
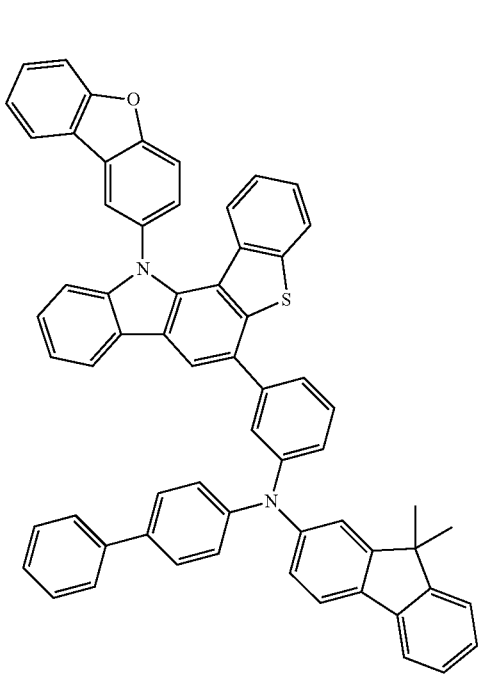
1-97
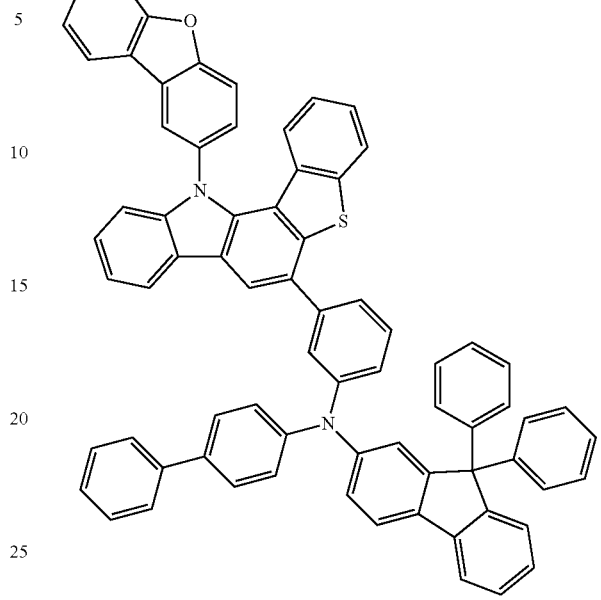
1-98
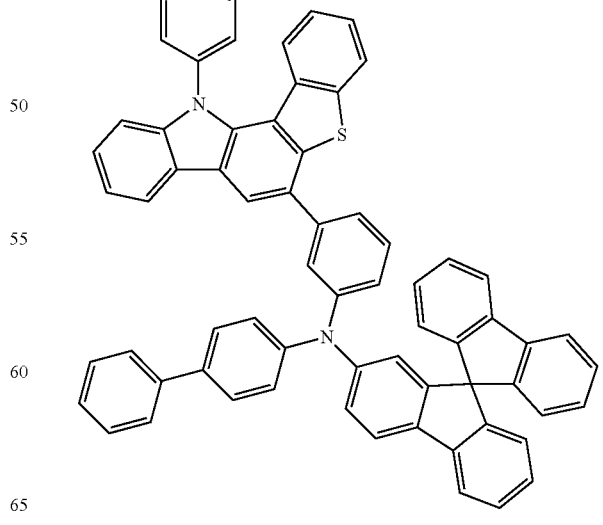

1-99
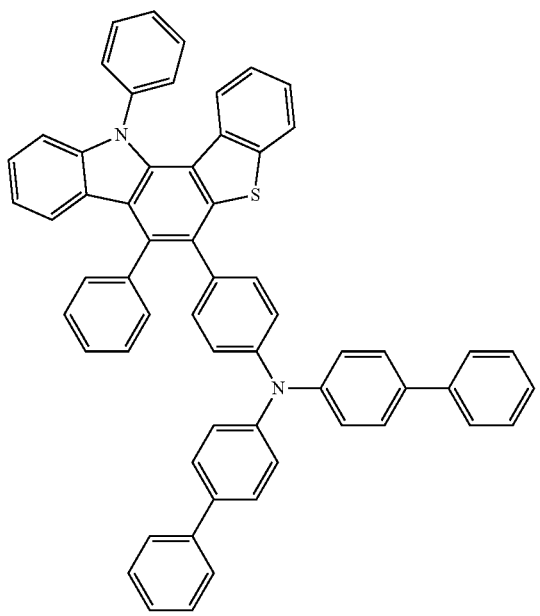
1-100
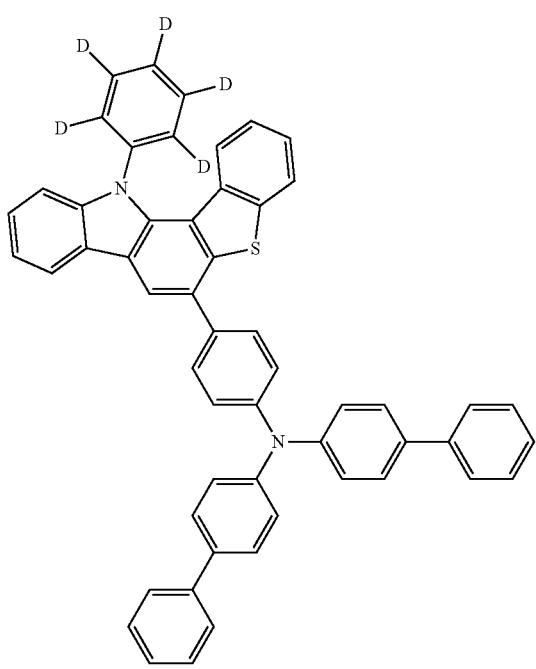
1-101
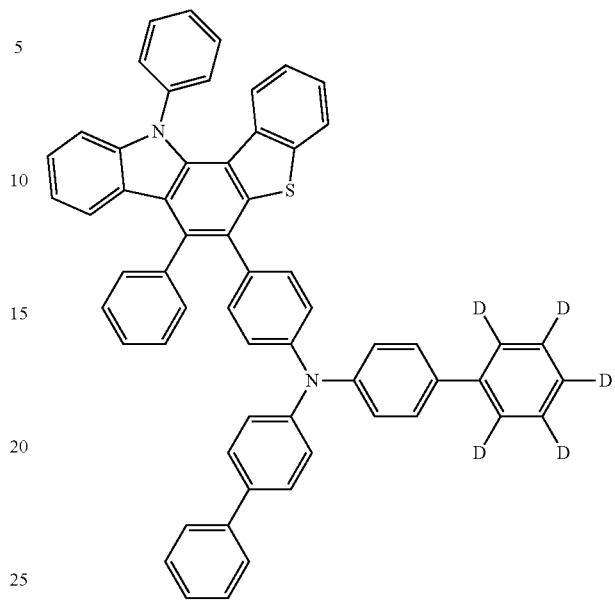
1-102
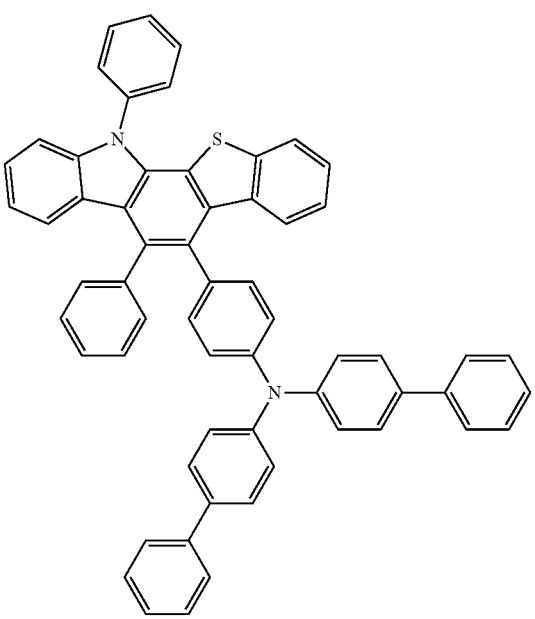

1-103
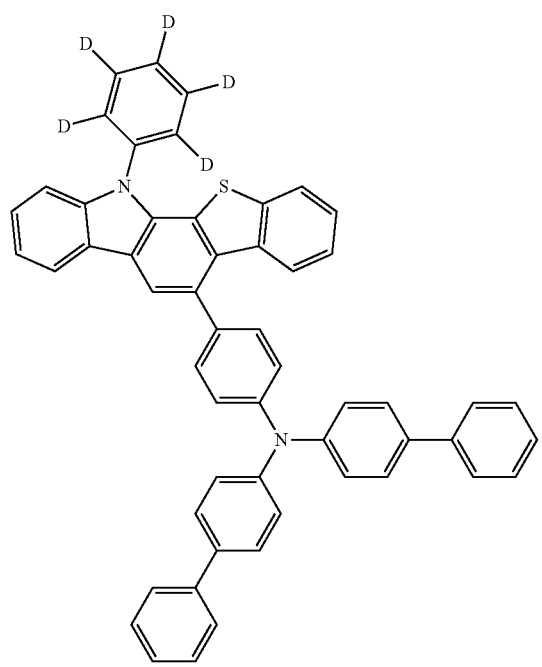
1-104
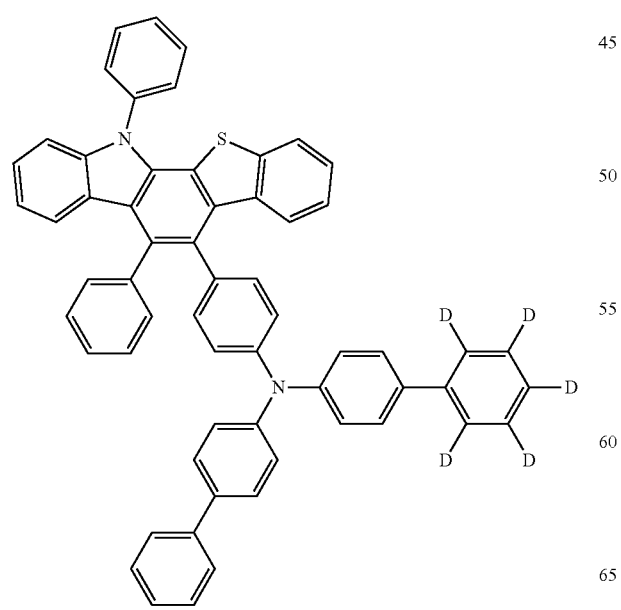
1-105
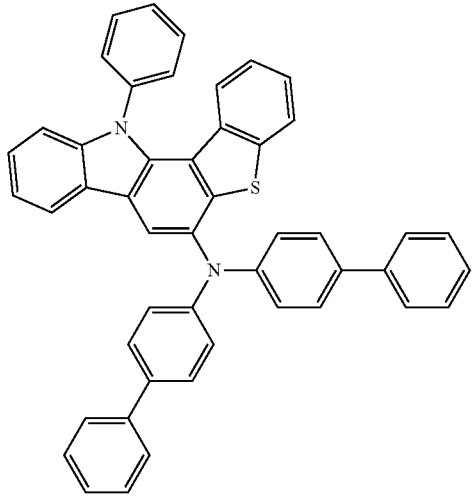
1-106
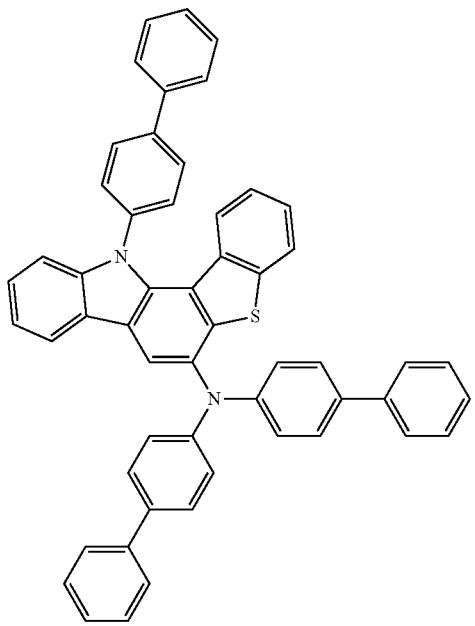
1-107
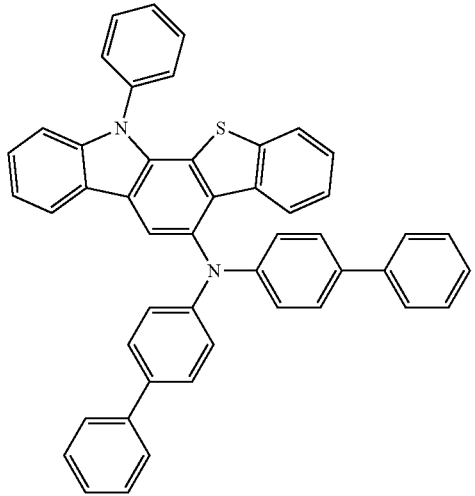

1-108
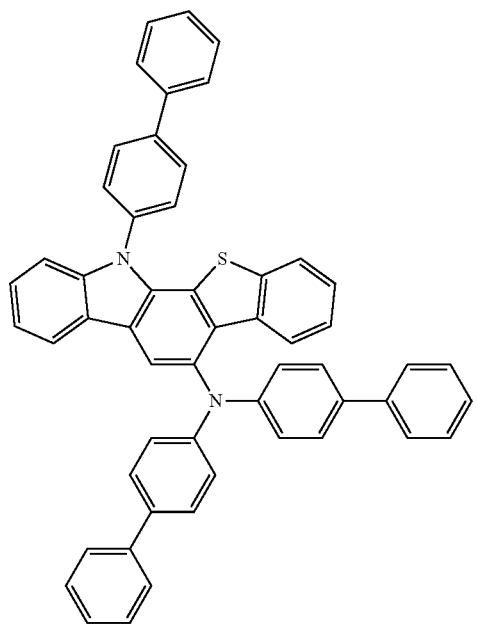
1-110
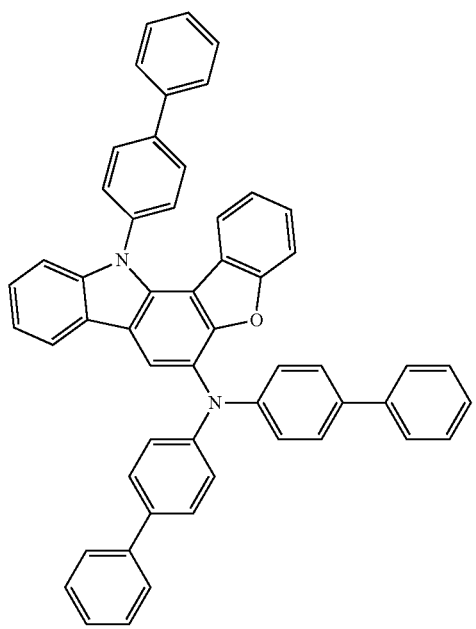
1-109
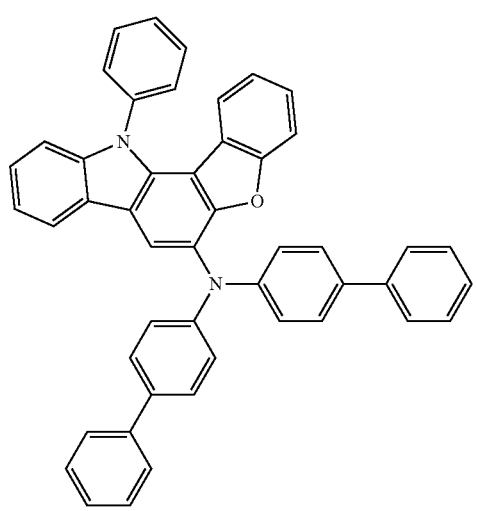
1-111
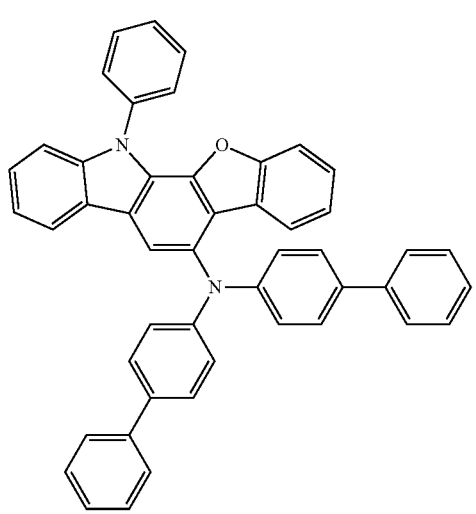

1-112
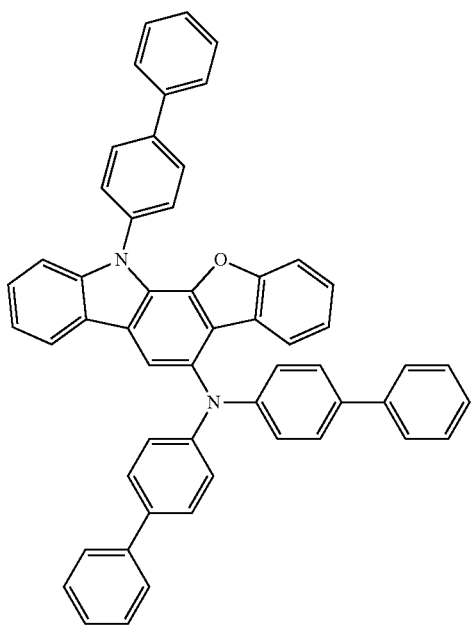
1-113
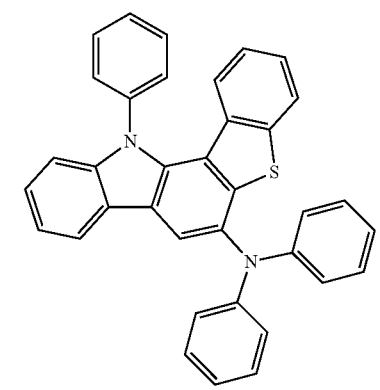
1-114
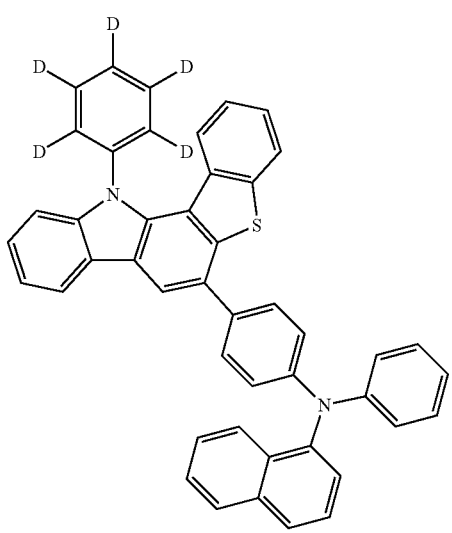
1-115
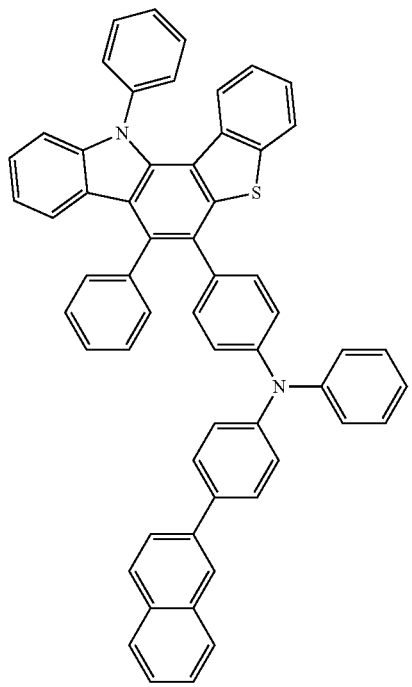
1-116
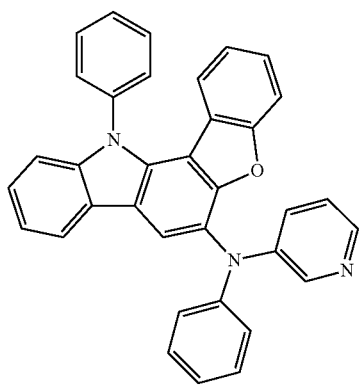
1-117
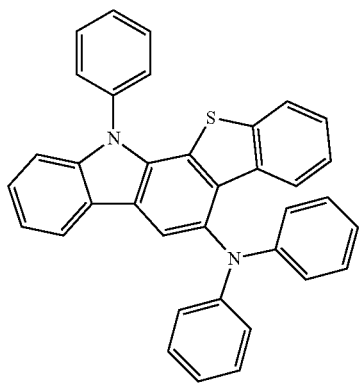

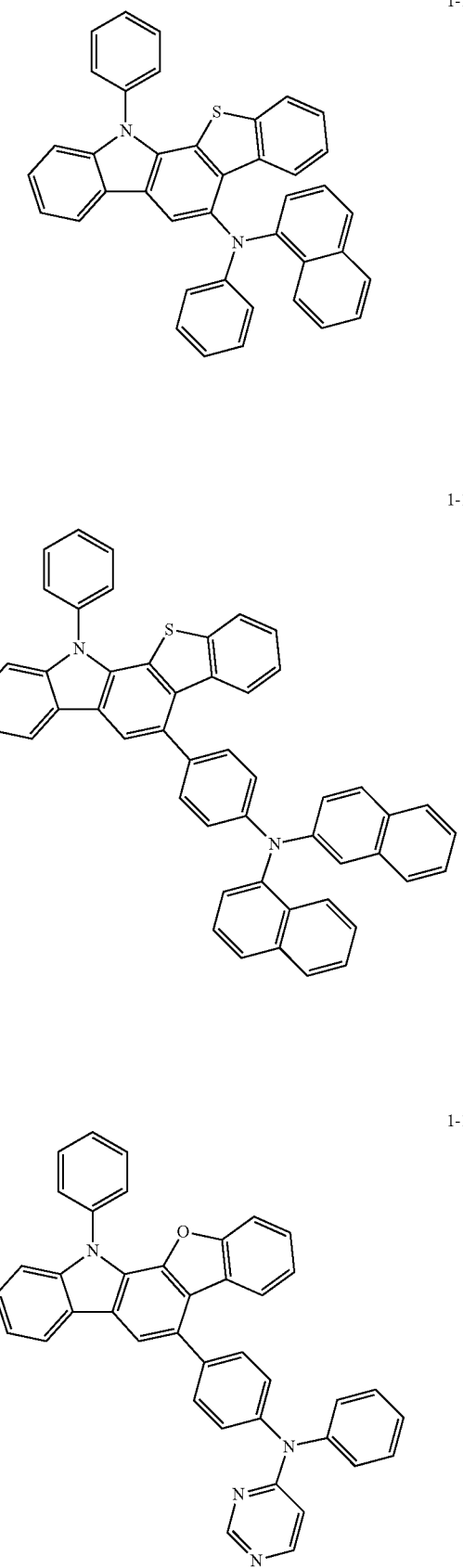
1-118
1-119
1-120
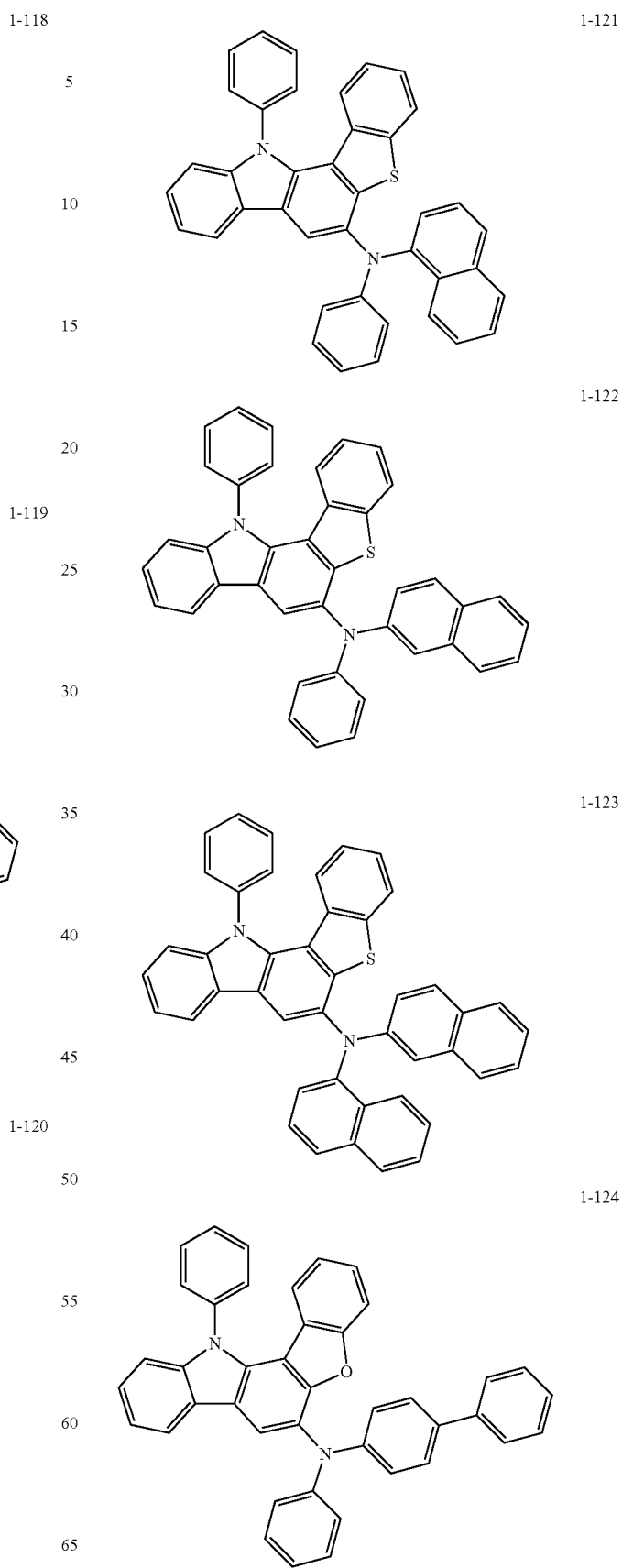
1-121
1-122
1-123
1-124

-continued 1-125
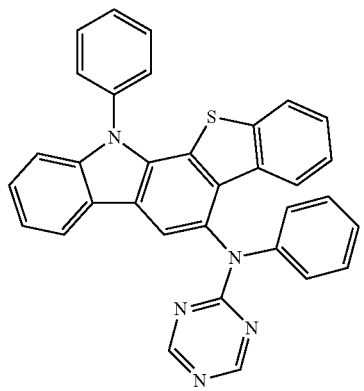

1-126
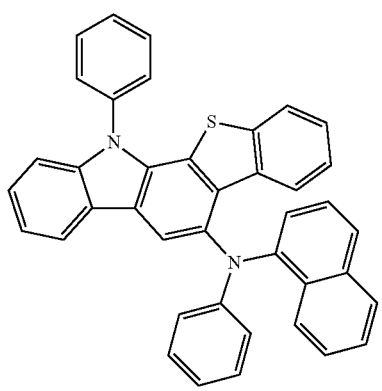

1-127

1-128
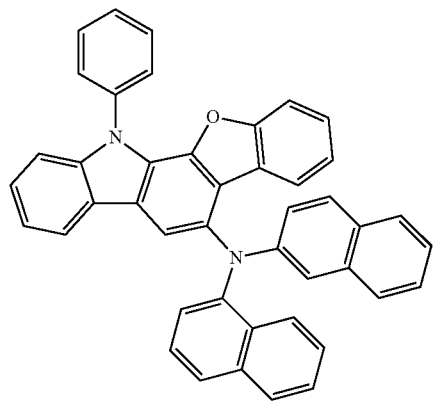

In another aspect of the present invention, the present invention provides an organic electric element comprising a first electrode, a second electrode, and an organic material layer formed between the first electrode and the second electrode. The organic material layer may comprise at least one layer of a hole injection layer, a hole transport layer, an emission-auxiliary layer, a light emitting layer, an electron transport-auxiliary layer, an electron transport layer and an electron injection layer, and at least one compound of the above compounds may be comprised in the organic material layer. That is, the organic material layer may be formed as a single compound or a mixture of two or more kinds represented by Formula 1.

Hereinafter, Synthesis method of the compound represented by Formula 1 according to one embodiment of the present invention and Preparation method of an organic electric element will be described in detail by way of examples. However, the present invention is not limited to the following examples.

Synthesis Example

The compound (final products) represented by Formula 1 according to the present invention are synthesized by reacting Sub 1 and Sub 2 as shown in Reaction Scheme, but are not limited thereto.

<Reaction Scheme 1>

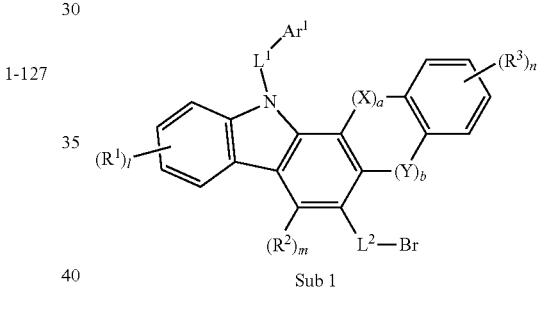

Sub 1

Sub 2

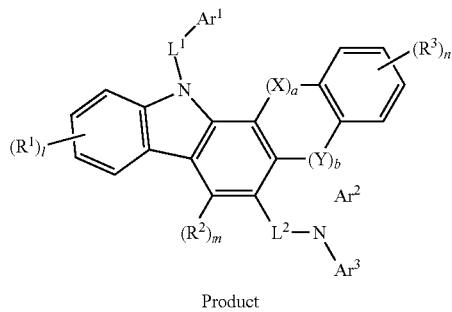

Product

I. Synthesis of Sub 1

Sub 1 of the above Reaction Scheme 1 can be synthesized by the following Reaction Scheme 2.

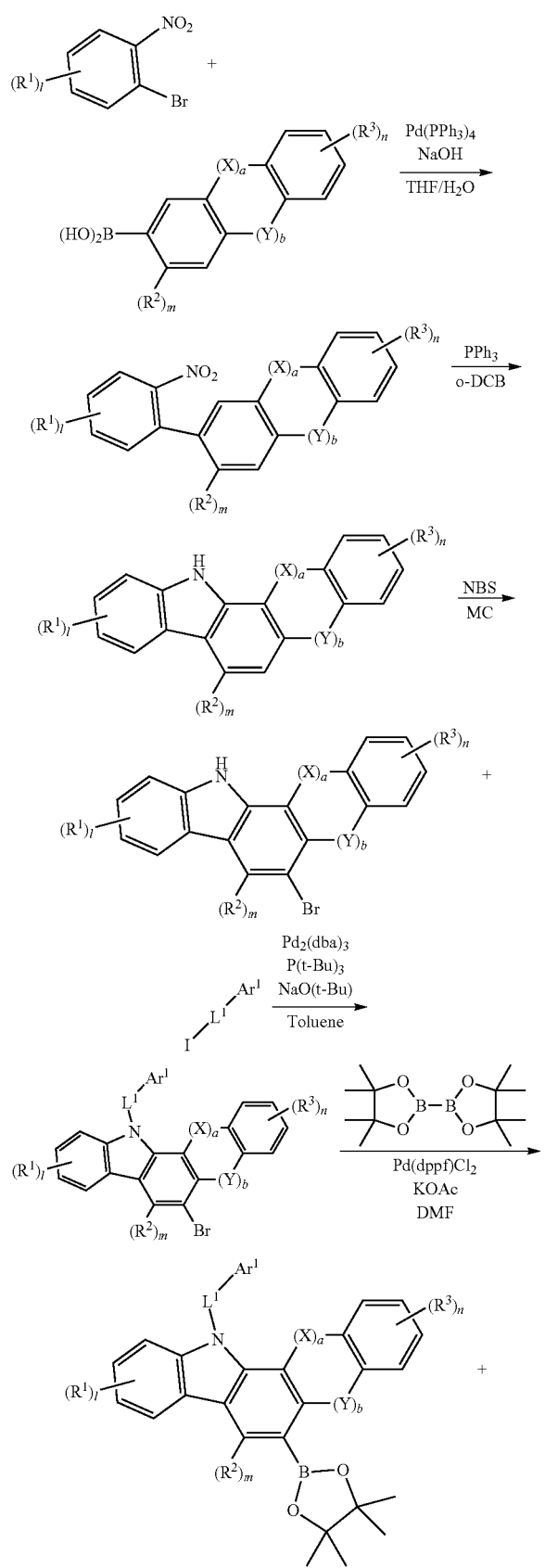
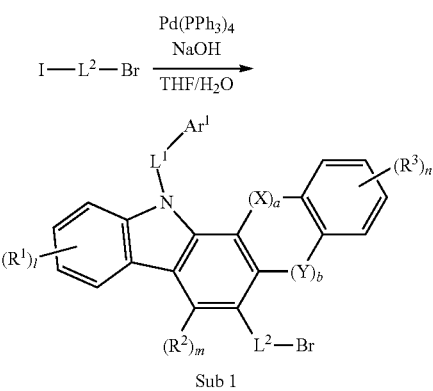
Sub 1
Also, for example, compounds belong to Sub 1 when b is "0" in Sub 1 can be synthesized by the reaction route of the following Reaction Scheme 3.
<Reaction Scheme 3>
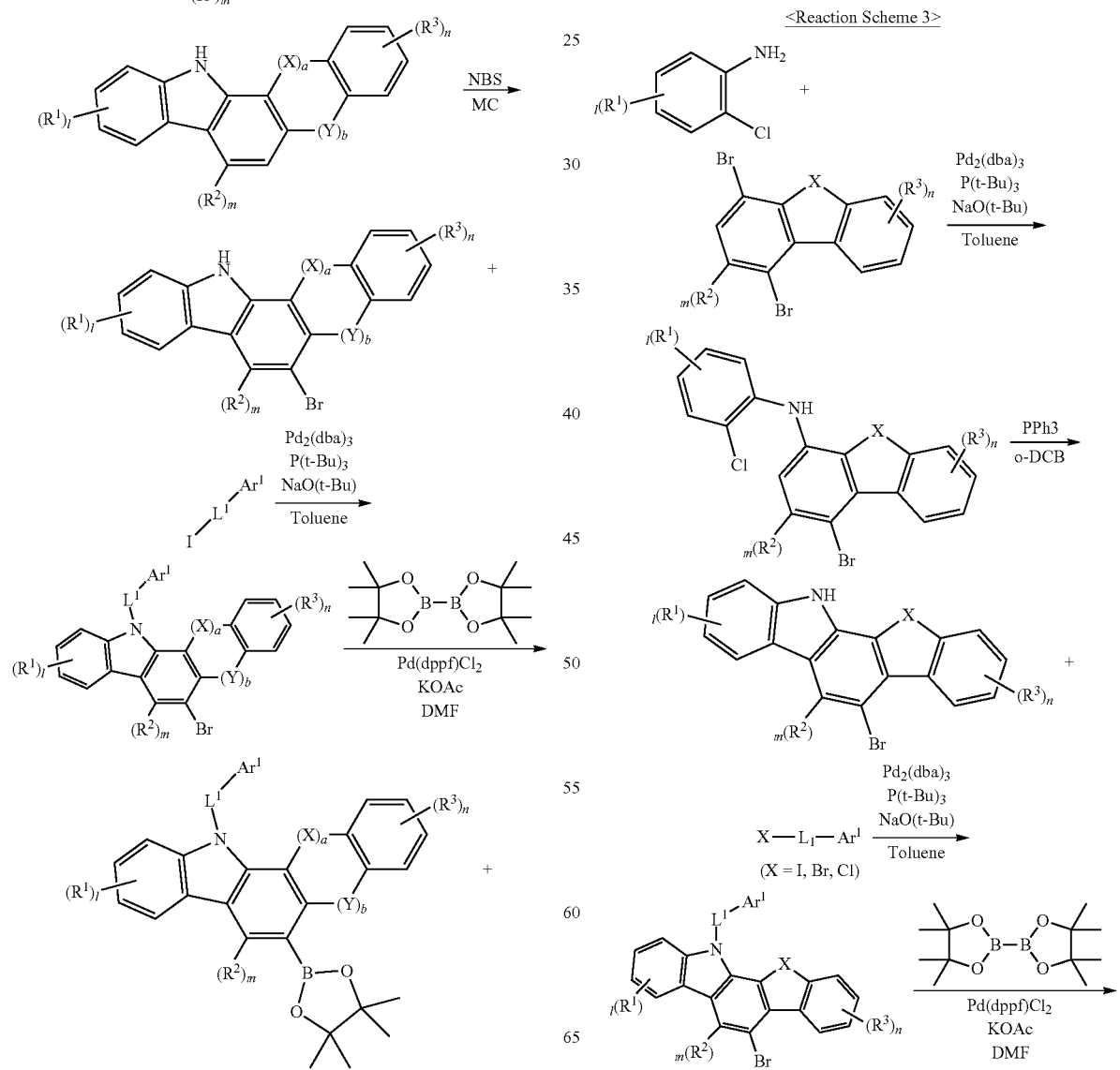

73
-continued
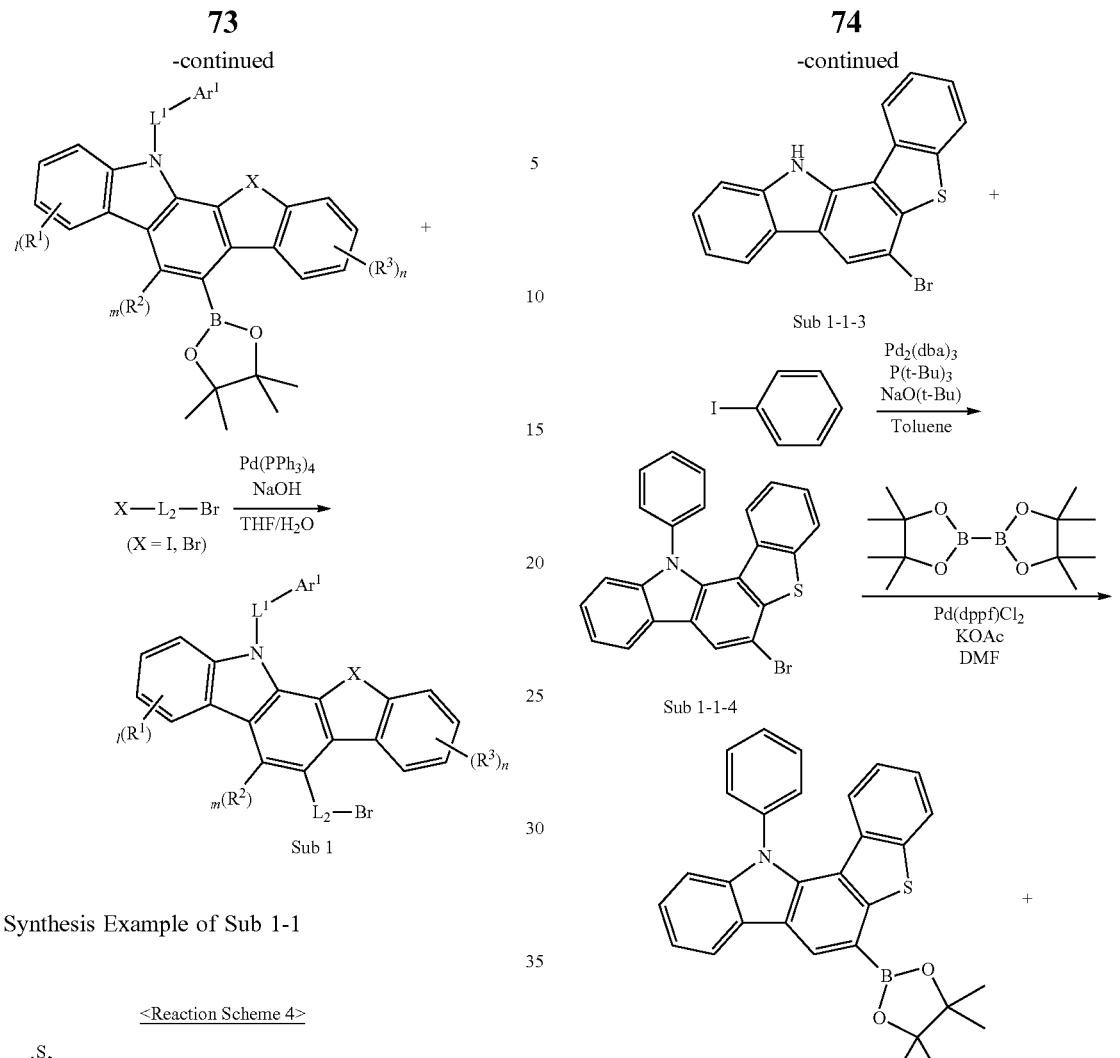
1.1. Synthesis Example of Sub 1-1
<Reaction Scheme 4>
74
-continued
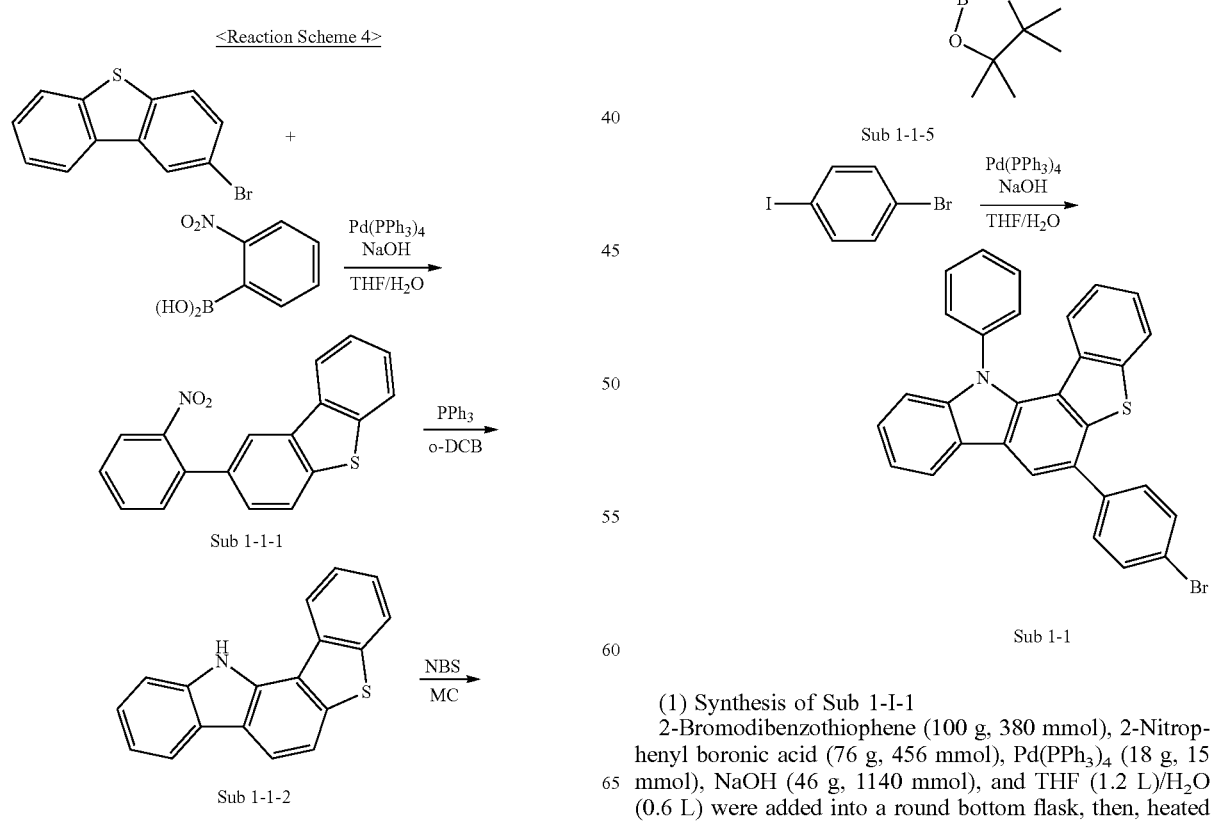
(1) Synthesis of Sub 1-I-1
2-Bromodibenzothiophene (100 g, 380 mmol), 2-Nitrophenyl boronic acid (76 g, 456 mmol), Pd(PPh₃)₄ (18 g, 15 mmol), NaOH (46 g, 1140 mmol), and THF (1.2 L)/H₂O (0.6 L) were added into a round bottom flask, then, heated and refluxed at 70° C. for 4 hours. When the reaction was completed, the reaction product was diluted with distilled water at room temperature, and then with Methylene chloride (CH₂Cl₂) and water. The organic layer was dried with MgSO₄ and concentrated. The concentrate was recrystallized with Methylene chloride and Hexane to obtain 99 g of the product Sub 1-1-1 (Yield: 85%).

(2) Synthesis Method of Sub 1-1-2

Sub 1-1-1 (99 g, 323 mmol), PPh₃ (218 g, 808 mmol), and o-Dichlorobenzene (1.0 L) were added into a round bottom flask, then, heated and refluxed at 180° C. for 24 hours. When the reaction was completed, the reaction product was cooled to room temperature and concentrated. The concentrate was passed through silica gel column, and then recrystallized to obtain the product Sub 1-1-2 (70 g, 80%).

(3) Synthesis Method of Sub 1-1-3

Sub 1-1-2 (70 g, 293 mmol), N-Bromosuccinimide (52 g, 293 mmol), and Methylene chloride (1 L) were added into a round bottom flask, then, stirred at room temperature for 4 hours. When the reaction was completed, distilled water was added. The resultant was extracted with Methylene chloride and water. The organic layer was dried with MgSO₄ and concentrated. The concentrate was recrystallized with Methylene chloride and Hexane to obtain 86 g of the product Sub 1-1-3 (Yield: 83%).

(4) Synthesis Method of Sub 1-1-4

Sub 1-1-3 (30 g, 84 mmol), Iodobenzene (20.7 g, 102 mmol), Pd₂(dba)₃ (3 g, 3.3 mmol), P(t-Bu)₃ (1.8 g, 8.4 mmol), NaO(t-Bu) (24.6 g, 255 mmol), and Toluene (240 mL) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO₄ and concentrated. The concentrate was recrystallized with Methylene chloride and Hexane to obtain 28 g of the product Sub 1-1-4 (Yield: 76%).

(5) Synthesis Method of Sub 1-1-5

Sub 1-1-4 (20 g, 47 mmol), 4,4,4',4',5,5,5',5'-octamethyl-2,2'-bi(1,3,2-dioxaborolane) (14.3 g, 56 mmol), Pd(dppf)Cl₂ (1.5 g, 1.9 mmol), KOAc (13.8 g, 141 mmol), and DMF (150 mL) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO₄ and concentrated. The concentrate was dissolved in Methylene chloride, then, filtered through silica gel column and concentrated. The final concentrate recrystallized with Methylene chloride and Hexane to obtain 17 g of the product Sub 1-1-5 (Yield: 76%).

(6) Synthesis Method of Sub 1-1

Sub 1-1-5 (17 g, 35.8 mmol), 1-Bromo-4-iodobenzene (12.1 g, 42.9 mmol), Pd(PPh₃)₄ (1.7 g, 1.4 mmol), NaOH (4.3 g, 107 mmol), and THF (160 mL)/H₂O (80 ml) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO₄ and concentrated. The concentrate was dissolved in Methylene chloride, then, filtered through silica gel column and concentrated. The final concentrate recrystallized with Methylene chloride and Hexane to obtain 12 g of the product Sub 1-1 (Yield: 65%).

2. Synthesis Method of Sub 1-2

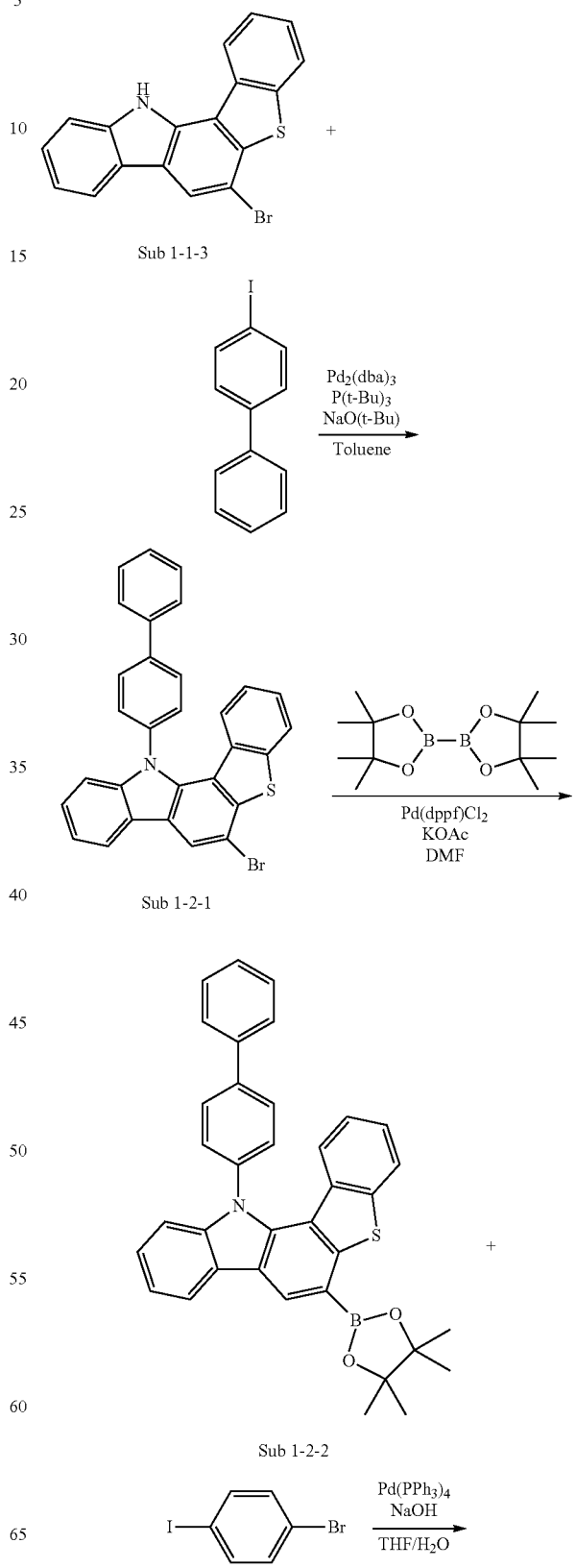

<Reaction Scheme 5>

-continued

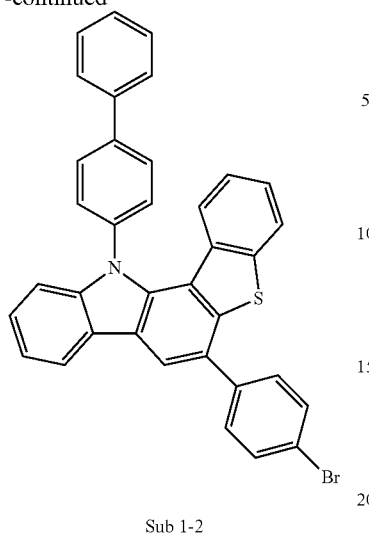

Sub 1-2

(1) Synthesis Method of Sub 1-2-1

Sub 1-1-3 (30 g, 84 mmol) being intermediate product of Reaction Scheme 4, 4-Iodo-1,1'-biphenyl (28.6 g, 102 mmol), Pd₂(dba)₃ (3 g, 3.3 mmol), P(t-Bu)₃ (1.8 g, 8.4 mmol), NaO(t-Bu) (24.6 g, 255 mmol), and Toluene (240 mL) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO₄ and concentrated. The concentrate was recrystallized with Methylene chloride and Hexane to obtain 32 g of the product Sub 1-2-1 (Yield: 76%).

(2) Synthesis Method of Sub 1-2-2

Sub 1-2-1 (23.7 g, 47 mmol), 4,4,4',4',5,5,5',5'-octamethyl-2,2'-bi(1,3,2-dioxaborolane) (14.3 g, 56 mmol), Pd(dppf)Cl₂ (1.5 g, 1.9 mmol), KOAc (13.8 g, 141 mmol), and DMF (150 mL) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO₄ and concentrated. The concentrate was dissolved in Methylene chloride, then, filtered through silica gel column and concentrated. The final concentrate recrystallized with Methylene chloride and Hexane to obtain 22 g of the product Sub 1-2-2 (Yield: 84%).

(3) Synthesis Method of Sub 1-2

Sub 1-2-2 (19.7 g, 35.8 mmol), 1-Bromo-4-iodobenzene (12.1 g, 42.9 mmol), Pd(PPh₃)₄ (1.7 g, 1.4 mmol), NaOH (4.3 g, 107 mmol), and THF (160 mL)/H₂O (80 ml) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO₄ and concentrated. The concentrate was dissolved in Methylene chloride, then, filtered through silica gel column and concentrated. The final concentrate recrystallized with Methylene chloride and Hexane to obtain 14.5 g of the product Sub 1-1 (Yield: 70%).

3. Synthesis Method of Sub 1-4

<Reaction Scheme 6>

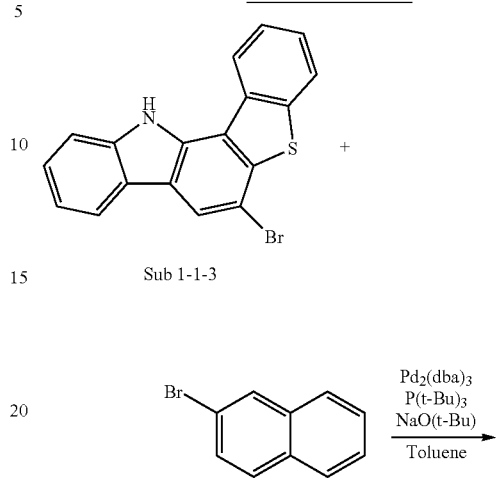

Sub 1-1-3

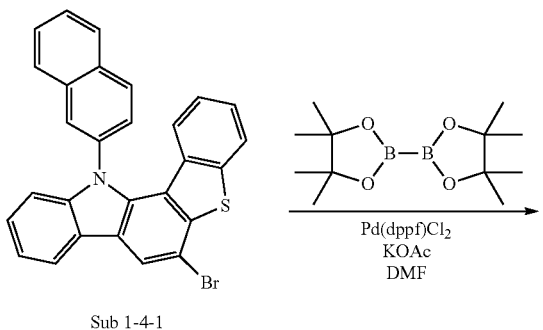

Sub 1-4-1

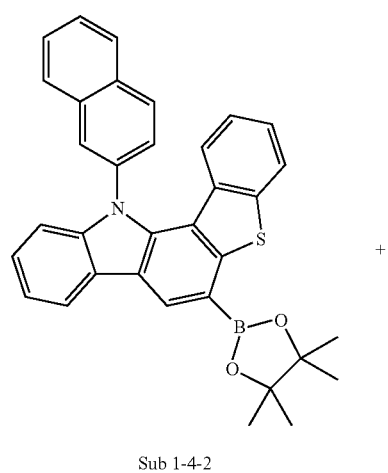

Sub 1-4-2

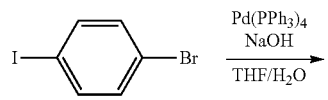

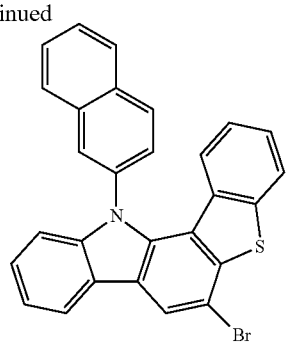

Sub 1-4

(1) Synthesis Method of Sub 1-4-1

Sub 1-1-3 (30 g, 84 mmol) being intermediate product of Reaction Scheme 4, 2-Bromonaphthalene (21.1 g, 102 mmol), Pd$_2$(dba)$_3$ (3 g, 3.3 mmol), P(t-Bu)$_3$ (1.8 g, 8.4 mmol), NaO(t-Bu) (24.6 g, 255 mmol), and Toluene (240 mL) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO$_4$ and concentrated. The concentrate was recrystallized with Methylene chloride and Hexane to obtain 34.6 g of the product Sub 1-4-1 (Yield: 86%).

(2) Synthesis Method of Sub 1-4-2

Sub 1-4-1 (22.5 g, 47 mmol), 4,4,4',4',5,5,5',5'-octamethyl-2,2'-bi(1,3,2-dioxaborolane) (14.3 g, 56 mmol), Pd(dppf)Cl$_2$ (1.5 g, 1.9 mmol), KOAc (13.8 g, 141 mmol), and DMF (150 mL) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO$_4$ and concentrated. The concentrate was dissolved in Methylene chloride, then, filtered through silica gel column and concentrated. The final concentrate recrystallized with Methylene chloride and Hexane to obtain 22.7 g of the product Sub 1-4-2 (Yield: 92%).

(3) Synthesis Method of Sub 1-4

Sub 1-4-2 (18.8 g, 35.8 mmol), 1-Bromo-4-iodobenzene (12.1 g, 42.9 mmol), Pd(PPh$_3$)$_4$ (1.7 g, 1.4 mmol), NaOH (4.3 g, 107 mmol), and THF (160 mL)/H$_2$O (80 ml) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO$_4$ and concentrated. The concentrate was dissolved in Methylene chloride, then, filtered through silica gel column and concentrated. The final concentrate recrystallized with Methylene chloride and Hexane to obtain 13.9 g of the product Sub 1-4 (Yield: 70%).

4. Synthesis Method of Sub 1-6

<Reaction Scheme 7>

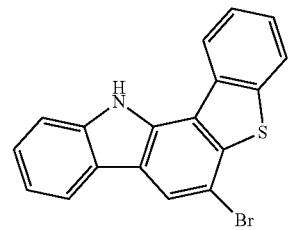

Sub 1-1-3

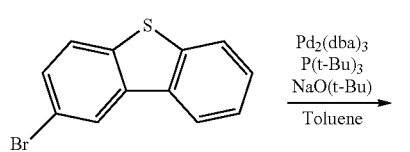

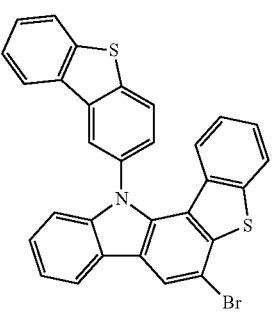

Sub 1-6-1

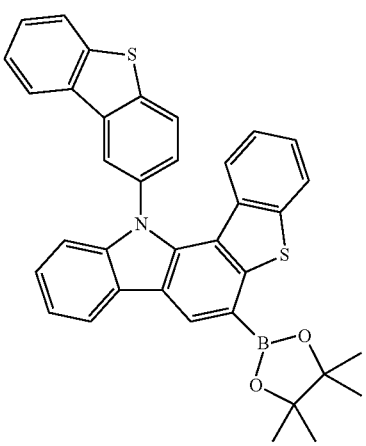

Sub 1-6-2

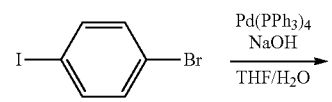

-continued

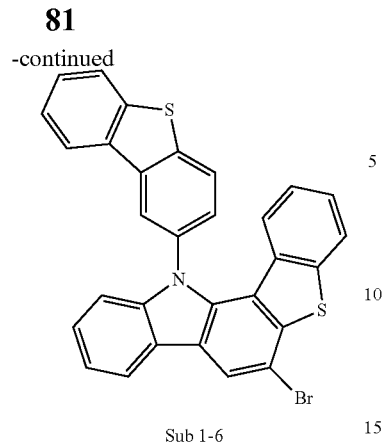

Sub 1-6

(1) Synthesis Method of Sub 1-6-1

Sub 1-1-3 (30 g, 84 mmol) being intermediate product of Reaction Scheme 4, 2-Bromodibenzothiophene (26.8 g, 102 mmol), Pd$_2$(dba)$_3$ (3 g, 3.3 mmol), P(t-Bu)$_3$ (1.8 g, 8.4 mmol), NaO(t-Bu) (24.6 g, 255 mmol), and Toluene (240 mL) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO$_4$ and concentrated. The concentrate was recrystallized with Methylene chloride and Hexane to obtain 32 g of the product Sub 1-6-1 (Yield: 72%).

(2) Synthesis Method of Sub 1-6-2

Sub 1-6-1 (25 g, 47 mmol), 4,4,4',4',5,5,5',5'-octamethyl-2,2'-bi(1,3,2-dioxaborolane) (14.3 g, 56 mmol), Pd(dppf)Cl$_2$ (1.5 g, 1.9 mmol), KOAc (13.8 g, 141 mmol), and DMF (150 mL) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO$_4$ and concentrated. The concentrate was dissolved in Methylene chloride, then, filtered through silica gel column and concentrated. The final concentrate recrystallized with Methylene chloride and Hexane to obtain 23.5 g of the product Sub 1-4-2 (Yield: 86%).

(3) Synthesis Method of Sub 1-6

Sub 1-6-2 (20.8 g, 35.8 mmol), 1-Bromo-4-iodobenzene (12.1 g, 42.9 mmol), Pd(PPh$_3$)$_4$ (1.7 g, 1.4 mmol), NaOH (4.3 g, 107 mmol), and THF (160 mL)/H$_2$O (80 ml) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO$_4$ and concentrated. The concentrate was dissolved in Methylene chloride, then, filtered through silica gel column and concentrated. The final concentrate recrystallized with Methylene chloride and Hexane to obtain 12 g of the product Sub 1-6 (Yield: 55%).

5. Synthesis Method of Sub 1-8

<Reaction Scheme 8>

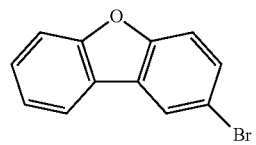 +

-continued

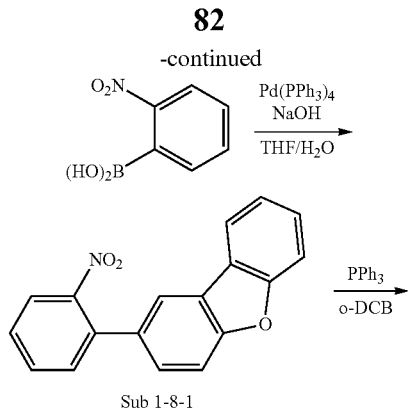

Sub 1-8-1

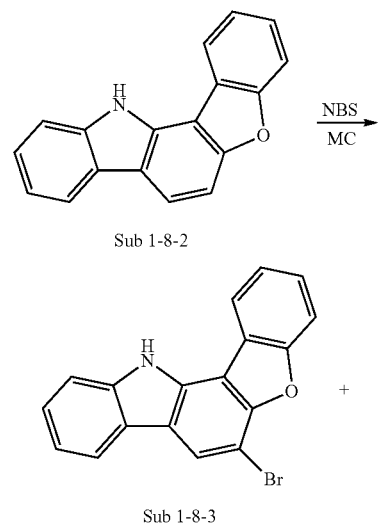

Sub 1-8-2

Sub 1-8-3

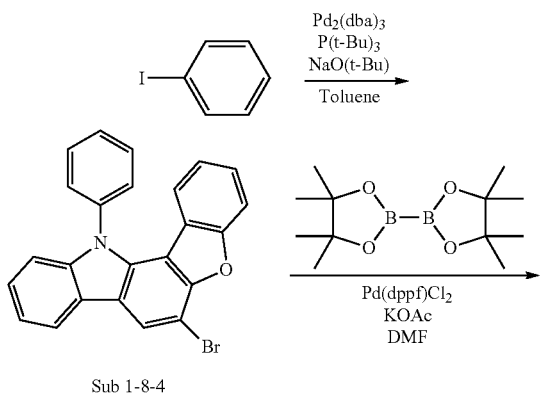

Sub 1-8-4

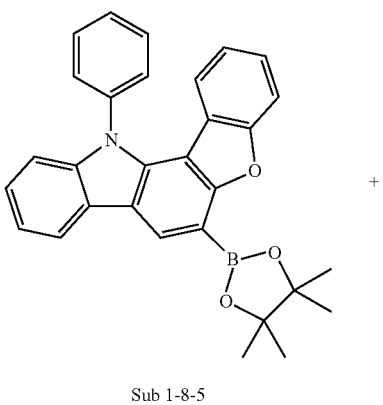

Sub 1-8-5

-continued

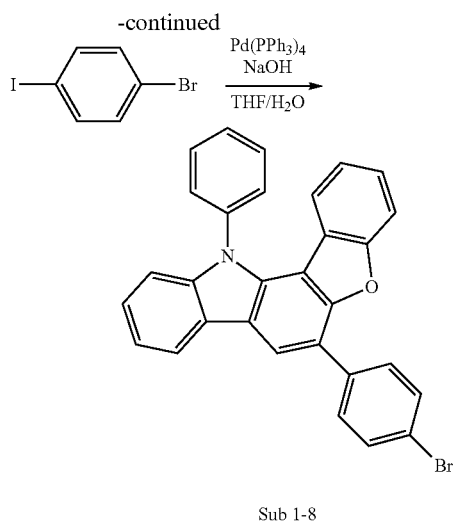

Sub 1-8

(1) Synthesis Method of Sub 1-8-1

2-Bromodibenzofuran (50 g, 202 mmol), 2-Nitrophenyl boronic acid (40.5 g, 242 mmol), Pd(PPh$_3$)$_4$ (9.3 g, 8 mmol), NaOH (24 g, 606 mmol), and THF (600 mL)/H$_2$O (300 mL) were added into a round bottom flask, then, heated and refluxed at 70° C. for 4 hours. When the reaction was completed, the reaction product was diluted with distilled water at room temperature, then, extracted with Methylene chloride and water. The organic layer was dried with MgSO$_4$ and concentrated. The concentrate was recrystallized with Methylene chloride and Hexane to obtain 43 g of the product Sub 1-8-1 (Yield: 74%).

(2) Synthesis Method of Sub 1-8-2

Sub 1-8-1 (43 g, 110 mmol), PPh$_3$ (72 g, 276 mmol), and o-Dichlorobenzene (350 mL) were added into a round bottom flask, then, heated and refluxed at 180° C. for 24 hours. When the reaction was completed, the reaction product was cooled to room temperature and concentrated. The concentrate was passed through silica gel column, and then recrystallized to obtain 23 g of the product Sub 1-8-2 (Yield: 82%).

(3) Synthesis Method of Sub 1-8-3

Sub 1-8-2 (23 g, 89 mmol), N-Bromosuccinimide (16 g, 89 mmol), and Methylene chloride (300 mL) were added into a round bottom flask, then, stirred at room temperature for 4 hours. When the reaction was completed, distilled water was added. The resultant was extracted with Methylene chloride and water. The organic layer was dried with MgSO$_4$ and concentrated. The concentrate was recrystallized with Methylene chloride and Hexane to obtain 21 g of the product Sub 1-8-3 (Yield: 70%).

(4) Synthesis Method of Sub 1-8-4

Sub 1-8-3 (21 g, 62 mmol), Iodobenzene (15.3 g, 75 mmol), Pd$_2$(dba)$_3$ (2.3 g, 2.5 mmol), P(t-Bu)$_3$ (1.3 g, 6.2 mmol), NaO(t-Bu) (18 g, 187 mmol), and Toluene (200 mL) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO$_4$ and concentrated. The concentrate was recrystallized with Methylene chloride and Hexane to obtain 16 g of the product Sub 1-8-4 (Yield: 63%).

(5) Synthesis Method of Sub 1-8-5

Sub 1-8-4 (19.4 g, 47 mmol), 4,4,4',4',5,5,5',5'-octamethyl-2,2'-bi(1,3,2-dioxaborolane) (14.3 g, 56 mmol), Pd(dppf)Cl$_2$ (1.5 g, 1.9 mmol), KOAc (13.8 g, 141 mmol), and DMF (150 mL) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO$_4$ and concentrated. The concentrate was dissolved in Methylene chloride, then, filtered through silica gel column and concentrated. The final concentrate recrystallized with Methylene chloride and Hexane to obtain 18 g of the product Sub 1-8-5 (Yield: 84%).

(6) Synthesis Method of Sub 1-8

Sub 1-8-5 (16.4 g, 35.8 mmol), 1-Bromo-4-iodobenzene (12.1 g, 42.9 mmol), Pd(PPh$_3$)$_4$ (1.7 g, 1.4 mmol), NaOH (4.3 g, 107 mmol), and THF (160 mL)/H$_2$O (80 ml) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO$_4$ and concentrated. The concentrate was dissolved in Methylene chloride, then, filtered through silica gel column and concentrated. The final concentrate recrystallized with Methylene chloride and Hexane to obtain 10 g of the product Sub 1-8 (Yield: 58%).

6. Synthesis Method of Sub 1-15

<Reaction Scheme 9>

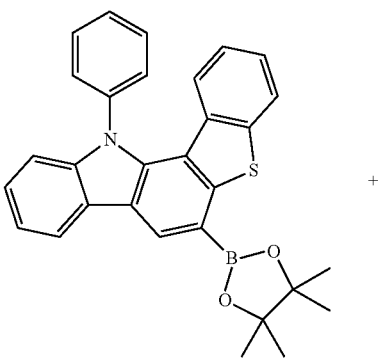

Sub 1-1-5

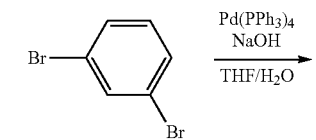

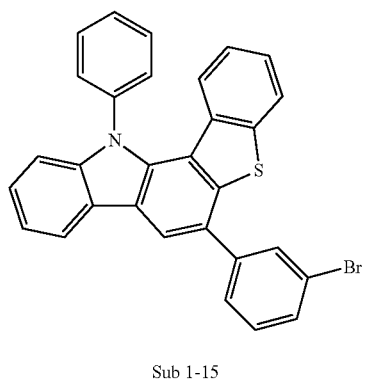

Sub 1-15

Sub 1-1-5 (17 g, 35.8 mmol) being intermediate product of Reaction Scheme 4, 1,3-Dibromobenzene (10.1 g, 42.9 mmol), Pd(PPh₃)₄ (1.7 g, 1.4 mmol), NaOH (4.3 g, 107 mmol), and THF (160 mL)/H₂O (80 ml) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO₄ and concentrated. The concentrate was recrystallized with Methylene chloride and Hexane to obtain 9.8 g of the product Sub 1-15 (Yield: 54%).

7. Synthesis Method of Sub 1-16

<Reaction Scheme 10>

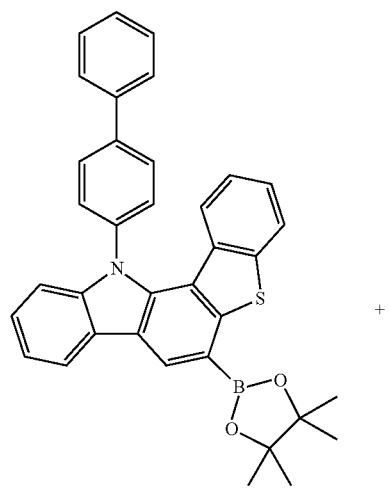

Sub 1-2-2

+

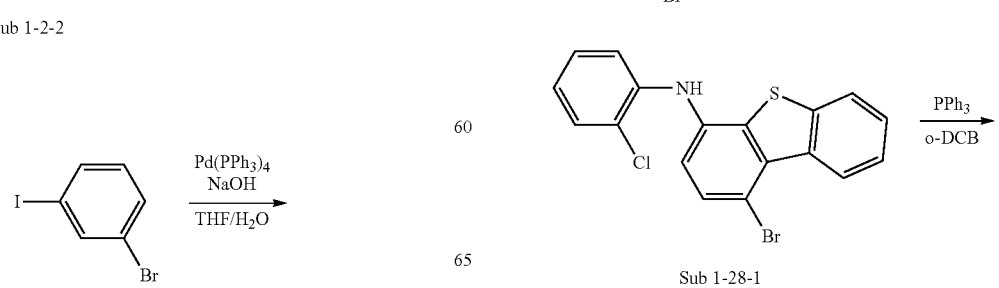

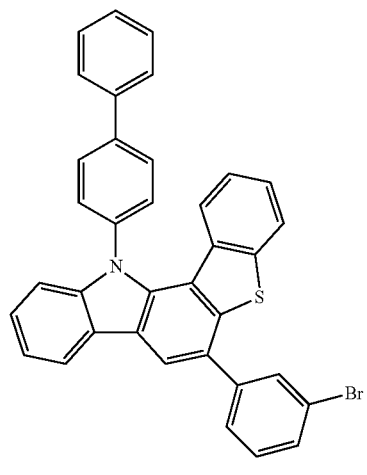

Sub 1-16

Sub 1-2-2 (19.7 g, 35.8 mmol) being produced of Reaction Scheme 5, 1,3-Dibromoenzene (10.1 g, 42.9 mmol), Pd(PPh₃)₄ (1.7 g, 1.4 mmol), NaOH (4.3 g, 107 mmol), and THF (160 mL)/H₂O (80 ml) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO₄ and concentrated. The concentrate was dissolved in Methylene chloride, then, filtered through silica gel column and concentrated. The final concentrate recrystallized with Methylene chloride and Hexane to obtain 13 g of the product Sub 1-16 (Yield: 62%).

8. Synthesis Method of Sub 1-28

<Reaction Scheme 11>

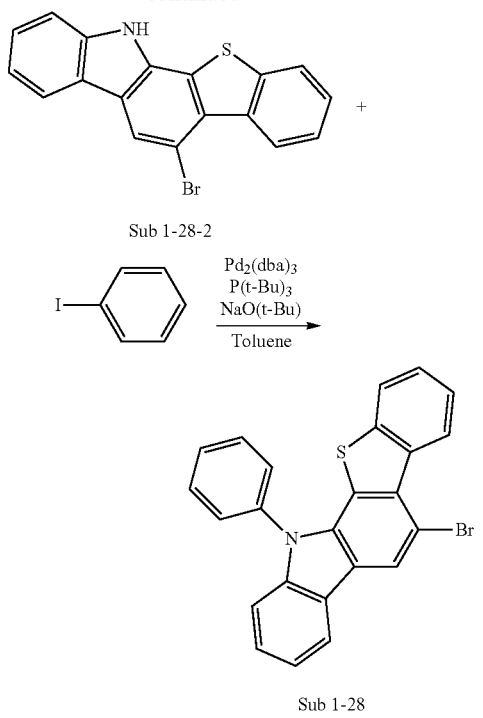

Sub 1-28-2

Sub 1-28

9. Synthesis Method of Sub 1-32

<Reaction Scheme 12>

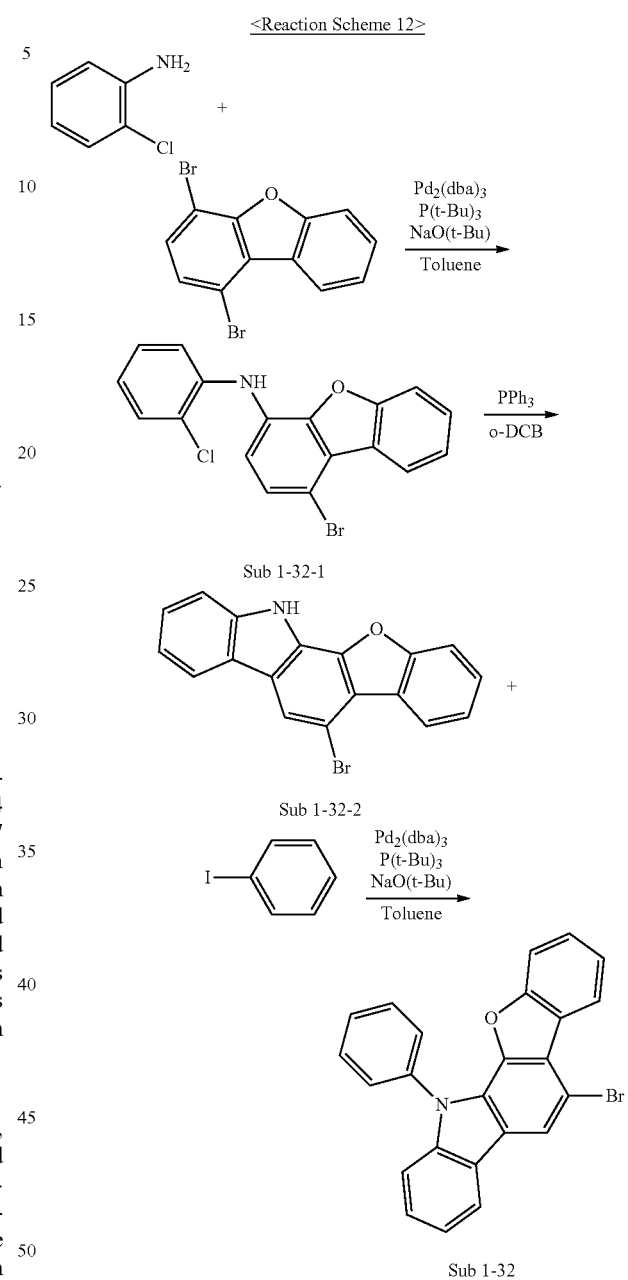

Sub 1-32-1

Sub 1-32-2

Sub 1-32

(1) Synthesis Method of Sub 1-28-1

2-Chloroaniline (67.2 g, 525 mmol), 1,4-Dibromodibenzothiophene (150 g, 438 mmol), Pd₂(dba)₃ (16.2 g, 17.4 mmol), P(t-Bu)₃ (15 g, 43.8 mmol), NaO(t-Bu) (126 g, 1317 mmol), and Toluene (1.5 L) were added into a round bottom flask, then, heated and refluxed at 70° C. for 4 hours. When the reaction was completed, the reaction product was diluted with distilled water at room temperature, then, extracted with Methylene chloride and water. The organic layer was dried with MgSO₄ and concentrated. The concentrate was recrystallized with Methylene chloride and Hexane to obtain 135 g of the product Sub 1-28-1 (Yield: 79%).

(2) Synthesis Method of Sub 1-28-2

Sub 1-28-1 (135 g, 348 mmol), PPh₃ (228 g, 867 mmol), and o-Dichlorobenzene (900 mL) were added into a round bottom flask, then, heated and refluxed at 180° C. for 24 hours. When the reaction was completed, the reaction product was cooled to room temperature and concentrated. The concentrate was passed through silica gel column, and then recrystallized to obtain 91.8 g of the product Sub 1-28-2 (Yield: 75%).

(3) Synthesis Method of Sub 1-28

Sub 1-28-2 (30 g, 84 mmol), Iodobenzene (20.7 g, 102 mmol), Pd₂(dba)₃ (3 g, 3.3 mmol), P(t-Bu)₃ (1.8 g, 8.4 mmol), NaO(t-Bu) (24.6 g, 255 mmol), and Toluene (240 mL) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO₄ and concentrated. The concentrate was recrystallized with Methylene chloride and Hexane to obtain 28 g of the product Sub 1-28 (Yield: 76%).

(1) Synthesis Method of Sub 1-32-1

2-Chloroaniline (67.2 g, 525 mmol), 1,4-Dibromodibenzofuran (143 g, 438 mmol), Pd₂(dba)₃ (16.2 g, 17.4 mmol), P(t-Bu)₃ (15 g, 43.8 mmol), NaO(t-Bu) (126 g, 1317 mmol), and Toluene (1.5 L) were added into a round bottom flask, then, heated and refluxed at 70° C. for 4 hours. When the reaction was completed, the reaction product was diluted with distilled water at room temperature, then, extracted with Methylene chloride and water. The organic layer was dried with MgSO₄ and concentrated. The concentrate was recrystallized with Methylene chloride and Hexane to obtain 129 g of the product Sub 1-32-1 (Yield: 79%).

(2) Synthesis Method of Sub 1-32-2

Sub 1-32-1 (129 g, 346 mmol), PPh₃ (227 g, 865 mmol), and o-Dichlorobenzene (900 mL) were added into a round bottom flask, then, heated and refluxed at 180° C. for 24 hours. When the reaction was completed, the reaction product was cooled to room temperature and concentrated. The concentrate was passed through silica gel column, and then recrystallized to obtain 87.2 g of the product Sub 1-32-2 (Yield: 75%).

(3) Synthesis Method of Sub 1-32

Sub 1-32-2 (28 g, 84 mmol), Iodobenzene (20.7 g, 102 mmol), Pd$_2$(dba)$_3$ (3 g, 3.3 mmol), P(t-Bu)$_3$ (1.8 g, 8.4 mmol), NaO(t-Bu) (24.6 g, 255 mmol), and Toluene (240 mL) were added into a round bottom flask, then, heated and refluxed at 110° C. for 8 hours. When the reaction was completed, the reaction product was diluted with distilled water at room temperature, then, extracted with Methylene chloride and water. The organic layer was dried with MgSO$_4$ and concentrated. The concentrate was recrystallized with Methylene chloride and Hexane to obtain 26 g of the product Sub 1-32 (Yield: 76%).

Exemplary compounds of Sub 1 are as followings, but not limited thereto, and Table 1 shows FD-MS (Field Desorption-Mass Spectrometry) values of compounds belonging to Sub 1.

Sub 1-1

Sub 1-2

Sub 1-3

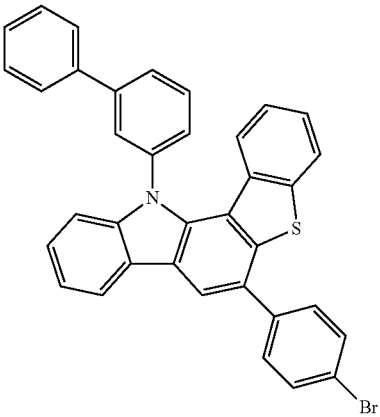

Sub 1-4

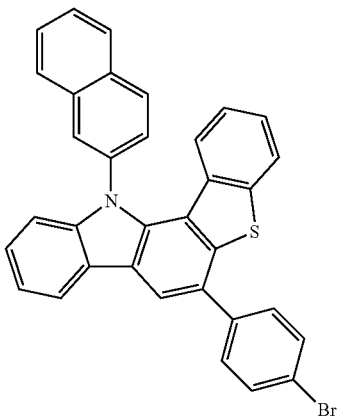

Sub 1-5

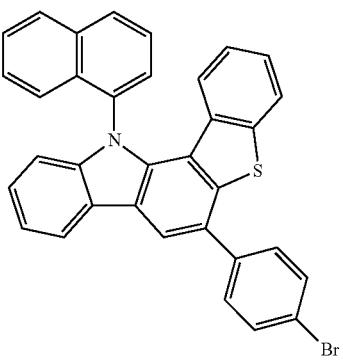

Sub 1-6
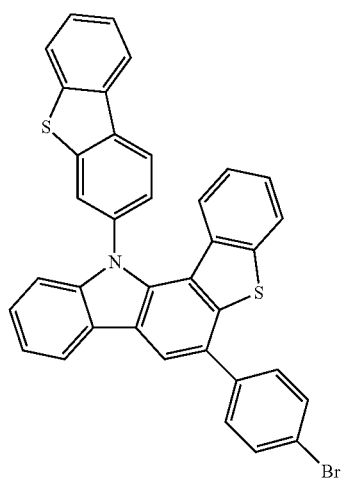
Sub 1-7
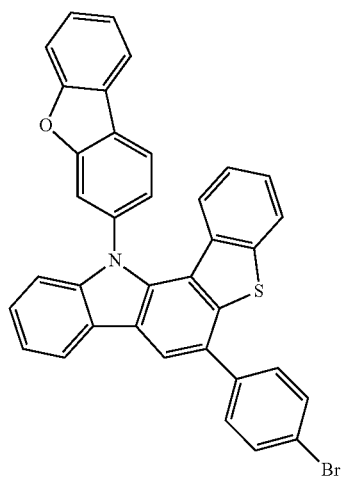
Sub 1-8
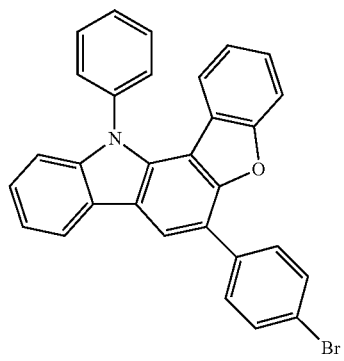
Sub 1-9
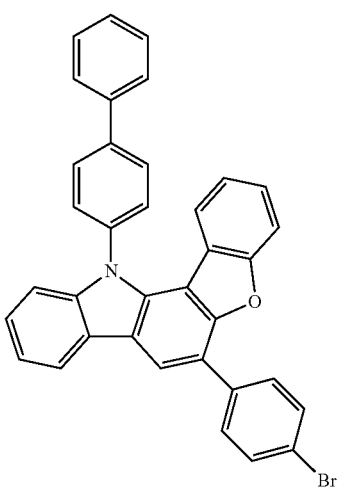
Sub 1-10
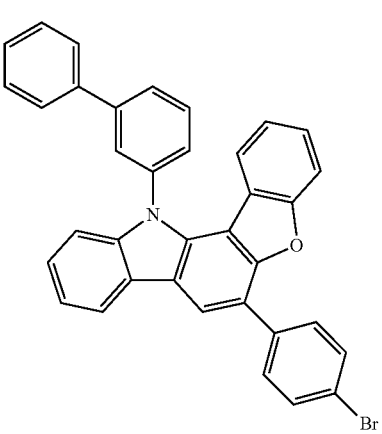
Sub 1-11
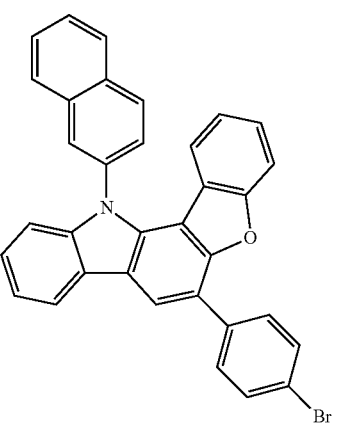

Sub 1-12
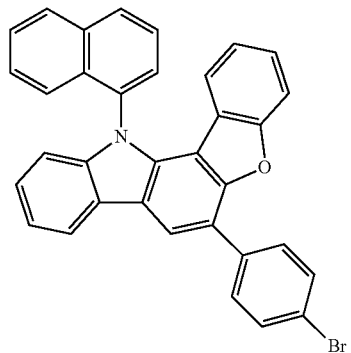
Sub 1-13
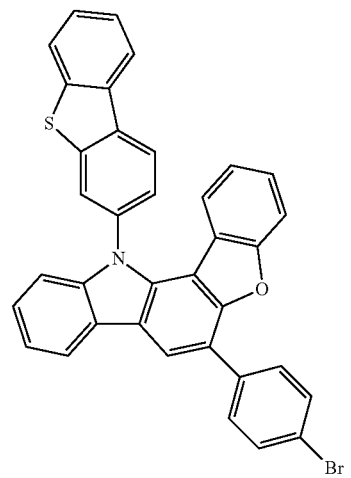
Sub 1-14
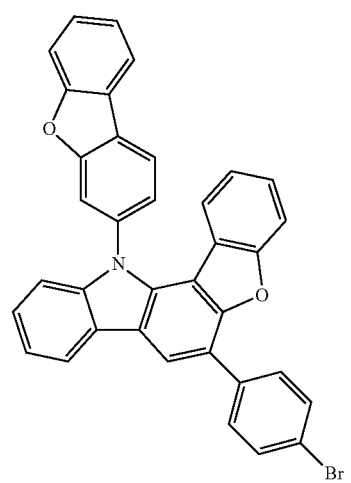
Sub 1-15
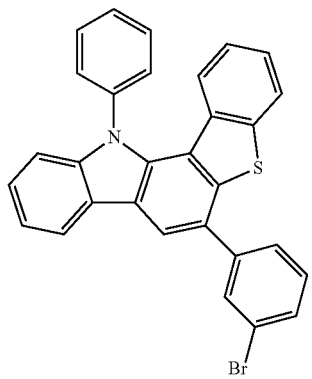
Sub 1-16
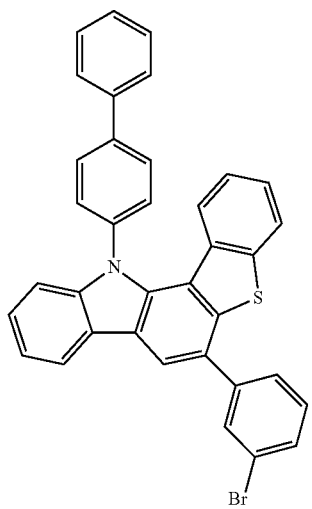
Sub 1-17
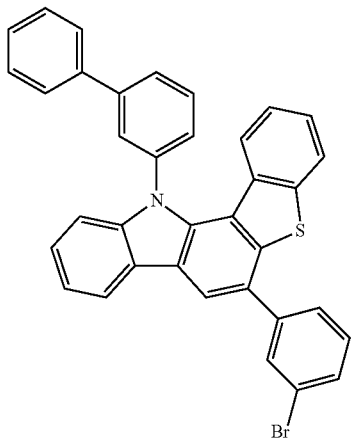

Sub 1-18
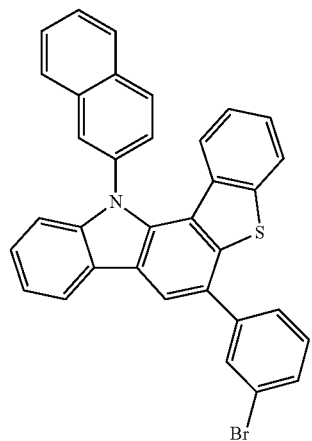
Sub 1-19
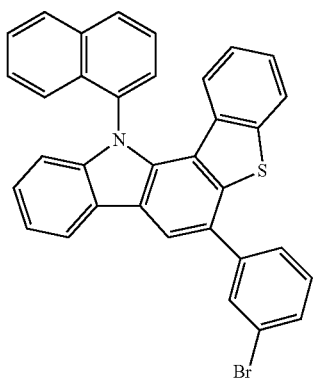
Sub 1-20
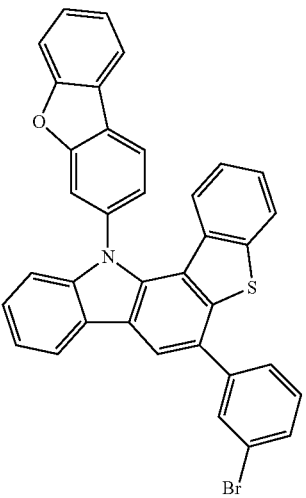
Sub 1-21
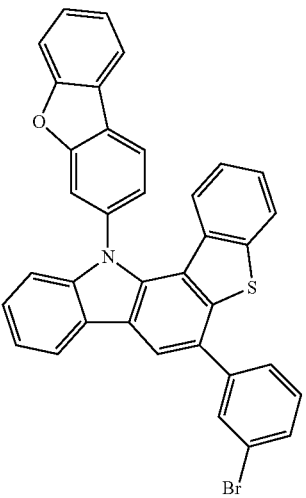
Sub 1-22
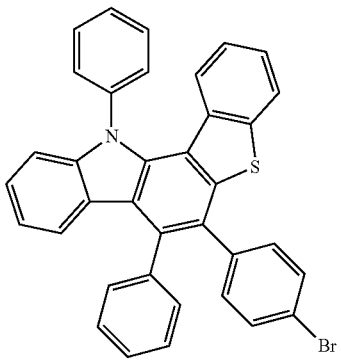
Sub 1-23
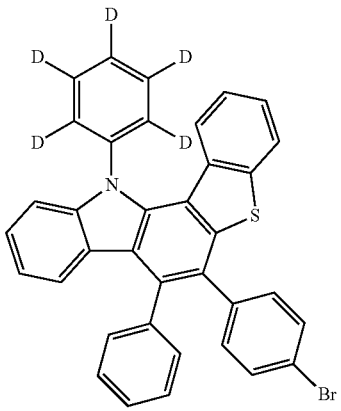
Sub 1-24
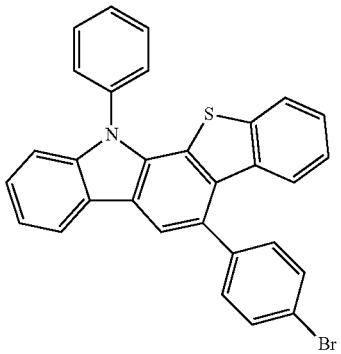

Sub 1-25
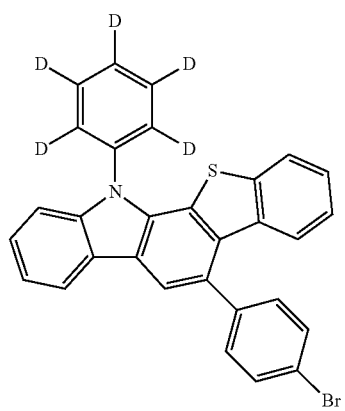
Sub 1-26
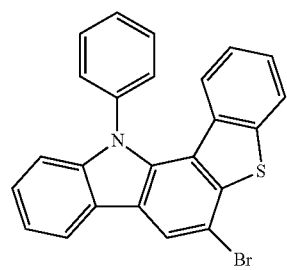
Sub 1-27
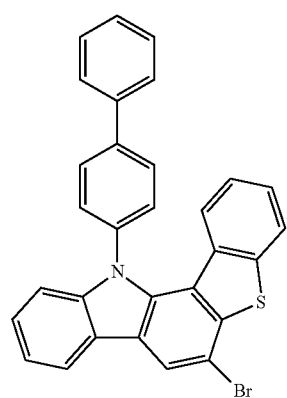
Sub 1-28
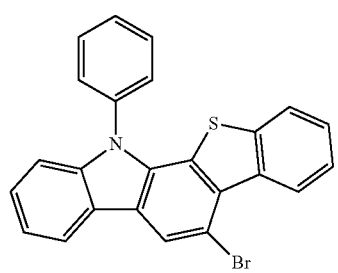
Sub 1-29
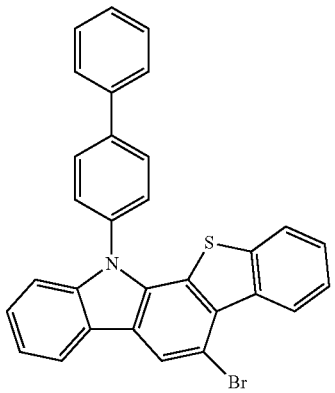
Sub 1-30
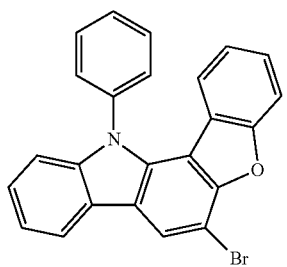
Sub 1-31
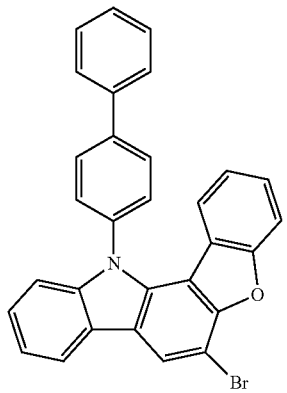
Sub 1-32
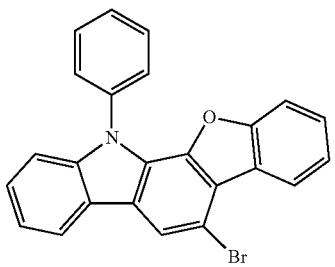

Sub 1-33

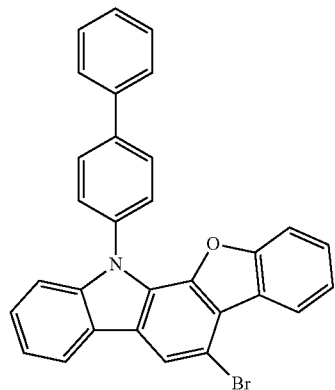

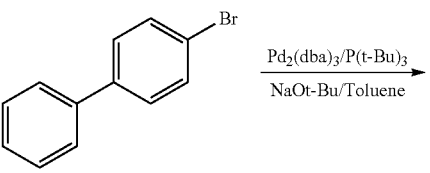

TABLE 1

| compound | FD-MS | compound | FD-MS |
|---|---|---|---|
| Sub 1-1 | m/z = 503.03($C_{30}H_{18}BrNS$ = 504.44) | Sub 1-2 | m/z = 579.07($C_{36}H_{22}BrNS$ = 580.54) |
| Sub 1-3 | m/z = 579.07($C_{36}H_{22}BrNS$ = 580.54) | Sub 1-4 | m/z = 553.05($C_{34}H_{20}BrNS$ = 554.50) |
| Sub 1-5 | m/z = 553.05($C_{34}H_{20}BrNS$ = 554.50) | Sub 1-6 | m/z = 609.02($C_{36}H_{20}BrNS_2$ = 610.58) |
| Sub 1-7 | m/z = 593.04($C_{36}H_{20}BrNOS$ = 594.52) | Sub 1-8 | m/z = 487.06($C_{30}H_{18}BrNO$ = 488.37) |
| Sub 1-9 | m/z = 563.09($C_{36}H_{22}BrNO$ = 564.47) | Sub 1-10 | m/z = 563.09($C_{36}H_{22}BrNO$ = 564.47) |
| Sub 1-11 | m/z = 537.07($C_{34}H_{20}BrNO$ = 538.43) | Sub 1-12 | m/z = 537.07($C_{34}H_{20}BrNO$ = 538.43) |
| Sub 1-13 | m/z = 593.04($C_{36}H_{20}BrNOS$ = 594.52) | Sub 1-14 | m/z = 577.07($C_{36}H_{20}BrNS_2$ = 578.45) |
| Sub 1-15 | m/z = 503.03($C_{30}H_{18}BrNS$ = 504.44) | Sub 1-16 | m/z = 579.07($C_{36}H_{22}BrNS$ = 580.54) |
| Sub 1-17 | m/z = 579.07($C_{36}H_{22}BrNS$ = 580.54) | Sub 1-18 | m/z = 553.05($C_{34}H_{20}BrNS$ = 554.50) |
| Sub 1-19 | m/z = 553.05($C_{34}H_{20}BrNS$ = 554.50) | Sub 1-20 | m/z = 609.02($C_{36}H_{20}BrNS_2$ = 610.58) |
| Sub 1-21 | m/z = 593.04($C_{36}H_{20}BrNOS$ = 594.52) | Sub 1-22 | m/z = 579.07($C_{36}H_{22}BrNS$ = 580.54) |
| Sub 1-23 | m/z = 584.10($C_{36}H_{17}D_5BrNS$ = 585.57) | Sub 1-24 | m/z = 503.03($C_{30}H_{18}BrNS$ = 504.44) |
| Sub 1-25 | m/z = 508.07($C_{30}H_{13}D_5BrNS$ = 509.47) | Sub 1-26 | m/z = 427.00($C_{24}H_{14}BrNS$ = 428.34) |
| Sub 1-27 | m/z = 503.03($C_{30}H_{18}BrNS$ = 504.44) | Sub 1-28 | m/z = 427.00($C_{24}H_{14}BrNS$ = 428.34) |
| Sub 1-29 | m/z = 503.03($C_{30}H_{18}BrNS$ = 504.44) | Sub 1-30 | m/z = 411.03($C_{24}H_{14}BrNO$ = 412.28) |
| Sub 1-31 | m/z = 487.06($C_{30}H_{18}BrNO$ = 488.37) | Sub 1-32 | m/z = 411.03($C_{24}H_{14}BrNO$ = 412.28) |
| Sub 1-33 | m/z = 487.06($C_{30}H_{18}BrNO$ = 488.37) | | |

Synthesis Example of Sub 2

Sub 2 of the Reaction Scheme 1 may be synthesized by the reaction route of the following Reaction Scheme 13.

<Reaction Scheme 13>

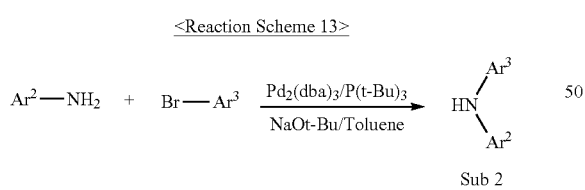

1. Synthesis Example of Sub 2-28

<Reaction Scheme 14>

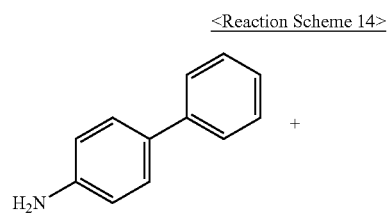

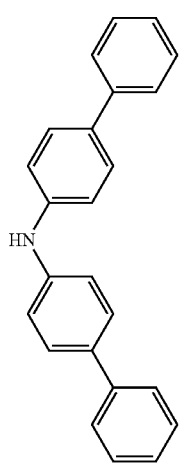

Sub 2-28

After dissolving 4-bromo-1,1'-biphenyl (5.6 g, 24 mmol) in toluene, [1,1'-biphenyl]-4-amine (3.4 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol), and toluene (300 mL) were added, then, stirred and refluxed at 100° C. for 24 hours. When the reaction was completed, the resultant was extracted with ether and water. The organic layer was dried with MgSO₄ and concentrated. The concentrate was passed through silica gel column, and then recrystallized to obtain 6.2 g of the product Sub 2-28 (Yield: 80%).

Exemplary compounds of Sub 2 may be, but not limited to, the following compounds, and Table 2 shows FD-MS values of compounds belonging to Sub 2.

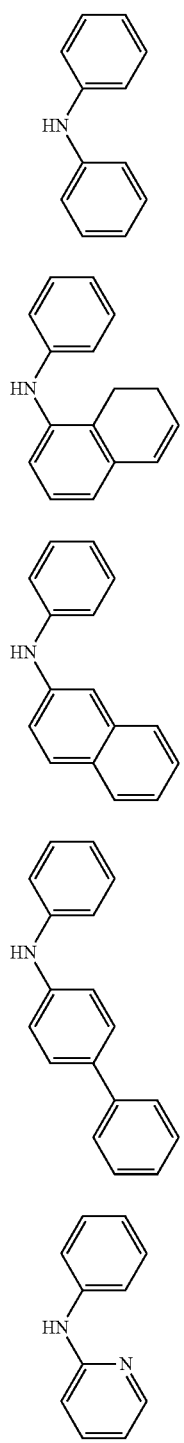

Sub 2-1

Sub 2-2

Sub 2-3

Sub 2-4

Sub 2-5

Sub 2-6

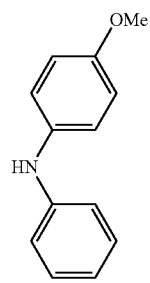

Sub 2-7

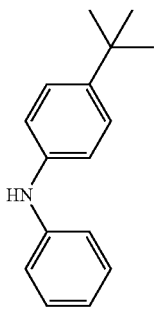

Sub 2-8

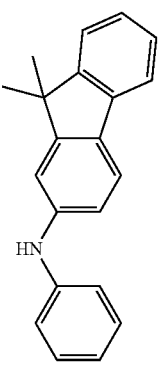

Sub 2-9

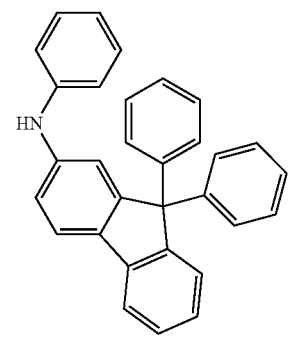

Sub 2-10

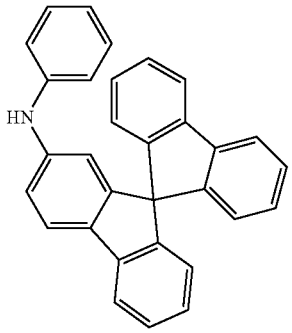

Sub 2-11
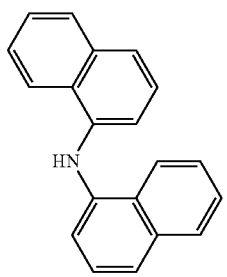
Sub 2-12
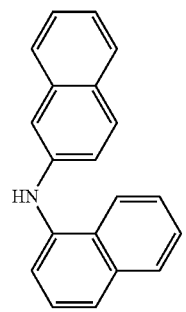
Sub 2-13
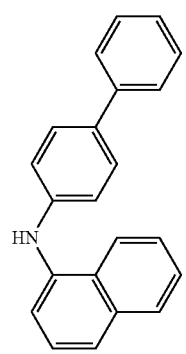
Sub 2-14
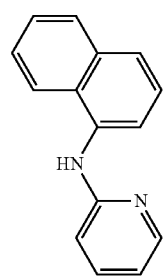
Sub 2-15
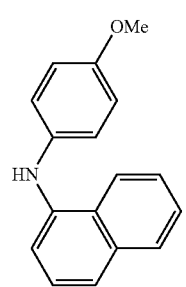
Sub 2-16
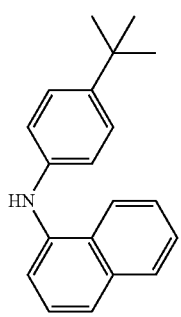
Sub 2-17
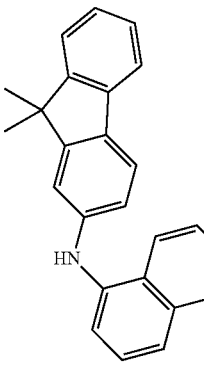
Sub 2-18
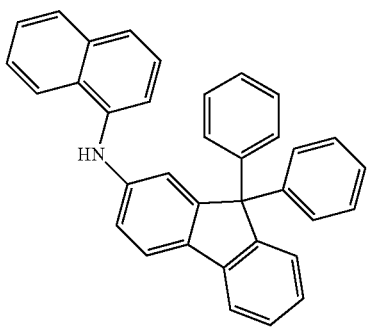
Sub 2-19
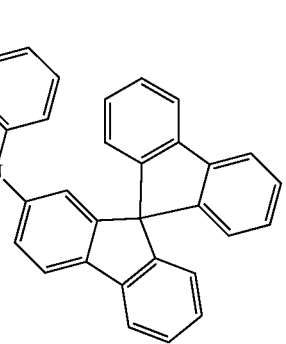

Sub 2-20
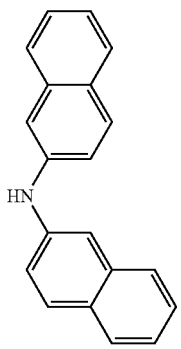
Sub 2-21
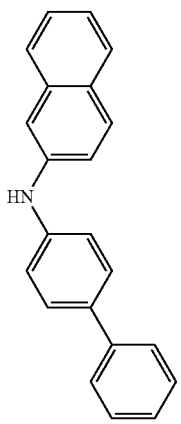
Sub 2-22
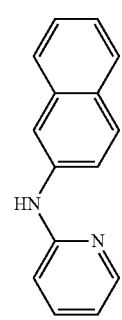
Sub 2-23
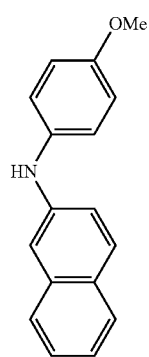
Sub 2-24
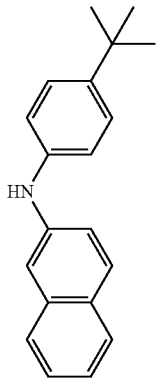
Sub 2-25
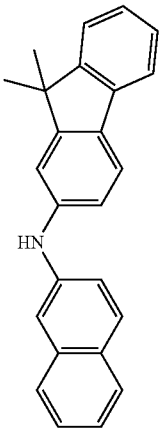
Sub 2-26
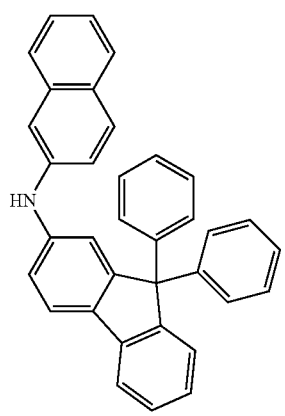
Sub 2-27
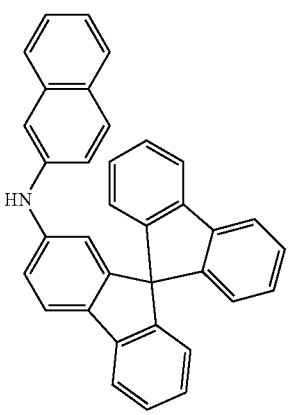

Sub 2-28
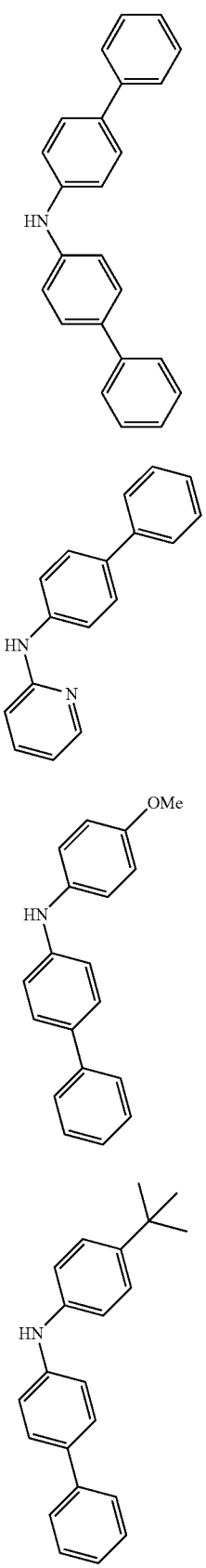
Sub 2-29
Sub 2-30
Sub 2-31
Sub 2-32
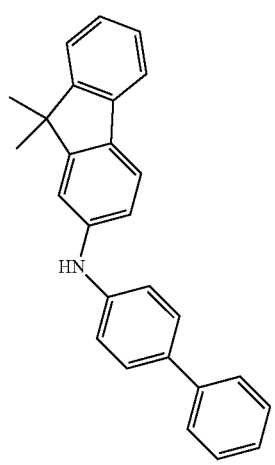
Sub 2-33
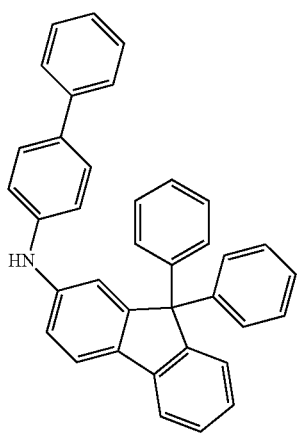
Sub 2-34
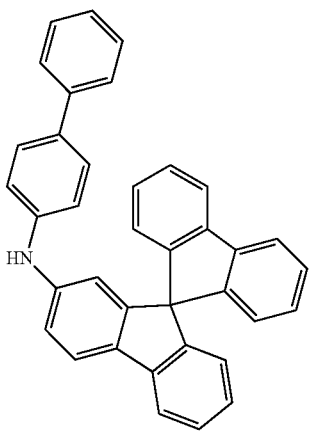
Sub 2-35
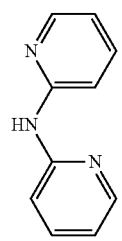

Sub 2-36 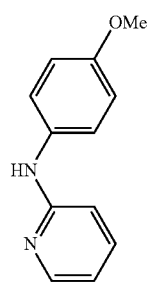
Sub 2-37 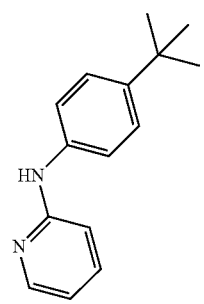
Sub 2-38 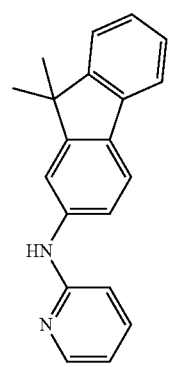
Sub 2-39 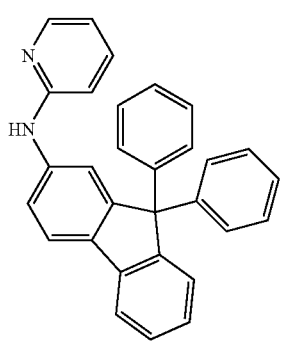
Sub 2-40 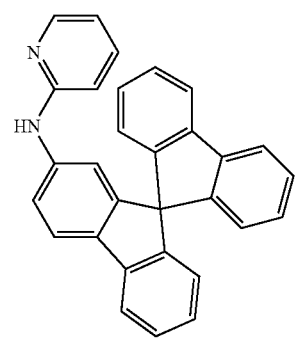
Sub 2-41 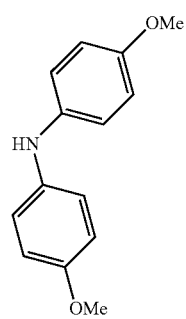
Sub 2-42 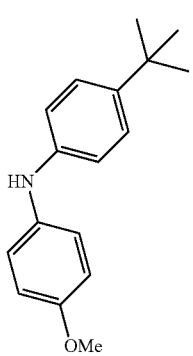
Sub 2-43 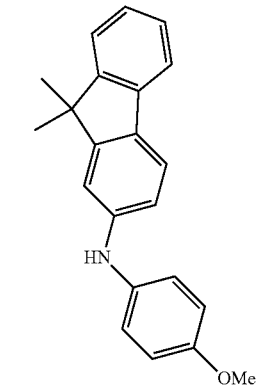
Sub 2-44 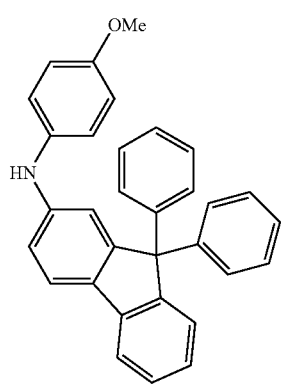

Sub 2-45
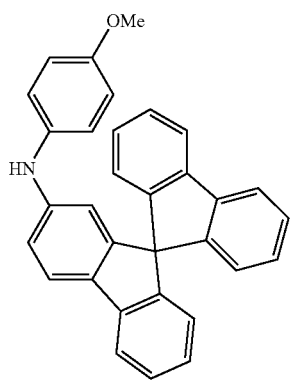
Sub 2-49
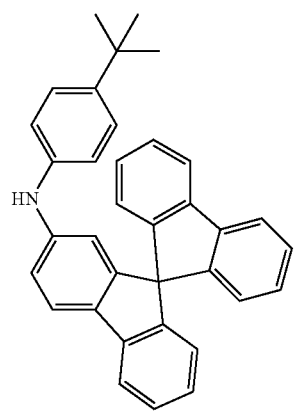
Sub 2-46
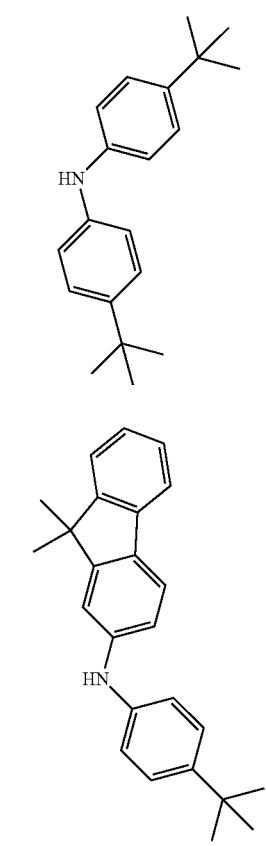
Sub 2-47
Sub 2-50
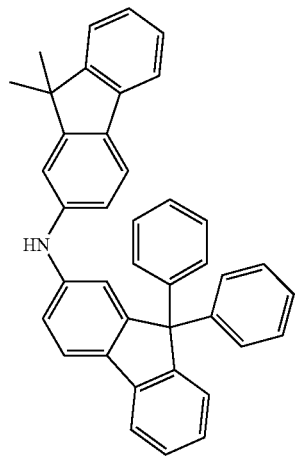
Sub 2-48
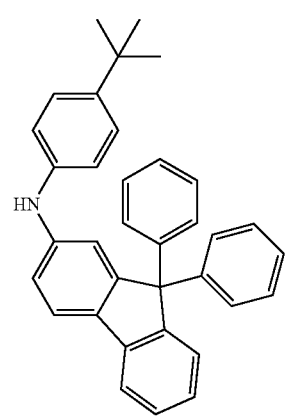
Sub 2-51

Sub 2-52
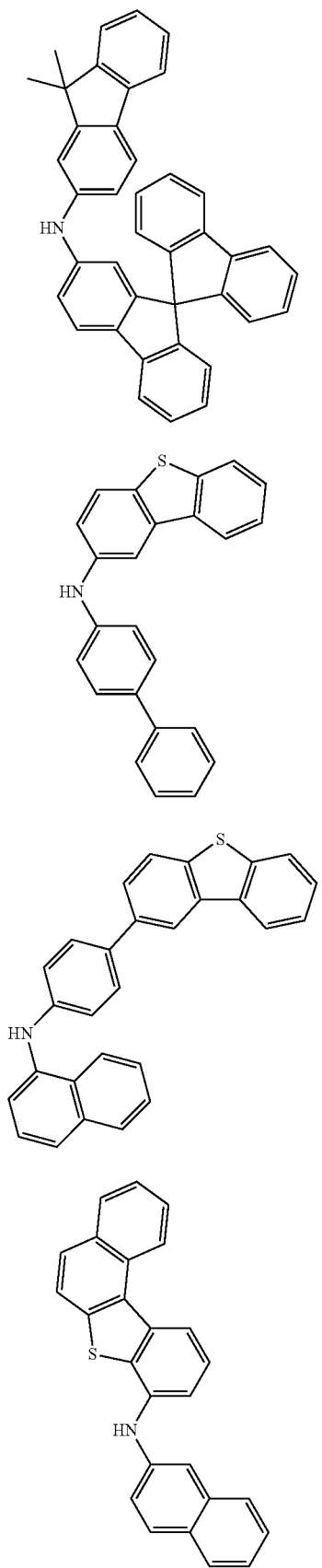
Sub 2-56
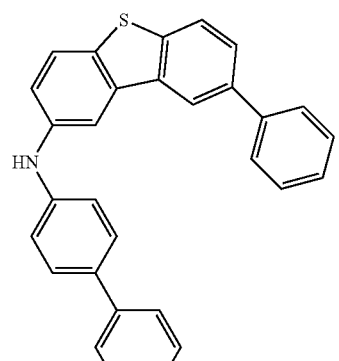
Sub 2-53
Sub 2-57
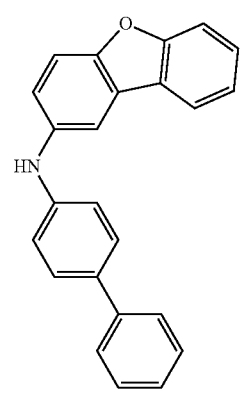
Sub 2-54
Sub 2-58
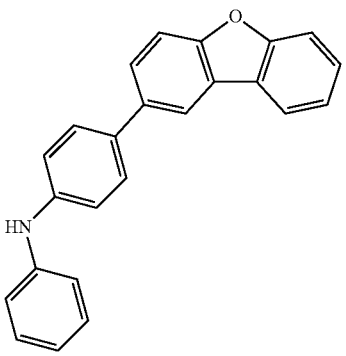
Sub 2-55
Sub 2-59
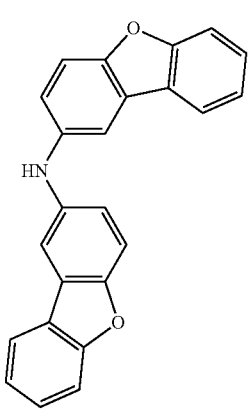

Sub 2-60
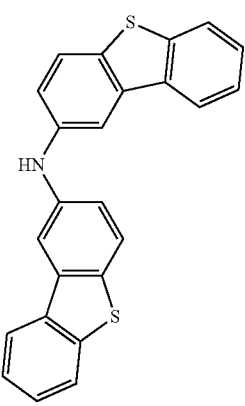
Sub 2-61
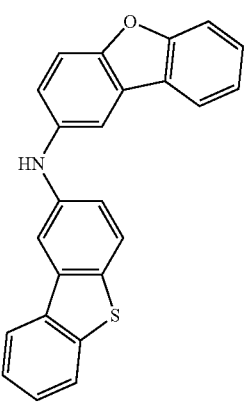
Sub 2-62
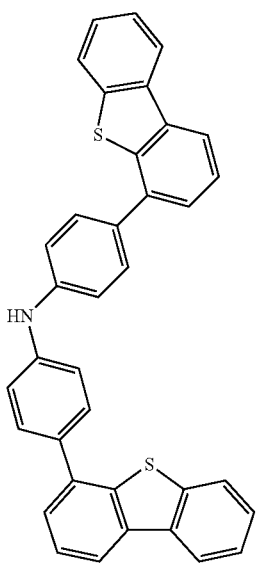
Sub 2-63
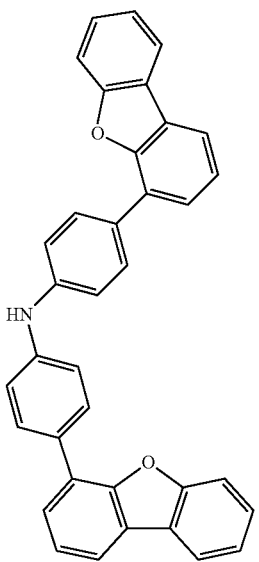
Sub 2-64
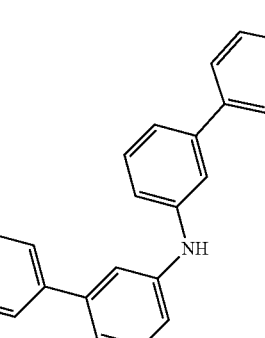
TABLE 2
| compound | FD-MS | compound | FD-MS |
|---|---|---|---|
| Sub 2-1 | m/z = 169.09($C_{12}H_{11}N$ = 169.22) | Sub 2-2 | m/z = 219.10($C_{16}H_{13}N$ = 219.28) |
| Sub 2-3 | m/z = 219.10($C_{16}H_{13}N$ = 219.28) | Sub 2-4 | m/z = 245.12($C_{18}H_{15}N$ = 245.32) |
| Sub 2-5 | m/z = 170.08($C_{11}H_{10}N_2$ = 170.21) | Sub 2-6 | m/z = 199.10($C_{10}H_{13}NO$ = 199.25) |
| Sub 2-7 | m/z = 225.15($C_{16}H_{19}N$ = 225.33) | Sub 2-8 | m/z = 285.15($C_{21}H_{19}N$ = 285.38) |
| Sub 2-9 | m/z = 409.18($C_{31}H_{23}N$ = 409.52) | Sub 2-10 | m/z = 407.17($C_{31}H_{21}N$ = 407.51) |
| Sub 2-11 | m/z = 269.12($C_{20}H_{15}N$ = 269.34) | Sub 2-12 | m/z = 269.12($C_{20}H_{15}N$ = 269.34) |
| Sub 2-13 | m/z = 295.14($C_{22}H_{17}N$ = 295.38) | Sub 2-14 | m/z = 220.10($C_{15}H_{12}N_2$ = 220.27) |

TABLE 2-continued

| compound | FD-MS | compound | FD-MS |
|---|---|---|---|
| Sub 2-15 | m/z = 249.12($C_{17}H_{12}NO$ = 249.31) | Sub 2-16 | m/z = 275.17($C_{20}H_{21}N$ = 275.39) |
| Sub 2-17 | m/z = 335.17($C_{25}H_{21}N$ = 335.44) | Sub 2-18 | m/z = 459.20($C_{35}H_{25}N$ = 459.58) |
| Sub 2-19 | m/z = 457.18($C_{35}H_{23}N$ = 457.56) | Sub 2-20 | m/z = 269.12($C_{20}H_{15}N$ = 269.34) |
| Sub 2-21 | m/z = 295.14($C_{22}H_{17}N$ = 295.38) | Sub 2-22 | m/z = 220.10($C_{15}H_{2}N_{2}$ = 220.27) |
| Sub 2-23 | m/z = 249.12($C_{17}H_{15}NO$ = 249.31) | Sub 2-24 | m/z = 275.17($C_{20}H_{21}N$ = 275.39) |
| Sub 2-25 | m/z = 335.17($C_{25}H_{21}N$ = 335.44) | Sub 2-26 | m/z = 459.20($C_{35}H_{25}N$ = 459.58) |
| Sub 2-27 | m/z = 457.18($C_{35}H_{23}N$ = 457.56) | Sub 2-28 | m/z = 321.15($C_{24}H_{19}N$ = 321.41) |
| Sub 2-29 | m/z = 246.12($C_{17}H_{14}N_{2}$ = 246.31) | Sub 2-30 | m/z = 275.13($C_{19}H_{17}NO$ = 275.34) |
| Sub 2-31 | m/z = 301.18($C_{22}H_{23}N$ = 301.42) | Sub 2-32 | m/z = 361.18($C_{27}H_{23}N$ = 361.48) |
| Sub 2-33 | m/z = 485.21($C_{37}H_{27}N$ = 485.62) | Sub 2-34 | m/z = 483.20($C_{37}H_{25}N$ = 483.60) |
| Sub 2-35 | m/z = 171.08($C_{10}H_{09}N_{3}$ = 171.20) | Sub 2-36 | m/z = 200.09($C_{12}H_{12}N_{2}O$ = 200.24) |
| Sub 2-37 | m/z = 226.15($C_{15}H_{18}N_{2}$ = 226.32) | Sub 2-38 | m/z = 286.15($C_{20}H_{18}N_{2}$ = 286.37) |
| Sub 2-39 | m/z = 410.18($C_{30}H_{22}N_{2}$ = 410.51) | Sub 2-40 | m/z = 408.16($C_{30}H_{20}N_{2}$ = 408.49) |
| Sub 2-41 | m/z = 229.11($C_{14}H_{15}NO_{2}$ = 229.27) | Sub 2-42 | m/z = 255.16($C_{17}H_{21}NO$ = 255.35) |
| Sub 2-43 | m/z = 315.16($C_{22}H_{21}NO$ = 315.41) | Sub 2-44 | m/z = 439.19($C_{32}H_{25}NO$ = 439.55) |
| Sub 2-45 | m/z = 437.18($C_{32}H_{23}NO$ = 437.53) | Sub 2-46 | m/z = 281.21($C_{20}H_{27}N$ = 281.44) |
| Sub 2-47 | m/z = 341.21($C_{25}H_{27}N$ = 341.49) | Sub 2-48 | m/z = 465.25($C_{35}H_{31}N$ = 465.63) |
| Sub 2-49 | m/z = 463.23($C_{35}H_{29}N$ = 463.61) | Sub 2-50 | m/z = 401.21($C_{30}H_{27}N$ = 401.54) |
| Sub 2-51 | m/z = 525.25($C_{40}H_{31}N$ = 525.68) | Sub 2-52 | m/z = 523.23($C_{40}H_{29}N$ = 523.66) |
| Sub 2-53 | m/z = 351.11($C_{24}H_{17}NS$ = 351.46) | Sub 2-54 | m/z = 401.12($C_{28}H_{19}NS$ = 401.52) |
| Sub 2-55 | m/z = 357.11($C_{26}H_{17}NS$ = 375.48) | Sub 2-56 | m/z = 427.14($C_{30}H_{21}NS$ = 427.56) |
| Sub 2-57 | m/z = 335.13($C_{24}H_{17}NO$ = 335.40) | Sub 2-58 | m/z = 335.13($C_{24}H_{17}NO$ = 335.40) |
| Sub 2-59 | m/z = 349.11($C_{24}H_{15}NO_{2}$ = 349.38) | Sub 2-60 | m/z = 381.06($C_{24}H_{15}NS_{2}$ = 381.51) |
| Sub 2-61 | m/z = 365.09($C_{24}H_{15}NOS$ = 365.45) | Sub 2-62 | m/z = 533.13($C_{36}H_{23}NS_{2}$ = 533.70) |
| Sub 2-63 | m/z = 501.17($C_{36}H_{23}NO_{2}$ = 501.57) | Sub 2-64 | m/z = 517.15($C_{36}H_{23}NOS$ = 349.38) |

Synthesis Method of Product

Compound Sub 1 (1 eq.), compound Sub 2 (1 eq.), $Pd_{2}(dba)_{3}$ (0.03~0.05 eq.), $P(t-Bu)_{3}$ (0.08 eq.), NaO(t-Bu) (3 eq.), and Toluene (3 mmol) were added into a round bottom flask, then, heated and refluxed at 100° C. When the reaction was completed, the reaction product was diluted with distilled water at room temperature, then, extracted with Methylene chloride and water. The organic layer was dried with $MgSO_{4}$ and concentrated. The concentrate was recrystallized with Toluene and Acetone to obtain product.

Synthesis of Compound 1-1

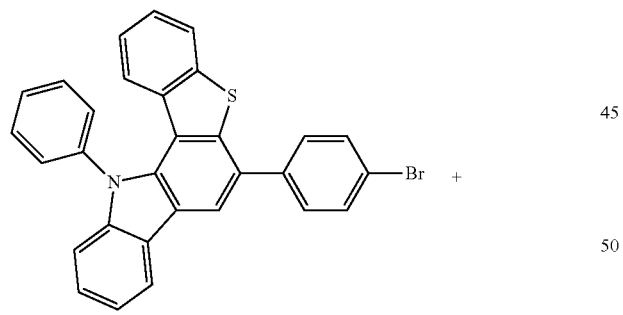

Sub 1-1

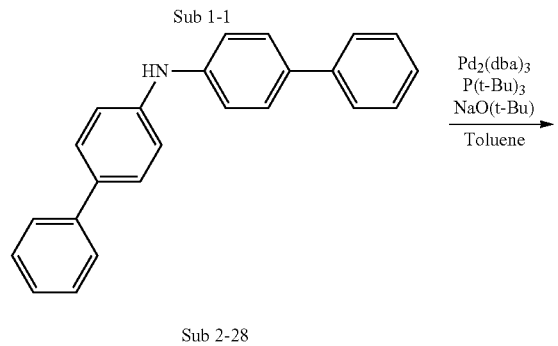

Sub 2-28

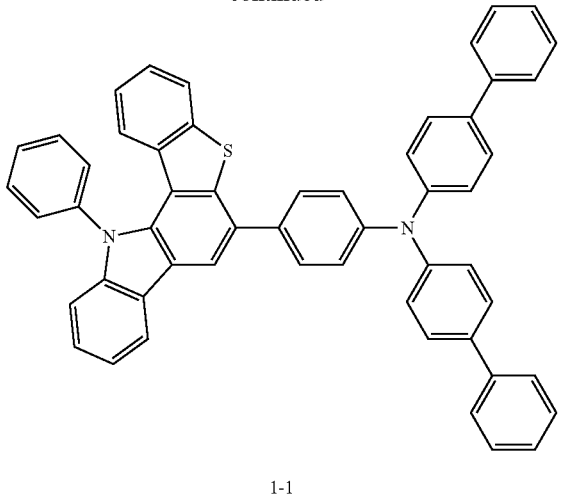

1-1

Sub 1-1 (5 g, 10 mmol), Sub 2-28 (3.2 g, 10 mmol), $Pd_{2}(dba)_{3}$ (3 g, 0.4 mmol), $P(t-Bu)_{3}$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with $MgSO_{4}$ and concentrated. The concentrate was dissolved in Toluene, then, filtered through silica gel column and concentrated. The final concentrate recrystallized with Toluene and Acetone to obtain 6.4 g of the product 1-1 (Yield: 86%).

Synthesis of Compound 1-2

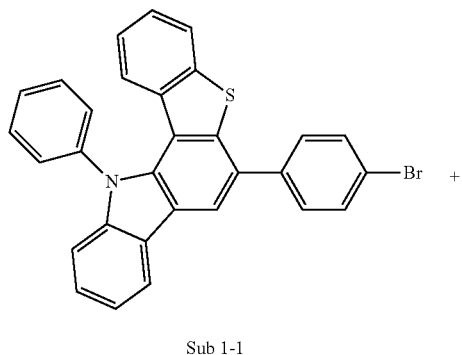

Sub 1-1

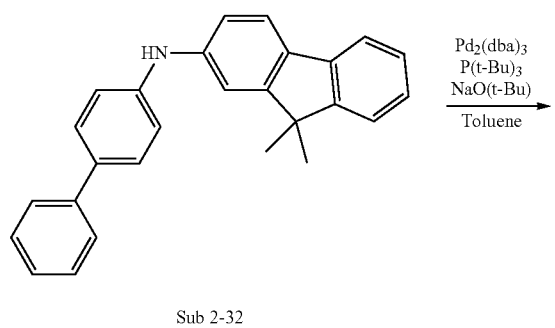

Sub 2-32

1-2

Synthesis of Compound 1-3

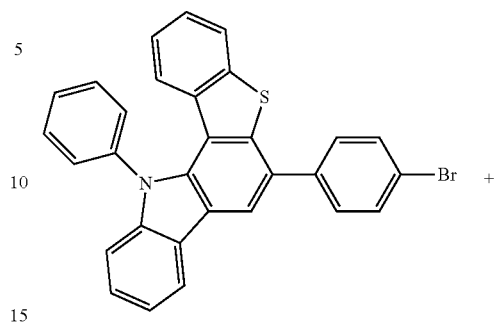

Sub 1-1

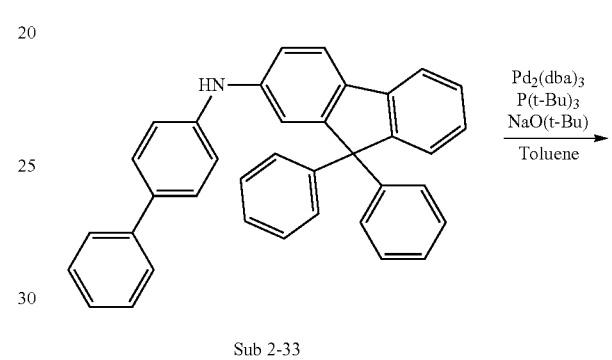

Sub 2-33

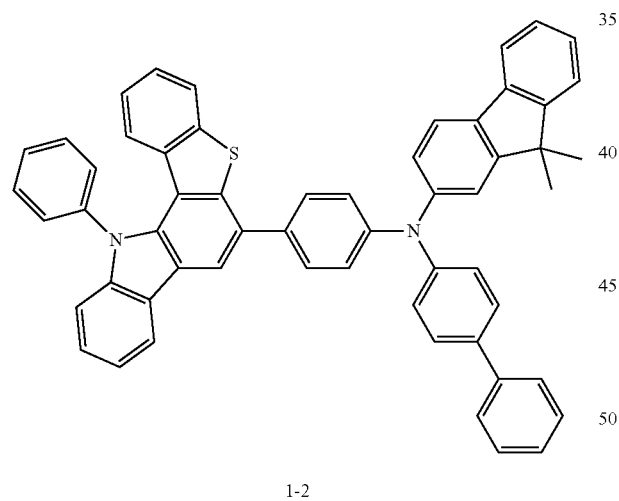

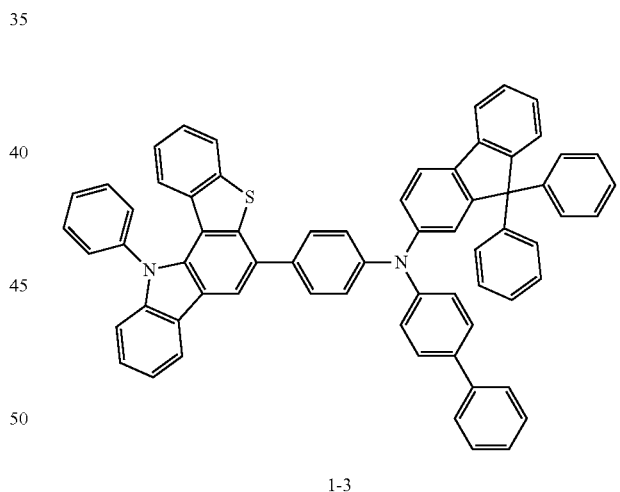

1-3

Sub 1-1 (5 g, 10 mmol), Sub 2-32 (3.6 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 5.8 g of the product 1-2 (Yield: 74%).

Sub 1-1 (5 g, 10 mmol), Sub 2-33 (4.9 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 6.8 g of the product 1-3 (Yield: 75%).

Synthesis of Compound 1-4

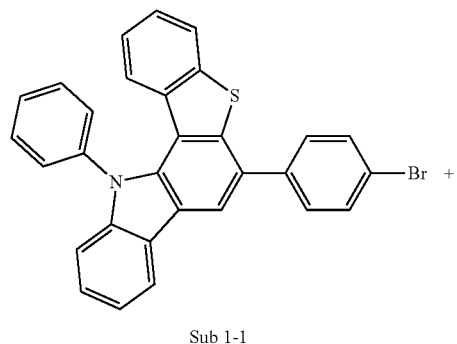
Sub 1-1

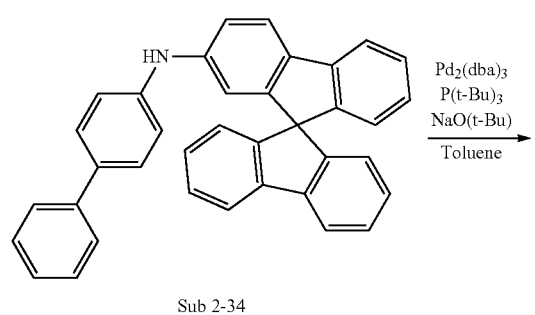
Sub 2-34

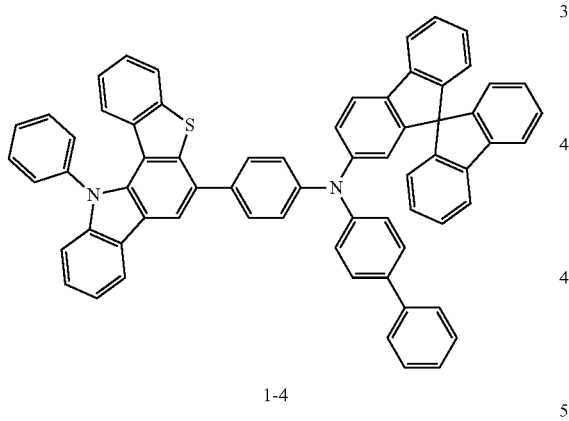
1-4

Sub 1-1 (5 g, 10 mmol), Sub 2-34 (4.9 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 7 g of the product 1-4 (Yield: 77%).

Synthesis of Compound 1-5

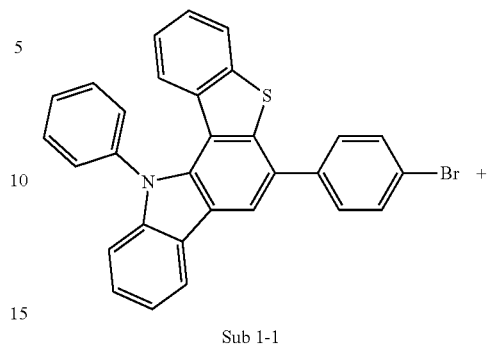
Sub 1-1

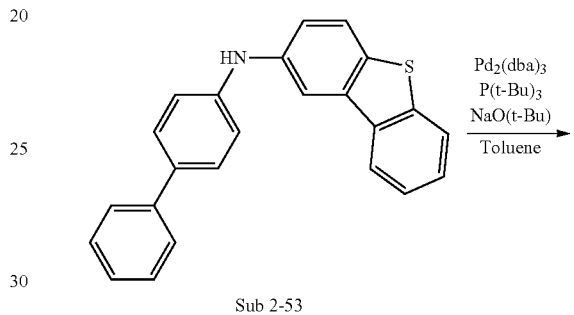
Sub 2-53

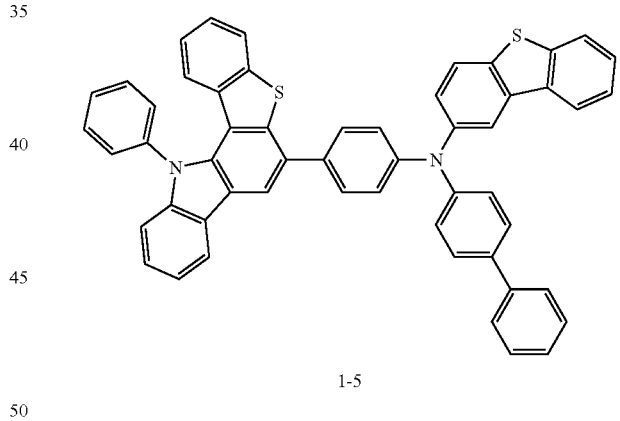
1-5

Sub 1-1 (5 g, 10 mmol), Sub 2-53 (3.5 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 6.8 g of the product 1-5 (Yield: 88%).

Synthesis of Compound 1-6

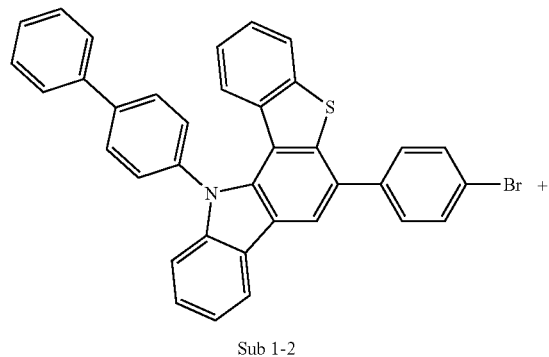
Sub 1-2

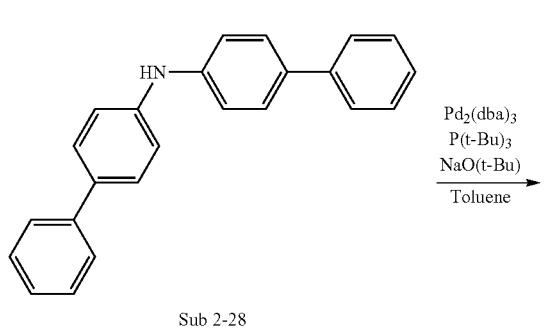
Sub 2-28

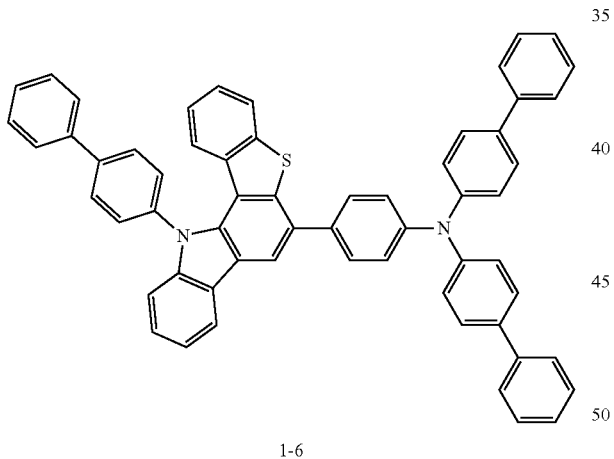
1-6

Synthesis of Compound 1-16

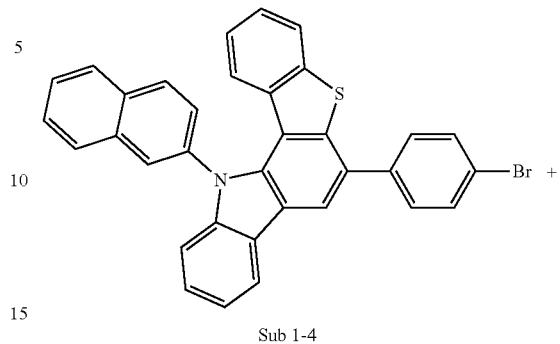
Sub 1-4

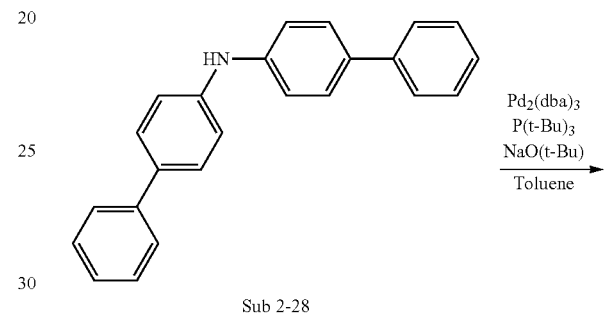
Sub 2-28

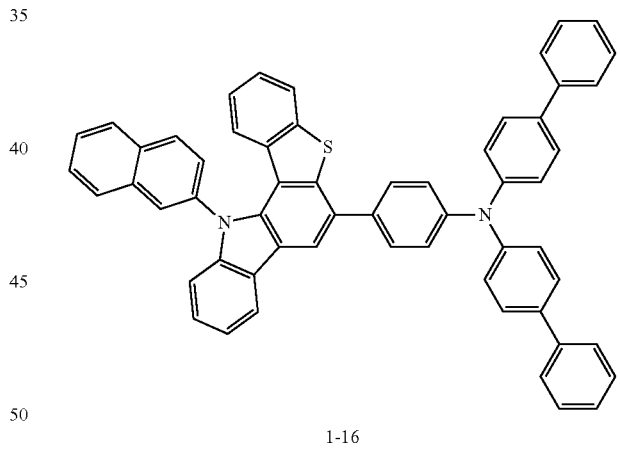
1-16

Sub 1-2 (5.8 g, 10 mmol), Sub 2-28 (3.2 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 6.2 g of the product 1-6 (Yield: 76%).

Sub 1-4 (5.5 g, 10 mmol), Sub 2-28 (3.2 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 5.4 g of the product 1-16 (Yield: 68%).

Synthesis of Compound 1-26

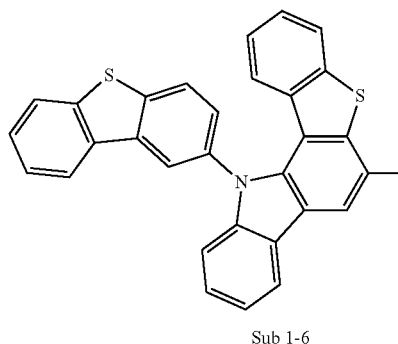

Sub 1-6

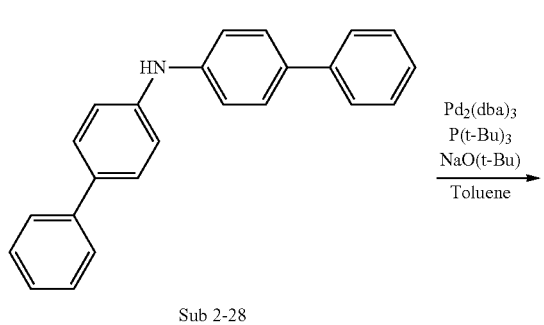

Sub 2-28

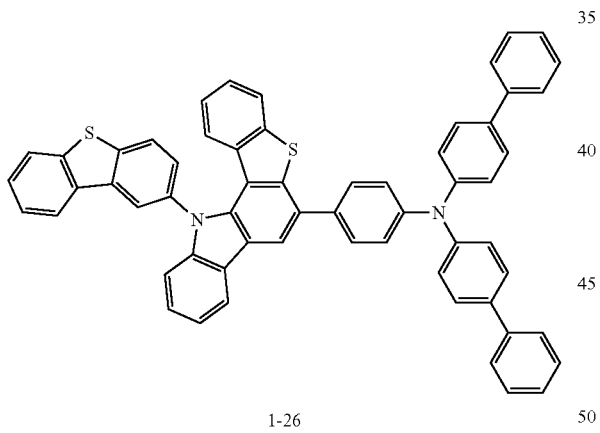

1-26

Synthesis of Compound 1-36

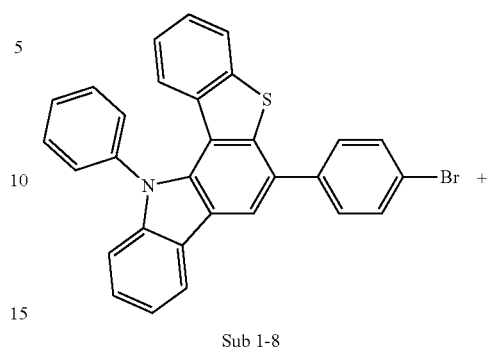

Sub 1-8

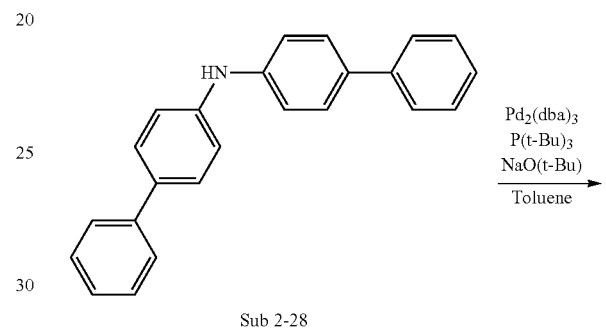

Sub 2-28

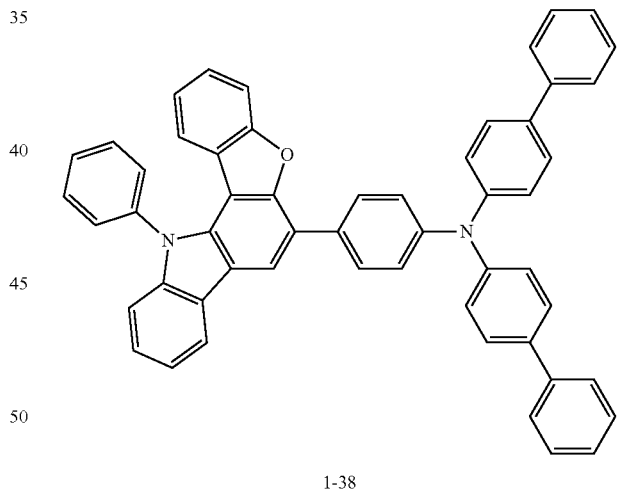

1-38

Sub 1-6 (6.1 g, 10 mmol), Sub 2-28 (3.2 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 6.3 g of the product 1-26 (Yield: 74%).

Sub 1-8 (4.9 g, 10 mmol), Sub 2-28 (3.2 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 6.5 g of the product 1-36 (Yield: 89%).

Synthesis of Compound 1-38

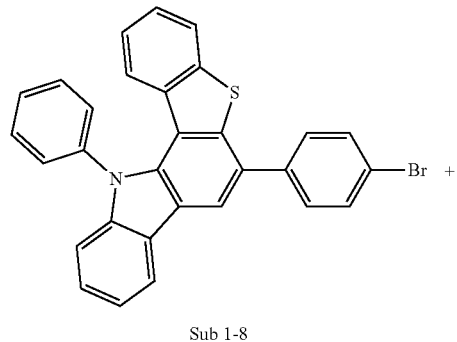

Synthesis of Compound 1-71

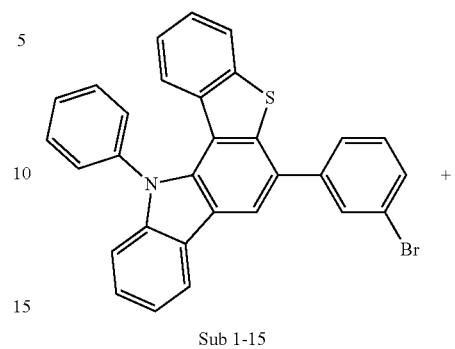

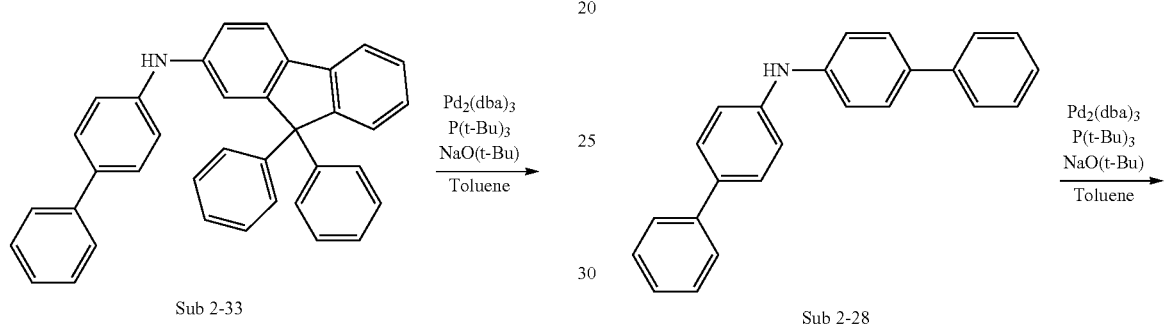

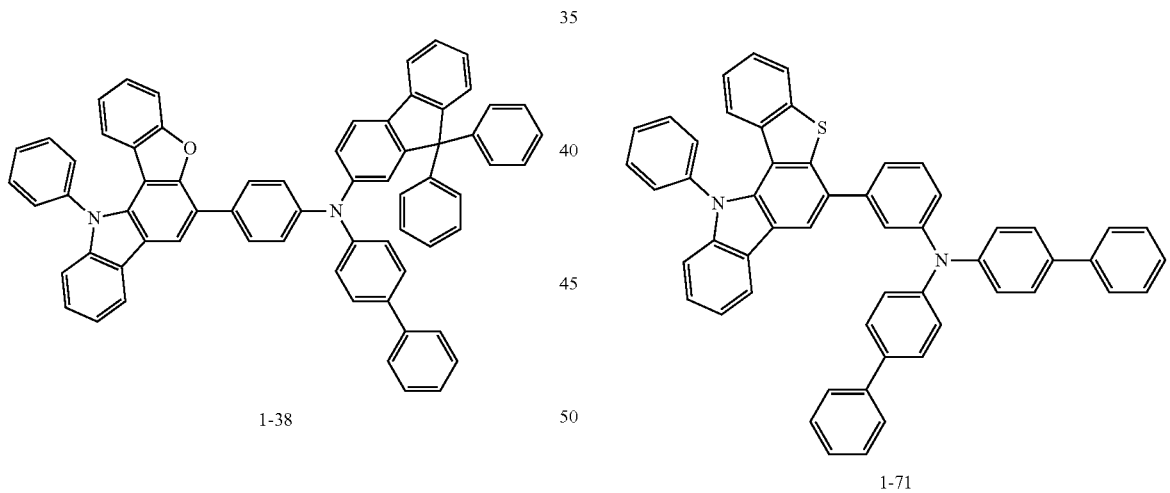

Sub 1-8 (4.9 g, 10 mmol), Sub 2-33 (4.9 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 7 g of the product 1-38 (Yield: 79%).

Sub 1-15 (5 g, 10 mmol), Sub 2-28 (3.2 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 6.3 g of the product 1-71 (Yield: 85%).

Synthesis of Compound 1-73

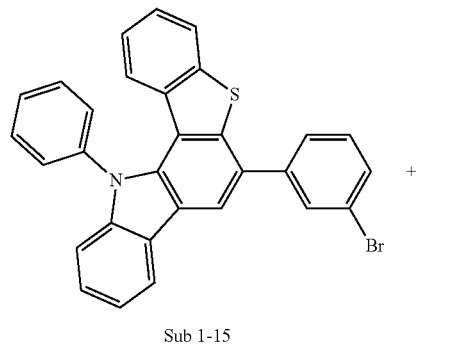

Sub 1-15

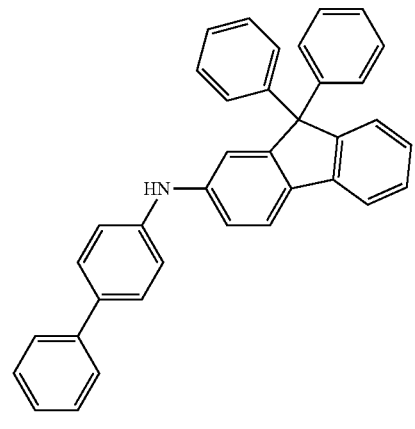

Sub 2-33

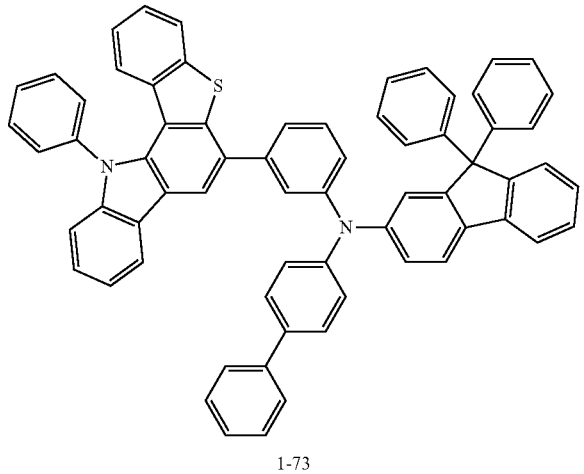

1-73

Sub 1-15 (5 g, 10 mmol), Sub 2-33 (4.9 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 6.7 g of the product 1-73 (Yield: 74%).

Synthesis of Compound 1-75

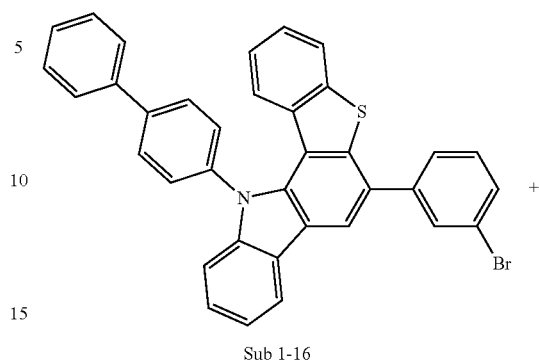

Sub 1-16

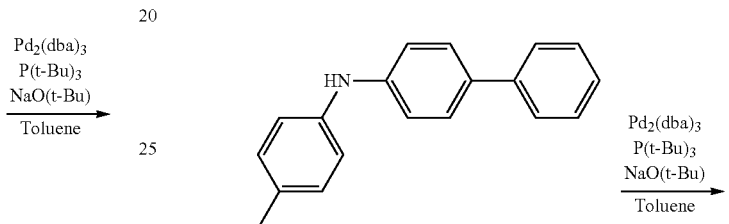

Sub 2-28

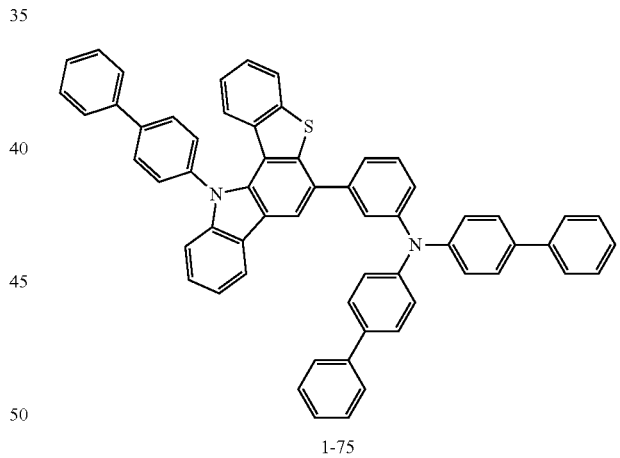

1-75

Sub 1-16 (5.8 g, 10 mmol), Sub 2-28 (3.2 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 6.3 g of the product 1-75 (Yield: 77%).

Synthesis of Compound 1-105

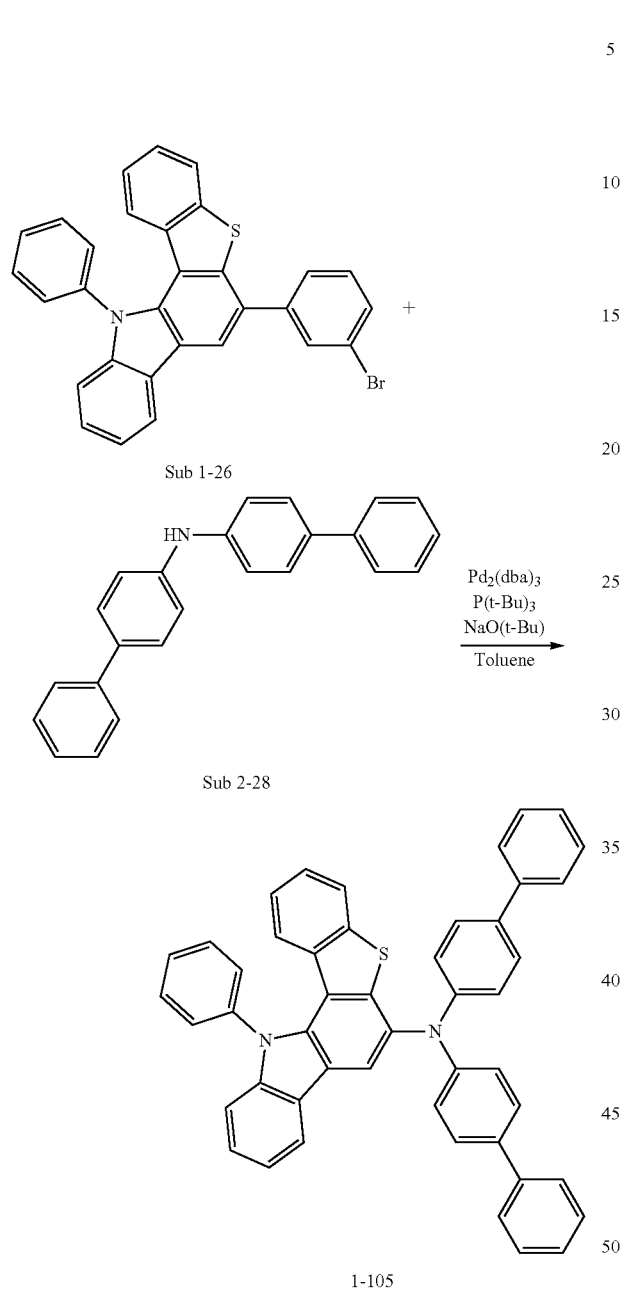

1-105

Synthesis of Compound 1-107

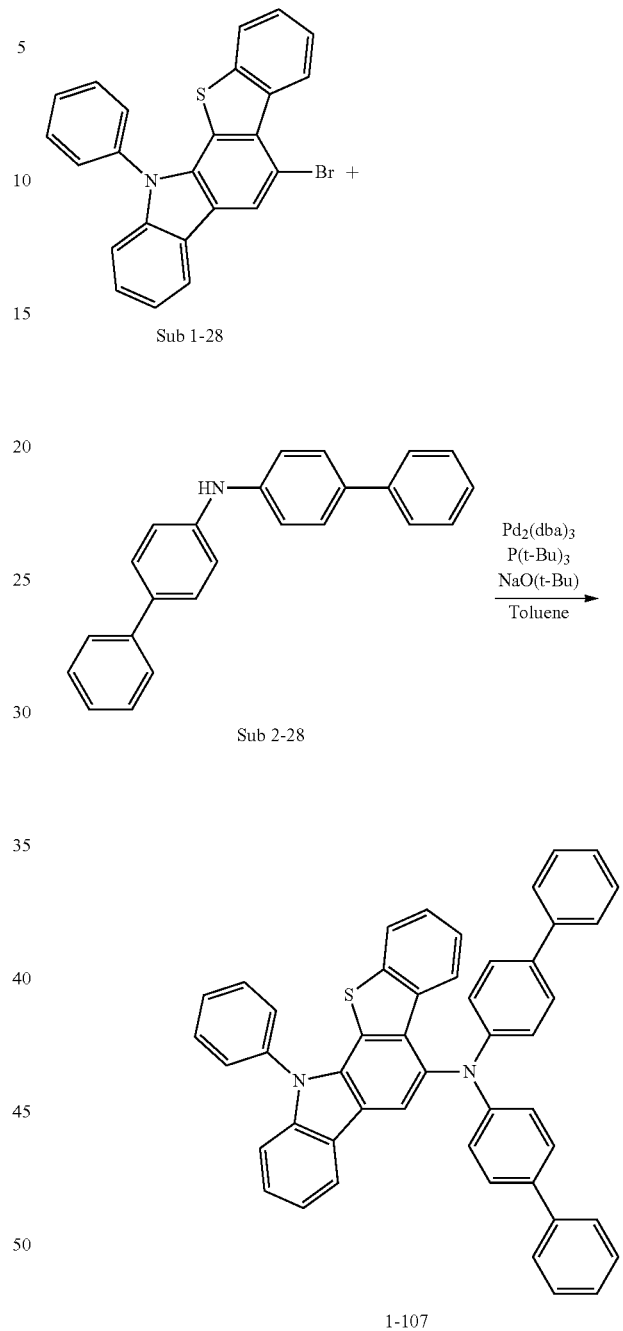

1-107

Sub 1-26 (4.3 g, 10 mmol), Sub 2-28 (3.2 g, 10 mmol), $Pd_2(dba)_3$ (3 g, 0.4 mmol), $P(t-Bu)_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with $MgSO_4$ and concentrated. The concentrate was dissolved in Toluene, then, filtered through silica gel column and concentrated. The final concentrate recrystallized with Toluene and Acetone to obtain 5.9 g of the product 1-105 (Yield: 88%).

Sub 1-28 (4.3 g, 10 mmol), Sub 2-28 (3.2 g, 10 mmol), $Pd_2(dba)_3$ (3 g, 0.4 mmol), $P(t-Bu)_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with $MgSO_4$ and concentrated. The concentrate was dissolved in Toluene, then, filtered through silica gel column and concentrated. The final concentrate recrystallized with Toluene and Acetone to obtain 4.3 g of the product 1-107 (Yield: 65%).

Synthesis of Compound 1-111

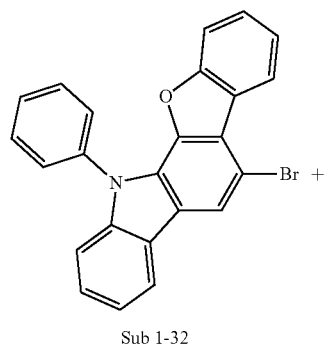

Sub 1-32

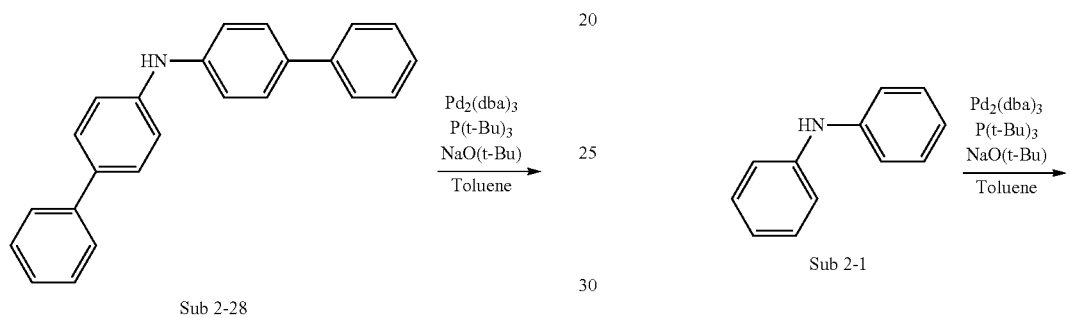

Sub 2-28

1-111

Sub 1-32 (4.1 g, 10 mmol), Sub 2-28 (3.2 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 3.8 g of the product 1-111 (Yield: 58%).

Synthesis of Compound 1-113

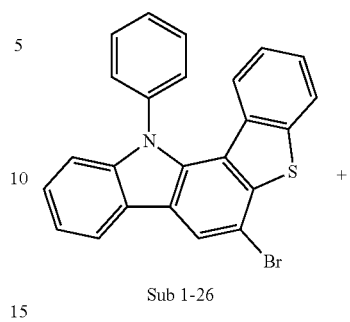

Sub 1-26

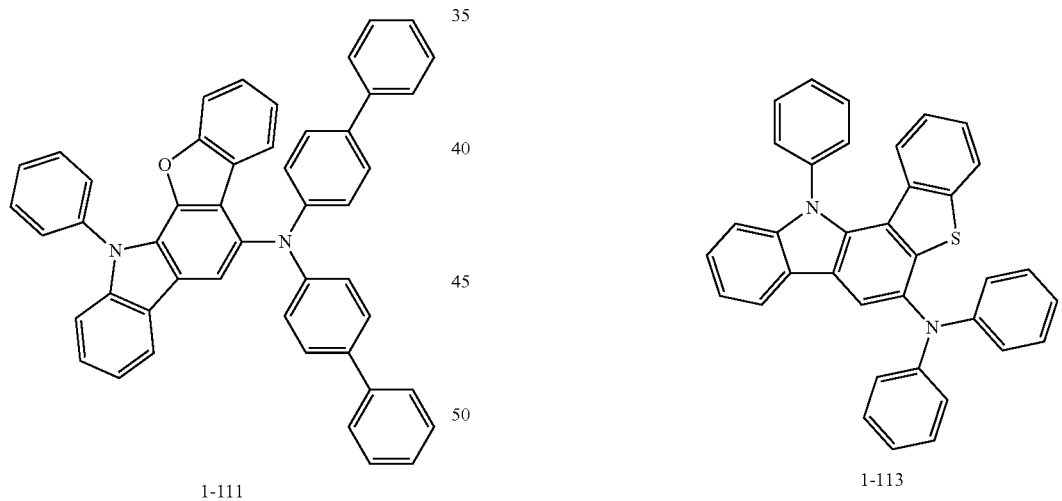

Sub 2-1

1-113

Sub 1-26 (4.3 g, 10 mmol), Sub 2-1 (1.7 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 3.0 g of the product 1-113 (Yield: 59%).

Synthesis of Compound 1-126

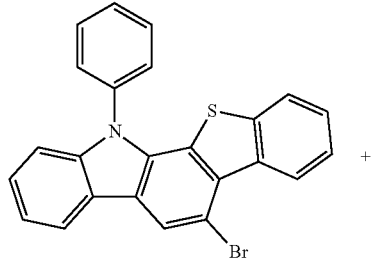

Sub 1-28

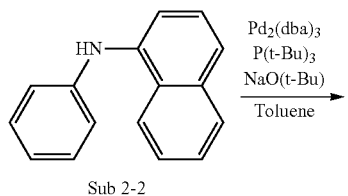

Sub 2-2

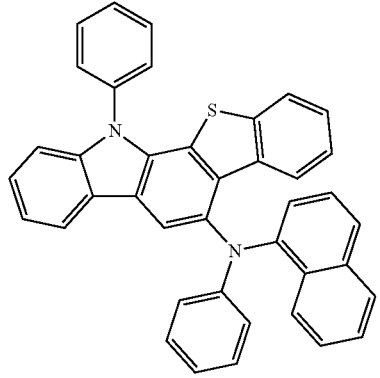

1-126

Sub 1-28 (4.3 g, 10 mmol), Sub 2-2 2.2 g, 10 mmol), Pd$_2$(dba)$_3$ (3 g, 0.4 mmol), P(t-Bu)$_3$ (1.8 g, 0.8 mmol), NaO(t-Bu) (24.6 g, 30 mmol), and Toluene (50 mL) were added into a round bottom flask, then, heated and refluxed at 110° C. for 3 hours. When the reaction was completed, the reaction product was diluted with distilled water at room temperature, then, extracted with Methylene chloride and water. The organic layer was dried with MgSO$_4$ and concentrated. The concentrate was dissolved in Toluene, then, filtered through silica gel column and concentrated. The final concentrate recrystallized with Toluene and Acetone to obtain 3.5 g of the product 1-126 (Yield: 62%).

TABLE 3

| compound | FD-MS | compound | FD-MS |
|---|---|---|---|
| 1-1 | m/z = 744.26(C$_{54}$H$_{36}$N$_2$S = 744.94) | 1-2 | m/z = 784.29(C$_{57}$H$_{40}$N$_2$S = 785.01) |
| 1-3 | m/z = 908.32(C$_{67}$H$_{44}$N$_2$S = 909.14) | 1-4 | m/z = 906.31(C$_{67}$H$_{42}$N$_2$S = 907.13) |
| 1-5 | m/z = 774.22(C$_{54}$H$_{34}$N$_2$S$_2$ = 774.99) | 1-6 | m/z = 820.29(C$_{60}$H$_{20}$N$_2$S = 821.04) |
| 1-7 | m/z = 860.32(C$_{63}$H$_{44}$N$_2$S = 861.10) | 1-8 | m/z = 984.35(C$_{73}$H$_{48}$N$_2$S = 985.24) |
| 1-9 | m/z = 982.34(C$_{73}$H$_{46}$N$_2$S = 983.22) | 1-10 | m/z = 850.25(C$_{60}$H$_{38}$N$_2$S$_2$ = 851.09) |
| 1-11 | m/z = 820.29(C$_{60}$H$_{20}$N$_2$S = 821.04) | 1-12 | m/z = 860.32(C$_{63}$H$_{44}$N$_2$S = 861.10) |
| 1-13 | m/z = 984.35(C$_{73}$H$_{48}$N$_2$S = 985.24) | 1-14 | m/z = 982.34(C$_{73}$H$_{46}$N$_2$S = 983.22) |
| 1-15 | m/z = 850.25(C$_{60}$H$_{38}$N$_2$S$_2$ = 851.09) | 1-16 | m/z = 794.28(C$_{58}$H$_{38}$N$_2$S = 795.00) |
| 1-17 | m/z = 834.31(C$_{61}$H$_{42}$N$_2$S = 835.06) | 1-18 | m/z = 958.34(C$_{71}$H$_{46}$N$_2$S = 959.20) |
| 1-19 | m/z = 956.32(C$_{71}$H$_{44}$N$_2$S = 957.29) | 1-20 | m/z = 824.23(C$_{58}$H$_{36}$N$_2$S$_2$ = 825.05) |
| 1-21 | m/z = 794.28(C$_{58}$H$_{38}$N$_2$S = 795.00) | 1-22 | m/z = 834.31(C$_{61}$H$_{42}$N$_2$S = 835.06) |
| 1-23 | m/z = 958.34(C$_{71}$H$_{46}$N$_2$S = 959.20) | 1-24 | m/z = 956.32(C$_{71}$H$_{44}$N$_2$S = 957.29) |
| 1-25 | m/z = 824.23(C$_{58}$H$_{36}$N$_2$S$_2$ = 825.05) | 1-26 | m/z = 850.25(C$_{60}$H$_{38}$N$_2$S$_2$ = 851.09) |
| 1-27 | m/z = 890.28(C$_{63}$H$_{42}$N$_2$S$_2$ = 891.15) | 1-28 | m/z = 1014.31(C$_{73}$H$_{46}$N$_2$S$_2$ = 1015.29) |
| 1-29 | m/z = 1012.29(C$_{73}$H$_{44}$N$_2$S$_2$ = 1013.27) | 1-30 | m/z = 880.20(C$_{60}$H$_{36}$N$_2$S$_3$ = 881.14) |
| 1-31 | m/z = 834.27(C$_{68}$H$_{38}$N$_2$OS = 835.02) | 1-32 | m/z = 874.30(C$_{63}$H$_{42}$N$_2$OS = 875.09) |
| 1-33 | m/z = 998.33(C$_{73}$H$_{46}$N$_2$OS = 999.22) | 1-34 | m/z = 996.32(C$_{73}$H$_{44}$N$_2$OS = 997.21) |
| 1-35 | m/z = 864.23(C$_{60}$H$_{36}$N$_2$OS$_2$ = 865.07) | 1-36 | m/z = 728.28(C$_{54}$H$_{36}$N$_2$O = 728.88) |
| 1-37 | m/z = 768.31(C$_{57}$H$_{40}$N$_2$O = 768.94) | 1-38 | m/z = 892.35(C$_{67}$H$_{44}$N$_2$O = 893.08) |
| 1-39 | m/z = 890.33(C$_{67}$H$_{42}$N$_2$O = 891.06) | 1-40 | m/z = 758.24(C$_{54}$H$_{34}$N$_2$OS = 758.93) |
| 1-41 | m/z = 804.31(C$_{60}$H$_{40}$N$_2$O = 804.97) | 1-42 | m/z = 844.35(C$_{63}$H$_{44}$N$_2$O = 845.04) |
| 1-43 | m/z = 968.38(C$_{73}$H$_{48}$N$_2$O = 969.18) | 1-44 | m/z = 966.36(C$_{73}$H$_{46}$N$_2$O = 967.16) |
| 1-45 | m/z = 834.27(C$_{60}$H$_{38}$N$_2$OS = 835.02) | 1-46 | m/z = 804.31(C$_{60}$H$_{40}$N$_2$O = 804.97) |
| 1-47 | m/z = 844.35(C$_{63}$H$_{44}$N$_2$O = 845.04) | 1-48 | m/z = 968.38(C$_{73}$H$_{48}$N$_2$O = 969.18) |
| 1-49 | m/z = 966.36(C$_{73}$H$_{46}$N$_2$O = 967.16) | 1-50 | m/z = 834.27(C$_{60}$H$_{38}$N$_2$OS = 835.02) |
| 1-51 | m/z = 778.30(C$_{58}$H$_{38}$N$_2$O = 778.94) | 1-52 | m/z = 818.33(C$_{61}$H$_{42}$N$_2$O = 819.00) |
| 1-53 | m/z = 942.36(C$_{71}$H$_{46}$N$_2$O = 943.14) | 1-54 | m/z = 940.35(C$_{71}$H$_{44}$N$_2$O = 941.12) |
| 1-55 | m/z = 808.25(C$_{58}$H$_{36}$N$_2$OS = 808.98) | 1-56 | m/z = 778.30(C$_{58}$H$_{38}$N$_2$O = 778.94) |
| 1-57 | m/z = 818.33(C$_{61}$H$_{42}$N$_2$O = 819.00) | 1-58 | m/z = 942.36(C$_{71}$H$_{46}$N$_2$O = 943.14) |
| 1-59 | m/z = 940.35(C$_{71}$H$_{44}$N$_2$O = 941.12) | 1-60 | m/z = 808.25(C$_{58}$H$_{36}$N$_2$OS = 808.98) |
| 1-61 | m/z = 834.27(C$_{68}$H$_{38}$N$_2$OS = 835.02) | 1-62 | m/z = 874.30(C$_{63}$H$_{42}$N$_2$OS = 875.09) |
| 1-63 | m/z = 998.33(C$_{73}$H$_{46}$N$_2$OS = 999.22) | 1-64 | m/z = 996.32(C$_{73}$H$_{44}$N$_2$OS = 997.21) |
| 1-65 | m/z = 864.23(C$_{60}$H$_{36}$N$_2$OS$_2$ = 865.07) | 1-66 | m/z = 818.29(C$_{60}$H$_{38}$N$_2$O$_2$ = 818.96) |
| 1-67 | m/z = 858.32(C$_{63}$H$_{42}$N$_2$O$_2$ = 859.02) | 1-68 | m/z = 982.36(C$_{73}$H$_{46}$N$_2$O$_2$ = 983.16) |
| 1-69 | m/z = 980.34(C$_{73}$H$_{44}$N$_2$O$_2$ = 981.14) | 1-70 | m/z = 848.25(C$_{60}$H$_{36}$N$_2$O$_2$S = 849.01) |
| 1-71 | m/z = 744.26(C$_{54}$H$_{36}$N$_2$S = 744.94) | 1-72 | m/z = 784.29(C$_{57}$H$_{40}$N$_2$S = 785.01) |
| 1-73 | m/z = 908.32(C$_{67}$H$_{44}$N$_2$S = 909.14) | 1-74 | m/z = 906.31(C$_{67}$H$_{42}$N$_2$S = 907.13) |
| 1-75 | m/z = 820.29(C$_{60}$H$_{20}$N$_2$S = 821.04) | 1-76 | m/z = 860.32(C$_{63}$H$_{44}$N$_2$S = 861.10) |
| 1-77 | m/z = 984.35(C$_{73}$H$_{48}$N$_2$S = 985.24) | 1-78 | m/z = 982.34(C$_{73}$H$_{46}$N$_2$S = 983.22) |
| 1-79 | m/z = 820.29(C$_{60}$H$_{20}$N$_2$S = 821.04) | 1-80 | m/z = 86032(C$_{63}$H$_{44}$N$_2$S = 861.10) |
| 1-81 | m/z = 984.35(C$_{73}$H$_{48}$N$_2$S = 985.24) | 1-82 | m/z = 982.34(C$_{73}$H$_{46}$N$_2$S = 983.22) |

TABLE 3-continued

| compound | FD-MS | compound | FD-MS |
|---|---|---|---|
| 1-83 | m/z = 794.28($C_{58}H_{38}N_2S$ = 795.00) | 1-84 | m/z = 834.31($C_{61}H_{42}N_2S$ = 835.06) |
| 1-85 | m/z = 958.34($C_{71}H_{46}N_2S$ = 959.20) | 1-86 | m/z = 956.32($C_{71}H_{44}N_2S$ = 957.29) |
| 1-87 | m/z = 794.28($C_{58}H_{38}N_2S$ = 795.00) | 1-88 | m/z = 834.31($C_{61}H_{42}N_2S$ = 835.06) |
| 1-89 | m/z = 958.34($C_{71}H_{46}N_2S$ = 959.20) | 1-90 | m/z = 956.32($C_{71}H_{44}N_2S$ = 957.29) |
| 1-91 | m/z = 850.25($C_{60}H_{38}N_2S_2$ = 851.09) | 1-92 | m/z = 890.28($C_{63}H_{42}N_2S_2$ = 891.15) |
| 1-93 | m/z = 1014.31($C_{73}H_{46}N_2S_2$ = 1015.29) | 1-94 | m/z = 1012.29($C_{73}H_{44}N_2S_2$ = 1013.27) |
| 1-95 | m/z = 834.27($C_{68}H_{38}N_2OS$ = 835.02) | 1-96 | m/z = 874.30($C_{63}H_{42}N_2OS$ = 875.09) |
| 1-97 | m/z = 998.33($C_{73}H_{46}N_2OS$ = 999.22) | 1-98 | m/z = 996.32($C_{73}H_{44}N_2OS$ = 997.21) |
| 1-99 | m/z = 820.29($C_{60}H_{40}N_2S$ = 821.04) | 1-100 | m/z = 749.29($C_{54}H_{31}D_5N_2S$ = 749.97) |
| 1-101 | m/z = 825.32($C_{60}H_{35}D_5N_2S$ = 826.07) | 1-102 | m/z = 820.29($C_{60}H_{40}N_2S$ = 821.04) |
| 1-103 | m/z = 749.29($C_{54}H_{31}D_5N_2S$ = 749.97) | 1-104 | m/z = 825.32($C_{60}H_{35}D_5N_2S$ = 826.07) |
| 1-105 | m/z = 749.29($C_{54}H_{31}D_5N_2S$ = 749.97) | 1-106 | m/z = 956.32($C_{71}H_{44}N_2S$ = 957.29) |
| 1-107 | m/z = 749.29($C_{54}H_{31}D_5N_2S$ = 749.97) | 1-108 | m/z = 890.28($C_{63}H_{42}N_2S_2$ = 891.15) |
| 1-109 | m/z = 749.29($C_{54}H_{31}D_5N_2S$ = 749.97) | 1-110 | m/z = 1012.29($C_{73}H_{44}N_2S_2$ = 1013.27) |
| 1-111 | m/z = 749.29($C_{54}H_{31}D_5N_2S$ = 749.97) | 1-112 | m/z = 87430($C_{63}H_{42}N_2OS$ = 875.09) |
| 1-113 | m/z = 516.17($C_{36}H_{24}N_2S$ = 516.65) | 1-114 | m/z = 647.24($C_{46}H_{25}D_5N_2S$ = 647.84) |
| 1-115 | m/z = 794.28($C_{58}H_{38}N_2S$ = 796.00) | 1-116 | m/z = 501.18($C_{35}H_{23}N_3O$ = 501.58) |
| 1-117 | m/z = 516.17($C_{36}H_{24}N_2S$ = 516.65) | 1-118 | m/z = 566.18($C_{40}H_{26}N_2S$ = 566.71) |
| 1-119 | m/z = 692.23($C_{50}H_{32}N_2S$ = 692.87) | 1-120 | m/z = 578.21($C_{40}H_{26}N_4O$ = 578.66) |
| 1-121 | m/z = 566.18($C_{40}H_{26}N_2S$ = 566.71) | 1-122 | m/z = 566.18($C_{40}H_{26}N_2S$ = 566.71) |
| 1-123 | m/z = 616.20($C_{44}H_{28}N_2S$ = 616.77) | 1-124 | m/z = 576.22($C_{42}H_{28}N_2O$ = 576.68) |
| 1-125 | m/z = 519.15($C_{33}H_{21}N_5S$ = 519.62) | 1-126 | m/z = 566.18($C_{40}H_{26}N_2S$ = 566.71) |
| 1-127 | m/z = 632.23($C_{45}H_{32}N_2S$ = 632.81) | 1-128 | m/z = 600.22($C_{44}H_{28}N_2O$ = 600.71) |

Fabrication and Evaluation of Organic Electronic Element

[Example 1] Green OLED (A Hole Transport Layer)

Organic light emitting diodes (OLEDs) were fabricated according to a conventional method by using a compound of the present invention as a hole transport layer material. First, an ITO layer (anode) was formed on a glass substrate, and then 4,4',4"-tris[2-naphthyl(phenyl)amino]triphenylamine (hereinafter, "2-TNATA") was vacuum-deposited on the ITO layer to form a hole injection layer with a thickness of 60 nm. Subsequently, compound 1-1 of the present invention was vacuum-deposited with a thickness of 60 nm on the hole injection layer to form a hole transport layer. Subsequently, a light emitting layer with a thickness of 30 nm was formed on the hole transport layer by using 4,4'-N,N'-dicarbazole-biphenyl (hereinafter, "CBP") as a host material and tris(2-phenylpyridine)-iridium (hereinafter, "Ir(ppy)₃") as a dopant material in a weight ratio of 90:10. Next, ((1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and tris(8-quinolinolato)aluminum (hereinafter, "Alq₃") was formed with a thickness of 40 nm to form an electron transport layer. Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 128] Green OLED (A Hole Transport Layer)

The OLEDs were fabricated in the same manner as described in Example 1 except that the compounds 1-2 to 1-128 of the present invention described in Table 5 instead of the compound 1-1 of the present invention were used as the hole transport layer material.

[Comparative Example 1] to [Comparative Example 5] Green OLED (A Hole Transport Layer)

In case of Comparative Examples 1 to 5, the OLEDs were fabricated in the same manner as described in Example 1 except that the following Comparative Compounds A to E described instead of the compound 1-1 of the present invention were each used as the hole transport layer material.

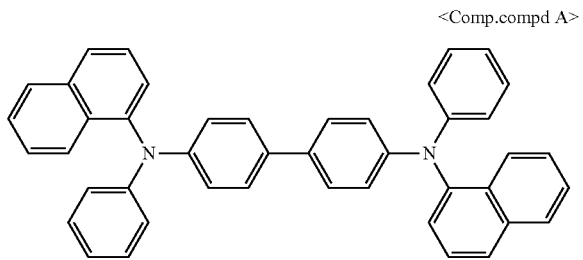

<Comp.compd A>

<Comp.compd B>

<Comp.compd C>

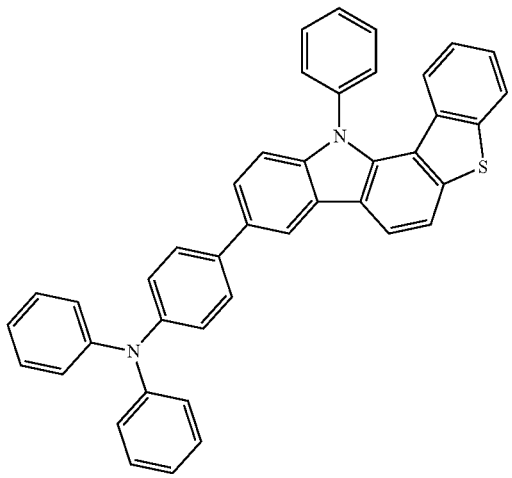

<Comp.compd D>

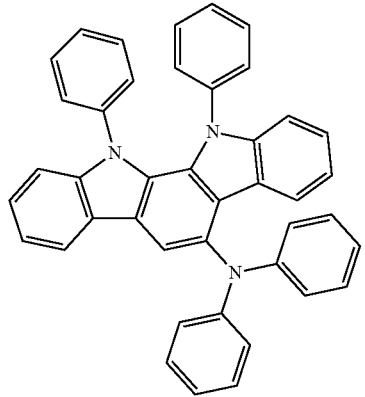

<Comp.compd E>

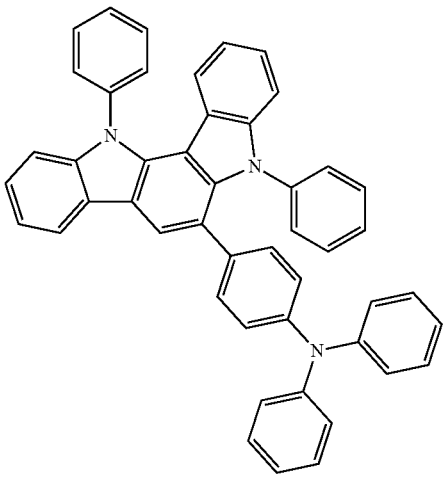

Electroluminescence (EL) characteristics were measured with a PR-650 (Photoresearch) by applying a forward bias DC voltage to the OLEDs prepared in Examples of the present invention and Comparative Examples. And, the T95 life time was measured using a life time measuring apparatus manufactured by Macscience Inc. at reference brightness of 5000 cd/m². The measurement results are shown in Table 5 below.

TABLE 5

|  | compound | Voltage (V) | Current Density (mA/cm²) | Brightness (cd/m²) | Efficiency (cd/A) | Lifetime T(95) | CIE (x, y) |
|---|---|---|---|---|---|---|---|
| comp. Ex(1) | comp. Com A | 6.6 | 20.8 | 5000.0 | 24.0 | 60.2 | (0.31, 0.60) |
| comp. Ex(2) | comp. Com B | 6.1 | 14.0 | 5000.0 | 35.7 | 97.4 | (0.31, 0.61) |
| comp. Ex(3) | comp. Com C | 6.0 | 12.9 | 5000.0 | 38.9 | 98.1 | (0.31, 0.60) |
| comp. Ex(4) | comp. Com D | 6.2 | 16.0 | 5000.0 | 31.2 | 76.4 | (0.33, 0.61) |
| comp. Ex(5) | comp. Com E | 6.2 | 15.5 | 5000.0 | 32.3 | 76.9 | (0.33, 0.61) |
| Ex. (1) | Com. (1-1) | 5.6 | 9.4 | 5000.0 | 53.0 | 118.8 | (0.30, 0.60) |
| Ex. (2) | Com. (1-2) | 5.7 | 9.4 | 5000.0 | 53.0 | 116.3 | (0.31, 0.61) |
| Ex. (3) | Com. (1-3) | 5.6 | 9.7 | 5000.0 | 51.5 | 117.4 | (0.31, 0.60) |
| Ex. (4) | Com. (1-4) | 5.5 | 9.6 | 5000.0 | 52.0 | 112.9 | (0.33, 0.61) |
| Ex. (5) | Com. (1-5) | 5.8 | 9.8 | 5000.0 | 51.1 | 111.3 | (0.32, 0.61) |
| Ex. (6) | Com. (1-6) | 5.5 | 9.6 | 5000.0 | 51.8 | 115.3 | (0.33, 0.60) |
| Ex. (7) | Com. (1-7) | 5.6 | 9.4 | 5000.0 | 53.2 | 116.5 | (0.32, 0.61) |
| Ex. (8) | Com. (1-8) | 5.7 | 9.4 | 5000.0 | 53.3 | 114.0 | (0.31, 0.60) |
| Ex. (9) | Com. (1-9) | 5.7 | 9.6 | 5000.0 | 52.1 | 115.1 | (0.31, 0.61) |
| Ex. (10) | Com. (1-10) | 5.6 | 9.4 | 5000.0 | 53.4 | 115.2 | (0.31, 0.60) |
| Ex. (11) | Com. (1-11) | 5.7 | 9.2 | 5000.0 | 54.5 | 115.0 | (0.33, 0.61) |
| Ex. (12) | Com. (1-12) | 5.6 | 9.2 | 5000.0 | 54.6 | 112.8 | (0.30, 0.60) |
| Ex. (13) | Com. (1-13) | 5.6 | 9.3 | 5000.0 | 53.8 | 117.8 | (0.31, 0.61) |
| Ex. (14) | Com. (1-14) | 5.6 | 9.2 | 5000.0 | 54.4 | 118.4 | (0.31, 0.60) |
| Ex. (15) | Com. (1-15) | 5.6 | 9.2 | 5000.0 | 54.5 | 112.7 | (0.33, 0.61) |
| Ex. (16) | Com. (1-16) | 5.7 | 9.7 | 5000.0 | 51.7 | 112.0 | (0.32, 0.61) |
| Ex. (17) | Com. (1-17) | 5.7 | 9.2 | 5000.0 | 54.1 | 116.4 | (0.33, 0.60) |
| Ex. (18) | Com. (1-18) | 5.7 | 9.7 | 5000.0 | 51.8 | 118.2 | (0.32, 0.61) |
| Ex. (19) | Com. (1-19) | 5.6 | 9.8 | 5000.0 | 50.8 | 111.4 | (0.31, 0.60) |
| Ex. (20) | Com. (1-20) | 5.7 | 9.4 | 5000.0 | 53.0 | 111.3 | (0.31, 0.61) |
| Ex. (21) | Com. (1-21) | 5.7 | 9.6 | 5000.0 | 51.9 | 115.5 | (0.31, 0.60) |
| Ex. (22) | Com. (1-22) | 5.7 | 9.7 | 5000.0 | 51.7 | 118.3 | (0.33, 0.61) |
| Ex. (23) | Com. (1-23) | 5.6 | 9.3 | 5000.0 | 53.6 | 117.7 | (0.30, 0.60) |
| Ex. (24) | Com. (1-24) | 5.7 | 9.9 | 5000.0 | 50.4 | 115.2 | (0.31, 0.61) |

TABLE 5-continued

|  | compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Ex. (25) | Com. (1-25) | 5.7 | 9.5 | 5000.0 | 52.6 | 115.9 | (0.31, 0.60) |
| Ex. (26) | Com. (1-26) | 5.8 | 9.7 | 5000.0 | 51.5 | 112.0 | (0.33, 0.61) |
| Ex. (27) | Com. (1-27) | 5.6 | 9.6 | 5000.0 | 52.2 | 113.5 | (0.32, 0.61) |
| Ex. (28) | Com. (1-28) | 5.5 | 9.3 | 5000.0 | 53.8 | 112.9 | (0.33, 0.60) |
| Ex. (29) | Com. (1-29) | 5.7 | 9.3 | 5000.0 | 53.9 | 111.2 | (0.31, 0.61) |
| Ex. (30) | Com. (1-30) | 5.6 | 9.6 | 5000.0 | 52.2 | 111.1 | (0.31, 0.60) |
| Ex. (31) | Com. (1-31) | 5.6 | 9.2 | 5000.0 | 54.6 | 119.5 | (0.33, 0.61) |
| Ex. (32) | Com. (1-32) | 5.6 | 9.8 | 5000.0 | 51.3 | 115.3 | (0.32, 0.61) |
| Ex. (33) | Com. (1-33) | 5.8 | 9.9 | 5000.0 | 50.5 | 118.1 | (0.33, 0.60) |
| Ex. (34) | Com. (1-34) | 5.5 | 9.5 | 5000.0 | 52.9 | 118.2 | (0.32, 0.61) |
| Ex. (35) | Com. (1-35) | 5.6 | 9.9 | 5000.0 | 50.4 | 113.1 | (0.31, 0.60) |
| Ex. (36) | Com. (1-36) | 5.5 | 10.2 | 5000.0 | 49.2 | 113.3 | (0.31, 0.61) |
| Ex. (37) | Com. (1-37) | 5.6 | 10.3 | 5000.0 | 48.7 | 110.6 | (0.31, 0.60) |
| Ex. (38) | Com. (1-38) | 5.8 | 10.5 | 5000.0 | 47.6 | 115.8 | (0.33, 0.61) |
| Ex. (39) | Com. (1-39) | 5.7 | 10.1 | 5000.0 | 49.4 | 113.9 | (0.30, 0.60) |
| Ex. (40) | Com. (1-40) | 5.8 | 10.2 | 5000.0 | 48.9 | 114.5 | (0.31, 0.61) |
| Ex. (41) | Com. (1-41) | 5.5 | 10.6 | 5000.0 | 47.1 | 113.6 | (0.31, 0.60) |
| Ex. (42) | Com. (1-42) | 5.5 | 10.5 | 5000.0 | 47.5 | 118.8 | (0.33, 0.61) |
| Ex. (43) | Com. (1-43) | 5.7 | 10.6 | 5000.0 | 47.3 | 110.8 | (0.32, 0.61) |
| Ex. (44) | Com. (1-44) | 5.6 | 10.5 | 5000.0 | 47.8 | 119.8 | (0.33, 0.60) |
| Ex. (45) | Com. (1-45) | 5.5 | 10.2 | 5000.0 | 49.2 | 118.0 | (0.32, 0.61) |
| Ex. (46) | Com. (1-46) | 5.7 | 10.2 | 5000.0 | 48.8 | 118.8 | (0.31, 0.60) |
| Ex. (47) | Com. (1-47) | 5.5 | 10.3 | 5000.0 | 48.3 | 114.4 | (0.31, 0.61) |
| Ex. (48) | Com. (1-48) | 5.7 | 10.8 | 5000.0 | 46.3 | 117.3 | (0.31, 0.60) |
| Ex. (49) | Com. (1-49) | 5.8 | 10.1 | 5000.0 | 49.6 | 111.2 | (0.33, 0.61) |
| Ex. (50) | Com. (1-50) | 5.5 | 10.1 | 5000.0 | 49.5 | 118.0 | (0.30, 0.60) |
| Ex. (51) | Com. (1-51) | 5.6 | 10.1 | 5000.0 | 49.6 | 113.0 | (0.31, 0.61) |
| Ex. (52) | Com. (1-52) | 5.6 | 10.7 | 5000.0 | 46.5 | 112.5 | (0.31, 0.60) |
| Ex. (53) | Com. (1-53) | 5.7 | 10.2 | 5000.0 | 49.2 | 112.5 | (0.33, 0.61) |
| Ex. (54) | Com. (1-54) | 5.8 | 10.2 | 5000.0 | 49.2 | 114.9 | (0.32, 0.61) |
| Ex. (55) | Com. (1-55) | 5.7 | 10.2 | 5000.0 | 49.0 | 115.9 | (0.33, 0.61) |
| Ex. (56) | Com. (1-56) | 5.6 | 10.7 | 5000.0 | 46.9 | 115.6 | (0.32, 0.61) |
| Ex. (57) | Com. (1-57) | 5.7 | 10.9 | 5000.0 | 45.7 | 111.9 | (0.31, 0.60) |
| Ex. (58) | Com. (1-58) | 5.8 | 10.3 | 5000.0 | 48.6 | 115.2 | (0.33, 0.61) |
| Ex. (59) | Com. (1-59) | 5.6 | 10.7 | 5000.0 | 46.8 | 115.5 | (0.30, 0.60) |
| Ex. (60) | Com. (1-60) | 5.5 | 10.0 | 5000.0 | 49.9 | 113.0 | (0.31, 0.61) |
| Ex. (61) | Com. (1-61) | 5.6 | 10.7 | 5000.0 | 46.8 | 110.5 | (0.31, 0.60) |
| Ex. (62) | Com. (1-62) | 5.7 | 11.0 | 5000.0 | 45.4 | 119.0 | (0.33, 0.61) |
| Ex. (63) | Com. (1-63) | 5.5 | 10.6 | 5000.0 | 47.3 | 110.7 | (0.32, 0.61) |
| Ex. (64) | Com. (1-64) | 5.6 | 11.1 | 5000.0 | 45.1 | 111.8 | (0.33, 0.60) |
| Ex. (65) | Com. (1-65) | 5.6 | 10.9 | 5000.0 | 45.7 | 112.6 | (0.32, 0.61) |
| Ex. (66) | Com. (1-66) | 5.7 | 10.8 | 5000.0 | 46.4 | 113.5 | (0.31, 0.60) |
| Ex. (67) | Com. (1-67) | 5.6 | 10.5 | 5000.0 | 47.4 | 113.5 | (0.31, 0.61) |
| Ex. (68) | Com. (1-68) | 5.5 | 10.3 | 5000.0 | 48.6 | 115.4 | (0.31, 0.60) |
| Ex. (69) | Com. (1-69) | 5.7 | 10.5 | 5000.0 | 47.6 | 112.6 | (0.33, 0.61) |
| Ex. (70) | Com. (1-70) | 5.7 | 10.6 | 5000.0 | 47.3 | 111.3 | (0.30, 0.60) |
| Ex. (71) | Com. (1-71) | 5.5 | 9.7 | 5000.0 | 51.6 | 118.7 | (0.31, 0.61) |
| Ex. (72) | Com. (1-72) | 5.6 | 9.7 | 5000.0 | 51.5 | 117.1 | (0.31, 0.60) |
| Ex. (73) | Com. (1-73) | 5.7 | 9.9 | 5000.0 | 50.4 | 110.7 | (0.33, 0.61) |
| Ex. (74) | Com. (1-74) | 5.6 | 10.0 | 5000.0 | 50.2 | 118.3 | (0.32, 0.61) |
| Ex. (75) | Com. (1-75) | 5.6 | 9.7 | 5000.0 | 51.6 | 119.8 | (0.33, 0.61) |
| Ex. (76) | Com. (1-76) | 5.6 | 9.8 | 5000.0 | 50.8 | 119.1 | (0.30, 0.60) |
| Ex. (77) | Com. (1-77) | 5.7 | 9.8 | 5000.0 | 50.9 | 116.3 | (0.31, 0.61) |
| Ex. (78) | Com. (1-78) | 5.7 | 10.0 | 5000.0 | 50.0 | 117.2 | (0.31, 0.60) |
| Ex. (79) | Com. (1-79) | 5.5 | 9.3 | 5000.0 | 53.6 | 119.8 | (0.33, 0.61) |
| Ex. (80) | Com. (1-80) | 5.6 | 9.1 | 5000.0 | 54.7 | 116.9 | (0.32, 0.61) |
| Ex. (81) | Com. (1-81) | 5.6 | 9.1 | 5000.0 | 54.7 | 111.5 | (0.33, 0.60) |
| Ex. (82) | Com. (1-82) | 5.7 | 9.6 | 5000.0 | 51.8 | 110.4 | (0.32, 0.61) |
| Ex. (83) | Com. (1-83) | 5.6 | 9.3 | 5000.0 | 53.5 | 110.4 | (0.31, 0.60) |
| Ex. (84) | Com. (1-84) | 5.7 | 10.0 | 5000.0 | 50.1 | 115.1 | (0.31, 0.61) |
| Ex. (85) | Com. (1-85) | 5.6 | 9.5 | 5000.0 | 52.8 | 115.2 | (0.31, 0.60) |
| Ex. (86) | Com. (1-86) | 5.5 | 9.7 | 5000.0 | 51.5 | 110.8 | (0.33, 0.61) |
| Ex. (87) | Com. (1-87) | 5.6 | 9.2 | 5000.0 | 54.6 | 115.7 | (0.30, 0.60) |
| Ex. (88) | Com. (1-88) | 5.6 | 9.7 | 5000.0 | 51.7 | 115.1 | (0.31, 0.61) |
| Ex. (89) | Com. (1-89) | 5.6 | 9.7 | 5000.0 | 51.3 | 110.2 | (0.31, 0.60) |
| Ex. (90) | Com. (1-90) | 5.8 | 9.2 | 5000.0 | 54.2 | 119.2 | (0.33, 0.61) |
| Ex. (91) | Com. (1-91) | 5.6 | 9.2 | 5000.0 | 54.5 | 118.2 | (0.32, 0.61) |
| Ex. (92) | Com. (1-92) | 5.7 | 10.0 | 5000.0 | 50.2 | 111.9 | (0.33, 0.60) |
| Ex. (93) | Com. (1-93) | 5.7 | 9.2 | 5000.0 | 54.6 | 117.3 | (0.31, 0.61) |
| Ex. (94) | Com. (1-94) | 5.5 | 9.4 | 5000.0 | 53.1 | 114.0 | (0.31, 0.60) |
| Ex. (95) | Com. (1-95) | 5.7 | 9.9 | 5000.0 | 50.3 | 120.0 | (0.33, 0.61) |
| Ex. (96) | Com. (1-96) | 5.5 | 9.1 | 5000.0 | 54.6 | 110.8 | (0.32, 0.61) |
| Ex. (97) | Com. (1-97) | 5.5 | 9.5 | 5000.0 | 52.6 | 114.4 | (0.33, 0.61) |
| Ex. (98) | Com. (1-98) | 5.7 | 9.9 | 5000.0 | 50.3 | 117.3 | (0.32, 0.61) |
| Ex. (99) | Com. (1-99) | 5.6 | 9.2 | 5000.0 | 54.5 | 111.0 | (0.31, 0.60) |
| Ex. (100) | Com. (1-100) | 5.6 | 9.5 | 5000.0 | 52.8 | 118.9 | (0.31, 0.61) |
| Ex. (101) | Com. (1-101) | 5.5 | 9.7 | 5000.0 | 51.7 | 114.4 | (0.31, 0.60) |

TABLE 5-continued

| | compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Ex. (102) | Com. (1-102) | 5.6 | 9.2 | 5000.0 | 54.2 | 118.0 | (0.33, 0.61) |
| Ex. (103) | Com. (1-103) | 5.6 | 9.6 | 5000.0 | 51.9 | 110.6 | (0.30, 0.60) |
| Ex. (104) | Com. (1-104) | 5.8 | 9.7 | 5000.0 | 51.5 | 112.1 | (0.31, 0.61) |
| Ex. (105) | Com. (1-105) | 5.6 | 9.3 | 5000.0 | 54.0 | 110.3 | (0.31, 0.60) |
| Ex. (106) | Com. (1-106) | 5.6 | 9.3 | 5000.0 | 53.7 | 119.4 | (0.33, 0.61) |
| Ex. (107) | Com. (1-107) | 5.8 | 9.1 | 5000.0 | 54.8 | 110.2 | (0.33, 0.61) |
| Ex. (108) | Com. (1-108) | 5.7 | 9.2 | 5000.0 | 54.4 | 119.9 | (0.30, 0.60) |
| Ex. (109) | Com. (1-109) | 5.6 | 10.2 | 5000.0 | 49.0 | 117.1 | (0.31, 0.61) |
| Ex. (110) | Com. (1-110) | 5.6 | 10.9 | 5000.0 | 45.9 | 119.4 | (0.31, 0.60) |
| Ex. (111) | Com. (1-111) | 5.7 | 10.0 | 5000.0 | 49.8 | 114.8 | (0.33, 0.61) |
| Ex. (112) | Com. (1-112) | 5.8 | 11.1 | 5000.0 | 45.0 | 118.6 | (0.32, 0.61) |
| Ex. (113) | Com. (1-113) | 5.5 | 9.5 | 5000.0 | 52.5 | 110.1 | (0.30, 0.60) |
| Ex. (114) | Com. (1-114) | 5.7 | 9.8 | 5000.0 | 51.1 | 115.6 | (0.31, 0.61) |
| Ex. (115) | Com. (1-115) | 5.7 | 9.5 | 5000.0 | 52.4 | 115.2 | (0.31, 0.60) |
| Ex. (116) | Com. (1-116) | 5.9 | 10.4 | 5000.0 | 48.0 | 114.0 | (0.33, 0.61) |
| Ex. (117) | Com. (1-117) | 5.6 | 9.5 | 5000.0 | 52.8 | 111.4 | (0.32, 0.61) |
| Ex. (118) | Com. (1-118) | 5.7 | 9.3 | 5000.0 | 53.7 | 111.8 | (0.33, 0.60) |
| Ex. (119) | Com. (1-119) | 5.6 | 9.2 | 5000.0 | 54.4 | 114.2 | (0.32, 0.61) |
| Ex. (120) | Com. (1-120) | 5.9 | 10.7 | 5000.0 | 46.7 | 115.0 | (0.31, 0.60) |
| Ex. (121) | Com. (1-121) | 5.8 | 9.2 | 5000.0 | 54.5 | 113.2 | (0.31, 0.61) |
| Ex. (122) | Com. (1-122) | 5.6 | 10.0 | 5000.0 | 50.1 | 110.6 | (0.31, 0.60) |
| Ex. (123) | Com. (1-123) | 5.5 | 9.3 | 5000.0 | 53.9 | 110.5 | (0.33, 0.61) |
| Ex. (124) | Com. (1-124) | 5.8 | 10.0 | 5000.0 | 49.8 | 112.5 | (0.30, 0.60) |
| Ex. (125) | Com. (1-125) | 5.6 | 9.5 | 5000.0 | 52.5 | 118.6 | (0.31, 0.61) |
| Ex. (126) | Com. (1-126) | 5.6 | 9.8 | 5000.0 | 51.1 | 116.6 | (0.31, 0.60) |
| Ex. (127) | Com. (1-127) | 5.7 | 9.5 | 5000.0 | 52.4 | 113.9 | (0.33, 0.61) |
| Ex. (128) | Com. (1-128) | 5.6 | 10.6 | 5000.0 | 47.0 | 117.3 | (0.30, 0.60) |

As can be seen from the results of Table 5, it is confirmed that the driving voltage is lowered and the luminous efficiency and the lifetime are remarkably improved when material for the organic electroluminescence device of the present invention is used as material of a hole transport layer. That is, the driving voltage, luminous efficiency and lifetime are remarkably improved in case of Comparative Examples 2 to 5 compared to Comparative Example 1, wherein NPB in Comparative Example 1, and Comparative Compounds B to E in Comparative Examples 2 to 5 are each used as material of a hole transport layer.

In addition, the compound of the present invention is different from Comparative compounds 2 and 3 in the position of the amine and Comparative compounds 4 and 5 in the type of the hetero atom. In case of Examples 1 to 128 using such compound of the present invention as a hole transport layer material, it was found that the efficiency and lifetime were improved while lowering the driving voltage of the device.

Consider the difference between the compound of the present invention and the Comparative compounds used in Comparative Example 2 and 3, wherein the Comparative compounds are the same in the kind of the hetero atom but different from the substitution position of the amine group. The HOMO level is dependent on the amine group, as the electron cloud distribution diagrams shown in FIGS. 2 and 3. The electron cloud distribution of Comparative Compounds B and C substituted with an amine group at the terminal is remarkably different from that of Compound A and B of the present invention substituted with an amine group at phenyl, wherein the phenyl is present in the center of the heterocyclic rings core having five rings. That is, comparing the Comparative compound B with the compound A (corresponding to compound 1-117) of the present invention, it is confirmed that the electron cloud of the HOMO of the Comparative compound B is formed from the amine group to the portion where S is substituted, whereas the electron cloud of the HOMO of compound A of the present invention is formed from the amine group to the portion where N is substituted.

As such, the energy level and the chemical properties of the compound are changed because the electron cloud of the HOMO is formed in different regions. The hole transporting property of the compound of the present invention having an appropriate energy level becomes better than the comparative compound. Therefore, it is inferred that the driving voltage, efficiency and life span of the inventive device can be improved.

Comparing Comparative compounds D and E with the compounds A and B of the present invention, wherein Comparative compounds D and E are the same in the substitution position of the amine group but different from the kind of the hetero atom, it is confirmed that the electron cloud distribution of the HOMO is remarkably changed depending on the kind of hetero atom. This is because compound of the present invention has an appropriate energy level, thereby increasing the charge balance of holes and electrons in a light emitting layer and emitting well in a light emitting layer not in the interface of a hole transport layer. As a result, the driving voltage of device can be lowered and efficiency and life span can be maximized.

In conclusion, it can be seen that the physical properties of the compound and the result of the device properties can be remarkably changed depending on the substitution position of the amine group and the kind of the hetero atom.

[Example 129] Red OLED (an Emission-Auxiliary Layer)

Organic light emitting diodes (OLEDs) were fabricated according to a conventional method by using a compound of the present invention as an emission-auxiliary layer material. First, an ITO layer (anode) was formed on a glass substrate, and a film of 2-TNATA was vacuum-deposited on the ITO layer to form a hole injection layer with a thickness of 60 nm. Subsequently, N,N'-Bis(1-naphthalenyl)-N,N'-bisphenyl-(1,1'-biphenyl)-4,4'-diamine (hereinafter, "NPB") was vacuum-deposited with a thickness of 60 nm on the hole injection layer to form a hole transport layer. Subsequently, a film of the compound 1-1 of the present invention was vacuum-deposited on the hole transport layer to form a emission-auxiliary layer with a thickness of 20 nm. A light emitting layer with a thickness of 30 nm was deposited on the emission-auxiliary layer by using the CBP as a host material and bis-(1-phenylisoquinolyl)iridium(III)acetylacetonate (hereinafter, "(piq)$_2$Ir(acac)") as a dopant material in a weight ratio of 95:5.

Next, a film of BAlq was vacuum-deposited with a thickness of 10 nm on the light emitting layer to form a hole case of Comparative Examples 7 to 10, the OLEDs were fabricated in the same manner as described in Example 129 except that the Comparative compounds B to E above instead of the compound 1-1 of the present invention were used as an emission-auxiliary layer material.

Electroluminescence (EL) characteristics were measured with a PR-650 (Photoresearch) by applying a forward bias DC voltage to the OLEDs prepared in Examples of the present invention and Comparative Examples. And, the T95 life time was measured using a life time measuring apparatus manufactured by Macscience Inc. at reference brightness of 2500 cd/m$^2$. The measurement results are shown in Table 6 below.

TABLE 6

|  | compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(6) | — | 6.4 | 32.9 | 2500.0 | 7.6 | 84.9 | 0.66 | 0.34 |
| comp. Ex(7) | comp. Com B | 6.6 | 29.1 | 2500.0 | 8.6 | 104.0 | 0.66 | 0.32 |
| comp. Ex(8) | comp. Com C | 6.5 | 28.4 | 2500.0 | 8.8 | 114.4 | 0.67 | 0.34 |
| comp. Ex(9) | comp. Com D | 6.7 | 29.4 | 2500.0 | 8.5 | 108.1 | 0.66 | 0.33 |
| comp. Ex(10) | comp. Com E | 6.5 | 30.1 | 2500.0 | 8.3 | 103.3 | 0.66 | 0.33 |
| Ex. (129) | Com. (1-1) | 6.1 | 19.2 | 2500.0 | 13.0 | 138.7 | 0.66 | 0.34 |
| Ex. (130) | Com. (1-7) | 6.0 | 18.5 | 2500.0 | 13.5 | 134.5 | 0.67 | 0.34 |
| Ex. (131) | Com. (1-13) | 6.1 | 19.2 | 2500.0 | 13.0 | 132.2 | 0.66 | 0.33 |
| Ex. (132) | Com. (1-19) | 6.1 | 17.5 | 2500.0 | 14.3 | 139.5 | 0.66 | 0.32 |
| Ex. (133) | Com. (1-25) | 6.1 | 35.2 | 5000.0 | 14.2 | 137.1 | 0.67 | 0.34 |
| Ex. (134) | Com. (1-29) | 6.2 | 33.8 | 5000.0 | 14.8 | 135.9 | 0.65 | 0.33 |
| Ex. (135) | Com. (1-33) | 6.1 | 34.7 | 5000.0 | 14.4 | 138.4 | 0.66 | 0.34 |
| Ex. (136) | Com. (1-37) | 6.1 | 21.5 | 2500.0 | 11.6 | 138.5 | 0.67 | 0.33 |
| Ex. (137) | Com. (1-41) | 6.1 | 21.0 | 2500.0 | 11.9 | 132.6 | 0.67 | 0.34 |
| Ex. (138) | Com. (1-47) | 6.2 | 23.2 | 2500.0 | 10.8 | 133.4 | 0.67 | 0.33 |
| Ex. (139) | Com. (1-53) | 6.2 | 23.7 | 2500.0 | 10.6 | 132.5 | 0.67 | 0.32 |
| Ex. (140) | Com. (1-59) | 6.2 | 21.5 | 2500.0 | 11.6 | 132.5 | 0.66 | 0.33 |
| Ex. (141) | Com. (1-65) | 6.0 | 24.7 | 2500.0 | 10.1 | 131.6 | 0.67 | 0.33 |
| Ex. (142) | Com. (1-69) | 6.0 | 23.9 | 2500.0 | 10.5 | 130.6 | 0.66 | 0.34 |
| Ex. (143) | Com. (1-72) | 6.1 | 18.6 | 2500.0 | 13.4 | 138.7 | 0.66 | 0.33 |
| Ex. (144) | Com. (1-75) | 6.0 | 17.6 | 2500.0 | 14.2 | 135.2 | 0.66 | 0.33 |
| Ex. (145) | Com. (1-80) | 6.2 | 18.4 | 2500.0 | 13.6 | 138.8 | 0.65 | 0.32 |
| Ex. (146) | Com. (1-85) | 6.1 | 18.4 | 2500.0 | 13.6 | 132.3 | 0.65 | 0.34 |
| Ex. (147) | Com. (1-94) | 6.2 | 19.0 | 2500.0 | 13.2 | 135.3 | 0.66 | 0.32 |
| Ex. (148) | Com. (1-97) | 6.1 | 17.8 | 2500.0 | 14.0 | 137.6 | 0.66 | 0.33 |
| Ex. (149) | Com. (1-100) | 6.2 | 18.1 | 2500.0 | 13.8 | 138.3 | 0.66 | 0.32 |
| Ex. (150) | Com. (1-104) | 6.2 | 17.3 | 2500.0 | 14.5 | 138.2 | 0.66 | 0.34 |
| Ex. (151) | Com. (1-109) | 6.1 | 23.7 | 2500.0 | 10.6 | 139.8 | 0.66 | 0.33 | blocking layer, and a film of Alq$_3$ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 130] to [Example 151] Red OLED (an Emission-Auxiliary Layer)

The OLEDs were fabricated in the same manner as described in Example 1-1 except that the compounds 1-2 to 1-109 of the present invention described in Table 6, instead of the compound 1-1 of the present invention, were used as an emission-auxiliary layer material.

[Comparative Example 6] to [Comparative Example 10]

In case of Comparative Example 6, the OLED was fabricated in the same manner as described in Example 129 except that an emission-auxiliary layer was not formed. In From the results shown in Table 6, it can be seen that the driving voltage, luminous efficiency and lifetime of the organic electroluminescent device are remarkably improved when compounds of the present invention were used as an emission-auxiliary layer material. That is, it is confirmed that the luminescent efficiency and lifetime are remarkably improved while the driving voltage are slightly increased when Comparative Compounds were used as an emission-auxiliary layer material, compared with case of an emission-auxiliary layer not being formed (Comparative Example 6). Further, the driving voltage can be lowered and the luminescent efficiency and lifetime can be maximized when an emission-auxiliary layer is formed as compound of the present invention compared with Comparative Compounds B to E.

As already explained, this is because the energy level of the compound is changed depending on the substitution position of the amine group and the hetero atom. Comparing the compounds of the present invention with the comparative compounds, the compounds of the present invention have more appropriate HOMO and LUMO energies, so that the charge balance of holes and electrons in the light emitting layer is improved, thereby improving characteristics of the device. These results suggest that the properties of the compound and the result of the device properties may be significantly changed depending on the substitution position of the amine group and the kind of the hetero atom.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:
1. A compound of Formula 1 below:

[Formula 1]

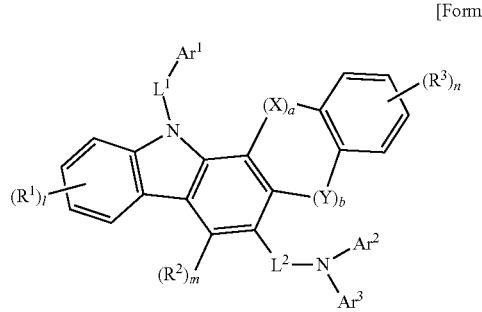

wherein

X and Y are each independently O or S, a and b are each an integer of 0 or 1, and at least one of a and b is 1, $Ar^1$ to $Ar^3$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, $C_1$-$C_{60}$ alkyl group, a fused ring group of a $C_6$-$C_{60}$ aromatic ring and a $C_3$-$C_{60}$ aliphatic ring, and -L-N(R')(R''), $R^1$ to $R^3$ are each independently selected from the group consisting of deuterium, tritium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_6$-$C_{60}$ aromatic ring and a $C_3$-$C_{60}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group, and -L'-N(R')(R''), and neighboring groups of $R^1$, neighboring groups of $R^2$ or neighboring groups of $R^3$ may be optionally linked each other to form a ring when a plurality of neighboring $R^1$ to $R^3$ exist, l and n are each an integer of 0-4, and m is an integer of 0 or 1, $L^1$, $L^2$ and L' are each independently selected from the group consisting of a single bond, a $C_6$-$C_{60}$ arylene group, a fluorenylene group, a $C_2$-$C_{60}$ heterocyclic group containing at least one heteroatom selected from O, N, S, Si, and P, a fused ring group of a $C_6$-$C_{60}$ aromatic ring and a $C_3$-$C_{60}$ aliphatic ring, and a aliphatic hydrocarbon group, R' and R'' are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_6$-$C_{60}$ aromatic ring and a $C_3$-$C_{60}$ aliphatic ring, and when $Ar^1$ to $Ar^3$, $R^1$ to $R^3$, R' and R'' are each the aryl group, fluorenyl group, heterocyclic group, or fused ring group, when $Ar^1$ to $Ar^3$ are each the alkyl group, when $R^1$ to $R^3$ are each the alkyl group, alkenyl group, alkynyl group, alkoxyl group or aryloxy group, or when $L^1$, $L^2$ and L' are each the arylene group, fluorenylene group, heterocyclic group, or fused ring group, each of them may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

2. The compound of claim 1, wherein Formula 1 above is represented by Formula 2 below:

[Formula 2]

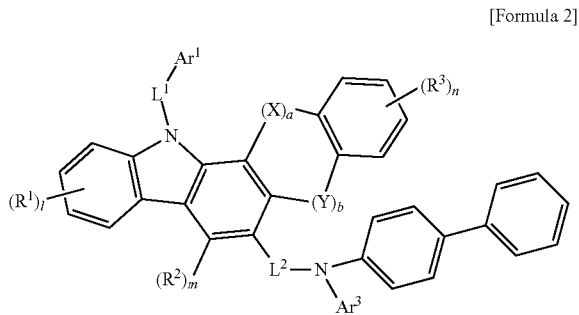

in formula 2, X, Y, $Ar^1$, $Ar^3$, $R^1$ to $R^3$, $L^1$, $L^2$, a, b, l, m, and n are each the same as defined in claim 1.

3. The compound of claim 1, wherein Formula 1 above is represented by formula 3 or formula 4 below:

[Formula 3]

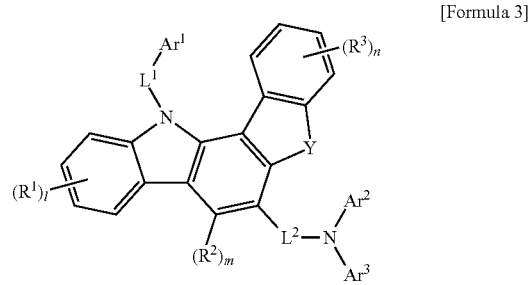

[Formula 4]
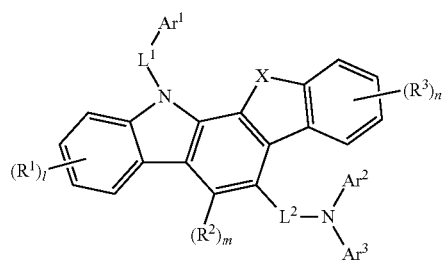
in formula 3 or formula 4, X, Y, $Ar^1$ to $Ar^a$, $R^1$ to $R^3$, $L^1$, $L^2$, l, m, and n are each the same as defined in claim 1.
4. The compound of claim 1, wherein Formula 1 is any one of the compounds below:
1-1
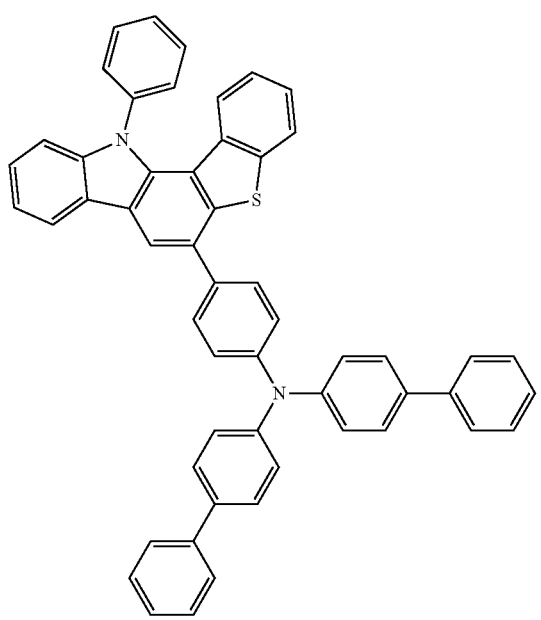
1-2
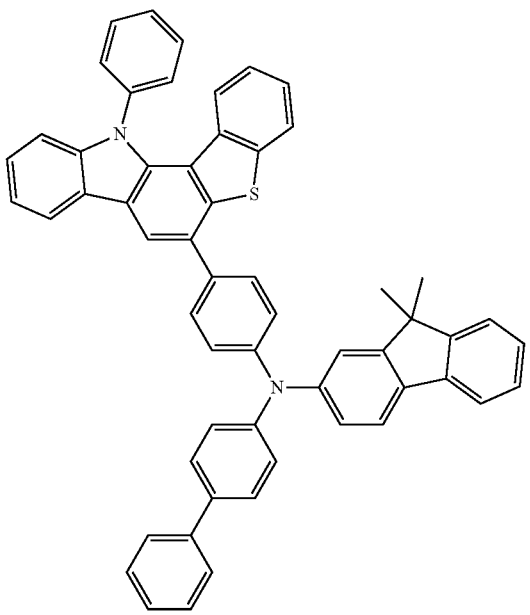
1-3
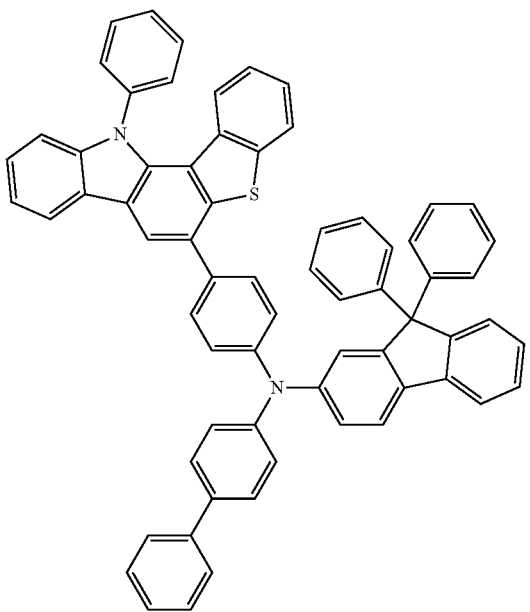

1-4
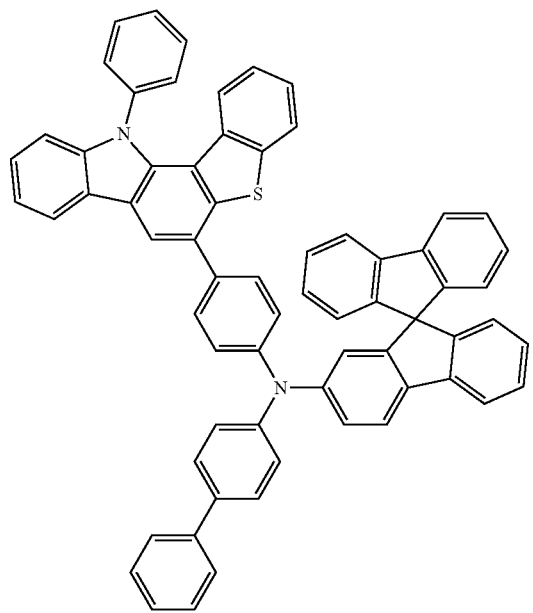
1-5
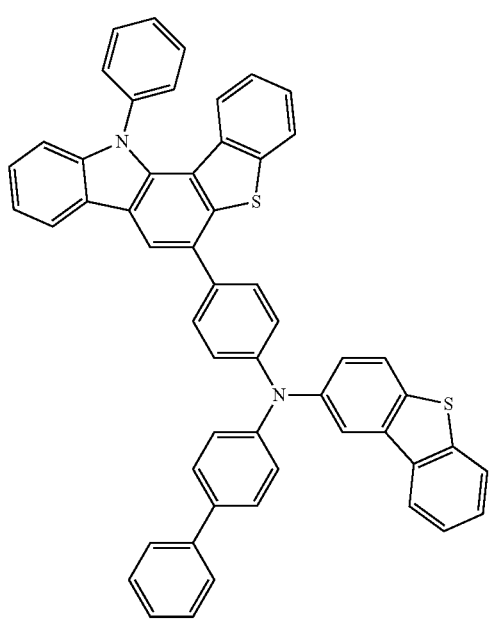
1-6
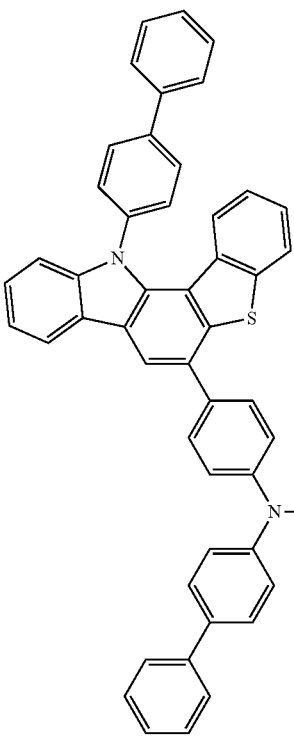
1-7
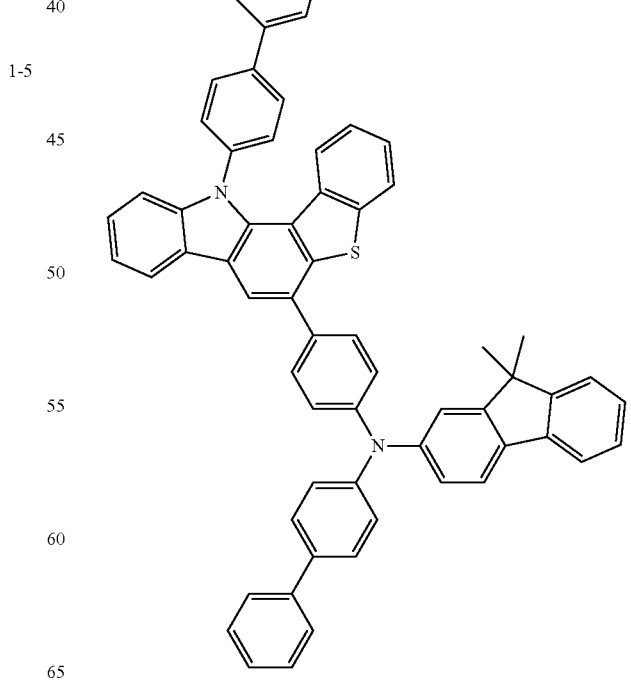

1-8
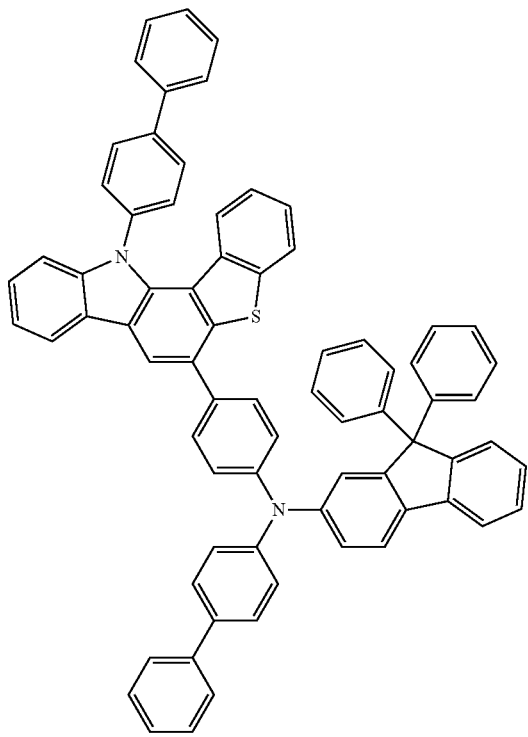
1-10
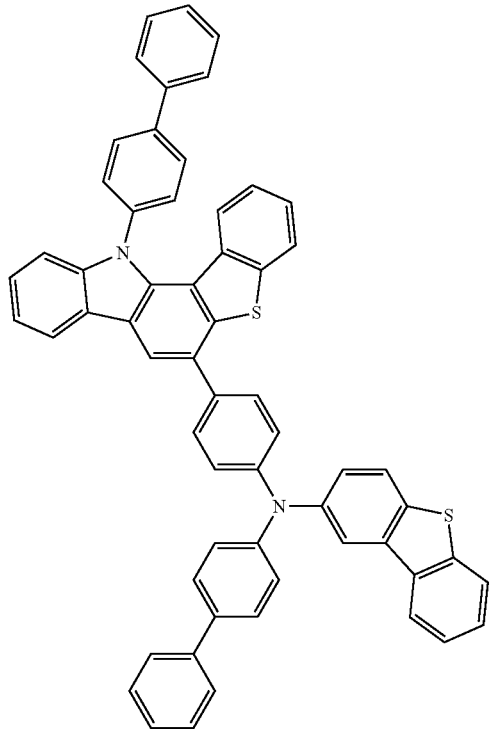
1-9
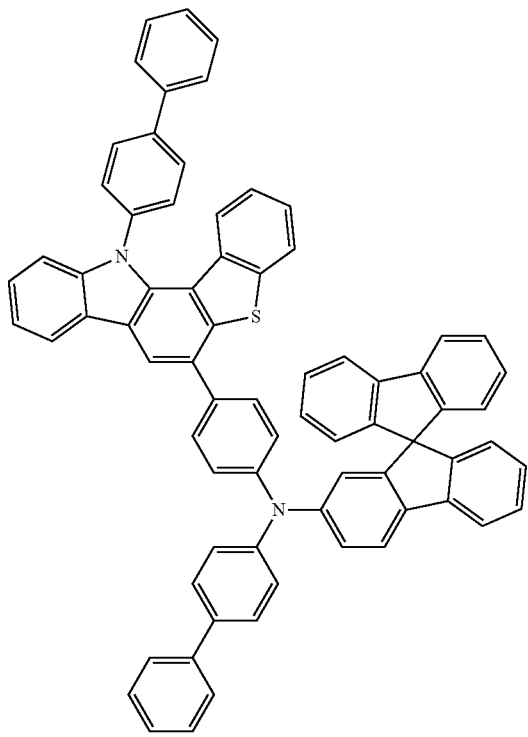
1-11
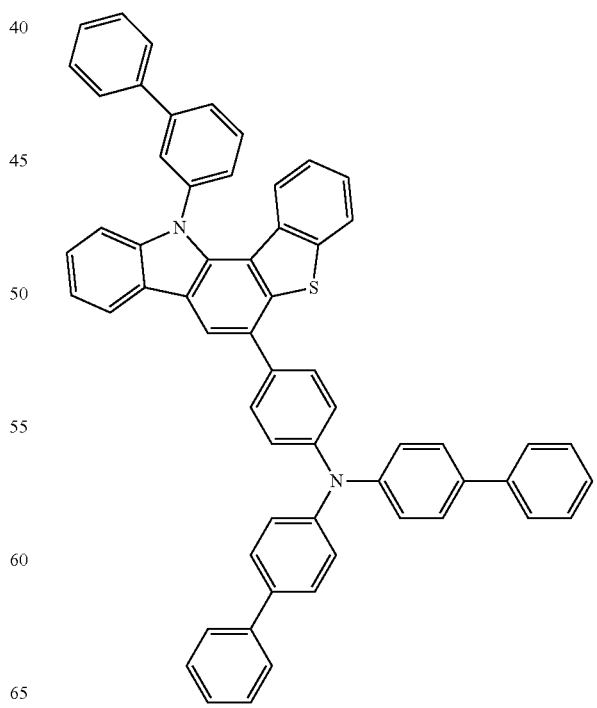

1-12
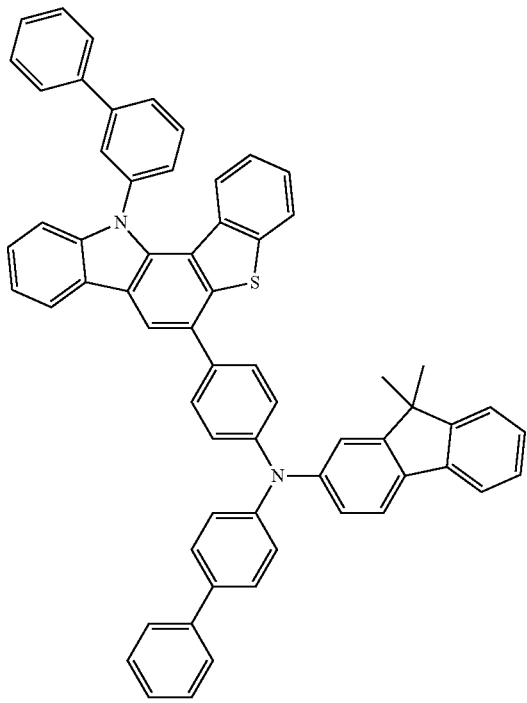
1-13
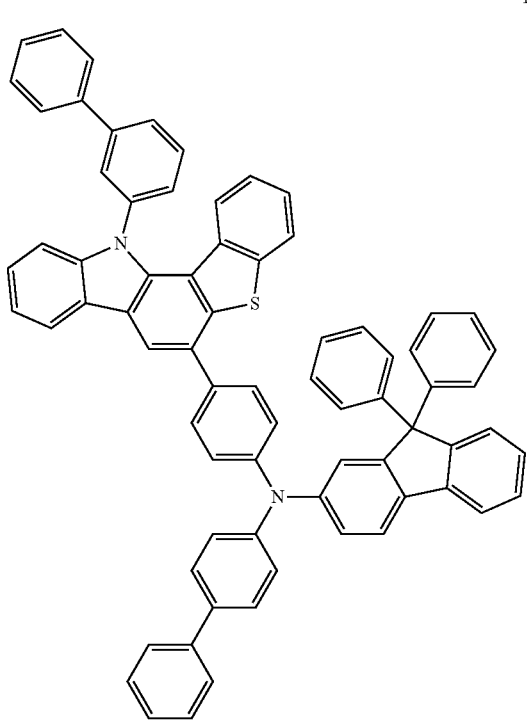
1-14
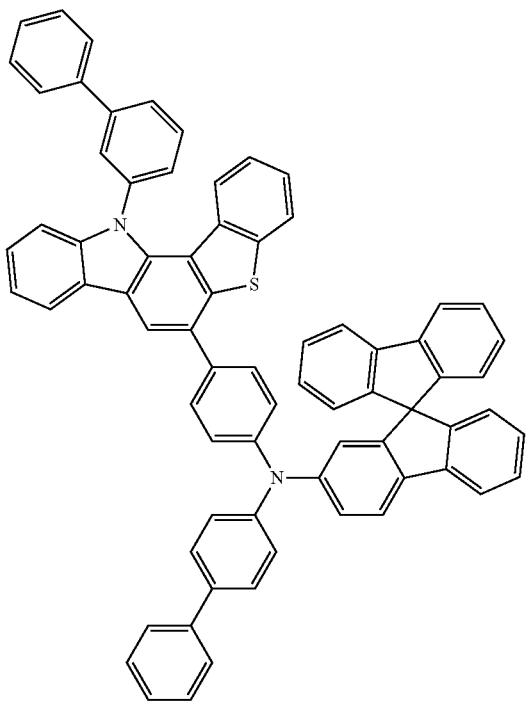
1-15
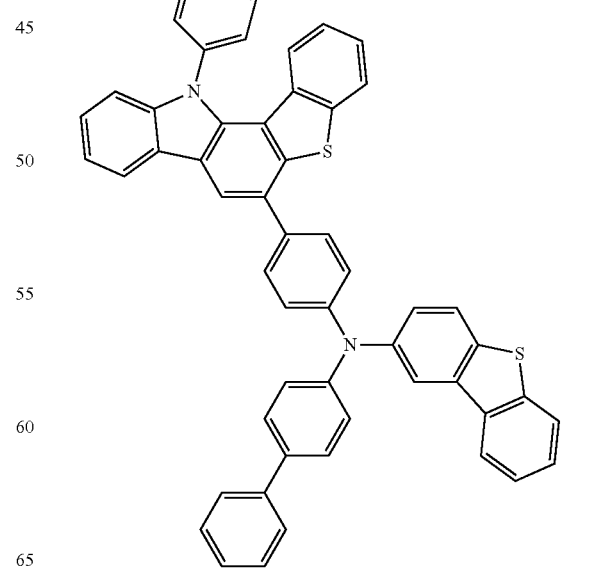

-continued
1-16
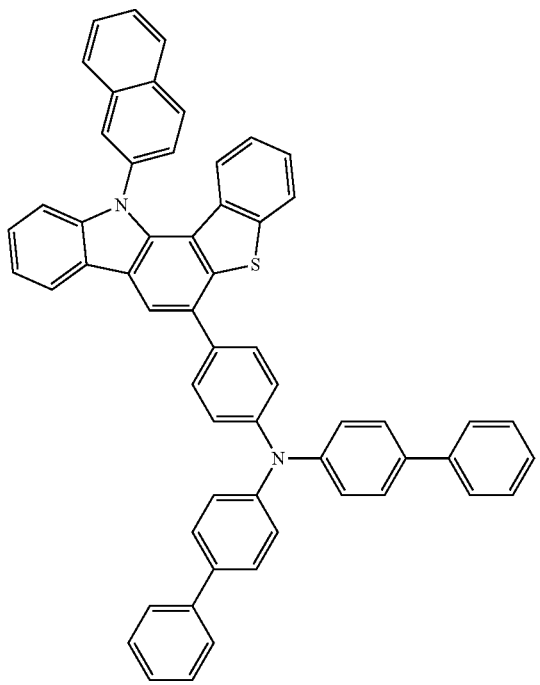
1-17
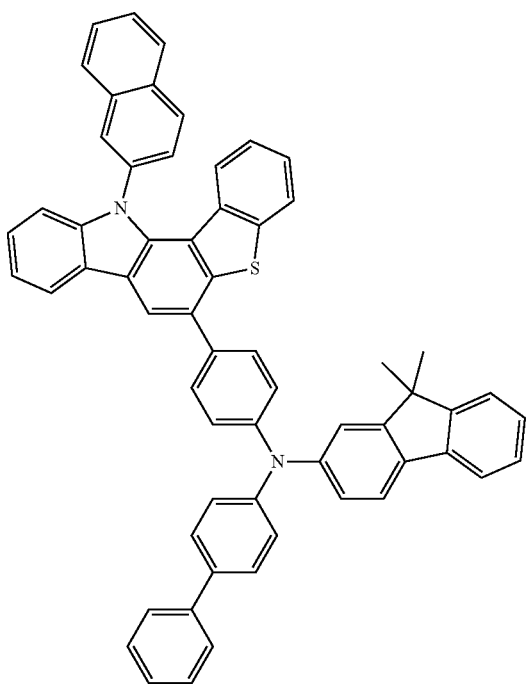
1-18
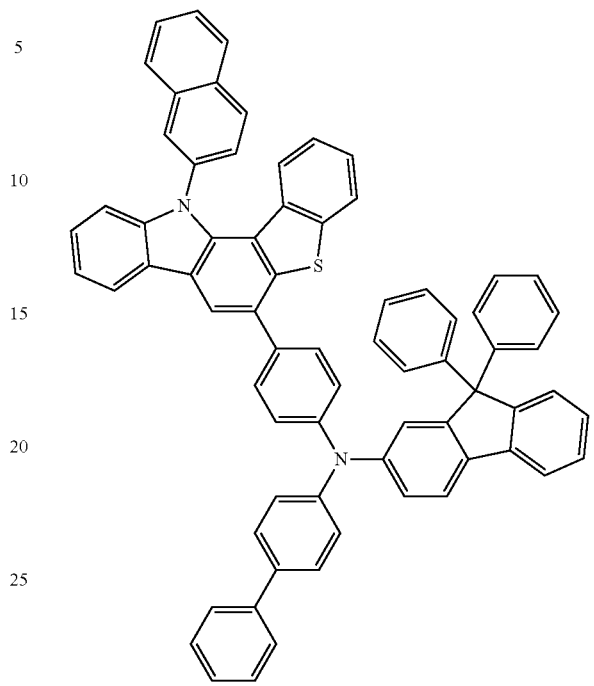
1-19
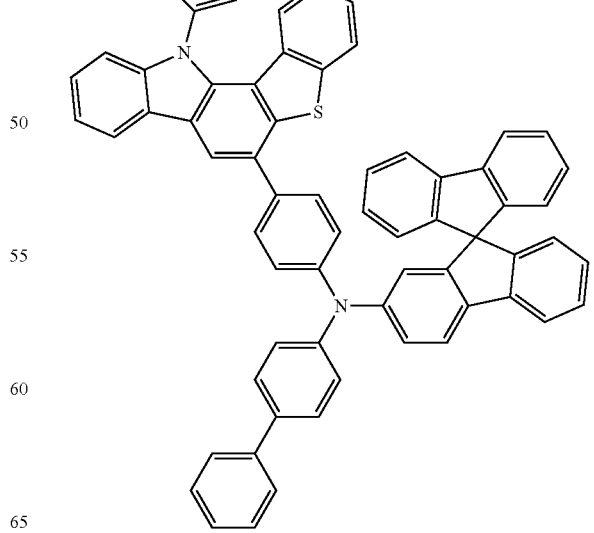

1-20
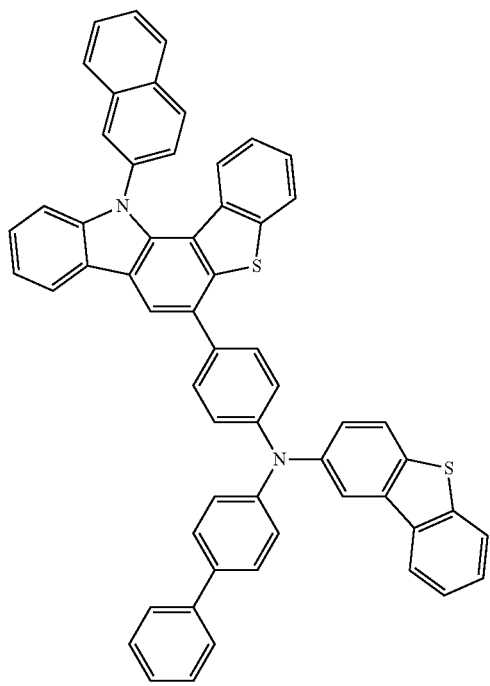
1-21
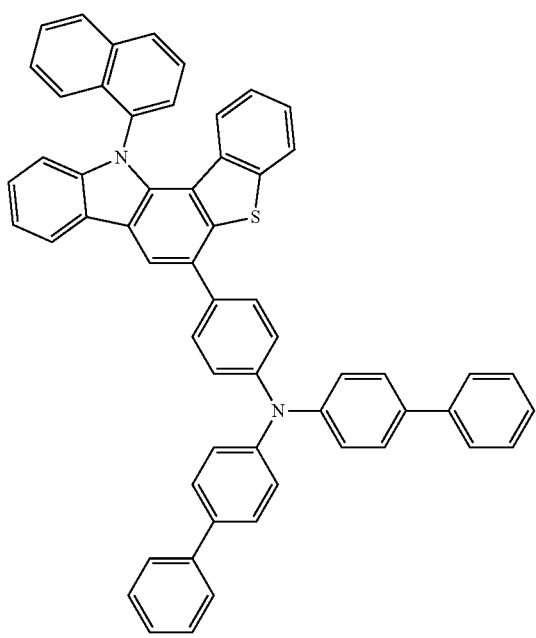
1-22
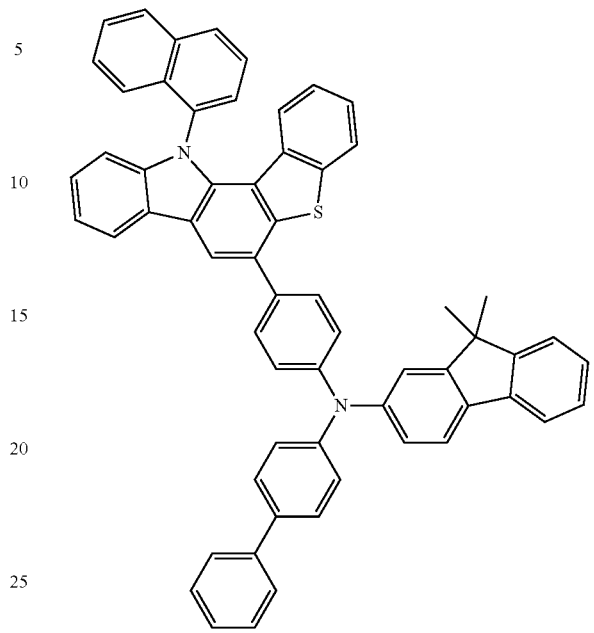
1-23
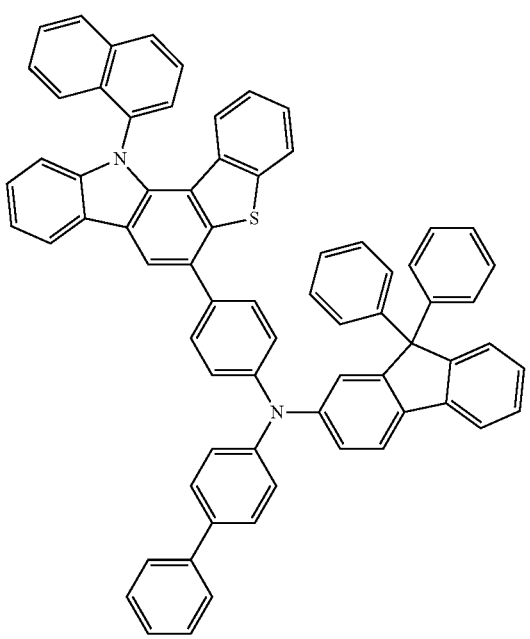

1-24
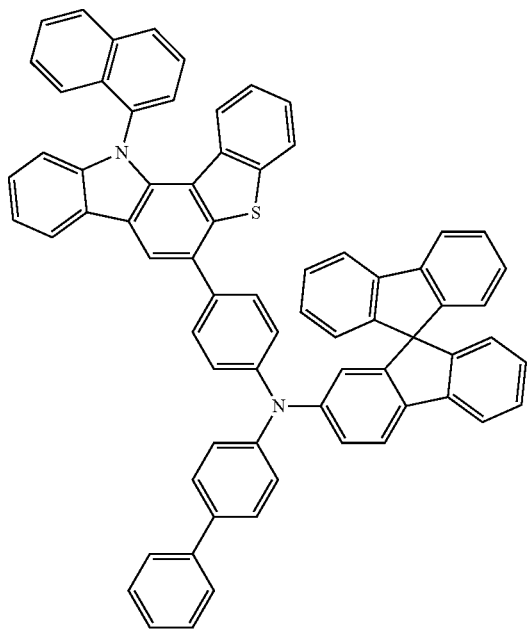
1-26
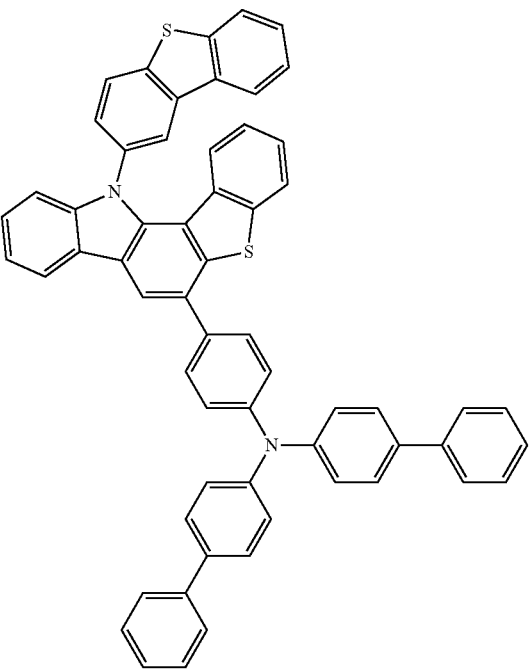
1-25
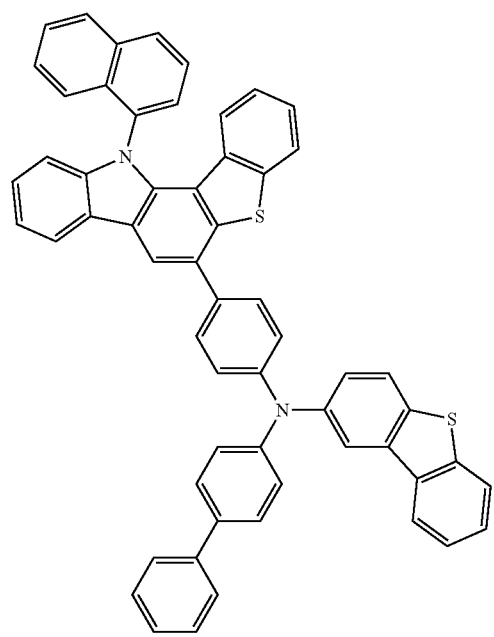
1-27
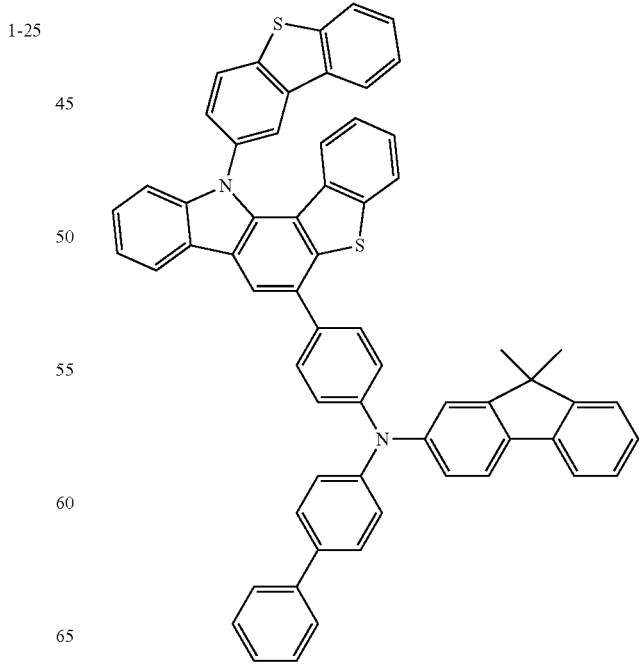

1-28
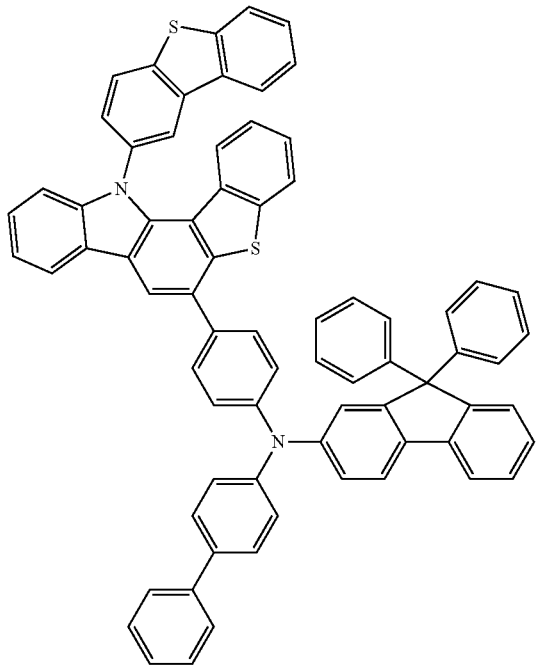
1-30
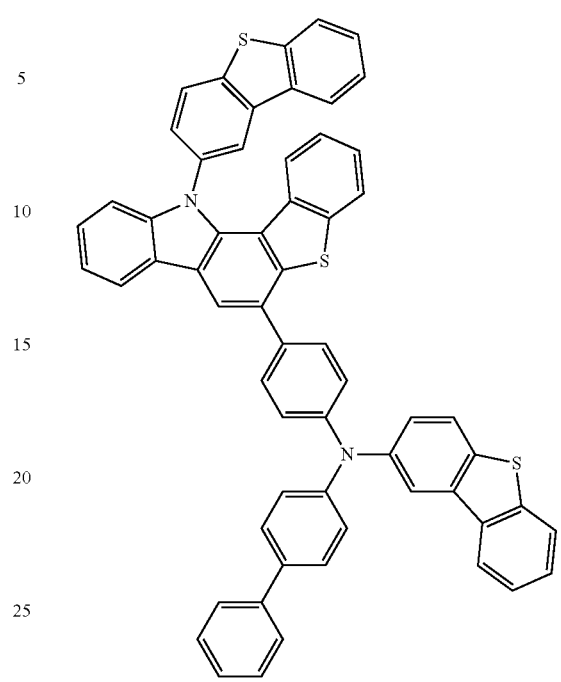
1-29
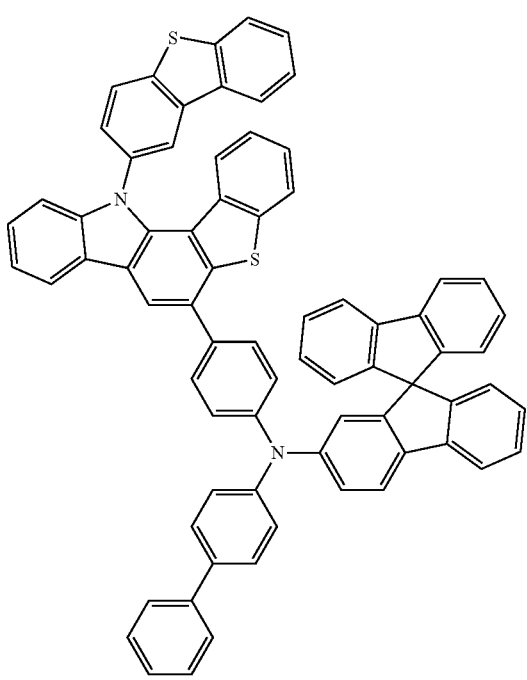
1-31
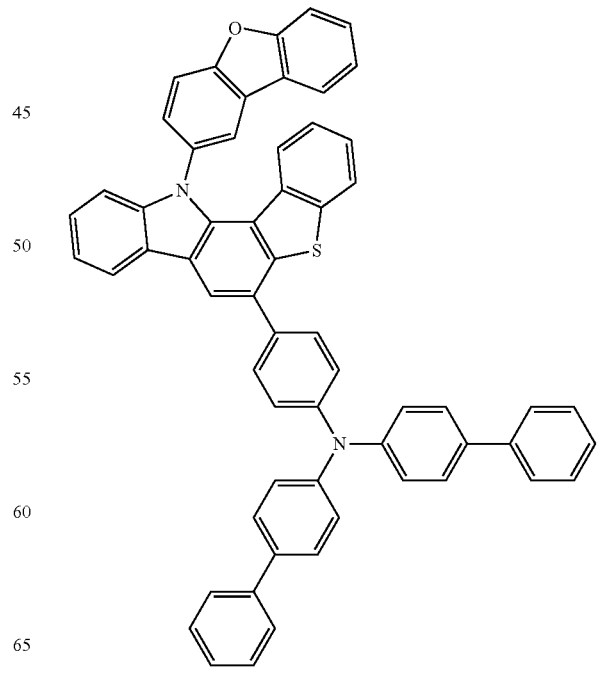

1-32
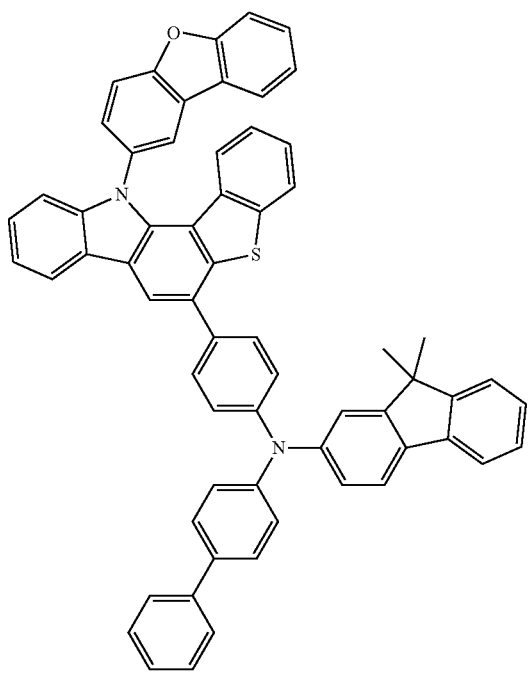
1-34
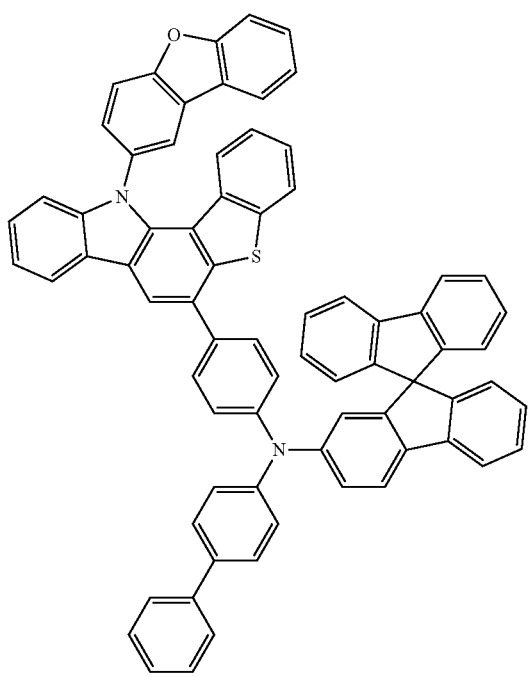
1-33
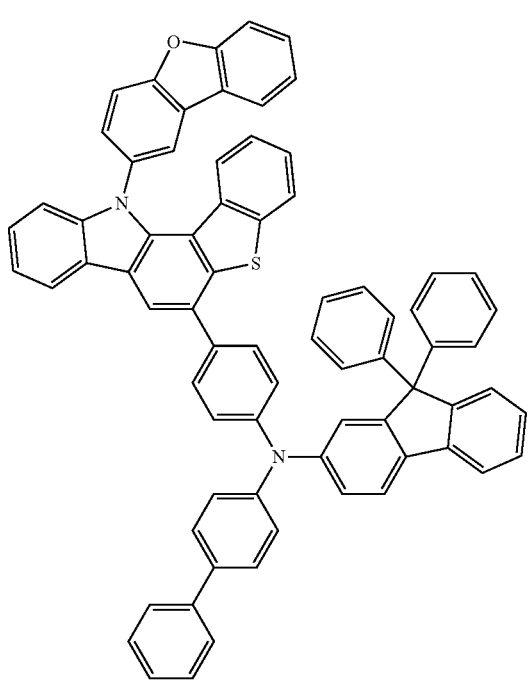
1-35
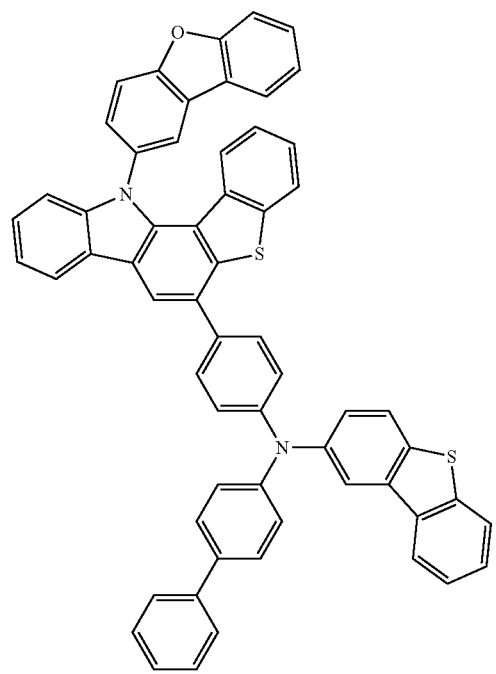

-continued
1-36
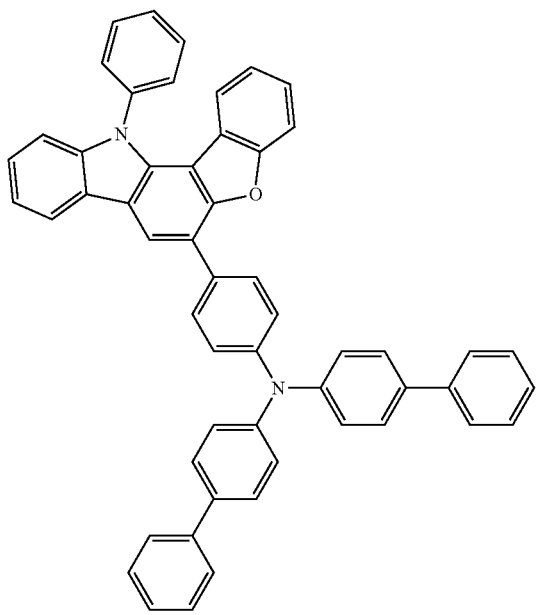
1-38
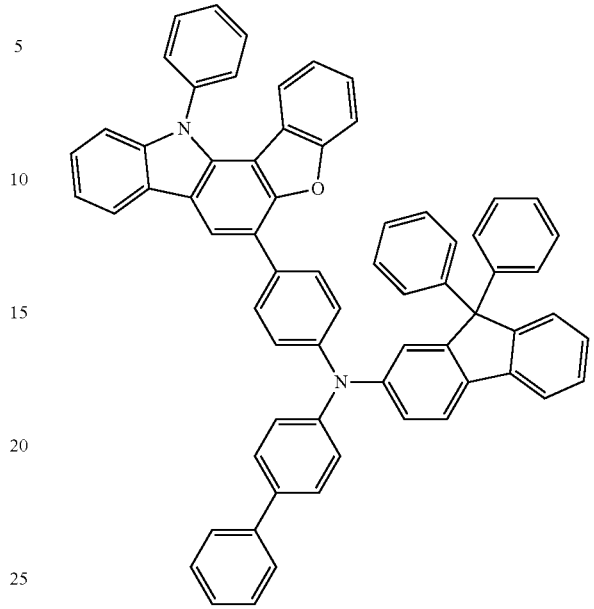
1-37
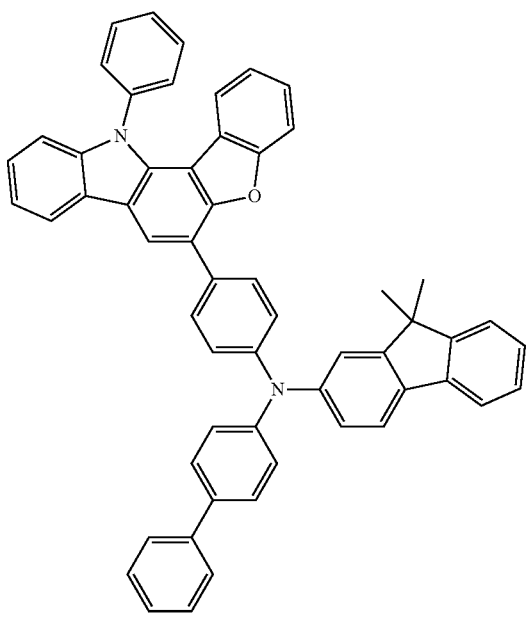
1-39
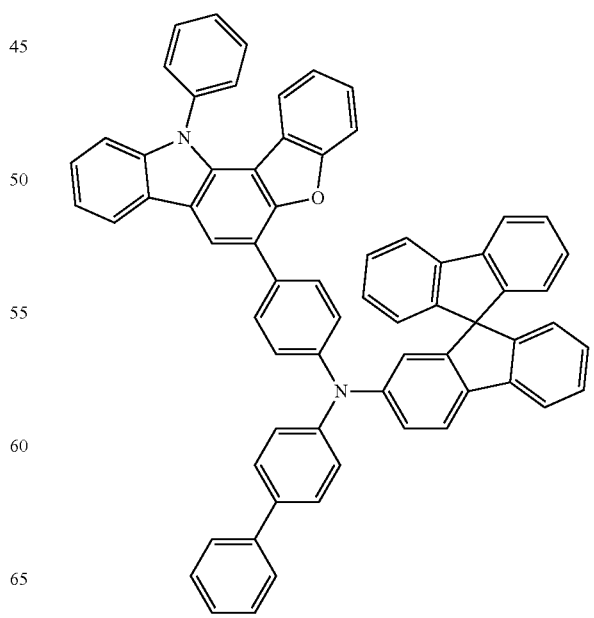

1-40
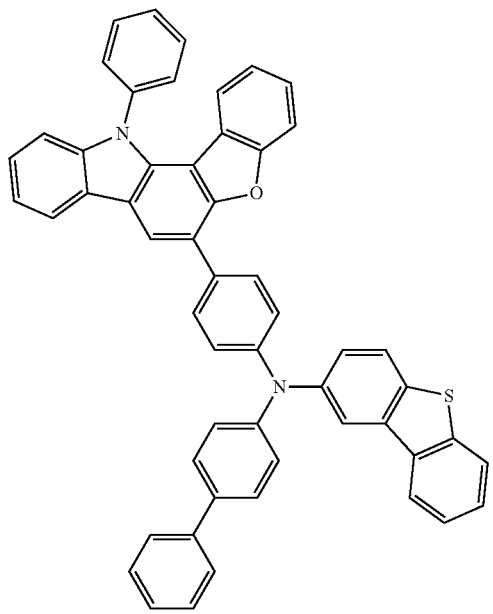
1-41
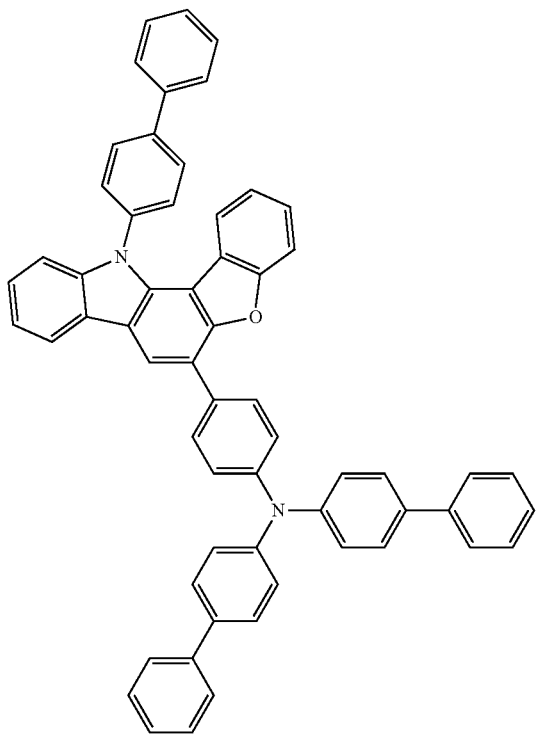
1-42
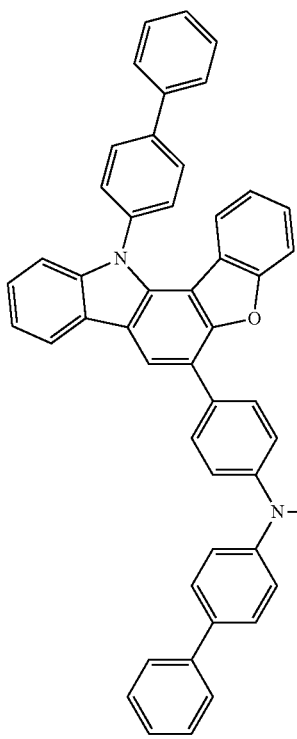
1-43
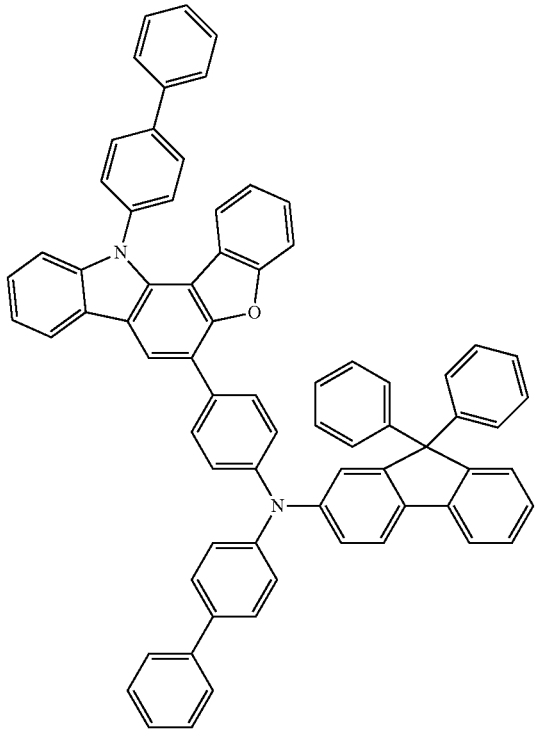

1-44
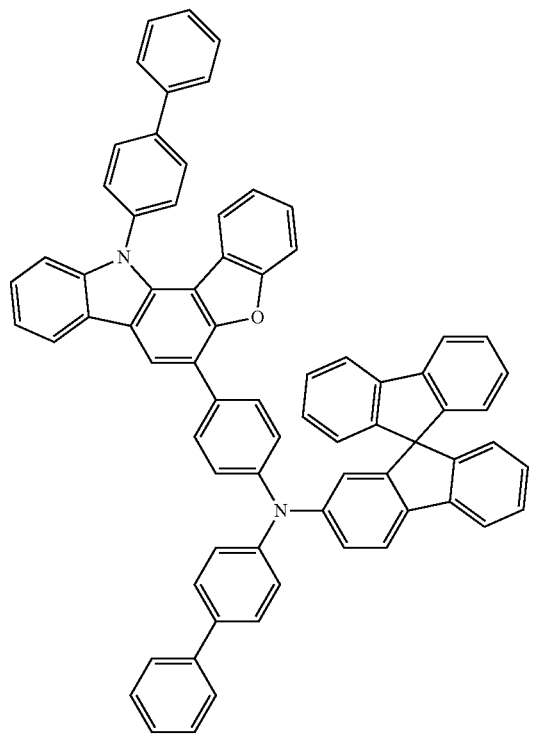
1-45
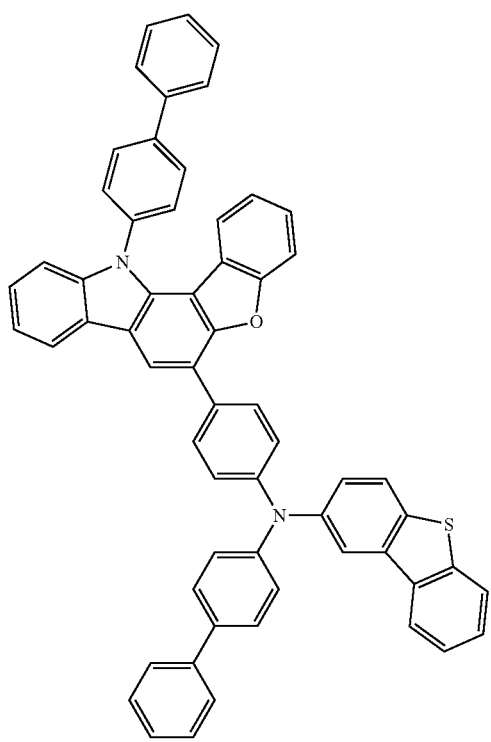
1-46
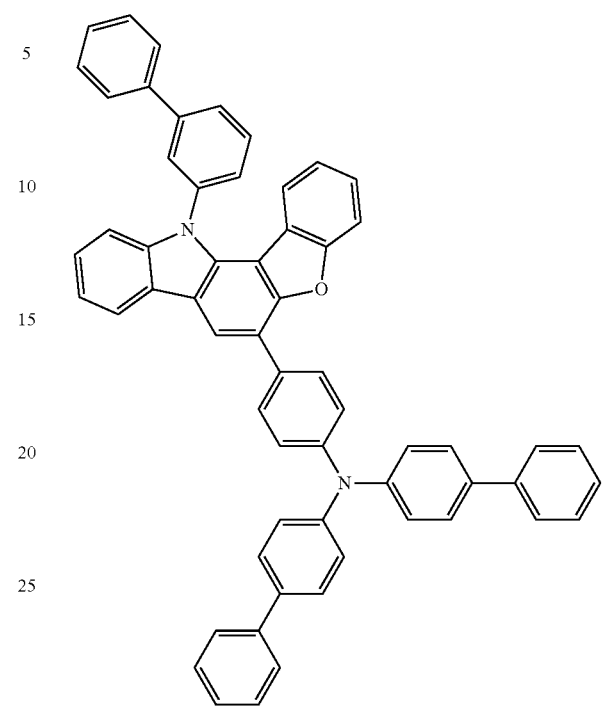
1-47
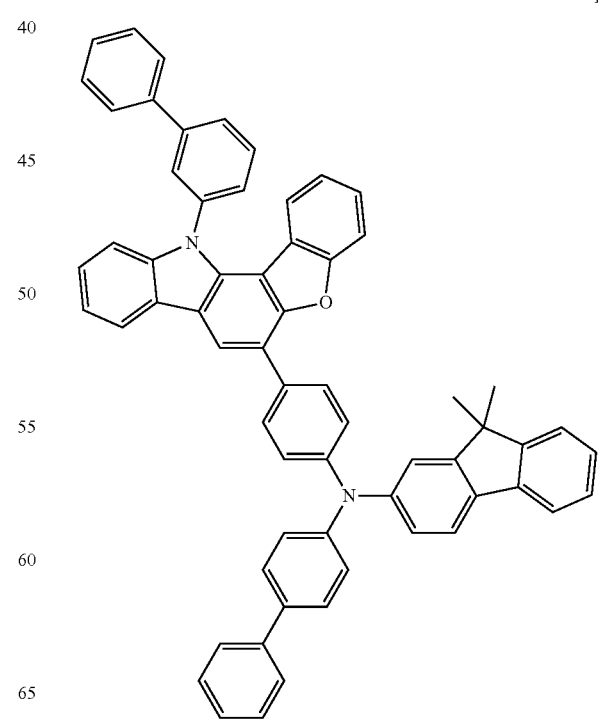

-continued
1-48
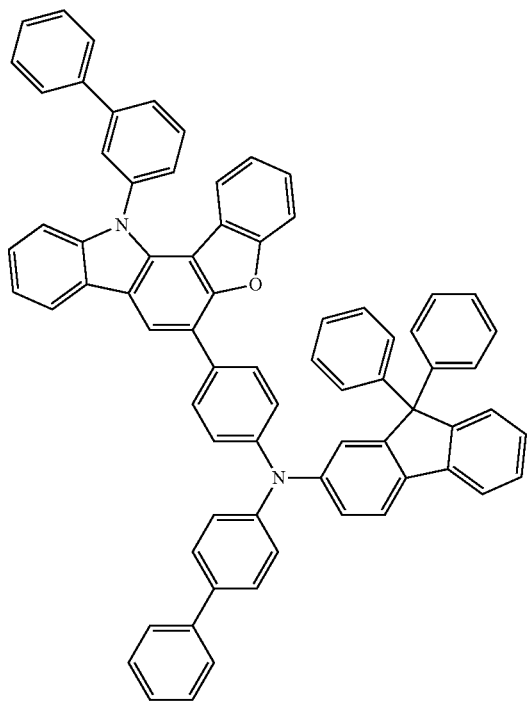
1-50
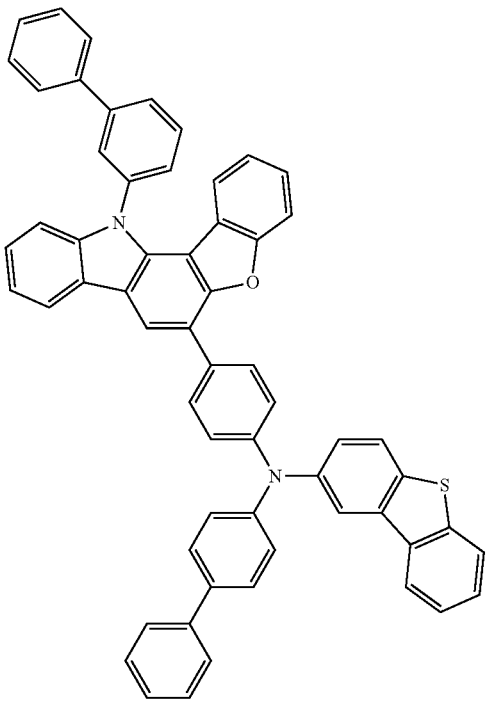
1-49
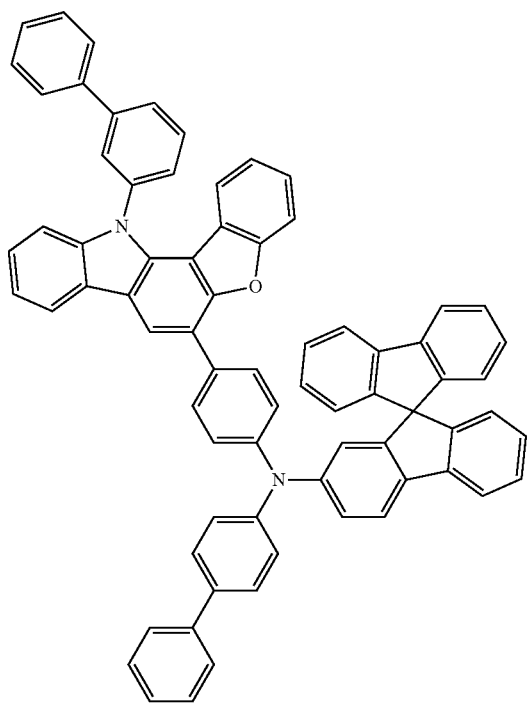
1-51
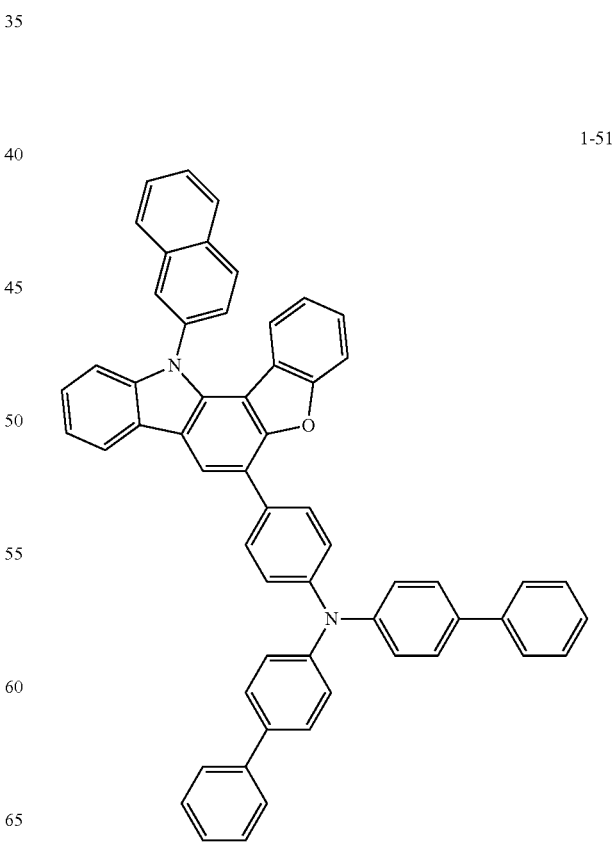

1-52
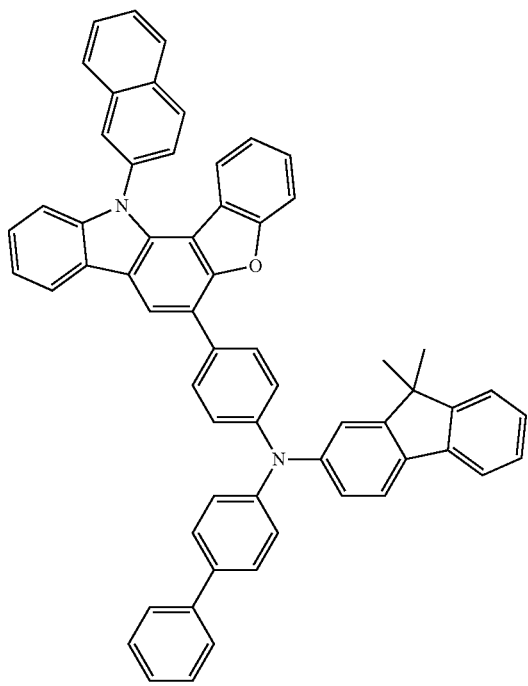
1-54
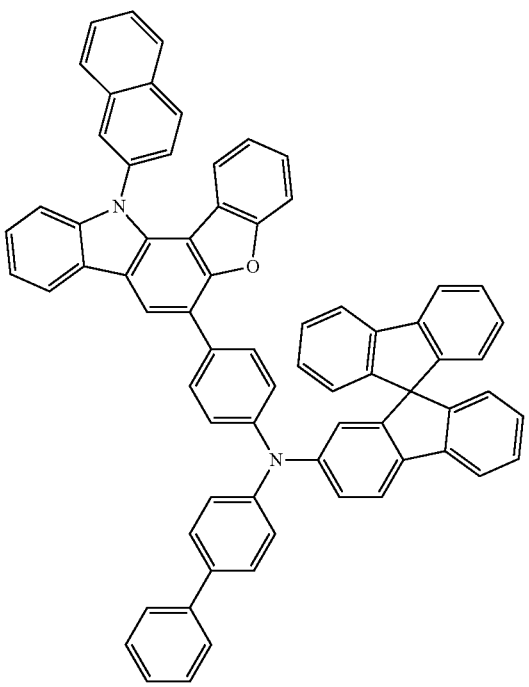
1-53
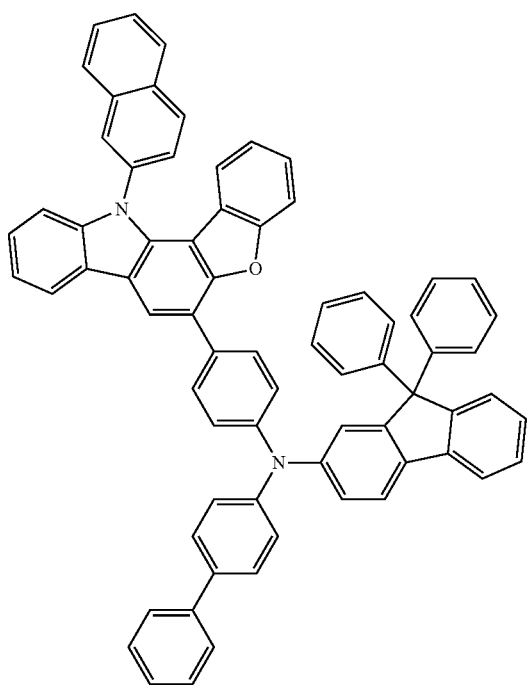
1-55
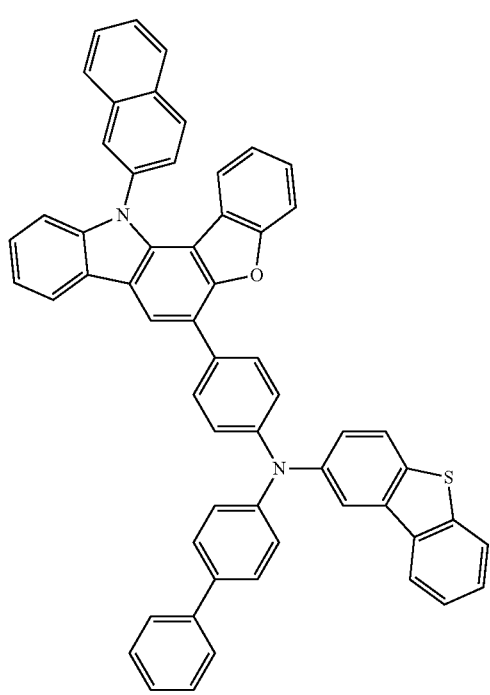

1-56
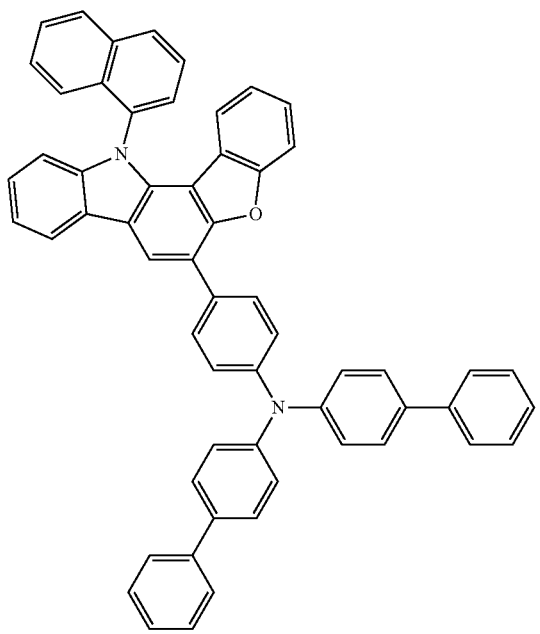
1-57
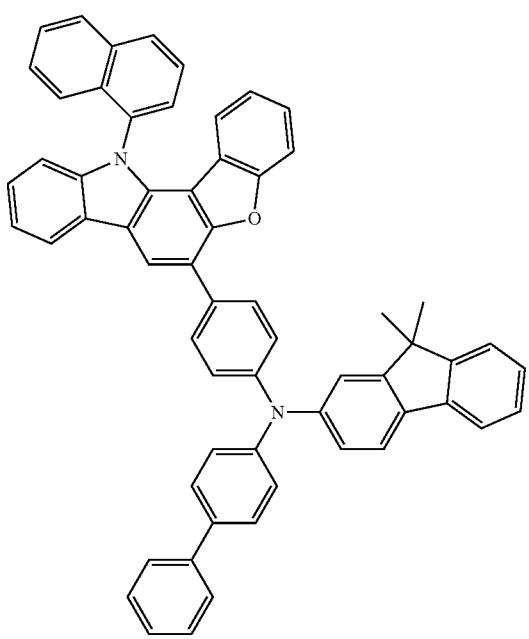
1-58
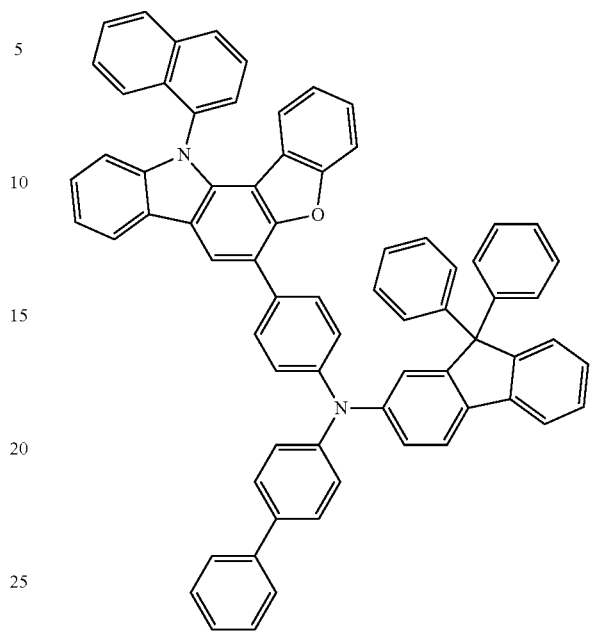
1-59

1-60
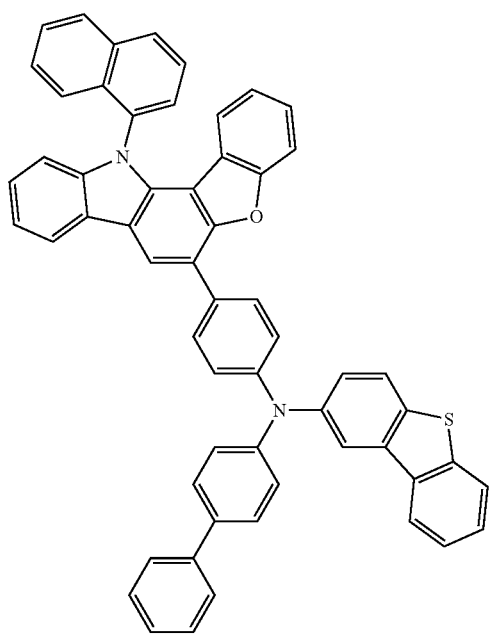
1-61
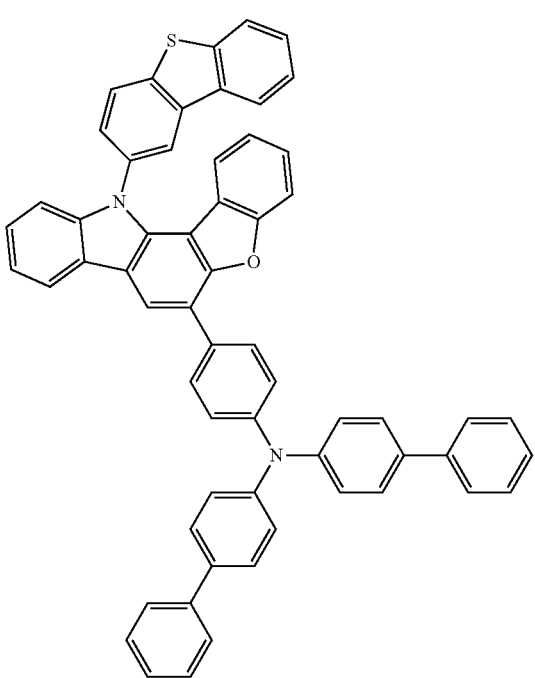
1-62
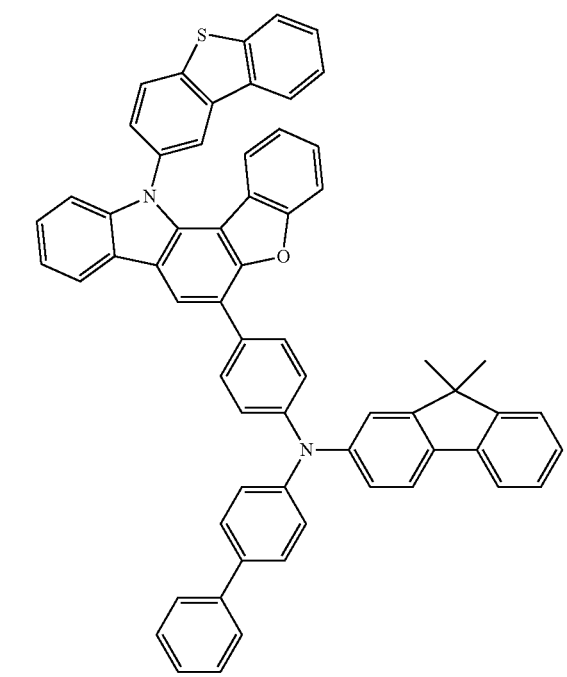
1-63
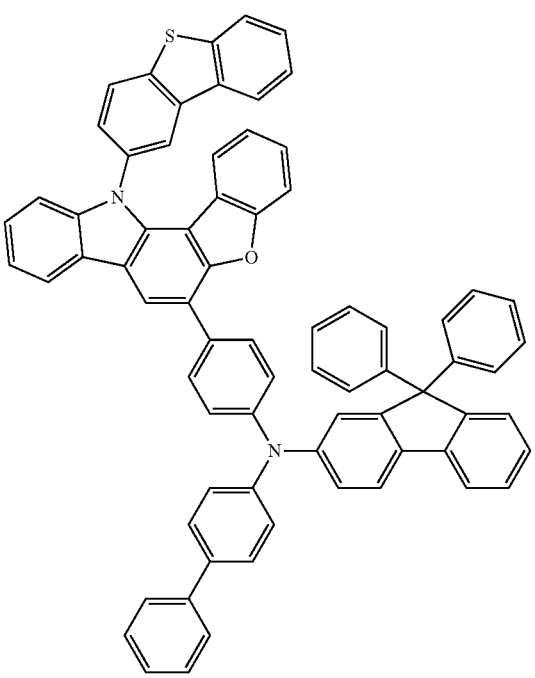

1-64
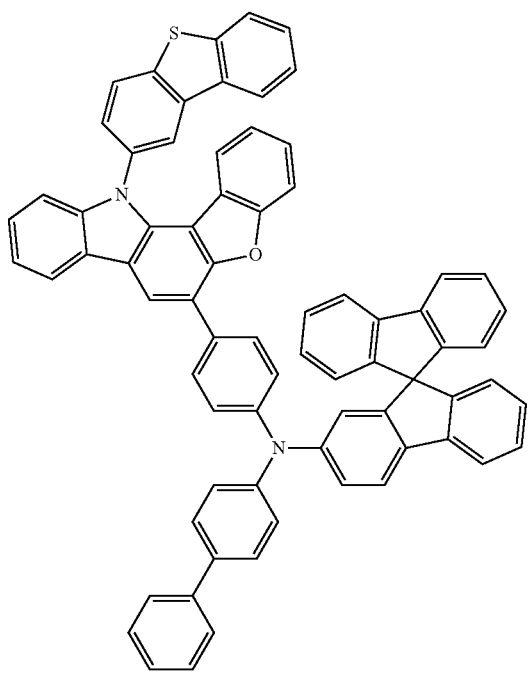
1-65
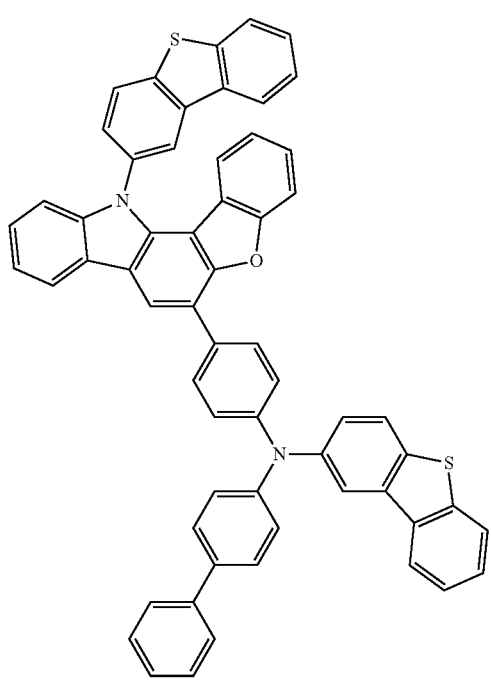
1-66
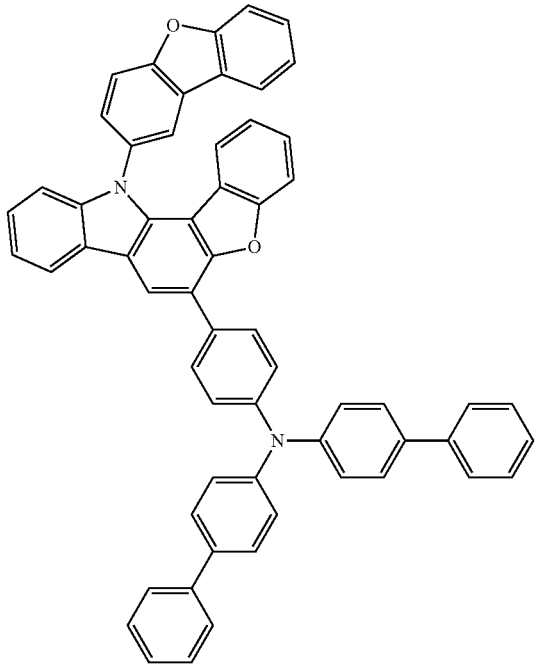
1-67
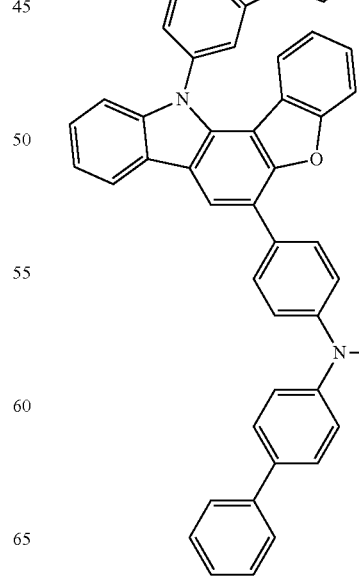

1-68
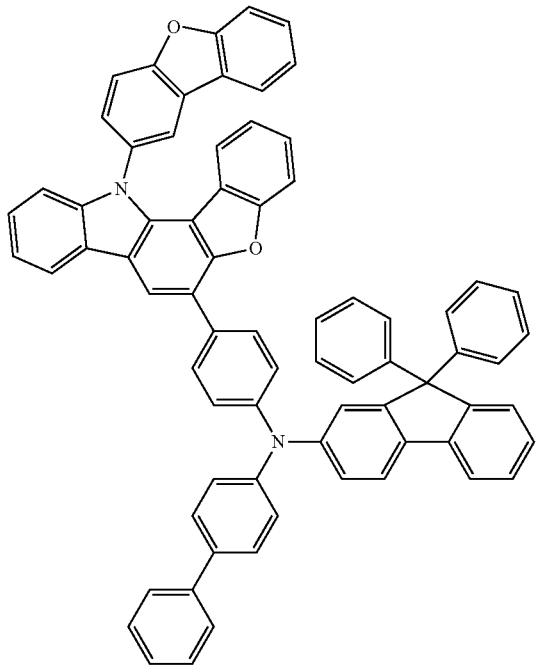
1-69
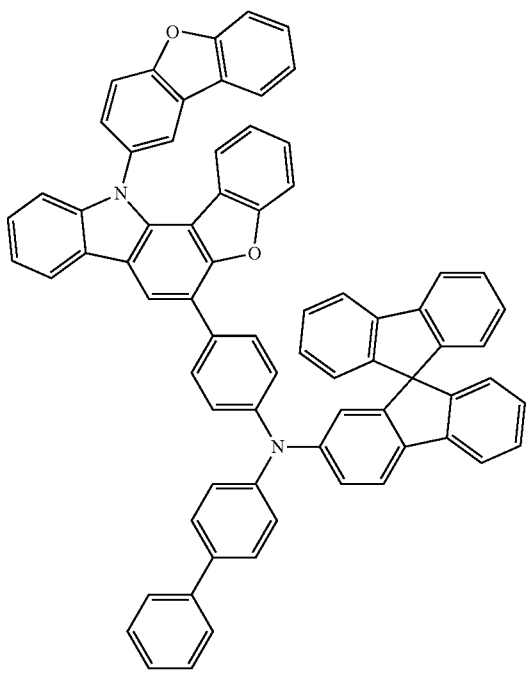
1-70
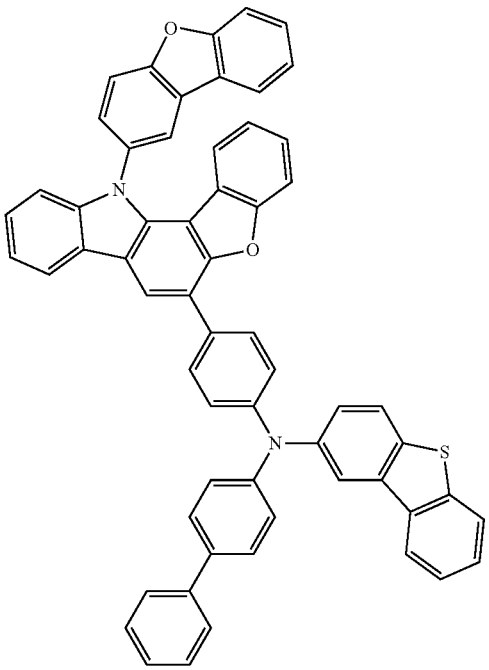
1-71
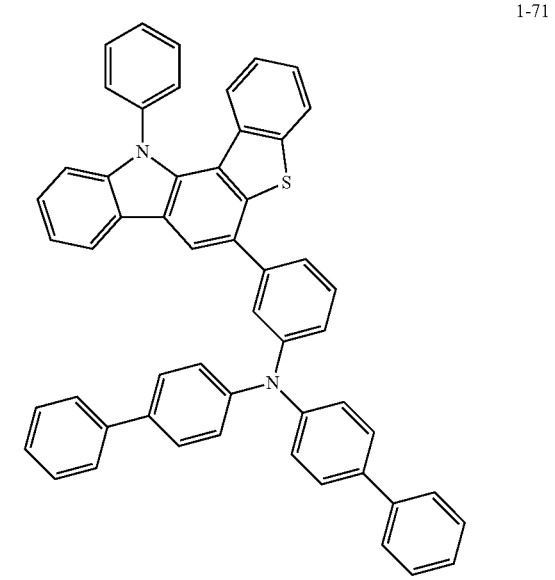

1-72
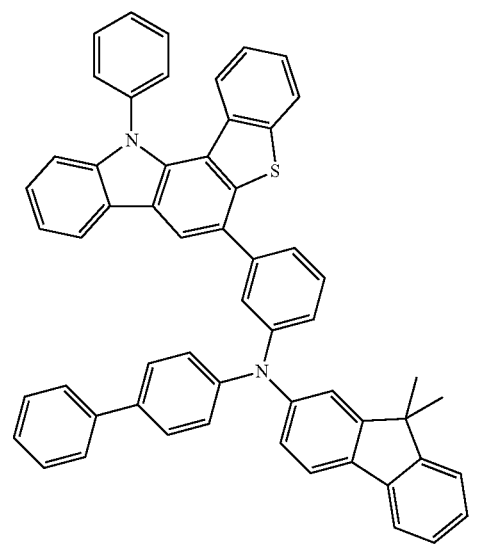
1-73
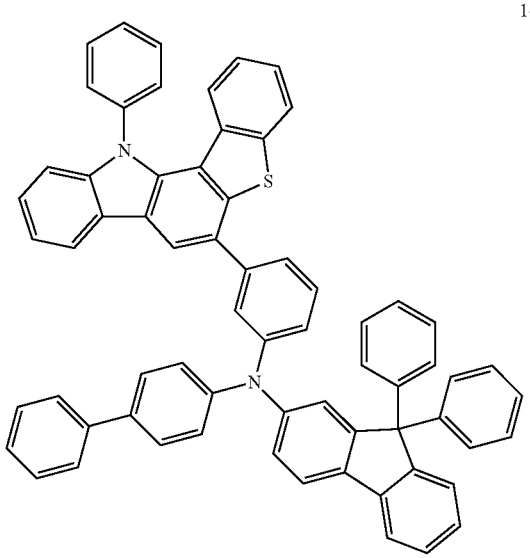
1-74
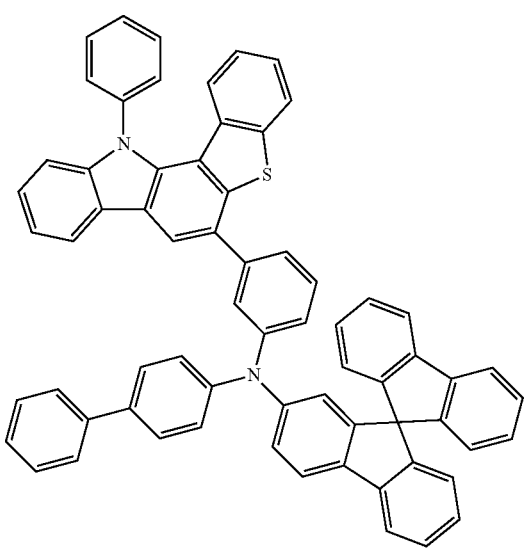
1-75
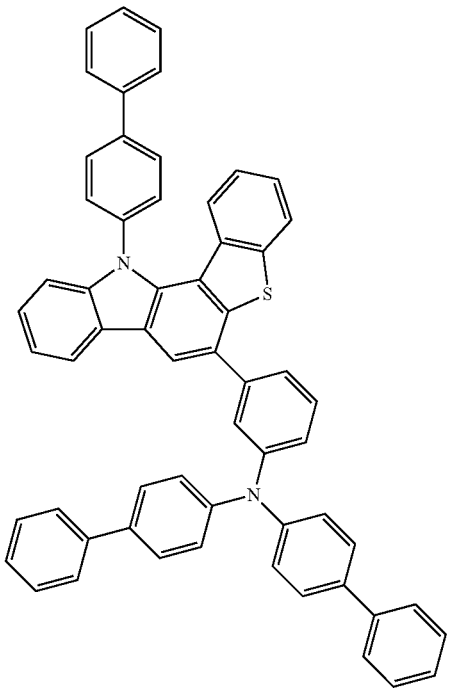
1-76
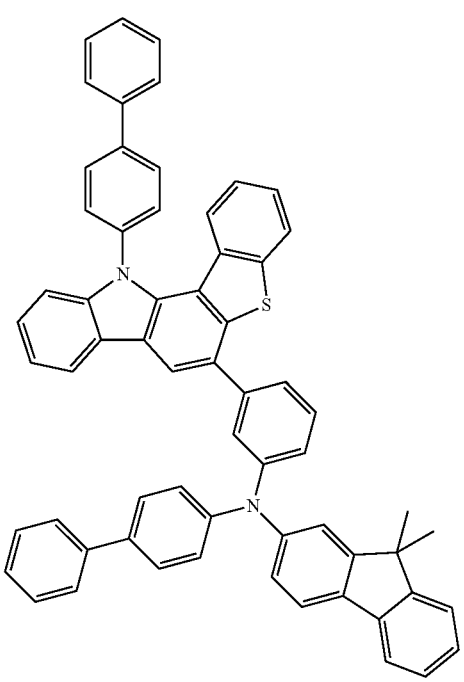

1-77
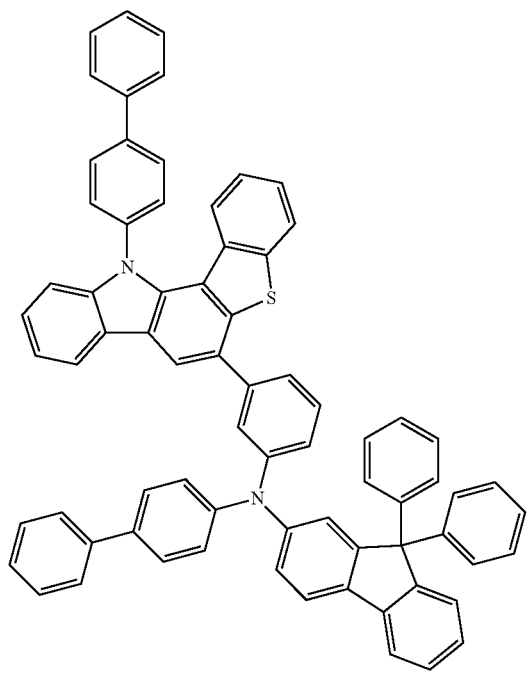
1-78
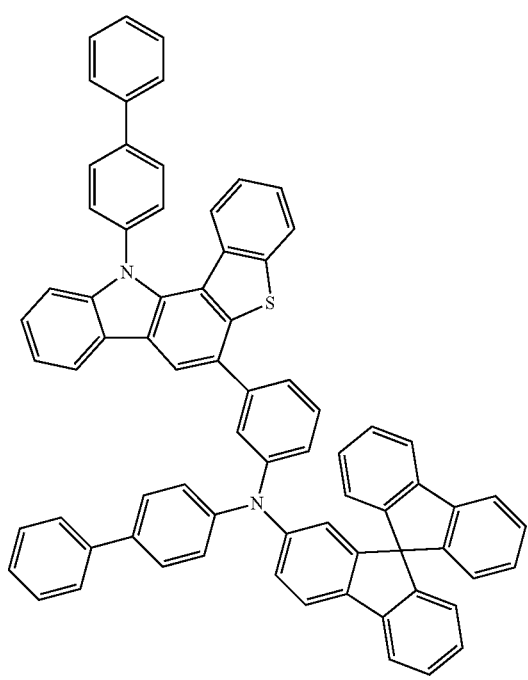
1-79
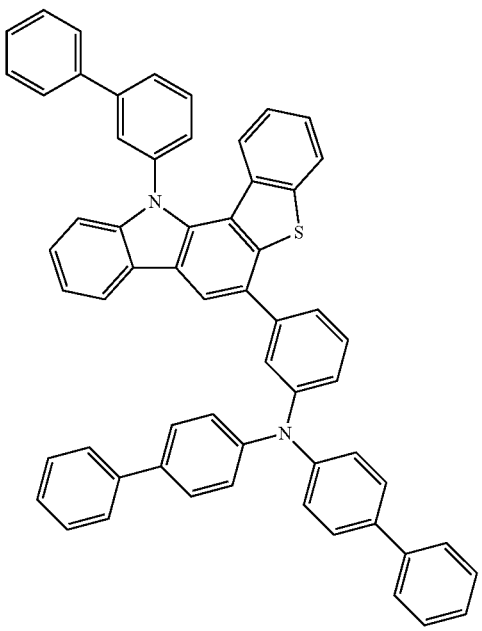
1-80
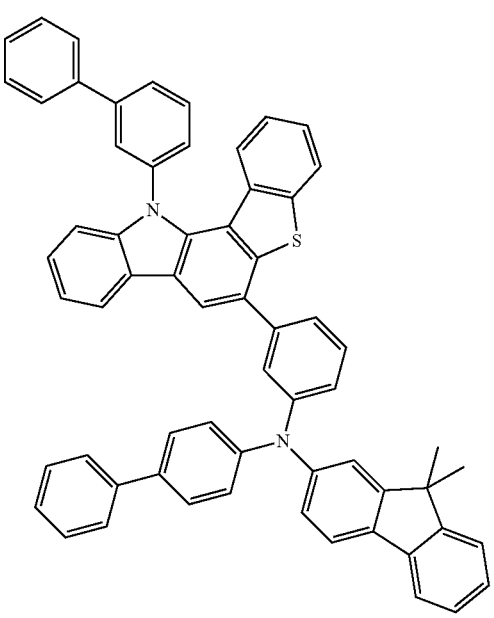

1-81
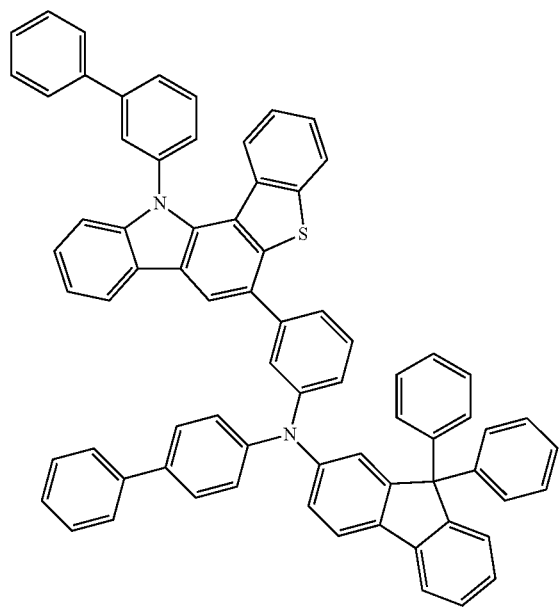
1-83
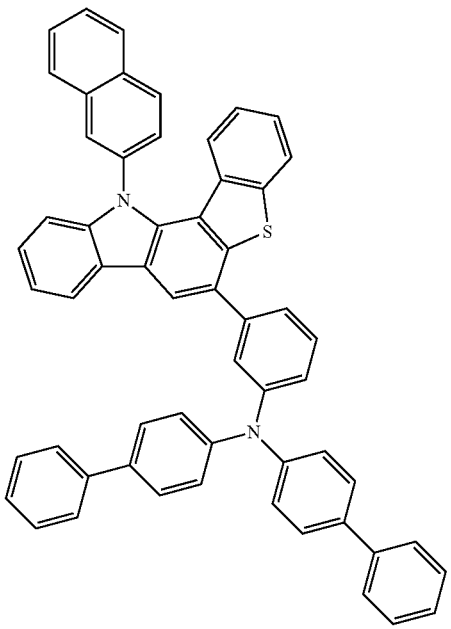
1-82
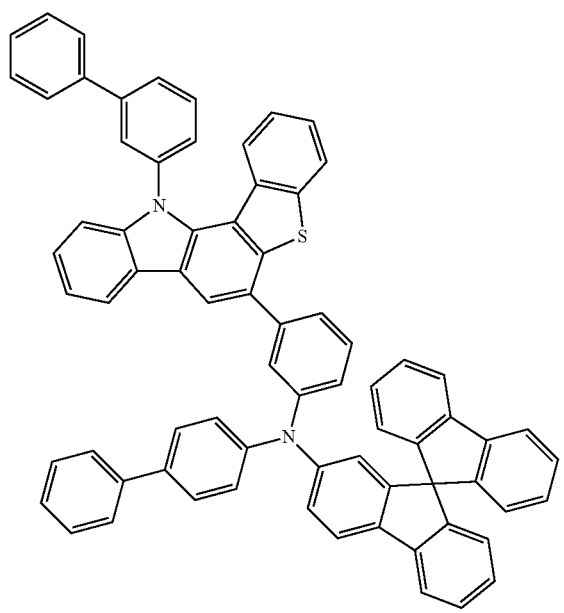
1-84
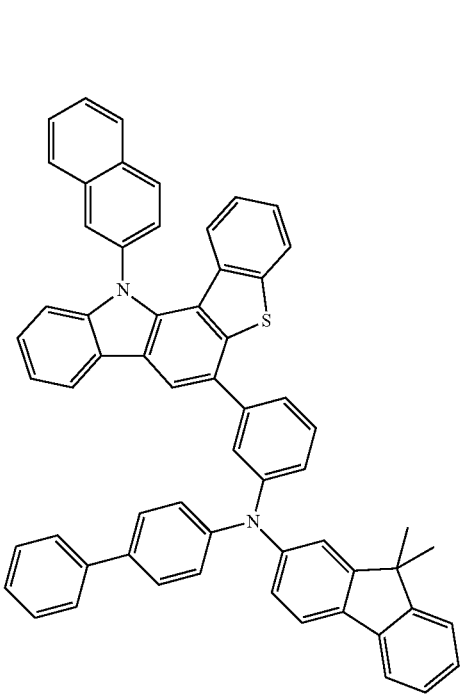

1-85
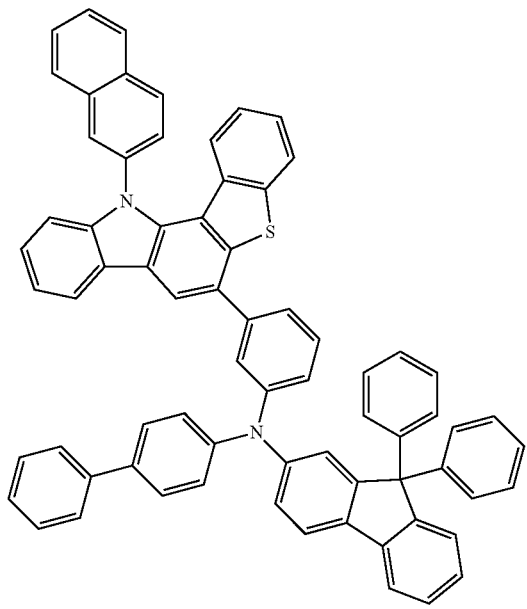
1-86
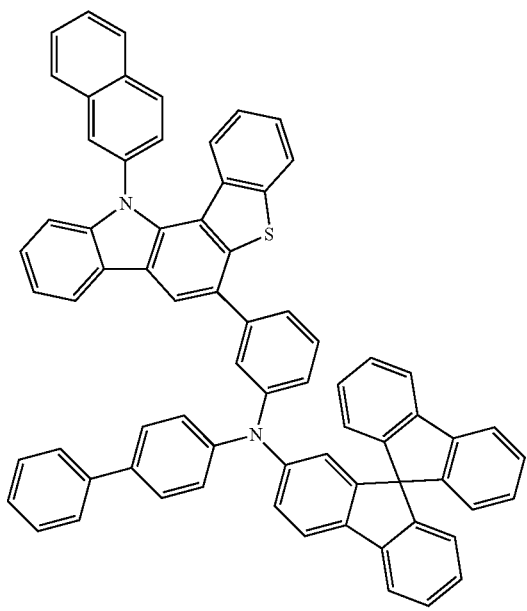
1-87
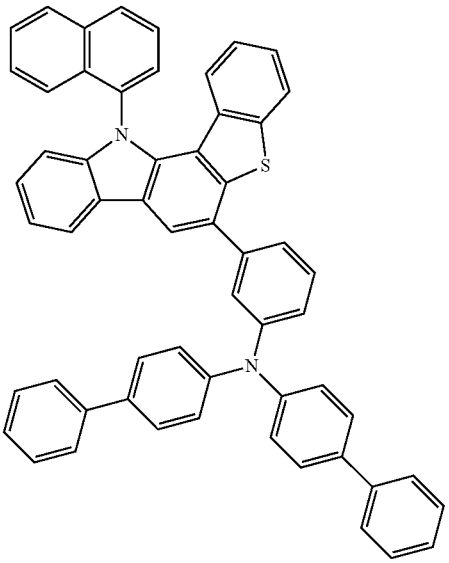
1-88
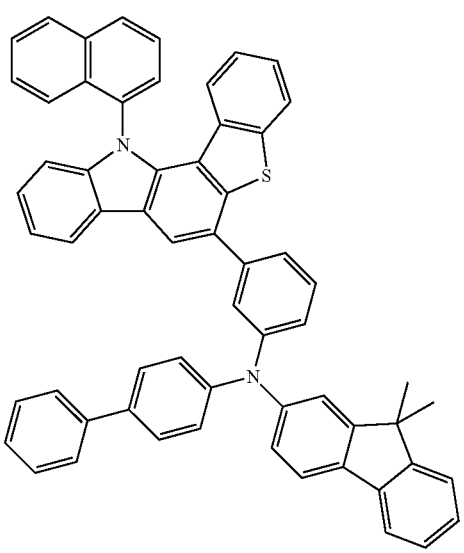
1-89
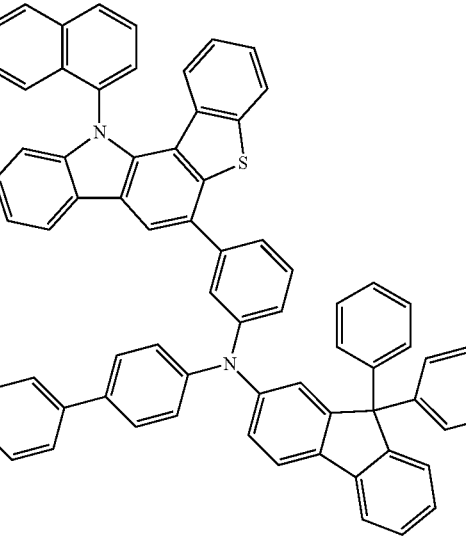

1-90
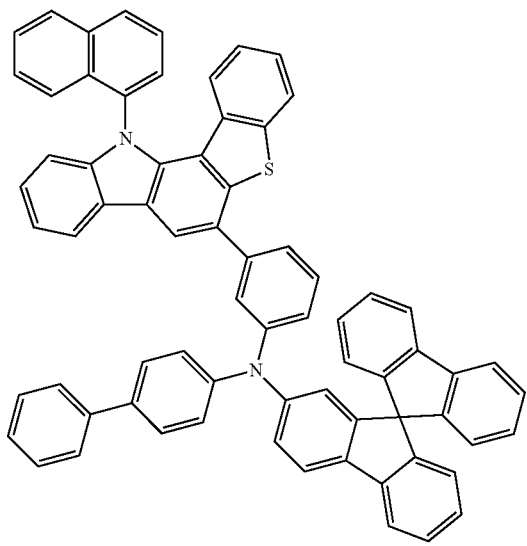
1-91
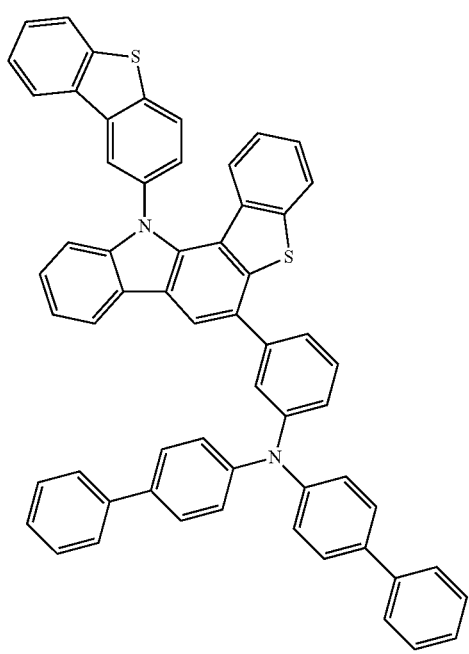
1-92
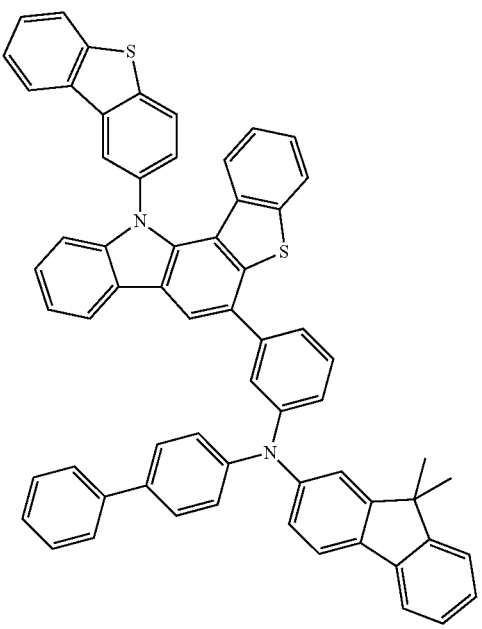
1-93
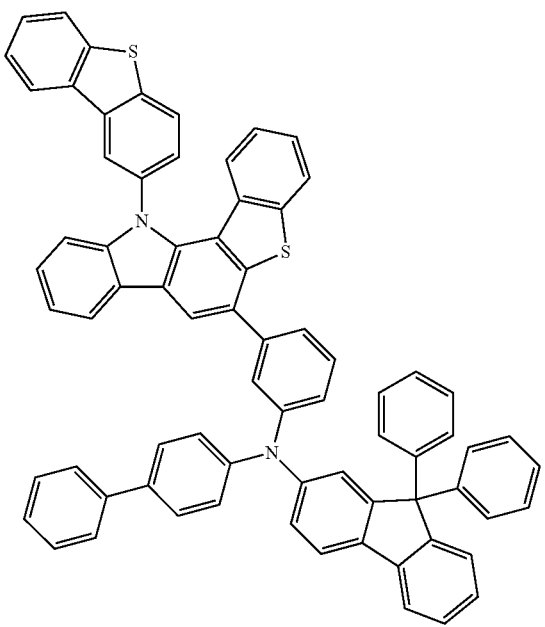

1-94
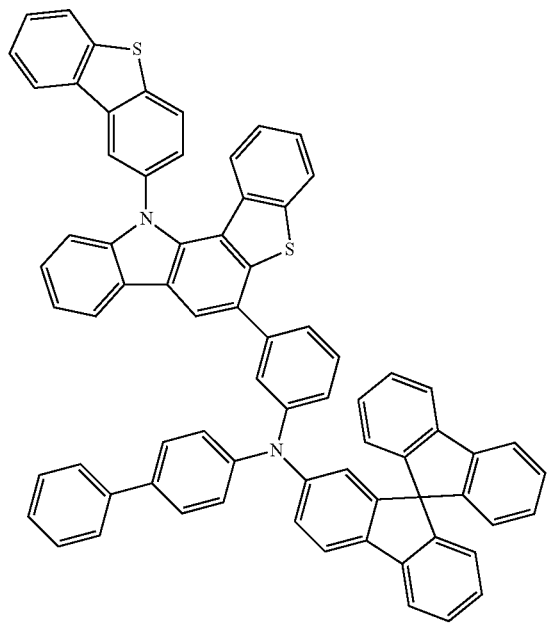
1-96
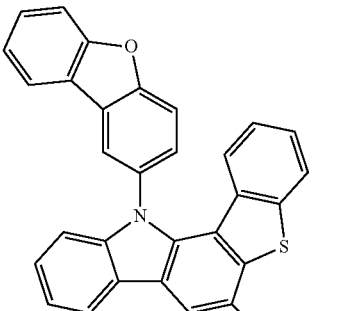
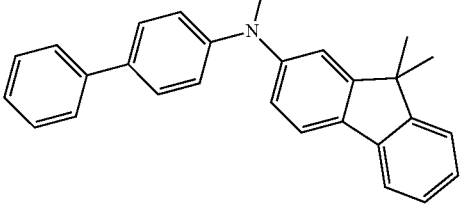
1-95
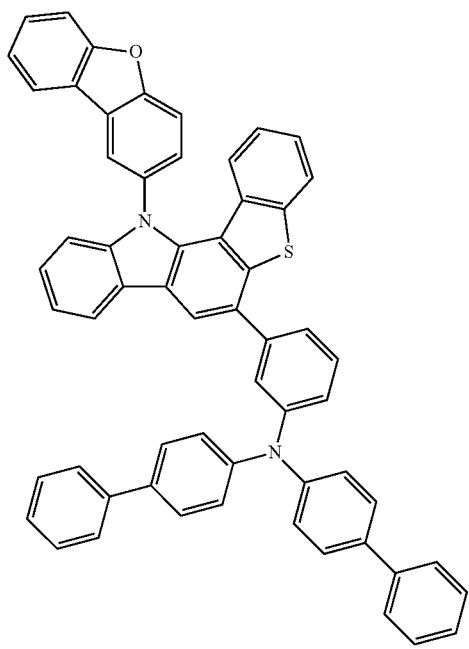
1-97
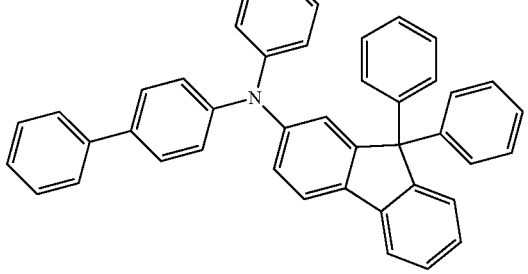

1-98
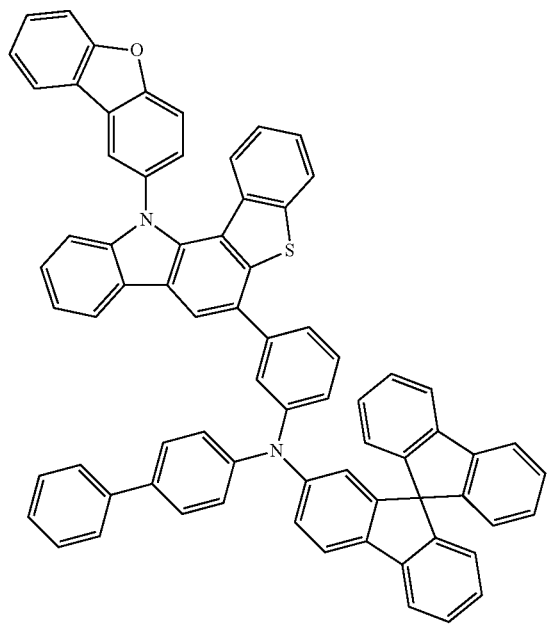
1-99
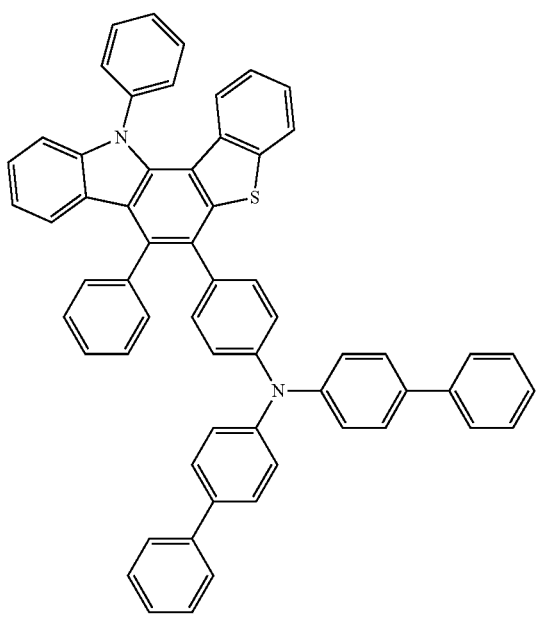
1-100
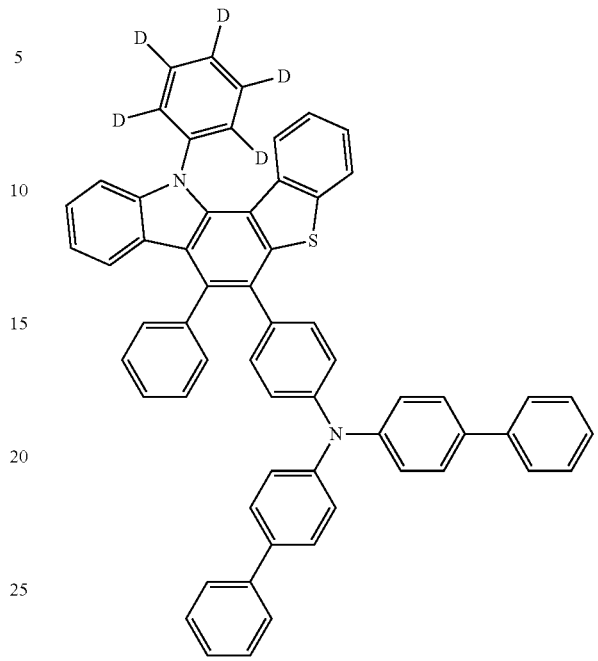
1-101
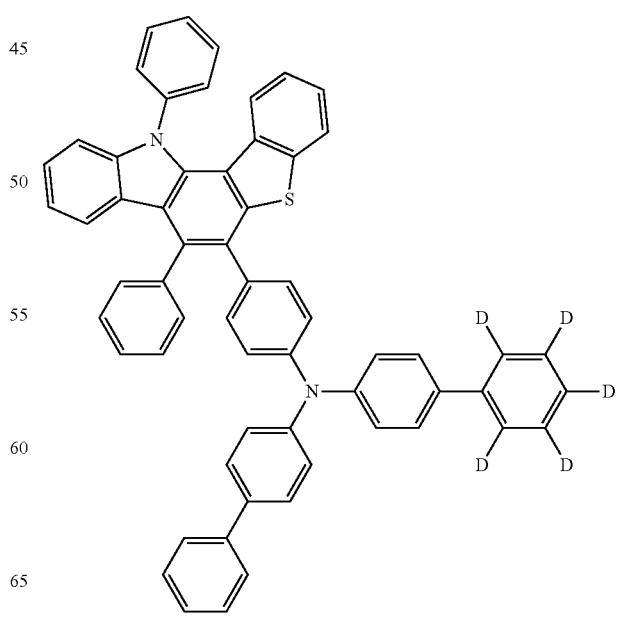

-continued
1-102
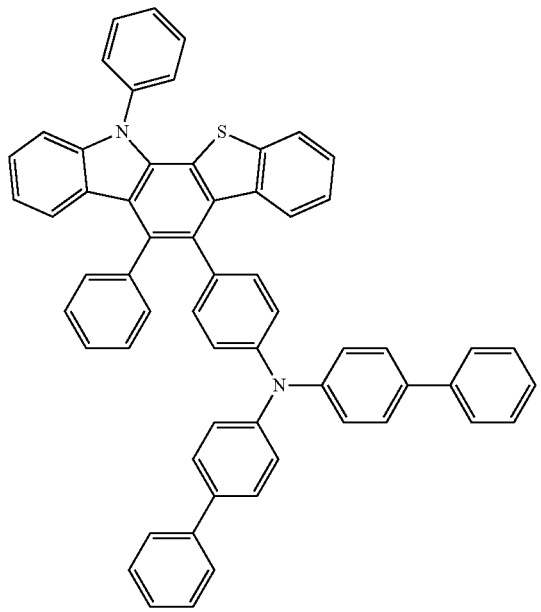
1-104
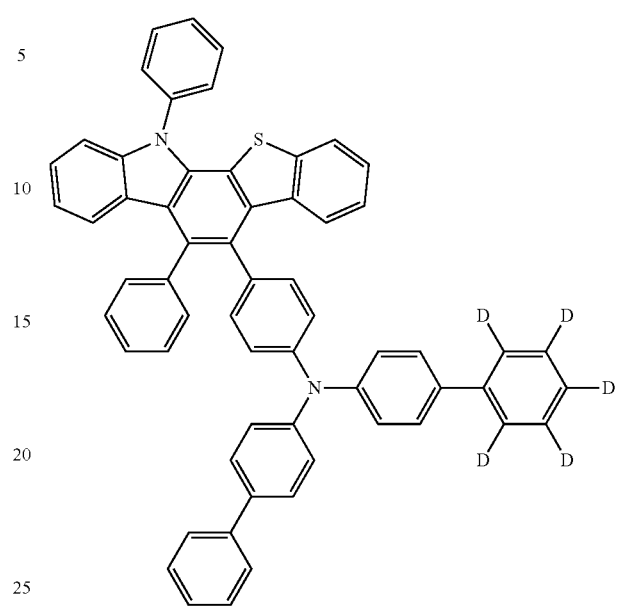
1-103
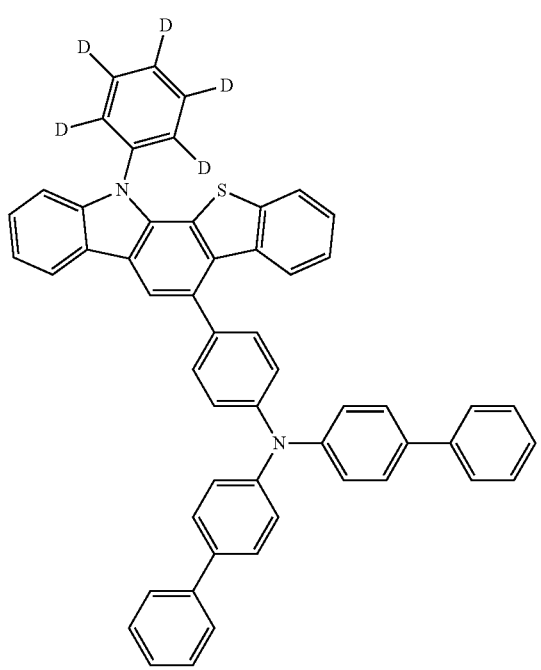
1-105
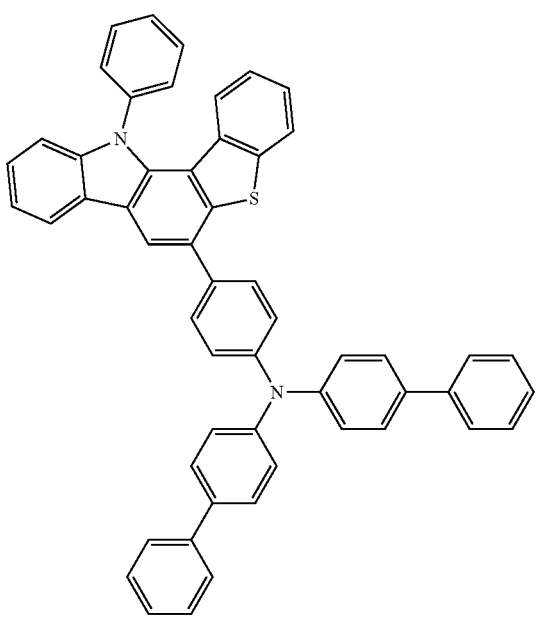

1-106
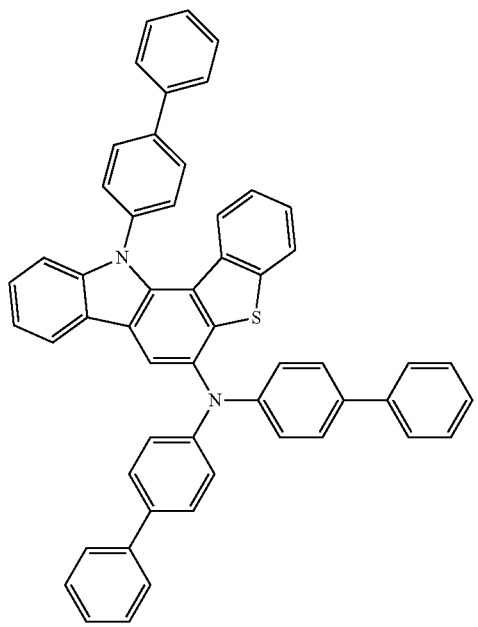
1-108
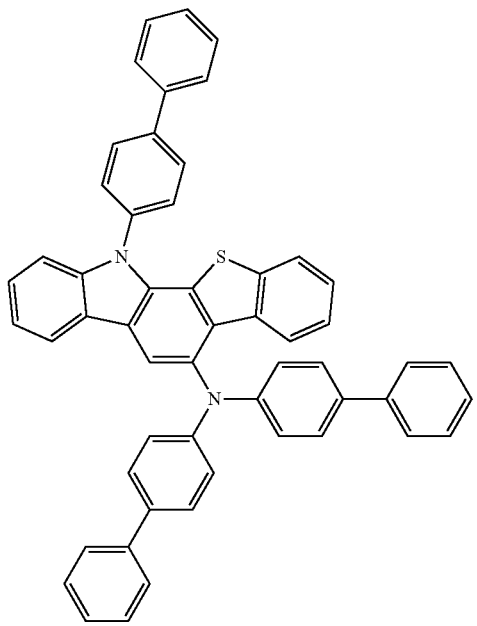
1-107
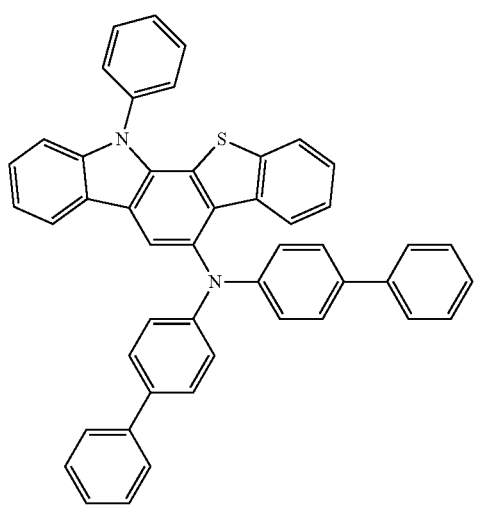
1-109
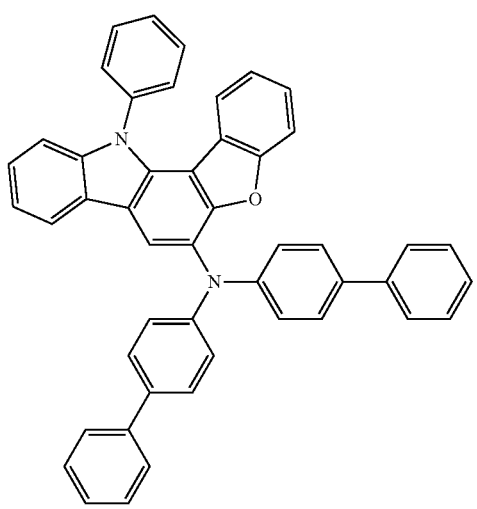

1-110
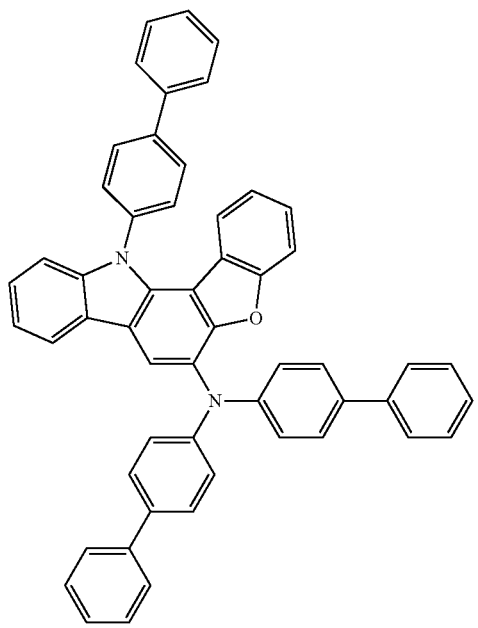
1-111
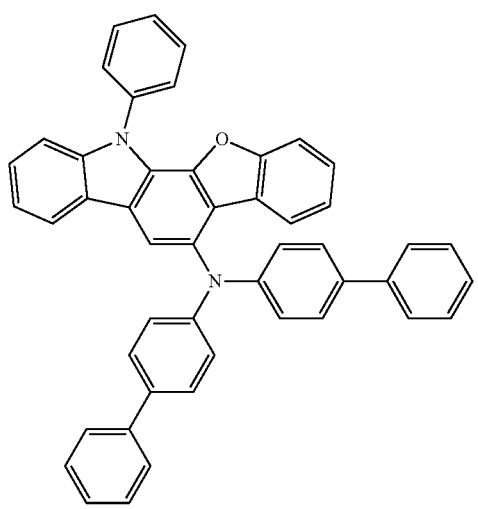
1-112
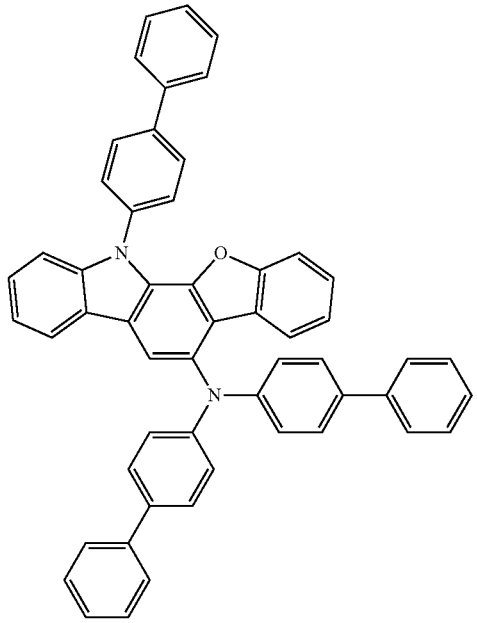
1-113
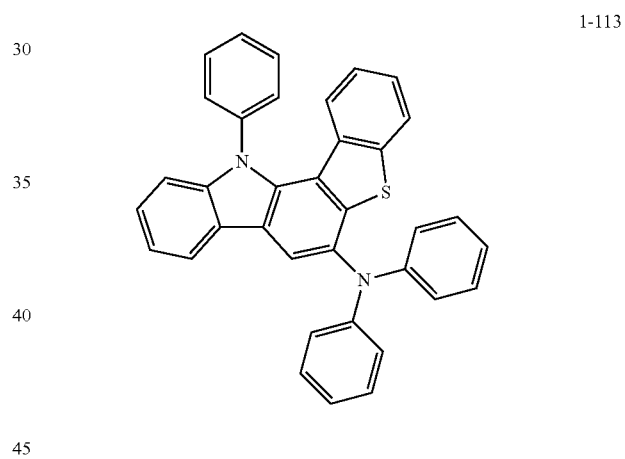
1-114
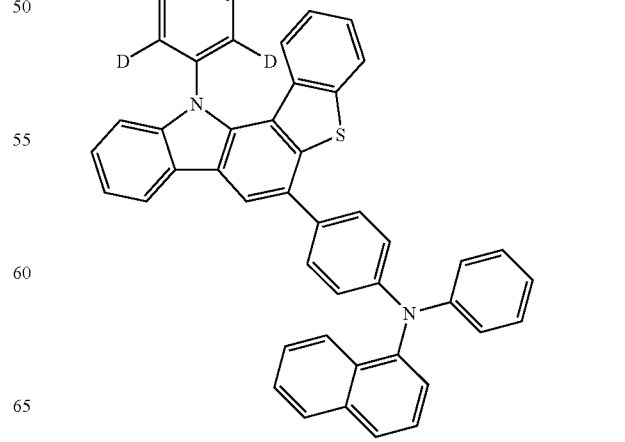

1-115
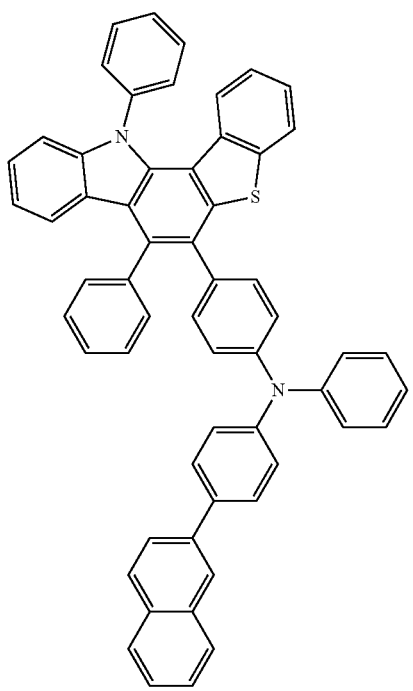
1-116
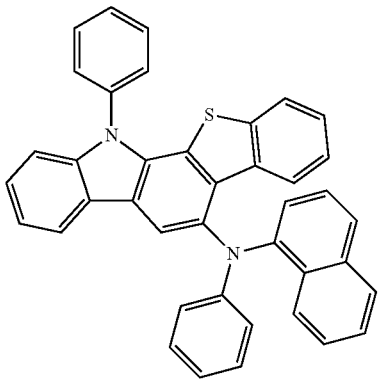
1-117
1-118
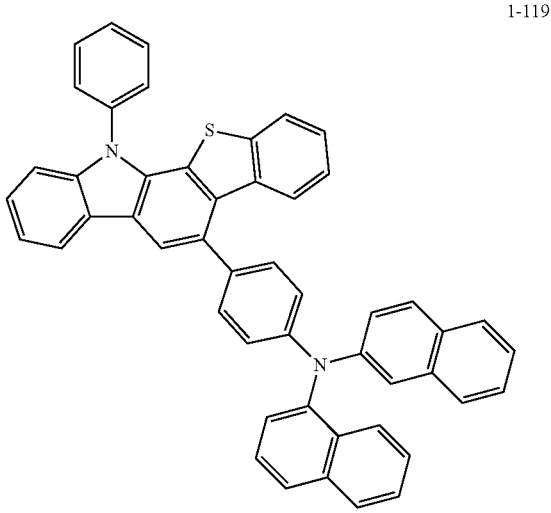
1-119
1-120
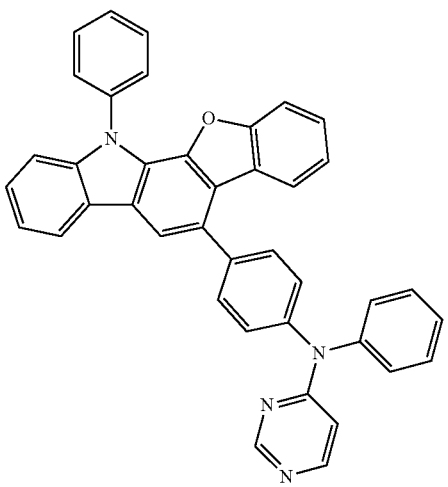

207
-continued
1-121
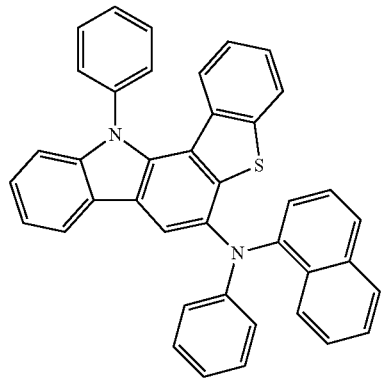
1-122
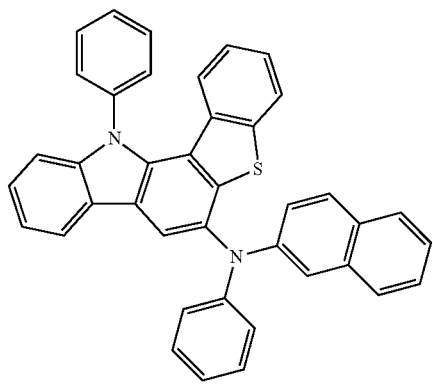
1-123
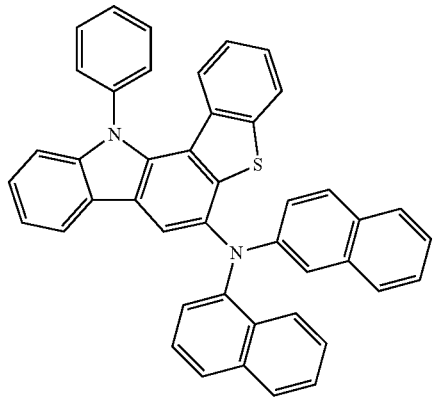
1-124
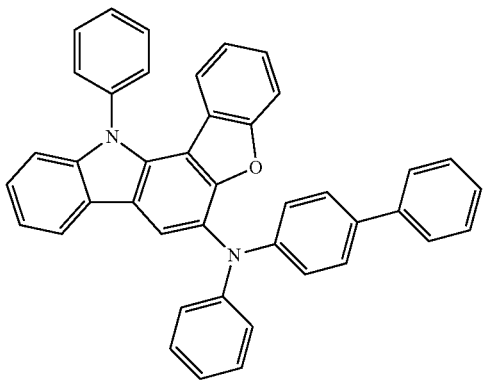
208
-continued
1-125
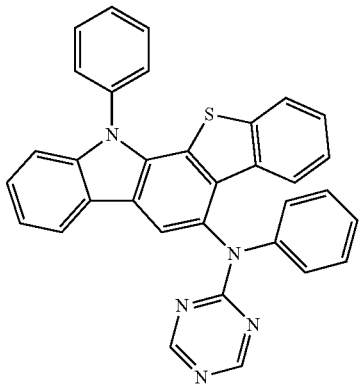
1-126
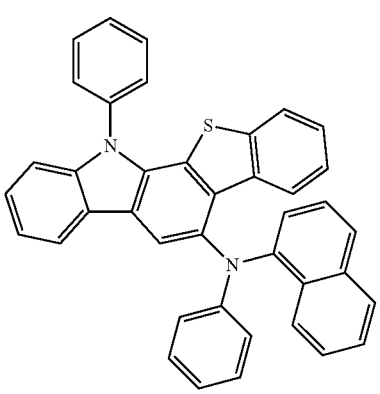
1-127
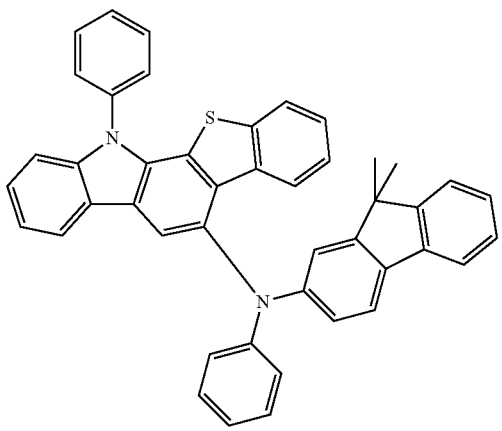
1-128
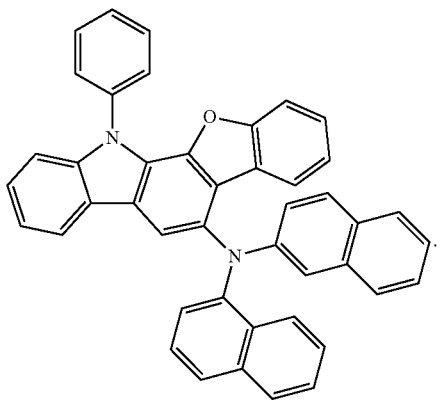

5. An organic electric element comprising a first electrode, a second electrode, and an organic material layer formed between the first electrode and the second electrode, wherein the organic material layer comprises the compound of claim 1.

6. The organic electric element of claim 5, wherein the compound is comprised in at least one layer of a hole injection layer, a hole transport layer, an emission-auxiliary layer, an light emitting layer, an electron transport-auxiliary layer, an electron transport layer and an electron injection layer, and the compound is a single compound or a mixture of two or more different kinds.

7. The organic electric element of claim 5, wherein the organic material layer is formed by any one of the processes of spin coating, nozzle printing, inkjet printing, slot coating, dip coating and roll-to-roll.

8. The organic electric element of claim 5, wherein the organic electric element further comprises a layer for improving luminous efficiency formed on at least one side of the first and second electrodes opposite to the organic material layer.

9. An electronic device comprising a display device and a control unit for driving the display device, wherein the display device comprises the organic electric element of claim 5.

10. The electronic device of claim 9, wherein the organic electric element is at least one of an organic light emitting diode, an organic solar cell, an organic photo conductor, an organic transistor, and an element for monochromatic or white illumination.

\* \* \* \* \*